United States Patent
Zeng et al.

(10) Patent No.: US 12,410,400 B2
(45) Date of Patent: Sep. 9, 2025

(54) METHODS FOR GENERATING MIMETIC INNATE IMMUNE CELLS FROM PLURIPOTENT STEM CELLS

(71) Applicant: Agency for Science, Technology and Research, Singapore (SG)

(72) Inventors: Jieming Zeng, Singapore (SG); Shu Wang, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 559 days.

(21) Appl. No.: 16/484,349

(22) PCT Filed: Feb. 7, 2018

(86) PCT No.: PCT/SG2018/050051
§ 371 (c)(1),
(2) Date: Aug. 7, 2019

(87) PCT Pub. No.: WO2018/147801
PCT Pub. Date: Aug. 16, 2018

(65) Prior Publication Data
US 2019/0359940 A1  Nov. 28, 2019

(30) Foreign Application Priority Data

| Feb. 7, 2017 | (SG) | 10201700937P |
| Jul. 6, 2017 | (SG) | 10201705582S |

(51) Int. Cl.
C12N 5/0783 (2010.01)
A61K 40/15 (2025.01)
A61K 40/42 (2025.01)

(52) U.S. Cl.
CPC ............ C12N 5/0636 (2013.01); A61K 40/15 (2025.01); A61K 40/42 (2025.01); C12N 5/0646 (2013.01); *C12N 2501/125* (2013.01); *C12N 2501/2307* (2013.01); *C12N 2501/2315* (2013.01); *C12N 2501/26* (2013.01); *C12N 2502/1358* (2013.01); *C12N 2502/45* (2013.01); *C12N 2506/02* (2013.01); *C12N 2510/00* (2013.01)

(58) Field of Classification Search
CPC .............. C12N 5/0646; C12N 5/0636; C12N 2501/125; C12N 2501/2307; C12N 2501/2315; C12N 2501/26; C12N 2502/1358; C12N 2502/45; C12N 2506/02; C12N 2510/00; A61K 35/17
See application file for complete search history.

(56) References Cited

U.S. PATENT DOCUMENTS

| 7,749,760 | B2 | 7/2010 | Okamura et al. |
| 8,945,922 | B2 | 2/2015 | Watarai et al. |
| 2011/0044962 | A1 | 2/2011 | Beck |
| 2013/0078226 | A1 | 3/2013 | Nakauchi et al. |
| 2013/0287751 | A1 | 10/2013 | Kaufman et al. |
| 2013/0303380 | A1* | 11/2013 | Ogg ................ G01N 33/54313 506/18 |
| 2020/0017837 | A1 | 1/2020 | Aoi |

FOREIGN PATENT DOCUMENTS

| CN | 1791433 A | 6/2006 |
| CN | 103087991 A | 5/2013 |
| CN | 108473961 B | 11/2022 |
| EP | 2336303 A1 | 6/2011 |
| EP | 2853590 A1 | 4/2015 |
| JP | 2003111595 A | 4/2003 |
| JP | 7092281 B2 | 6/2022 |
| WO | WO-2006/006720 A1 | 1/2006 |
| WO | WO-2010/027094 A1 | 3/2010 |
| WO | WO-2010/051634 A1 | 5/2010 |
| WO | WO-2010/141801 A2 | 12/2010 |

(Continued)

OTHER PUBLICATIONS

Thibault et al ("Compared TCR and CD3e Expression on αβ and γδ T Cells: Evidence for the Association of Two TCR Heterodimers with Three CD3 Chains in the TCR/CD3 Complex," J Immunol 1995; 154:3814-3820 )(Thibault). (Year: 1995).*
Poccia et al ("CD94/NKC2 Inhibitory Receptor Complex Modulates Both Anti-Viral and Anti-Tumoral Responses of Polyclonal Phosphoantigen-Reactive Vγ9Vδ2 T Lymphocytes," J Immunol (1997) 159 (12): 6009-6017 (Year: 1997).*
Battistini et al ("Phenotypic and Cytokine Analysis of Human Peripheral Blood T Cells Expressing NK Cell Receptors," J Immunol (1997) (Year: 1997).*
Smith et al ("Ex vivo expansion of human T cells for adoptive immunotherapy using the novel Xeno-free CTS Immune Cell Serum Replacement," Clinical & Translational Immunology (2015) 4, e31), (Year: 2015).*
Watarai et al ("Murine induced pluripotent stem cells can be derived from and differentiate into natural killer T cells," J Clin Invest. 2010;120(7):2610-2618). (Year: 2010).*

(Continued)

*Primary Examiner* — Anoop K Singh
(74) *Attorney, Agent, or Firm* — Joseph G. Chu; JCIP

(57) ABSTRACT

Human pluripotent stem cells (hPSCs), especially induced pluripotent stem cells (iPSCs) provide a promising starting material to produce mimetic innate immune cells such as natural killer (NK) cells and γδ T-cells for cancer immunotherapy. To facilitate consistent mass production, an overall manufacturing scheme to make mimetic innate immune cells from hPSCs was designed and demonstrated. Particularly, a robust protocol to differentiate hPSCs into NK cells or γδ T-cells through sequential hematopoietic differentiation on stromal cell line deficient in expressing M-CSF and lymphoid commitment on stromal cell line deficient in expressing M-CSF ectopically expressing DLL1 without employing CD34+ cell enrichment and spin embryoid body formation is established. Using this two-stage protocol, the generation of functional mimetic NK cells and functional mimetic γδ NKT-cells was demonstrated from hPSCs, including hESCs, peripheral blood cell-derived iPSCs (PBC-iPSCs). non-T cell-derived iPSCs or γδ T cell-derived iPSCs and the use of these mimetic innate immune cells in killing cancer cells.

6 Claims, 13 Drawing Sheets

Specification includes a Sequence Listing.

(56) References Cited

FOREIGN PATENT DOCUMENTS

| WO | WO-2016/123100 A1 | 8/2016 |
|---|---|---|
| WO | WO-2016/205680 A1 | 12/2016 |
| WO | WO-2017/100403 A1 | 6/2017 |
| WO | WO-2018/143243 A1 | 8/2018 |

OTHER PUBLICATIONS

Nishimura et al ("Generation of Rejuvenated Antigen-Specific T Cells by Reprogramming to Pluripotency and Redifferentiation," Cell Stem Cell 12, 114-126, Jan. 3, 2013) (Year: 2013).*
Giannotta Frontiers in Immunology, 14, 1-12 (Year: 2023).*
Kabelitz et al Cellular & Molecular Immunology 17:925-939). (Year: 2020).*
Silva Santos (Nature Reviews Cancer 19, 392-404 (Year: 2019).*
Halary et al Eur. J. Immunol. .27: 2812-2821 (Year: 1997).*
Watanabe, Daisuke; Azuma, Takeshi; Aoi, Takashi S Gastroenterology, vol. 152, No. 5, Suppl. 1, p. S641 (pp. 1-2 abstract) ( Year: 2017).*
Pellicci et al Nature Review, 20, 756-770 (Year: 2020).*
Watarai et al (J Clin Invest. ; 120(7):2610-2618 (Year: 2010).*
Zeng et al PLoS One , 1-20 (Year: 2012).*
Deniger et al Frontiers in Immunology, 5(1)1-10 (Year: 2014).*
Beck, R.C. et al., The Notch Ligands Jagged2, Delta1, and Delta4 Induce Differentiation and Expansion of Functional Human NK Cells from CD34+ Cord Blood Hematopoietic Progenitor Cells, Biol Blood Marrow Transplant, 15(9): 1026-1037 (2009).
Brown, M.E. et al., Derivation of Induced Pluripotent Stem Cells from Human Peripheral Blood T Lymphocytes, PLoS One, 5(6):1-9 (2010).
Bueno, C. et al., Reprogramming human B cells into induced pluripotent stem cells and its enhancement by C/EBPa, Leukemia, 30(3):674-682 (2015).
International Search Report for PCT/SG2018/050051, 8 pages (mailed Jul. 5, 2018).
Loh, Y.H. et al., Reprogramming of T Cells from Human Peripheral Blood, Cell Stem Cell, 7(1):15-19 (2010).
Raab, S. et al., A Comparative View on Human Somatic Cell Sources for iPSC Generation. Stem Cells Int, 2014: 1-12 (2014).
Seki, T. et al., Generation of Induced Pluripotent Stem Cells from Human Terminally Differentiated Circulating T Cells, Cell Stem Cell, 7(1):11-14 (2010).
Staerk, J. et al., Reprogramming of Human Peripheral Blood Cells to Induced Pluripotent Stem Cells, Cell Stem Cell, 7(1):20-24 (2010).
Timmermans, F. et al., Generation of T Cells from Humab Embryonic Stem Cell-Derived Hematopoietic Zones, J Immunol, 182(11):6879-6888 (2009).
Tomchuck, S.L. et al., Enhanced Cytotoxic Function of Natural Killer and CD3+CD56+ Cells in Cord Blood after Culture, Biol Blood Marrow Transplant, 21(1):39-49 (2014).
Vizcardo, R. et al., Regeneration of Human Tumor Antigen-Specific T Cells from iPSCs Derived from Mature CD8* T Cells, Cell Stem Cell, 12(1):31-36 (2013).
Watanabe, D. et al., The Generation of Human γσT Cell-Derived Induced Pluripotent Stem Cells from Whole Peripheral Blood Mononuclear Cell Culture, Stem Cells Transl. Med., 7(1):34-44 (2017).
Written Opinion for PCT/SG2018/050051, 10 pages (mailed Jul. 5, 2018).
Zeng, J. et al., Generation of "Off-the-Shelf" Natural Killer Cells from Peripheral Blood Cell-Derived Induced Pluripotent Stem Cells, Stem Cell Reports, 9(6):1796-1812 (2017).
Watanabe, D. et al., Development of a new gastrointestinal cancer treatment method using iPS cell-derived $V\gamma9V\delta2$ T cells, Japan Dig. Dis. Week 24th Japan Gastroenter. Soc. Weekly, Abstract p. 413 (2016).
Lian, R.H., et al., Orderly and Nonstochastic Acquisition of CD94/NKG2 Receptors by Developing NK Cells Derived from Embryonic Stem Cells In Vitro, The Journal of Immunology, 168:4980-4987 (2002).
Chinese Office Action and Search Report dated Nov. 24, 2022 for Chinese Application No. 201880022790.X.
Notice of Granting Patent Right for Invention and Chinese supplemental Search Report dated Jun. 19, 2023 for Chinese Application No. 201880022790.X.
Rosemary K. Lees et al., Tissue-specific segregation of TCR gamma delta+ NKT cell according to phenotype TCR repertoire and activation status: parallels with TCR alpha beta+ NKT cell, Eur. J. Immunol. 2001. 31: 2901-2909.
Catherine C. Yin et al., The Tec Kinase ITK Regulates Thymic Expansion, Emigration, and Maturation of Gamma Delta NKT Cells, The Journal of Immunology, 2013, 190: 2659-2669.
Pablo Pereira et al., Critical Role of TCR Specificity in the Development of Vgamma1Vdetla6.3+ Innate NKT gamma delta Cells, The Journal of Immunology, 2013, 191: 1716-1723.
Taras Kreslavsky et al., TCR-inducible PLZF trancription factor required for innate phenotype of a subset of gamma delta T cells with restricted TCR diversity, PNAS, Jul. 28, 2009, vol. 106, No. 30, 12453-12458.
First Examination Report dated Jul. 27, 2023 for European Application No. 18751284.3.
Modified Substantive Examination Adverse Report dated Sep. 27, 2023 for Malaysian Application No. PI2019004546.

* cited by examiner

METHODS FOR GENERATING MIMETIC INNATE IMMUNE CELLS FROM PLURIPOTENT STEM CELLS

CROSS REFERENCE TO RELATED APPLICATIONS

This application is a national stage filing under 35 U.S.C. § 371 of International Patent Application Serial No. PCT/SG2018/050051, filed Feb. 7, 2018, which claims the priority to Singapore Application No. 10201700937P, filed Feb. 7, 2017 and Singapore Application No. 10201705582S, filed Jul. 6, 2017, the contents of each of which are incorporated herein by reference.

FIELD

The present invention relates to methods and kits for generating innate immune cells, preferably natural killer cells or gamma delta T-cells and methods of using the innate immune cells in treatment and methods of generating induced pluripotent stem cells.

BACKGROUND

In 2015, about 90.5 million people had cancer and about 14.1 million new cases occur each year (GBD 2015, Lancet. 388 (10053) 1545-1602). Cancer is often treated with some combination of radiation therapy, surgery, chemotherapy, and/or targeted therapy. While there are many treatments available 8.8 million people die from cancer each year and there is a constant need for new treatments.

Cancer immunotherapies exploiting innate immune cells are the new hope for cancer treatment (Woo et al. *Annual review of immunology* 33, 445-474 (2015)). These innate immune cells including natural killer (NK) cells and γδ T cells can recognize a wide range of cancer cells through major histocompatibility complex (MHC)-independent mechanisms (Scheper, et al. Leukemia 28, 1181-1190 (2014). This unique feature allows the use of innate immune cells to treat cancers in many recipients without MHC-restriction of conventional αβ T cell-based strategies. Currently, healthy donor-derived blood cells are the commonly used cell source to generate a large number of innate immune cells (Kondo, et al. *Cytotherapy* 10, 842-856 (2008)). However, these donor blood cell-dependent platforms are challenging for centralized, standardized and large-scale production due to the use of variable and limited starting materials and the complicated logistics.

Gamma delta T-cells (γδ T cells) are innate immune cells that recognize cancer cells via major histocompatibility complex-independent mechanisms. This feature allows the use of donor-derived γδ T cells to treat cancers in different patients. γδ T cells account for 1-10% of peripheral blood lymphocytes. Among these circulating γδ T cells, Vγ9Vδ2 T cells are the major subset that reacts to phosphoantigens through their Vγ9Vδ2 T-cell receptors (TCRs), and thus recognizes infected cells or malignant cells. During in vivo development, somatic recombination of TCRG and TCRD genes is an early crucial step for γδ cells to obtain their TCR γ chain and δ chain. To generate γδ T cells from iPSCs, a logical strategy would be to accurately recapitulate this process of somatic recombination of TCRG and TCRD genes during in vitro differentiation to produce functional γδ TCRs. But such a strategy remains very difficult for current technology.

Natural killer cells (NK cells) are lymphocytes of the innate immune system that are able to kill a broad spectrum of malignant cells and virus-infected cells (Domogala, et al. Frontiers in immunology 6, 264 (2015)). The target recognition and activation of NK cells depend on an array of activating receptors and inhibitory receptors, which are different from the MHC-restricted αβ T-cell receptor (TCR)-dependent mechanism of αβ T cells (Moretta, et al. Frontiers in immunology 5, 87 (2014)). Thus, it is possible to use allogeneic NK cells to treat cancer with less chance of causing graft-versus-host-disease (GVHD) (Leung. Clinical cancer research: an official journal of the American Association for Cancer Research 20, 3390-3400 (2014)). The distinct target recognition mechanism of NK cells significantly extends the potential cell sources that can be used in adoptive immunotherapy for cancer beyond autologous NK cells.

In current clinical trials, large dosages of NK cells ranging from $5 \times 10^8$-$5 \times 10^7$/kg body weight are required (Lapteva et al. Critical reviews in oncogenesis 19, 121-132 (2014)). One typical approach to derive such large amounts of allogeneic NK cells is NK cell enrichment from large volumes of donor peripheral blood. Starting from donor-derived leukapheresis products, different protocols have been established to produce NK cell products by immunemagnetic depletion of T cells and B cells and selection of CD56+ cells (Koehl, et al. Frontiers in oncology 3, 118 (2013)). The purities of such products are especially crucial for clinical application in an allogeneic setting, in which the residual T cells may cause GVHD and prohibit the infusion of high dosages. Current generation of high-purity NK cell products requires a prolonged procedure that not only compromises the recovery of NK cells but also affects their viability and potency. With a low recovery rate, it is difficult to obtain sufficient NK cells from a single leukapheresis product. Another popular approach to produce NK cell therapeutics is NK cell expansion using feeder cells, such as K562 cells modified with membrane-bound molecules such as interleukin (IL)-15 and 4-1BB ligand (K562-mb15-41BBL) (Fujisaki, et al. Cancer research 69, 4010-4017 (2009)). These feeder cells can rapidly expand the NK cells from peripheral blood mononuclear cells (PBMCs) by 21.6-fold (Fujisaki, et al.) or from cryopreserved apheresis products by 70-fold (Lapteva et al.). Yet the purities of such NK cell products are about 70% and further, time consuming methods of depletion of concomitant CD3+ T cells is necessary for allogeneic use (Lapteva et al.). The above-mentioned two approaches are feasible to generate NK cell therapeutics from donor cells, but like any other donor cell-dependent manufacturing processes, generating NK cell products from primary cells of various donors is difficult to be standardized due to the variable starting materials. It demands particular skills and facilities, complicated logistics and high operation cost, thus it is not amenable to bulk manufacturing.

Currently, healthy donor-derived blood cells are the commonly used cell source to generate a large number of innate immune cells. However, these donor blood cell-dependent platforms are challenging for centralized, standardized and large-scale production due to the use of variable and limited starting materials and the complicated logistics. Another hurdle faced by current strategies for NK cell production is that NK cells express clonally distributed inhibitory receptors known as killer cell immunoglobulin-like receptors (KIRs) (Parham, 2005 Nat. Rev. Immunol. 5, 201-214). Each individual KIR recognizes a specific human leukocyte antigen (HLA) class I molecule known as KIR ligand, e.g., KIR2DL1 binds HLA-C2, KIR2DL2 and KIR2DL3 bind HLA-C1, KIR3DL1 binds HLABw4, and KIR3DL2 binds HLA-A3 and HLA-A11 (Thielens et al., 2012 Curr. Opin. Immunol. 24, 239-245). Binding of KIR ligands to inhibitory KIRs suppresses cytotoxicity of NK cells. To alleviate such inhibition on NK cells and thus to enhance their cytotoxicity against a patient's cancer cells, elaborately selecting an NK cell donor for that particular patient to obtain a KIR-HLA mismatch in an anti-cancer direction is critical (Thielens et al., 2012). This selection is based on donor KIR typing and recipient HLA typing. A donor is suitable if an inhibitory KIR is present in the donor but the KIR ligand is absent in the recipient (Leung, 2014 Clin. Cancer Res. 20, 3390-3400). The involvement of both KIR and HLA, two highly diverse gene families in human immune system, decides that current donor cell-dependent manufacturing platforms can only produce "custom-made" NK cell products for limited patients instead of "off-the-shelf" ones for a wide range of patients. Therefore, it is imperative to explore alternative manufacturing strategy that circumvents these aforementioned issues.

In the age of pluripotency, human pluripotent stem cells (hPSCs), especially induced pluripotent stem cells (iPSCs) have emerged as a reliable and standardizable starting material to generate immune cells like dendritic cells (Zeng, et al. Journal of immunology 188, 4297-4304 (2012)) as well as NK cells (Woll, et al. Blood 113, 6094-6101 (2009)). Although a couple of protocols have been developed to generate NK cells from hPSCs, the requirements of enriching CD34+ cells (Woll, et al. Blood 113, 6094-6101 (2009)) or spin embryoid body (EB) formation (Knorr, D. A. et al. Stem cells translational medicine 2, 274-283 (2013)) determine that these existing protocols are very complex and time consuming thus more suitable for laboratory use rather than industrial manufacturing. Moreover, using these current methods, the resulting NK cells express high-level KIRs (Knorr et al., 2013), which restrict their applications to recipients of certain HLA typing. Up to now a robust protocol to consistently generate NK cells from various hPSC sources is yet to be established.

Inducing hematopoietic differentiation of hPSCs is a crucial first step for generating NK cells from hPSCs. One approach is to co-culture hPSCs with bone marrow stromal cells such as S17 and M2-10B4 to obtain CD34+ hematopoietic precursors (Woll, et al. Blood 113, 6094-6101 (2009)). However, this method requires a prolonged co-culture of up to 21 days and a subsequent sorting of CD34+ cells before their further differentiation into NK cells. This sorting step will not only complicate the protocol, but also affect the yield of NK cells due to the exclusion of many other hematopoietic progenitors that also have NK cell differentiation potential. Another approach to generate hematopoietic cells is to form EBs (Tabatabaei-Zavareh, et al. PloS one 2, e232 (2007)) and recently spin EBs Knorr, (D. A. et al. Stem cells translational medicine 2, 274-283 (2013)). This random differentiation approach, however, is highly hPSC line-dependent and thus not robust enough for various hPSC sources. Moreover, the spin EBs formation requires a prior time-consuming adaptation of hPSCs to TrypLE digestion for at least 10 passages, which may not work for every hPSC line. These TrypLE-adapted hPSCs are then seeded into 96-well plate at a density of 3,000 cells per well and spun down for spin EB formation. This is followed by harvesting and seeding the spin EBs at a density of 6 spin EBs per well in 24-well plate for further NK cell differentiation. Apparently, this labor-intensive and skill-demanding spin EB approach is difficult for scale-up in commercial production.

Co-culturing with stromal cells to promote further differentiation of hematopoietic progenitors is the second step for generating NK cells from hPSCs. Several stromal cell lines have been used for coculturing. Although stromal cell lines such as MS-5 and AFT024 have been proved to support NK cell development, the resulting cells are a heterogeneous population containing both CD56+ and CD56− cells (Woll, et al. Blood 113, 6094-6101 (2009)). A stromal cell line EL08-1D2 has showed better support for NK cell development (McCullar, V. et al. Experimental hematology 36, 598-608 (2008)); however, its efficacy has only been demonstrated with sorted CD34+ cells or spin EBs (Woll, et al. Blood 113, 6094-6101 (2009)).

SUMMARY

An object of the invention is to ameliorate some of the above mentioned difficulties preferably by using a reliable, unlimited and standardizable starting cell source of human pluripotent stem cells such as induced pluripotent stem cells (iPSCs) to generate mimetic innate immune cells for use in immunotherapy treatment.

Accordingly, a first aspect of the invention includes a method of generating mimetic innate immune cells, the method comprising:
  (a) co-culturing human pluripotent stem cells with a stromal cell line deficient in expressing macrophage colony stimulating factor to generate progenitors of innate immune cells;
  (b) co-culturing the progenitors of innate immune cells with a stromal cell line deficient in expressing macrophage colony stimulating factor and ectopically expressing Notch ligand, Delta like 1 (DLL1) in a media comprising stem cell factor (SCF), Fms-related tyrosine kinase 3 ligand (FLT3L), interleukin 7 (IL7) and/or interleukin 15 (IL15) to generate differentiated mimetic innate immune cells;
  (c) passaging the differentiated mimetic innate immune cells weekly for 3 to 5 weeks.

Another aspect of the invention includes mimetic innate immune cells comprising cells expressing at least one of CD56, CD16, NKp30, NKp44, NKp46, NKG2D, DNAM-1, FASL, TRAIL NKG2A/CD94 or a combination thereof and with low or no expression of killer cell immunoglobulin-like receptors (KIR).

Another aspect of the invention includes mimetic innate immune cells as described herein for use in a treatment.

Another aspect of the invention includes mimetic innate immune cells as described herein for use in treating cancer.

Another aspect of the invention includes use of mimetic innate immune cells as described herein for manufacture of a medicament in the treatment of cancer.

Another aspect of the invention includes a kit for generating mimetic innate immune cells, the kit comprising:
  (a) a human pluripotent stem cell line;
  (b) a stromal cell line deficient in expressing macrophage colony stimulating factor (M-CSF);
  (c) a stromal cell line deficient in expressing macrophage colony stimulating factor and ectopically expressing Notch ligand, Delta like 1 (DLL1);
  (d) a first simple media for co-culturing a human pluripotent stem cells with the stromal cell line deficient in expressing M-CSF; and
  (e) a second media comprising stem cell factor (SCF), Fms-related tyrosine kinase 3 ligand (FLT3L), interleukin 7 (IL7) and/or interleukin 15 (IL15).

Another aspect of the invention includes a method of treating a patient with cancer comprising: administering to the patient mimetic innate immune cells expressing at least one of CD56, CD16, NKp30, NKp44, NKp46, NKG2D, DNAM-1, FASL, TRAIL NKG2A/CD94 or a combination thereof and with low or no expression of killer cell immunoglobulin-like receptors KIR generated by,
(a) co-culturing human pluripotent stem cells with a stromal cell line deficient in expressing macrophage colony stimulating factor to generate progenitors of innate immune cells;
(b) co-culturing the progenitors of innate immune cells with a stromal cell line deficient in expressing macrophage colony stimulating factor and ectopically expressing Notch ligand, Delta like 1 (DLL1) in a media comprising stem cell factor (SCF), Fms-related tyrosine kinase 3 ligand (FLT3L), interleukin 7 (IL7) and/or interleukin 15 (IL15) to generate differentiated mimetic innate immune cells;
(c) passaging the differentiated mimetic innate immune cells weekly for 3 to 5 weeks.

Another aspect of the invention includes a method of generating induced pluripotent stem cells (iPSC) from non-T cells of peripheral blood cells, comprising:
(a) incorporating reprogramming transcription factors into non-T cells;
(b) growing the non-T cells incorporated with the reprogramming transcription factors to become pluripotent stem cells.

Another aspect of the invention includes a method of generating induced pluripotent stem cells (iPSC) from gammadelta T cells (γδ T cells), comprising:
(a) incorporating reprogramming transcription factors into γδ T cells;
(b) growing the γδ T cells incorporated with the reprogramming transcription factors to become pluripotent stem cells.

Another aspect of the invention includes an induced pluripotent stem cells (iPSC) comprising a TCR gene arranged in a TCRG gene configuration or a TCR gene arranged in a TCRD gene configuration.

Another aspect of the invention includes a method of generating mimetic NK cells, the method comprising:
(a) co-culturing human pluripotent stem cells with a stromal cell line deficient in expressing macrophage colony stimulating factor (M-CSF) to generate primed innate immune cells;
(b) co-culturing the primed innate immune cells with a stromal cell line deficient in expressing M-CSF and ectopically expressing Notch ligand, Delta like 1 (DLL1) in a media comprising stem cell factor (SCF), Fms-related tyrosine kinase 3 ligand (FLT3L), interleukin 7 (IL7) and/or interleukin 15 (IL15) to generate differentiated mimetic innate immune cells;
(c) passaging the differentiated mimetic innate immune cells weekly for 3 to 5 weeks.

Another aspect of the invention includes a method of generating mimetic γδ T cells, the method comprising:
(a) co-culturing human pluripotent stem cells with a stromal cell line deficient in expressing macrophage colony stimulating factor (M-CSF) to generate primed innate immune cells;
(b) co-culturing the primed innate immune cells with a stromal cell line deficient in expressing M-CSF and ectopically expressing Notch ligand, Delta like 1 (DLL1) in a media comprising stem cell factor (SCF), Fms-related tyrosine kinase 3 ligand (FLT3L), interleukin 7 (IL7) and/or interleukin 15 (IL15) to generate differentiated mimetic innate immune cells;
(c) passaging the differentiated mimetic innate immune cells weekly for 3 to 5 weeks.

Another aspect of the invention includes mimetic NK cells comprising cells expressing at least one of CD56, CD16, NKp30, NKp44, NKp46, NKG2D, DNAM-1, FASL, TRAIL, NKG2A/CD94 or a combination thereof, with no CD3 expression and with low or no expression of killer cell immunoglobulin-like receptors KIR.

Another aspect of the invention includes mimetic γδ T cells comprising cells expressing (a) at least one of CD56, CD16, NKp30, NKp44, NKp46, NKG2D, DNAM-1, FASL, TRAIL, NKG2A/CD94 or a combination thereof; (b) γδ TCR; and (c) with low or no expression of killer cell immunoglobulin-like receptors KIR.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION

Figure 1:
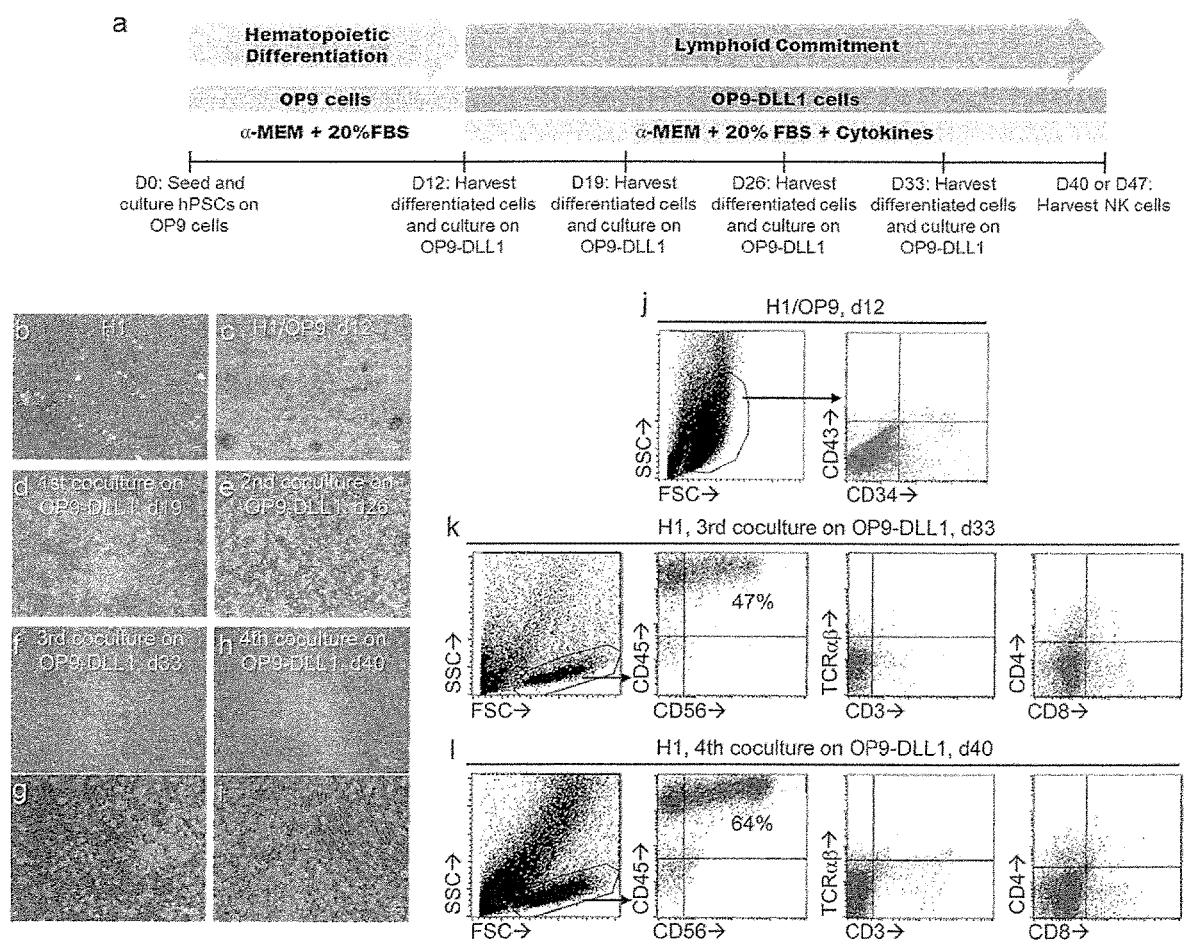
FIG. 1: Generation of NK cells from hPSCs. (a): A schematic of a two-stage protocol for NK cell derivation from hPSCs. (b-i): Morphological changes during differentiation of H1 cells into NK cells. Phase contrast images show (b): Undifferentiated H1 cells; (c): H1 and OP9 coculture day 12; (d): 1st differentiated cells and OP9-DLL1 coculture day 7 (day 19); (e): 2nd differentiated cells and OP9-DLL1 coculture day 7 (day 26); (f-g): 3rd differentiated cells and OP9-DLL1 coculture day 7 (day 33); (h-i): 4th differentiated cells and OP9-DLL1 coculture day 7 (day 40). (j-l): Phenotypic changes during differentiation of H1 cells into NK cells. Flow cytometric analysis shows U): CD34+ cells from H1 and OP9 coculture day 12; (k-l): CD56+CD45+ cells from 3rd (d33) and 4th (d40) coculture on OP9-DLL1.

A robust protocol to consistently generate innate immune cells from various hPSC sources is yet to be established. In this regard an overall manufacturing scheme for mass production of functional NK cells, has been designed and demonstrated not only from a classical hPSC source, human embryonic stem cells (hESCs), but also from a convenient hPSC source, peripheral blood cell (PBC)-derived iPSCs (PBC-iPSCs) without employing CD34+ cell enrichment or spin EB formation.

Human pluripotent stem cells (hPSCs), especially induced pluripotent stem cells (iPSCs) provide a promising starting material to produce mimetic innate immune cells such as mimetic natural killer (NK) cells and mimetic γδ T-cells for cancer immunotherapy. To facilitate consistent mass production, an overall manufacturing scheme to make mimetic innate immune cells from human pluripotent stem cells (hPSCs) was designed and demonstrated. Particularly, a robust protocol to differentiate hPSCs into mimetic NK cells or mimetic γδ T-cells with NK properties through sequential hematopoietic differentiation on OP9 cells and lymphoid commitment on OP9-DLL1 cells without employing CD34+ cell enrichment and spin embryoid body formation.

Accordingly, a first aspect of the invention includes a method of generating mimetic innate immune cells, the method comprising:
 (a) co-culturing human pluripotent stem cells with a stromal cell line deficient in expressing macrophage colony stimulating factor to generate primed innate immune cells;
 (b) co-culturing the primed innate immune cells with a stromal cell line deficient in expressing macrophage colony stimulating factor and ectopically expressing Notch ligand, Delta like 1 (DLL1) in a media comprising stem cell factor (SCF), Fms-related tyrosine kinase 3 ligand (FLT3L), interleukin 7 (IL7) and/or interleukin 15 (IL15) to generate differentiated mimetic innate immune cells;
 (c) passaging the differentiated mimetic innate immune cells weekly for 3 to 5 weeks.

In various embodiments using this protocol, functional mimetic NK cells and mimetic γδ T-cells with NK properties were generated.

As used herein the term 'mimetic innate immune cells' refers to cells that have been derived from pluripotent stem cells and have some similar features of the innate immune cells they mimic and some different features to the innate immune cells that they mimic. In various embodiments the mimetic innate immune cells are called iPSC-derived NK cells. For example, in various embodiments a mimetic innate immune cell such as PBC-iPSC derived NK cell or iPSC-derived γδ NKT cells have features of NK cells such as expression of NKp30, NKp44, NKp46, NKG2D, DNAM-1, FASL, TRAIL and/or NKG2A/CD94 but also new features not present on naturally occurring NK cells or γδ T cells such as no or low expression of killer cell immunoglobulin-like receptors (KIR). In various embodiments the mimetic innate immune cell such as PBC-iPSC-derived NK cell has features of NK cells such as expression of at least one of CD56, CD16, NKp30, NKp44, NKp46, NKG2D, DNAM-1, FASL, TRAIL, NKG2A/CD94 or a combination thereof. These features have the advantage of recognizing a broad spectrum of cancer cells. In this embodiment the cells also have new features such as no or low expression of killer cell immunoglobulin-like receptors (KIRs). In various other embodiments the mimetic innate immune cell such iPSC-derived γδ NKT cell expresses γδ TCRs that can recognize phospho-antigen besides having any one of the above-mentioned features present in the PBC-iPSC-derived NK cell. In various embodiments low KIR refers to less than 20% expression of KIR; or less than 10% expression of KIR; or less than 5% expression of KIR. In various embodiments the mimetic innate immune cell have 5% or less expression of KIR2DL1. In various embodiments the mimetic innate immune cell have 13% or less expression of KIR3DL1. In various embodiments the mimetic innate immune cells have 7% or less expression of KIR3DL1. In various embodiments the mimetic innate immune cells have 18% or less expression of KIR2DL2. A KIR-negative or KIR-low expression mimetic innate immune cell has the advantage that it may serve a wide range of recipients disregarding their HLA genotypes. Interestingly, starting with an autologous PBC-iPSC line, it is possible to generate autologous KIR-negative or KIR-low expression mimetic innate immune cell source to be used under an autologous setting without worrying about the inhibition imposed by self HLA molecules. With a reduced risk of immune rejection, these mimetic innate immune cells such as autologous PBC-iPSC-NK cells may survive longer and thus provide a prolonged anti-tumor activity.

In various embodiments the mimetic innate immune cell such as iPSC-derived γδ NKT cells have features of NK cells such as expression of at least one of CD56, CD16, NKp30, NKp44, NKp46, NKG2D, DNAM-1, FASL, TRAIL, NKG2A/CD94, or a combination thereof and new features such as no or low expression of killer cell immunoglobulin-like receptors (KIR) but also features of γδ T cells such as CD3+ and/or γδ T cell receptors such as V gamma 9V delta 2 (Vγ9Vδ2).

A stromal cell line deficient in expressing macrophage colony stimulating factor (M-CSF) may either have a deficient gene that is either not expressed or expresses a non-functional mutant or it may be knocked down using any known method such as antisense, siRNA, shRNA or any other method known in the art to knock down protein expression. In various embodiments the stromal cell line deficient in expressing M-CSF may be a mesenchymal stem cell such as a bone marrow mesenchymal stem cell. In various embodiments the stromal cell line deficient in expressing M-CSF may be an OP9 cell. In various embodiments the M-CSF functional cDNA is represented by nucleic acid sequence SEQ ID NO. 2, and a functional M-CSF protein is represented by amino acid sequence SEQ ID NO. 3. Any mutation to these sequences that results in a dysfunctional M-CSF would be sufficient.

In various embodiments to develop an industry-compatible differentiation protocol, it has been demonstrated that by co-culturing with OP9, a classical M-CSF-deficient stromal cell line, efficient hematopoietic differentiation of both hESCs and PBC-iPSCs can be consistently achieved in 12 days, which is significantly shorter than using other stromal cell lines. The harvested hematopoietic cells can be directly used for NK cell generation without sorting CD34+ cells. Thus, using OP9 to induce hematopoietic differentiation can significantly simplify the manufacturing process by avoiding CD34+ cell sorting and EB formation. In various embodiments a progenitor of innate immune cell comprises a hematopoietic cell.

A stromal cell line deficient in expressing macrophage colony stimulating factor (M-CSF) and ectopically expressing Notch ligand, Delta like 1 (DLL1) may be a stromal cell line deficient in expressing macrophage colony stimulating factor (M-CSF) as discussed above that has been engineered to express DLL1 exogenously or abnormally. Any method known in the art to artificially cause expression of DLL1 in the stromal cell line deficient in expressing M-CSF would be suitable. In various embodiments the stromal cell line deficient in expressing M-CSF ectopically expressing DLL1 may be a mesenchymal stem cell such as a bone marrow mesenchymal stem cell transduced with DLL1. In various embodiments the stromal cell line deficient in expressing M-CSF ectopically expressing DLL1 may be an OP9 DLL1 cell. In various embodiments the DLL1 cDNA is represented by nucleic acid sequence SEQ ID NO. 4, and a DII1 protein is represented by amino acid sequence SEQ ID NO. 5. Functional variations of the sequences that result in a functional DLL1 would be sufficient.

In various embodiments to provide a robust microenvironment for NK cell development, an OP9 cell line modified with DLL1 together with an NK cell-promoting cytokine combination including SCF, FLT3L, IL-7 and IL-15 was used. Using such an approach, the heterogeneous hematopoietic cells harvested from hPSC/OP9 co-cultures can be directly used for NK cell generation and the end product is a homogenous lymphoid population with more than 99% CD56+CD45+NK cells. The robustness of such method is likely due to the activation of Notch signaling pathway, which plays an important role in the development of innate lymphoid cells. This differentiation approach excludes the need for cell sorting, EB formation, spin EB formation, T or B cell depletion or NK cell enrichment.

Without being limited to any theories it is postulated that the deficiency of the macrophage colony stimulating factor (M-CSF) in step (a) sequentially differentiates the cells to hematopoietic cells and the combination of the deficiency of the macrophage colony stimulating factor (M-CSF) together with expression of DLL1 in the media in step (b) stimulates lymphoid commitment and this two phase process combination of the two different types of stromal cells used one after the other results in the mimetic innate immune cells with unique features. In various embodiments the process facilitates the expression of features of NK cells such as expression of CD56, CD16, NKp30, NKp44, NKp46, NKG2D, DNAM-1, FASL, TRAIL NKG2A/CD94 or a combination thereof as well as other features not common to NK cells such as no or low expression of killer cell immunoglobulin-like receptors (KIR).

In various embodiment the media used in step (b) also plays a large role and in various embodiments the media comprises stem cell factor (SCF) Fms-related tyrosine kinase 3 ligand (FLT3L), interleukin 7 (IL7). In various embodiments the media comprises stem cell factor (SCF) Fms-related tyrosine kinase 3 ligand (FLT3L), interleukin 15 (IL15). In various other embodiments the media comprises stem cell factor (SCF) Fms-related tyrosine kinase 3 ligand (FLT3L), interleukin 7 (IL7) and interleukin 15 (IL15). While all three combinations are able to generate the mimetic innate immune cells with unique features. Surprisingly, the use of interleukin 15 (IL15) alone or in combination with interleukin 7 (IL7) significantly increased the percentage of mimetic innate immune cells generated although the use of interleukin 7 (IL7) alone still successfully generated the mimetic innate immune cells with unique features. Other lymphocyte culture medium known in the art can also be used as basal medium.

As used herein the term 'passage', 'passaging' or 'passaged' refers to sub-culturing some or all of the cells into fresh media. This may involve any of the methods commonly known or used in the art. In various embodiments the differentiated mimetic innate immune cells are passaged after every 7 days of co-culturing 3 times and the final mimetic innate immune cells are harvested after 21 days, preferably by 33 days. In various embodiments the differentiated mimetic innate immune cells are passaged after every 7 days of co-culturing 4 times and the final mimetic innate immune cells are harvested after 28 days, preferably by 40 days. In various embodiments the differentiated mimetic innate immune cells are passaged after every 7 days of co-culturing 5 times and the final mimetic innate immune cells are harvested after 35 days, preferably by 47 days.

In various embodiments the human pluripotent stem cells in step (a) are co-cultured for 12 days with the stromal cell line deficient in expressing M-CSF. In various embodiments human pluripotent stem cells in step (a) are co-cultured in a simple media comprising alpha Minimum Essential Medium (αMEM) and Fetal Bovine Serum (FBS) and the co-cultures were fed every 3-4 days by changing half the simple media. Other stem cell differentiation media known in the art may also be used.

In various embodiments the media used in step (b) further comprises Fetal Bovine Serum (FBS); alpha Minimum Essential Medium (αMEM); or a combination thereof.

In various embodiments the human pluripotent stem cells are human embryonic stem cells (hESC). hESCs are a good option in terms of safety, but the derivation of hESCs is always ethically controversial and the applications of hESC derivatives are limited to allogeneic settings.

In various embodiments the human pluripotent stem cells are induced from peripheral blood cells (PBC (iPSC)). Using iPSC has the advantage that they can be generated from a reliable, unlimited and standardizable starting cell source such as peripheral blood mononuclear cells (PBMC) isolated from donors or patients allowing iPSCs derivatives to be used in both autologous and allogeneic applications and it further doesn't have any of the ethical concerns of using hESC Currently, most iPSCs are generated by reprogramming adult somatic cells. The choice of starting somatic cells will affect not only the efficiency and kinetic of reprogramming, but also the practicality of generating GMP-grade iPSCs. Although fibroblasts are the most commonly used somatic cells, they are not very GMP-compliant. Skin sample collection through punch biopsy is invasive and growing fibroblasts from skin biopsy sample is time-consuming (up to 3 weeks). The derivation of fibroblasts under GMP itself is already a daunting task. In contrast, using PBCs to generate iPSCs is a more practical option since peripheral blood collection is convenient and isolation of mononuclear cells from peripheral blood sample only takes 15 minutes. The easiness of implementing GMP in sample collection, transportation and processing renders PBCs an attractive starting material for iPSC derivation. Most importantly, using the two-stage differentiation protocol, for the first time the generation of high-purity, functional and expandable mimetic innate immune cells such as NK cells from PBC-derived iPSCs was demonstrated.

In various embodiments reprogramming transcription factors are incorporated into the peripheral blood cells and grown to generate induced pluripotent stem cells (iPSC).

In various embodiments the reprogramming transcription factors include the traditional Yamanaka transcription factors Oct 4, Sox2, Klf4 and c-myc. In various other embodiments the reprogramming transcription factors may be Oct 3/4 and a member of the Sox family including any one of Sox 1, Sox 2, Sox 3 or Sox 15. Alternatively, in various other embodiments the reprogramming transcription factors may be Oct 3/4; a member of the Sox family of transcription factors including any one of Sox 1, Sox 2, Sox 3 or Sox 15; NANOG and LIN28. Alternatively, in various other embodiments the reprogramming transcription factors may be Oct 3/4; a member of the Sox family of transcription factors including any one of Sox 1, Sox 2, Sox 3 or Sox 15; a member of the Klf family of transcription factors including Klf1, Klf 2, Klf4 or Klf5 and a member of the Myc family of transcription factors including c-myc, L-myc or N-myc. Alternatively, in various other embodiments the reprogramming transcription factors may be Oct 3/4; a member of the Sox family of transcription factors including any one of Sox 1, Sox 2, Sox 3 or Sox 15; a member of the Klf family of transcription factors including Klf1, Klf 2, Klf4 or Klf5 and Glis1 or any reprogramming transcription factors known in the art to effectively generate pluripotent cells that express stage-specific embryonic antigens (SSEA-3, and SSEA-4), and/or epitopes recognized by TRA-1-60, TRA-1-81 antibodies, initiated from a differentiated adult cell.

In various embodiments the reprogramming transcription factors may be incorporated into the peripheral blood cells by retroviral transduction. In various embodiments the reprogramming transcription factors may be incorporated into the peripheral blood cells by lentiviral expression system. In various embodiments the reprogramming transcription factors may be incorporated into the peripheral blood using a single cassette reprogramming vector in which each of the reprogramming factors are separated by a self-cleaving peptide signal such as STEMCCA. In various embodiments the reprogramming transcription factors may be incorporated into the peripheral blood cells by adenovirus expression system. In various embodiments the reprogramming transcription factors may be incorporated into the peripheral blood cells by sendai virus expression system. In various embodiments the reprogramming transcription factors may be incorporated into the peripheral blood cells by diffusion of the proteins into the cell. In various embodiments the reprogramming transcription factors may be incorporated into the peripheral blood cells by mRNA transfection. In various embodiments the reprogramming transcription factors may be incorporated into the peripheral blood cells by miRNA infection or transfection. In various embodiments the reprogramming transcription factors may be incorporated into the peripheral blood cells by a Piggy-Bac system that exploits the use of a transposon system. In various embodiments the reprogramming transcription factors may be incorporated into the peripheral blood cells by minicircle vectors containing only a eukaryotic promotor and the cDNA to be expressed. In various embodiments the reprogramming transcription factors may be incorporated into the peripheral blood cells by transient expression of the reprogramming factors in an episomal plasmid or any other method known in the art to deliver the reprogramming transcription factors into the peripheral blood cells to efficiently generate an induced pluripotent stem cells (iPSC).

In various embodiments the method further comprises expanding peripheral blood cells in the presence of an amino-bisphosphonate and interleukin 2 (IL2) prior to incorporating reprogramming transcription factors into the peripheral blood cells to generate induced pluripotent stem cells (iPSC).

In various embodiments amino-bisphosphonate and interleukin 2 (IL2) are used to induce the expansion of γδ T cells generally that are found to express Vγ9Vδ2 T cells. Without being limited to any theories it is postulated that as Vγ9Vδ2 T cells reacts to phosphoantigens the amino-bisphosphonate stimulates the formation of such Vγ9Vδ2 T cells.

In various embodiments the amino-bisphosphonate is zoledronate or zoledronic acid or salts thereof commercially known as Zometa. Preferably because zoledronic acid is easily obtainable commercially however any amino-bisphosphonate would be suitable. The formula for zoledronate is as follows.

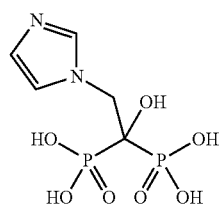 [SMILES: O=P(O)(O)C(O)(Cn1ccnc1)P(=O)(O)O]

In various embodiments the iPSC comprises a TCR gene arranged in the TCRG gene configuration. In various embodiments a TCRG gene configuration comprises the somatic recombination of TCR to TCRG and may also include TCRD gene configuration comprising the somatic recombination of TCR to TCRD. In various embodiments the TCRG gene configuration is represented by nucleic acid sequence SEQ ID NO. 1, functional variations of the sequence that result in the expression of a functional TCRγ would also be included. In various embodiments the iPSC comprises a TCR gene arranged in the TCRD gene configuration. In various embodiments a TCRD gene configuration comprises the somatic recombination of TCR to TCRD of any known TCRD sequence that results in the expression of a functional TCRδ would be suitable.

As used herein a TCR gene arranged in the TCRG gene configuration comprises a nucleic acid molecule which molecule typically encodes a γTCR polypeptide, allelic variant, or analog, including fragments, thereof. Specifically provided are DNA molecules for use in screening for the TCRG gene configuration and DNA molecules for securing expression of a γTCR polypeptide selected from the group consisting of: (a) DNA molecules set out in SEQ ID NO: 1, or fragments thereof; (b) DNA molecules that hybridize to the DNA molecules defined in (a) or hybridisable fragments thereof; and (c) DNA molecules that code on expression for the amino acid sequence encoded by any of the foregoing DNA molecules.

A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

"TCRG gene sequence," "TCRG gene," "TCRG nucleic acids" or "TCRG polynucleotide" each refer to polynucleotides that are likely to be expressed in normal T-cells, Mutations at the TCRG gene sequence that are capable of expressing a functional γTCR polypeptide are included.

The TCRG gene sequence is intended to include coding sequences, intervening sequences and regulatory elements controlling transcription and/or translation. The TCRG gene sequence is intended to include all allelic variations of the DNA sequence that are capable of expressing a γTCR polypeptide.

A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95-98% of the nucleotide bases.

Other preferred polynucleotides comprise a contiguous sequence having greater than 40, 50, 60, or 70% identity, more preferably greater than 80, 90, 95 or 97% identity to the sequence of SEQ ID NO: 1 that encodes amino acids for γTCR.

Detection of the TCRG gene configuration may be done in accordance with methods known in the art including techniques such as Southern blot hybridisation, polymerase chain reaction, or other suitable methods may be used.

In various embodiments this has the advantage of being the first demonstration of using γδ T cell-derived iPSCs to generate γδ T cells. An industry-compatible production scheme and method to derive iPSCs from γδ T cells and use these iPSCs to generate γδ T cells and a novel immune cell type—γδ natural killer T cells is derived.

In various embodiments the method further comprises expanding mimetic innate immune cells in the presence of feeder cells in a media comprising stem cell factor (SCF); Fetal Bovine Serum (FBS); Fms-related tyrosine kinase 3 ligand (FLT3L), interleukin 15 (IL15) and interleukin 7 (IL7).

In various embodiments the feeder cells are irradiated cell line able to expand NK cells. In various embodiments the feeder cells are gamma irradiated K562-mbIL15-41BBL.

In various embodiments the PBC-iPSC-derived mimetic NK cells could be expanded by 74-fold in 9 days and by 38.5-fold after cryopreservation using a feeder cell line. These expanded mimetic NK cells became more potent functionally as shown by the increased cytotoxicity against K562 cells. The possibility to generate iPSCs from both fresh and frozen PBCs provides even more flexibility for GMP manufacturing. To this end, the feasibility to derive iPSCs from frozen PBCs was demonstrated in this study.

Another aspect of the invention includes mimetic innate immune cells comprise cells expressing at least one of CD56, CD16, NKp30, NKp44, NKp46, NKG2D, DNAM-1, FASL, TRAIL, NKG2A/CD94 or a combination thereof, and with low or no expression of killer cell immunoglobulin-like receptors (KIR). These mimetic innate immune cells are optionally cells with or without γδ TCR expression.

In various embodiments the mimetic innate immune cells comprise cells expressing CD56, and with low or no expression of killer cell immunoglobulin-like receptors (KIR). In various embodiments the mimetic innate immune cells comprise cells expressing CD16, and with low or no expression of killer cell immunoglobulin-like receptors (KIR) as described above herein. In various embodiments the mimetic innate immune cells comprise cells expressing NKp30 and with low or no expression of killer cell immunoglobulin-like receptors (KIR). In various embodiments the mimetic innate immune cells comprise cells expressing NKp44 and with low or no expression of killer cell immunoglobulin-like receptors (KIR). In various embodiments the mimetic innate immune cells comprise cells expressing NKp46 and with low or no expression of killer cell immunoglobulin-like receptors (KIR). In various embodiments the mimetic innate immune cells comprise cells expressing NKG2D and with low or no expression of killer cell immunoglobulin-like receptors (KIR). In various embodiments the mimetic innate immune cells comprise cells expressing DNAM-1 and with low or no expression of killer cell immunoglobulin-like receptors (KIR). In various embodiments the mimetic innate immune cells comprise cells expressing FASL and with low or no expression of killer cell immunoglobulin-like receptors (KIR). In various embodiments the mimetic innate immune cells comprise cells expressing TRAIL and with low or no expression of killer cell immunoglobulin-like receptors (KIR). In various embodiments the mimetic innate immune cells comprise cells expressing NKG2A/CD94 and with low or no expression of killer cell immunoglobulin-like receptors (KIR). In various embodiments the mimetic innate immune cells comprise cells expressing a combination of any 2, or any 3, or any 4, or any 5, or any 6, or any 7, or any 8, or any 9, or all of CD56, CD16, NKp30, NKp44, NKp46, NKG2D, DNAM-1, FASL, TRAIL, NKG2A/CD94 and with low or no expression of killer cell immunoglobulin-like receptors (KIR).

In various embodiments cell expression profiles may be determined by any means known in the art for measuring protein expression. For example chromatography methods such HPLC, LCMS, or polyacrylamide gel electrophoresis. Alternatively antibody methods where an antibody that hybridizes to the protein is tagged for detection such as ELISA, flow cytometry, protein immunoprecipitation, immune-electrophoresis, or western blotting. In various embodiments an antibody with a conjugated tag, such as a colour tag, a magnetic tag, a fluorescent tag, a radioactive tag, a protein tag with known properties, is able to hybridise to a portion of any one of the protein sequences CD56 represented by amino acid sequence SEQ ID NO: 6, CD16 represented by amino acid sequence SEQ ID NO: 7, NKp30 represented by amino acid sequence SEQ ID NO: 8, NKp44 represented by amino acid sequence SEQ ID NO: 9, NKp46 represented by amino acid sequence SEQ ID NO: 10, NKG2D represented by amino acid sequence SEQ ID NO: 11, DNAM-1 represented by amino acid sequence SEQ ID NO: 12, FASL represented by amino acid sequence SEQ ID NO: 13, TRAIL represented by amino acid sequence SEQ ID NO: 14, or NKG2A/CD94 represented by amino acid sequence SEQ ID NO: 15.

In various embodiments the mimetic innate immune cells are cells with or without γδ TCR expression.

In various embodiments the mimetic innate immune cells are as described herein.

In various embodiments the mimetic innate immune cells further comprise expression of CD3+a feature of some T-cells.

In various embodiments the mimetic innate immune cells further comprise expression of gamma delta TCR a feature of gamma/delta T-cells.

In various embodiments the gamma delta TCR comprises a V gamma 9V delta 2 (Vγ9Vδ2).

In various embodiments the technology has demonstrated a best possible method to generate γδ T cells and a novel immune cell type—γδ natural killer T cells from iPSCs.

In various embodiments to develop γδ T cells into unlimited "off-the-shelf" products, it was demonstrated for the first time the generation of γδ T cells from induced pluripotent stem cells (iPSCs). Starting with γδ T cell-enriched blood cell cultures, iPSC lines were generated and identified as those derived from γδ T cells. In various embodiment using these γδ T cell-derived iPSCs (GDT-iPSCs), γδ T cells were generated, which were γδ TCR+CD3+ and Vγ9Vδ2+. Moreover, by differentiating GDT-iPSCs with the herein disclosed protocol for generating NK cells from iPSCs, the generated γδ T cells were further armed with many "cancer-fighting" molecules of NK cells, which include activating receptors, natural cytotoxicity receptors and death-inducing molecules. Thus, equipped with anticancer features of both γδ T cells and NK cells, these novel iPSC-derived "γδ natural killer T cells" have great therapeutic activity to target a broad range of cancer cells.

Another aspect of the invention includes mimetic innate immune cells as described herein for use in a treatment.

In various embodiments the mimetic innate immune cells may be suitable for treating viral infections, bacterial infections, fungal infections any other infections or cancer.

Another aspect of the invention includes mimetic innate immune cells as described herein for use in treating cancer.

In various embodiments the mimetic innate immune cells may be suitable for treating cancer including sarcomas, carcinomas, and lymphomas, leukemia, breast cancer, colorectal cancer, or ovarian cancer.

In various embodiments the mimetic innate immune cells may be suitable for treating solid tumor cancer. In various embodiments the solid tumor includes sarcomas, carcinomas, or lymphomas.

In various embodiments the mimetic innate immune cells may be suitable for treating breast adenocarcinoma, colorectal adenocarcinoma, breast ductal carcinoma, ovary adenocarcinoma breast ductal carcinoma, ovary adenocarcinoma or leukemia.

In various embodiments leukemia comprises chronic myelogenous leukemia or Burkitt's lymphoma.

In various embodiments the mimetic innate immune cells were shown to be toxic against cancer cells such as human myelogenous leukemia cells, breast adenocarcinoma cells, colorectal adenocarcinoma cells, breast ductal carcinoma cells, and ovary adenocarcinoma cells.

Another aspect of the invention includes use of mimetic innate immune cells as described herein for manufacture of a medicament in the treatment of cancer.

In various embodiments the cancer is a solid tumor cancer or leukemia.

In various embodiments the solid tumor cancer comprises breast adenocarcinoma, colorectal adenocarcinoma, breast ductal carcinoma, or ovary adenocarcinoma. In various embodiments the leukemia comprises acute lymphoblastic leukemia, acute myeloid leukemia, chronic lymphocytic leukemia or chronic myeloid leukemia.

In various embodiments cancer includes sarcomas, carcinomas, lymphomas, leukemia, breast cancer, colorectal cancer, or ovarian cancer.

The mimetic innate immune cells were shown to be toxic against cancer cells such as human myelogenous leukemia cells, breast adenocarcinoma cells, colorectal adenocarcinoma cells, breast ductal carcinoma cells, and ovary adenocarcinoma cells.

Another aspect of the invention includes a kit for generating mimetic innate immune cells, the kit comprising:
(a) a human pluripotent stem cell line;
(b) a stromal cell line deficient in expressing macrophage colony stimulating factor (M-CSF);
(c) a stromal cell line deficient in expressing macrophage colony stimulating factor and ectopically expressing Notch ligand, Delta like 1 (DLL1);
(d) a first simple media for co-culturing a human pluripotent stem cells with the stromal cell line deficient in expressing M-CSF; and
(e) a second media comprising Stem cell Factor (SCF), Fms-related tyrosine kinase 3 ligand (FLT3L), interleukin 7 (IL7) and/or interleukin 15 (IL15).

In various embodiments the human pluripotent stem cell line may include a human embryonic stem cell (hESC). In various other embodiments the human pluripotent stem cell line may include a Peripheral Blood Cell-derived iPSC line that may be a non-T cell-derived iPSC line or a γδ cell-derived iPSC line.

The stromal cell line deficient in expressing macrophage colony stimulating factor (M-CSF) and the stromal cell line deficient in expressing macrophage colony stimulating factor and ectopically expressing Notch ligand, Delta like 1 (DLL1) are as described herein above.

In various embodiments the first simple media comprises alpha Minimum Essential Medium (αMEM) or other stem cell differentiation medium and Fetal Bovine Serum (FBS).

In various embodiments the second media comprises Stem cell Factor (SCF), Fms-related tyrosine kinase 3 ligand (FLT3L), interleukin 7 (IL7). In various embodiments the media comprises Stem cell Factor (SCF), Fms-related tyrosine kinase 3 ligand (FLT3L), Interleukin 15 (IL15). In various other embodiments the media comprises Stem cell Factor (SCF), Fms-related tyrosine kinase 3 ligand (FLT3L), interleukin 7 (IL7) and interleukin 15 (IL15). While all three combinations are able to generate the mimetic innate immune cells with unique features. Surprisingly, the use of interleukin 15 (IL15) alone or in combination with interleukin 7 (IL7) significantly increased the percentage and/or amount of mimetic innate immune cells generated although the use of interleukin 7 (IL7) alone still successfully generated the mimetic innate immune cells with unique features.

In various embodiments the second media further comprises Fetal Bovine Serum (FBS); alpha Minimum Essential Medium (αMEM) or other lymphocyte culture medium; or a combination thereof.

In various embodiments the kit further comprises an amino-bisphosphonate and interleukin 2 (IL2). In various embodiments the amino-bisphosphonate is zoledronic acid or salts thereof.

Another aspect of the invention includes a method of treating a patient with cancer comprising: administering to the patient mimetic innate immune cells expressing at least one of CD56, CD16, NKp30, NKp44, NKp46, NKG2D, DNAM-1, FASL, TRAIL NKG2A/CD94 or a combination thereof and low or no expression of killer cell immunoglobulin-like receptors KIR generated by
  (a) co-culturing human pluripotent stem cells with a stromal cell line deficient in expressing macrophage colony stimulating factor to generate progenitors of innate immune cells;
  (b) co-culturing the progenitors of innate immune cells with a stromal cell line deficient in expressing macrophage colony stimulating factor and ectopically expressing Notch ligand, Delta like 1 (DLL1) in a media comprising Fms-related tyrosine kinase 3 ligand (FLT3L), interleukin 7 (IL7) and/or interleukin 15 (IL15) to generate differentiated mimetic innate immune cells;
  (c) passaging the differentiated mimetic innate immune cells weekly for 3 to 5 weeks.

In various embodiments the cancer is a solid tumor cancer as described herein. In various embodiments the cancer is a leukemia as described herein.

In various embodiments the solid tumor cancer comprises breast adenocarcinoma, colorectal adenocarcinoma, breast ductal carcinoma, or ovary adenocarcinoma. In various embodiments the leukemia comprises acute lymphoblastic leukemia, acute myeloid leukemia, chronic lymphocytic leukemia or chronic myeloid leukemia.

Another aspect of the invention includes a method of generating induced pluripotent stem cells (iPSC) from peripheral blood mononuclear cells, comprising:
  (a) incorporating reprogramming transcription factors into peripheral blood mononuclear cells;
  (b) growing the peripheral blood mononuclear cells incorporated with the reprogramming transcription factors into pluripotent stem cells.

In various embodiments the mononuclear peripheral blood cells are γδ T cells. This is the first demonstration of generating iPSCs from γδ T-cells. In various other embodiments the mononuclear peripheral blood cells are non-T cells of peripheral blood cells.

In various embodiments the method further comprises expanding peripheral blood cells in the presence of an amino-bisphosphonate and interleukin 2 (IL2) prior to incorporating reprogramming transcription factors into the gamma delta T-cells.

In various embodiments the amino-bisphosphonate is zoledronic acid or salts thereof.

In various embodiments the iPSC comprises a TCR gene arranged in the TCRG gene configuration or a TCR gene arranged in the TCRD gene configuration. In various embodiments the TCRG gene configuration is represented by nucleic acid sequence SEQ ID NO. 1. Functional variations of the sequence that result in the expression of a functional TCRγ would also be sufficient. In various embodiments a TCRD gene configuration comprises the somatic recombination of TCR to TCRD of any known TCRD sequence that results in the expression of a functional TCRδ would be suitable.

Another aspect of the invention includes an induced pluripotent stem cells (iPSC) comprising a TCR gene arranged in the TCRG gene configuration or a TCR gene arranged in the TCRD gene configuration.

In various embodiments the rearranged TCRG gene is represented by nucleic acid sequence SEQ ID NO. 1. Functional variations of the sequences that result in the expression of a functional TCRγ would be sufficient. In various embodiments a TCRD gene configuration comprises the somatic recombination of TCR to TCRD of any known TCRD sequence that results in the expression of a functional TCRδ would be suitable.

Another aspect of the invention includes a method of generating mimetic NK cells, the method comprising:
  (a) co-culturing human pluripotent stem cells with a stromal cell line deficient in expressing macrophage colony stimulating factor (M-CSF) to generate progenitors of innate immune cells;
  (b) co-culturing the progenitors of innate immune cells with a stromal cell line deficient in expressing M-CSF and ectopically expressing Notch ligand, Delta like 1 (DLL1) in a media comprising stem cell factor (SCF), Fms-related tyrosine kinase 3 ligand (FLT3L), interleukin 7 (IL7) and/or interleukin 15 (IL15) to generate differentiated mimetic innate immune cells;
  (c) passaging the differentiated mimetic innate immune cells weekly for 3 to 5 weeks.

Another aspect of the invention includes a method of generating mimetic γδ cells, the method comprising:
  (a) co-culturing human pluripotent stem cells with a stromal cell line deficient in expressing macrophage colony stimulating factor (M-CSF) to generate primed innate immune cells;
  (b) co-culturing the primed innate immune cells with a stromal cell line deficient in expressing M-CSF and ectopically expressing Notch ligand, Delta like 1 (DLL1) in a media comprising stem cell factor (SCF), Fms-related tyrosine kinase 3 ligand (FLT3L), interleukin 7 (IL7) and/or interleukin 15 (IL15) to generate differentiated mimetic innate immune cells;
  (c) passaging the differentiated mimetic innate immune cells weekly for 3 to 5 weeks.

Another aspect of the invention includes mimetic NK cells comprising cells expressing at least one of CD56, CD16, NKp30, NKp44, NKp46, NKG2D, DNAM-1, FASL, TRAIL, NKG2A/CD94 or a combination thereof and with low or no expression of killer cell immunoglobulin-like receptors KIR.

In various embodiments the mimetic NK cells comprise cells expressing no CD3 or no γδ TCR.

Another aspect of the invention includes mimetic gamma delta T-cells comprising cells expressing at least one of CD56, CD16, NKp30, NKp44, NKp46, NKG2D, DNAM-1, FASL, TRAIL, NKG2A/CD94 or a combination thereof and with low or no expression of killer cell immunoglobulin-like receptors KIR.

In various embodiments the mimetic γδ T cells are cells with γδ TCR expression or CD3 expression.

Unless defined otherwise, all technical and scientific terms used herein have the same meaning as is commonly understood by a skilled person to which the subject matter herein belongs. As used herein, the following definitions are supplied in order to facilitate the understanding of the present invention.

Throughout this document, unless otherwise indicated to the contrary, the terms "comprising", "consisting of", "having" and the like, are to be construed as non-exhaustive, or in other words, as meaning "including, but not limited to".

Furthermore, throughout the specification, unless the context requires otherwise, the word "include" or variations such as "includes" or "including" will be understood to imply the inclusion of a stated integer or group of integers but not the exclusion of any other integer or group of integers.

As used in the specification and the appended claims, the singular form "a", and "the" include plural references unless the context clearly dictates otherwise.

EXAMPLES

Described is an overall scheme for mass production of innate immune cells from hPSCs. Comparing with the existing protocols, the approach is more industry-compliant and provides the conveniences required to produce NK cell therapeutics: (1) the starting material PBC-iPSCs are a convenient, highly accessible and GMP-compatible hPSC source; (2) the differentiation process is simplified by excluding cell sorting, EB formation and spin EB formation; (3) the generated PBC-iPSC-derived cells are already a high-purity and functional population, obviating the need for T-cell and B-cell depletion or innate immune cell enrichment; (4) both fresh and cryopreserved NK cells can be expanded in a short period of time, which eases the logistics of transporting and manufacturing of NK cell therapeutics; (5) further functional maturation can be achieved after expansion; (6) most of the PBC-iPSC-derived innate immune cells are KIR-negative, which means that these innate immune cells may serve as universal cell source for various recipients without concerning the inhibitory signaling that may reduce the cytotoxicity. Thus, using PBC-iPSCs to derive innate immune cells is an amenable platform for mass production of innate immune cell therapeutics.

Generation of Mimetic Innate Immune Cells

A robust protocol to consistently generate innate immune cells from various hPSC sources is yet to be established. In this regard an overall manufacturing scheme for mass production of functional NK cells, has been designed and demonstrated not only from a classical hPSC source, human embryonic stem cells (hESCs), but also from a convenient hPSC source, peripheral blood cell (PBC)-derived iPSCs (PBC-iPSCs) without employing CD34+ cell enrichment or spin EB formation.

Generation of NK Cells from hESCs.

Cell Culture.

An hPSC line, H1 (WiCell Research Institute, Madison, WI, http://www.wicell.org), was cultured with mTeSR1 (StemCell Technologies, Vancouver, BC, Canada, http://www.stemcell.com) on Matrigel (BD Biosciences, San Diego, CA, http://www.bdbiosciences.com)—coated six-well plates. OP9 cells (American Type Culture Collection [ATTC], Manassas, VA, http://www.atcc.org) and OP9/G-DLL1 cells (Riken BRC Cell Bank, Ibaraki, Japan, http://cell.brc.riken.jp/en/) were cultured with α-MEM (Thermo Fisher Scientific, Waltham, MA, http://corporate.thermofisher.com) supplemented with 20% fetal bovine serum (FBS) (HyClone, Logan, UT, http://www.hyclone.com).

Two-Stage Protocol.

In the first stage, OP9 cells were seeded on 0.1% gelatin (StemCell Technologies)—coated T75 flask. Upon confluence, the OP9 cell cultures were fed by changing half of the medium and overgrown for 4-6 days. 1-1.5×10$^6$ hESCs were then seeded and differentiated on the overgrown OP9 cells in α-MEM supplemented with 10% FBS for 12 days. The hESC/OP9 co-cultures were fed every 4 days by changing half of the medium. In the second stage, the differentiated cells were harvested from the hESC/OP9 co-cultures using 1 mg/ml collagenase IV (StemCell Technologies) and TrypLE Express (Thermo Fisher Scientific). OP9 cells were removed by plastic adherence for 45 minutes and the cell clumps were further removed by 100 μm cell strainers (BD Biosciences). The remaining non-adherent cells were then co-cultured with OP9-DLL1 grown on T75 flasks using α-MEM containing 10% FBS, 10 ng/ml SCF (PeproTech, Rocky Hill, NJ, http://www.peprotech.com), 5 ng/ml FLT3L (PeproTech) together with 5 ng/ml IL-7 (PeproTech) and/or 10 ng/ml IL-15 (PeproTech) for 7 days. Hereafter, the differentiated cells were harvested using Versene (Thermo Fisher Scientific) and co-cultured on new OP9-DLL1 grown on six-well plates on a weekly basis for another 3-4 weeks.

To establish a robust two-stage protocol for NK cell derivation from hPSCs (FIG. 1a), a widely used hESC line, H1 (FIG. 1b) was used. In the first stage, to induce hematopoietic differentiation, H1 cells were co-cultured with overgrown OP9 cells, a bone marrow stromal cell line. On day 12 of co-culture, a lot of differentiated colonies (FIG. 1c) and a small population of CD34+ cells (FIG. 1j) were consistently observed. In the second stage, to induce lymphoid commitment, these differentiated cells were harvested and co-cultured with OP9-DLL1, an OP9 cell line modified with a Notch ligand Delta-like-1 (DLL1), on weekly basis in the presence of stem cell factor (SCF), Fms-related tyrosine kinase 3 ligand (FLT3L) and IL-7 (FIG. 1a). Seven days after first co-culture with OP9-DLL1 (day 19), most differentiated cells still grew as adherent cells (FIG. 1d); after second co-culture (day 26), some bright round and semi-attached cells started to pop out (FIG. 1e); after third co-culture (day 33), these cells detached and assembled in the center of the well (FIGS. 1f, g); after fourth co-culture (day 40), more suspension cells appeared (FIGS. 1h, i). Morphologically, these suspension cells were small, round and bright lymphoid cells (FIGS. 1g, i); phenotypically, they were a defined population on the scatter plots (FIGS. 1k, l); most of them were CD45$^+$CD56$^+$, but CD3 TCRαβ$^-$CD4$^-$CD8$^-$ (FIGS. 1k, l), which is typical for NK cells. Thus, by going through hematopoietic differentiation and lymphoid commitment, NK cells can be derived from hESCs without enriching CD34+ cells or forming spin EBs.

Generation of NK Cells from iPSCs

Cell Culture.

OP9 cells (American Type Culture Collection [ATTC], Manassas, VA, http://www.atcc.org) and OP9/G-DLL1 cells (Riken BRC Cell Bank, Ibaraki, Japan, http://cell.brc.riken.jp/en/) were cultured with α-MEM (Thermo Fisher Scientific, Waltham, MA, http://corporate.thermofisher.com) supplemented with 20% fetal bovine serum (FBS) (HyClone, Logan, UT, http://www.hyclone.com).

Two-Stage Protocol.

In the first stage, OP9 cells were seeded on 0.1% gelatin (StemCell Technologies)—coated T75 flask. Upon confluence, the OP9 cell cultures were fed by changing half of the medium and overgrown for 4-6 days. $1-1.5 \times 10^6$ hESCs were then seeded and differentiated on the overgrown OP9 cells in α-MEM supplemented with 10% FBS for 12 days. The hESC/OP9 co-cultures were fed every 4 days by changing half of the medium. In the second stage, the differentiated cells were harvested from the hESC/OP9 co-cultures using 1 mg/ml collagenase IV (StemCell Technologies) and TrypLE Express (Thermo Fisher Scientific). OP9 cells were removed by plastic adherence for 45 minutes and the cell clumps were further removed by 100 μm cell strainers (BD Biosciences). The remaining non-adherent cells were then co-cultured with OP9-DLL1 grown on T75 flasks using α-MEM containing 10% FBS, 10 ng/ml SCF (PeproTech, Rocky Hill, NJ, http://www.peprotech.com), 5 ng/ml FLT3L (PeproTech) together with 5 ng/ml IL-7 (PeproTech) and/or 10 ng/ml IL-15 (PeproTech) for 7 days. Hereafter, the differentiated cells were harvested using Versene (Thermo Fisher Scientific) and co-cultured on new OP9-DLL1 grown on six-well plates on a weekly basis for another 3-4 weeks.

Generation of NK Cells from PBC-iPSCs.

Figure 2:
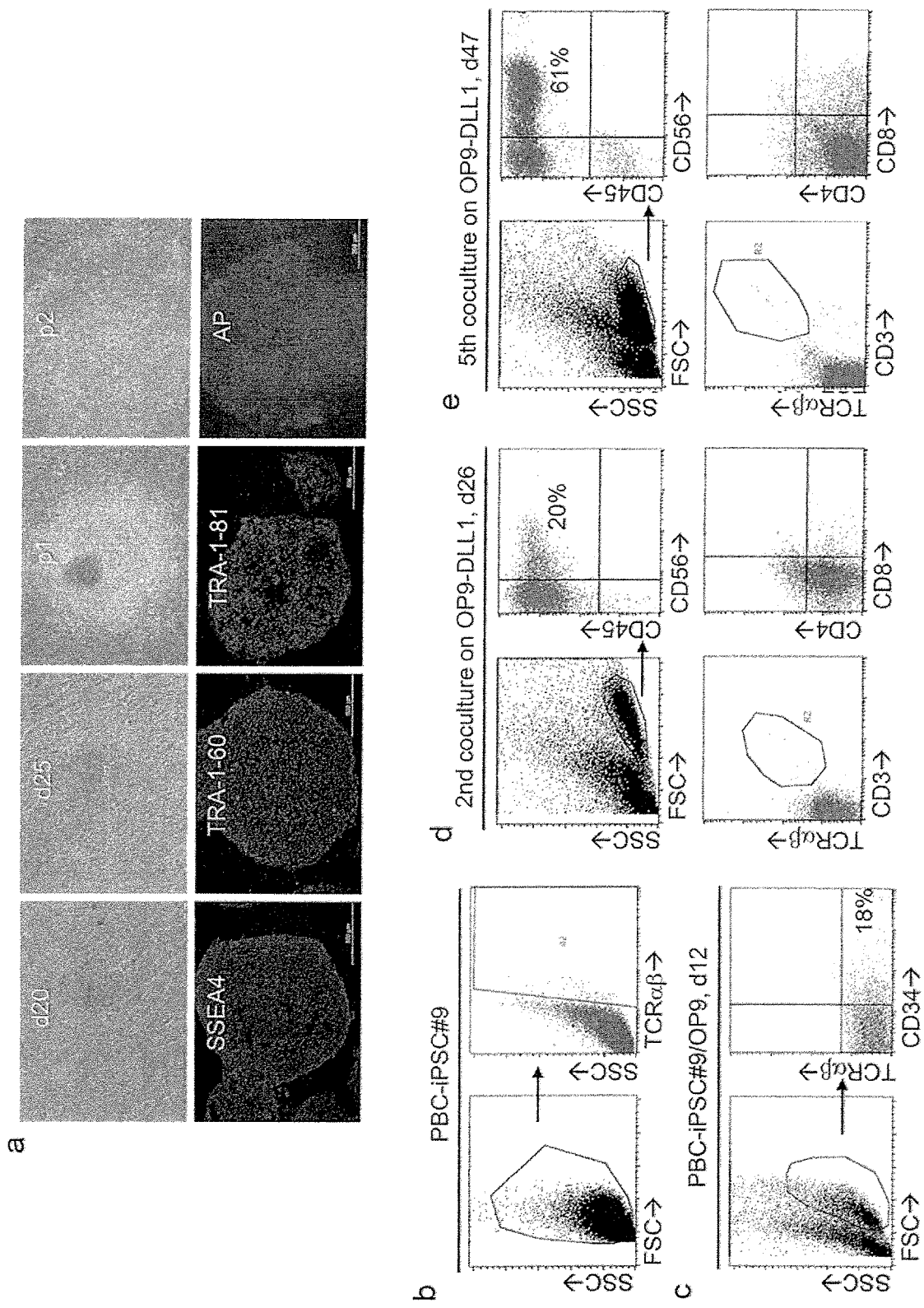
FIG. 2: Generation of NK cells from PBC-derived iPSCs. (a) Generation of iPSCs from PBCs. Typical morphology and phenotype of a PBC-derived iPSC (PBC-iPSC) colony and expanded iPSCs. Phase contrast images show a PBC-iPSC colony on day 20 and day 25 and an expanded iPSC line of passage 1 and passage 2. Fluorescence images show the immunostaining of SSEA-4, TRA-1-60, TRA-1-81 and alkaline phosphatase in a PBC-iPSC line. (b-e) Generation of NK cells from PBC-iPSCs. Phenotypic changes during differentiation of a PBC-iPSC line, PBC-iPSC #9 into NK cells are shown. Flow cytometric analysis shows the absence of TCRαβ expression during the differentiation process. Different cytokines were tested to enhance NK cell commitment. (f).

To further facilitate the production of NK cells from hPSCs under Good Manufacturing Practices (GMP), it is important to start with a convenient hPSC source that is GMP-compatible. Although hESCs and iPSCs generated from fibroblasts or umbilical cord blood CD34+ cells have been used to derive NK cells, iPSCs generated from peripheral blood cells (PBC-iPSCs) are a novel, but more accessible and practicable option from the standpoint of manufacturing. To demonstrate the feasibility of using PBC-iPSCs for NK cell generation, iPSC lines from PBCs using Sendai viral vectors carrying the reprogramming factors were first generated (FIG. 2a) and described below. These resulting PBC-iPSCs showed typical hPSC morphology and phenotype (FIG. 2a).

Next, the two-stage protocol for NK cell generation was examined to determine whether the method is still applicable to these PBC-iPSCs. Using a PBC-iPSC #9 line (FIG. 2b), differentiated cells containing a significant CD34+ population were derived after 12-day co-culture with OP9 (FIG. 2c). Without sorting the CD34+ cells, these differentiated cells were harvested and directly co-cultured with OP9-DLL1. A small CD45+CD56+ population appeared after second co-culture (day 26) (FIG. 2d); this population became much more apparent after fifth co-culture (day 47), which comprised 61% of the lymphoid cells (FIG. 2e). Neither TCRαβ nor CD3 expression was observed throughout the differentiation process: not in the pluripotent stem cells (FIG. 2b), hematopoietic cells (FIG. 2c) or lymphoid cells (FIG. 2d, e). Moreover, there was no obvious CD4 or CD8 expression in the lymphoid cells (FIG. 2d, e), confirming that the two-stage protocol can also be used for NK cell generation from PBC-iPSCs.

Improving Purity and Yield of NK Cells Derived from PBC-iPSCs.

Figure 2F:
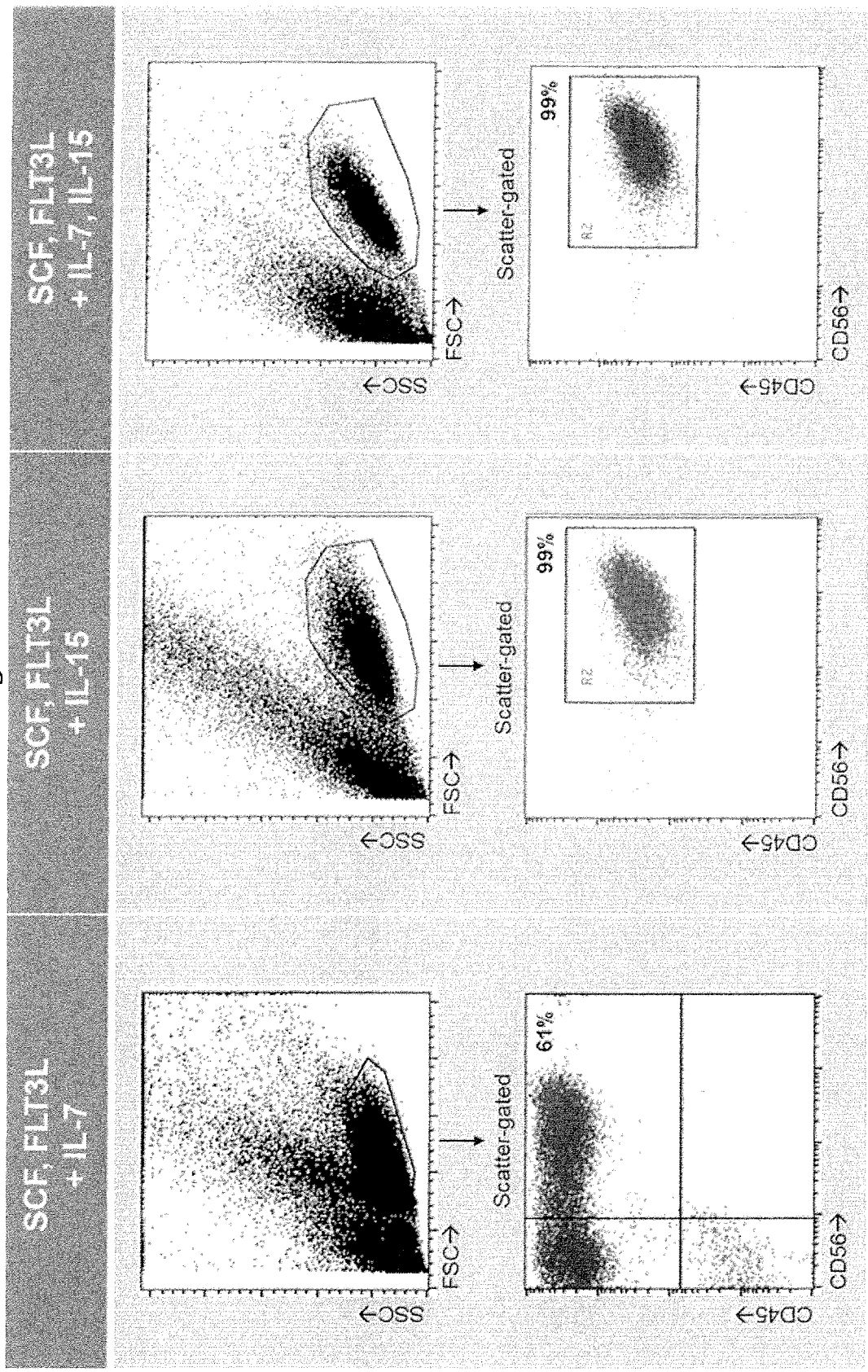

In addition to a GMP-compatible starting hPSC source, further improvement in purity and yield of NK cells derived from PBC-iPSCs will facilitate the production and translational use of this novel NK cell source. To this end, different cytokines were tested to enhance NK cell commitment (FIG. 2f). Results (Table 1) showed that the use of IL-7 together with SCF and FLT3L during lymphoid commitment brought about a purity of 61% and a yield of $0.21 \times 10^6$ CD56+CD45+ cells from $5\ 3 \times 10^6$ PBC-iPSCs on day 40 of differentiation; using IL-15 increased the purity to 99% and the yield to $0.75 \times 10^6$; while the combined use of IL-7 and IL-15 gave a purity of 99% and a yield of $7.93 \times 10^6$ on day 40, which further increased to $15 \times 10^6$ on day 47.

TABLE 1

Cytokines improve purity and yield of PBC-iPSC derived NK cells

| Cytokines | SCF, FLT3L, +IL7 | SCF, FLT3L, +IL15 | SCF, FLT3L, +IL7, IL15 |
|---|---|---|---|
| % of CD56+ CD45+ purity | 61% | 99% | 99% |
| Yield (number of CD56+ CD45+) | $0.2 \times 10^6 \pm 0.18 \times 10^6$ per $3 \times 10^6$ iPSCs (mean ± S, n = 4, day 40) | $0.75 \times 10^6 \pm 0.43 \times 10^6$ per $3 \times 10^6$ iPSCs (mean ± S, n = 3, day 40) | $7.93 \times 10^6 \pm 0.18 \times 10^6$ per $3 \times 10^6$ iPSCs (mean ± S, n = 6, day 40) |

Generation of γδ NKT Cells from iPSCs

Cell Culture.

The generated iPSC lines were cultured with mTeSR1 (StemCell Technologies, Vancouver, BC, Canada, http://www.stemcell.com) on Matrigel (BD Biosciences, San Diego, CA, http://www.bdbiosciences.com)—coated 6-well plates. Cell lines: OP9, (American Type Culture Collection [ATTC], Manassas, VA, http://www.atcc.org) were cultured as recommended by ATCC. Cell line OP9-DLL1 (Riken BRC Cell Bank, Ibaraki, Japan, http://cell.brc.riken.jp/en/) was cultured in α-MEM (Thermo Fisher Scientific, Waltham, MA, http://corporate.thermofisher.com) supplemented with 20% fetal bovine serum (FBS) (HyClone, Logan, UT, http://www.hyclone.com).

Generation of γδ T Cells from GDT-iPSCs.

To generate γδ T cells from GDT-iPSCs, a previously established two-stage protocol, described above for generating NK cells from iPSCs was used. In the first stage, $1-1.5 \times 10^6$ iPSCs were seeded and differentiated on the overgrown OP9 or OP9-DLL1 cells in α-MEM supplemented with 20% FBS for 12 days. The co-cultures were fed every 4 days by changing half medium. In the second stage, the differentiated cells were harvested from the co-cultures using 1 mg/ml collagenase IV (StemCell Technologies) and TrypLE Express (Thermo Fisher Scientific). OP9 or OP9-DLL1 cells were removed by plastic adherence for 45 minutes and the cell clumps were further removed by 100 □m cell strainers (BD Biosciences). The remaining non-adherent cells were then co-cultured with OP9-DLL1 cells grown on T75 flasks using α-MEM containing 20% FBS, 10 ng/ml SCF (PeproTech, Rocky Hill, NJ, http://www.peprotech.com), 5 ng/ml FLT3L (PeproTech) together with 5 ng/ml IL-7 (PeproTech) and/or 10 ng/ml IL-15 (PeproTech) for 7 days. Hereafter, the differentiated cells were harvested using Versene (Thermo Fisher Scientific) and cocultured with new OP9-DLL1 cells grown on 6-well plates on a weekly basis for another 3-4 weeks.

Figure 3:
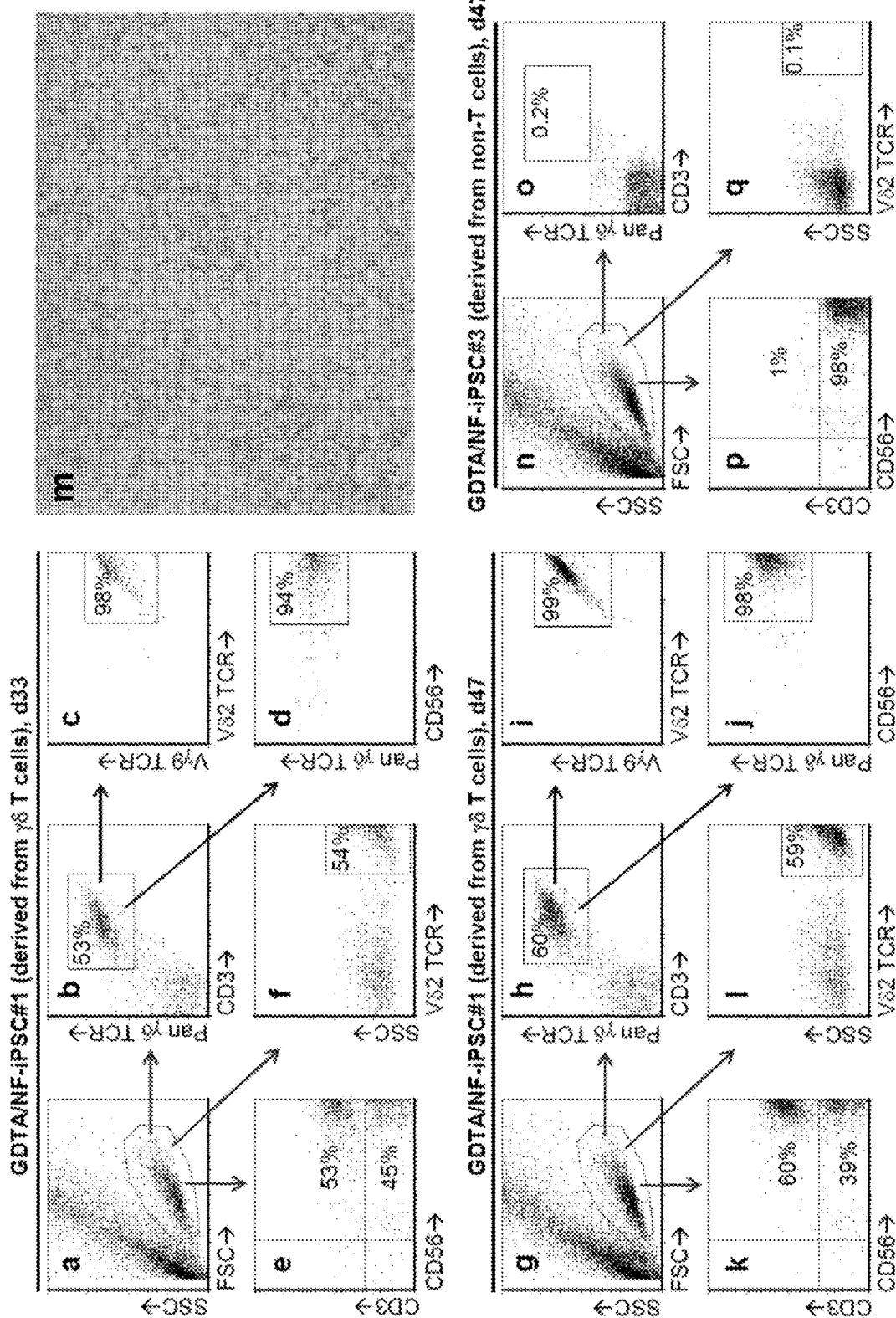
FIG. 3: Generation of γδ T cells from GDT-iPSCs. A γδ T cell-derived iPSC line, GDTA/NF-iPSC #1 was differentiated using established protocol in FIG. 1a. (a-l): Phenotype of differentiated cells from GDTA/NF-iPSC #1 line on day 33 and day 47 as analyzed by flow cytometry. (m): Morphology of differentiated cells from GDTA/NF-iPSC #1 line on day 47. A non T cell-derived iPSC line, GDTA/NF-iPSC #3 was differentiated as control. (n-q): Phenotype of differentiated cells from GDTA/NF-iPSC #3 line on day 47 as analyzed by flow cytometry.

To generate γδ T cells, the previously described above protocol was used for generating NK cells from iPSCs to differentiate the γδ T cell-derived GDTA/NF-iPSC #1 line described below. On day 33 of differentiation, a homogenous lymphoid population was observed (FIG. 3a), in which 53% was γδ TCR+CD3+ (FIG. 3b). Most of these γδ TCR+CD3+ cells were also Vγ9Vδ2+ (FIG. 3c) and CD56+ (FIG. 3d), indicating that these iPSC-derived γδ T cells were exclusively a Vγ9Vδ2 subset that may have an NK cell-like phenotype. This result tallied well with the findings that 53% of the lymphoid population was CD3+CD56+ and 45% was CD3-CD56+ (FIG. 3e) and that 54% was Vδ2+ (FIG. 3f). On day 47, the lymphoid population became more obvious (FIG. 3g, m). More γδ TCR+CD3+ cells appeared (FIG. 3h), which remained Vγ9V2+ (FIG. 3i) and CD56+ (FIG. 3j). This change was further confirmed by the increase of CD3+CD56+ population and Vδ2+ population and the decrease of CD3-CD56+ population (FIG. 3k, l). Likewise, when using the non-T cell-derived GDTA/NF-iPSC #3 for differentiation, an obvious lymphoid population was still observed on day 47 (FIG. 3n); however, this population was CD3-CD56+ (FIG. 3p) and there was no γδ TCR+CD3+ cells (FIG. 3o) or Vδ2+ cells (FIG. 3q) observed. These findings strongly suggest that generation of CD56+ Vγ9Vδ2 T cells from a γδ T cell-derived iPSC line occurred.

Characterization of Mimetic Innate Immune Cells
Mimetic NK Cells
Flow Cytometry.

To study the change of phenotype during hPSC differentiation, the cells were harvested and stained using antibodies against CD34, CD43, CD45, CD56, TCRαβ, CD3, CD4, CD8, NKp44, NKp46, NKG2D, CD16, NKG2A, CD94, CD158e1/e2, Cd158i, CD158a,h (BD Biosciences and Beckman Coulter, https://www.beckmancoulter.com) and analyzed with a FACSCalibur flow cytometer (BD Biosciences).

ELISPOT Assay.

To detect IFN-γ secretion, a Human IFN-γ ELISpotPro kit (MABTECH, Nacka Strand, Sweden, https://www.mabtech.com) was used. In brief, 0 to 10×104 PBC-iPSC-derived NK cells and 5×104 K562 or Raji cells were coincubated on a IFN-γ ELISPOT plate overnight. IFN-γ spots were stained according to the manufacturer's manual. To measure GrB secretion, a Human Granzyme B ELISpot Kit (R&D Systems, Minneapolis, MN, https://www.mdsystems.com) was used. In brief, 0 to 1.2×104 PBC-iPSC-derived NK cells were incubated with or without 5×104 K562 cells on a human GrB microplate for 4 hours. GrB spots were then stained as described in the manufacturer's manual. IFN-γ and GrB spots were counted using an ImmunoSpot Analyzer (CTL, Shaker Heights, OH, http://www.immunospot.com).

NK Cells Generated Using IL7 and IL15 Cytokine Combination.

Figure 4:
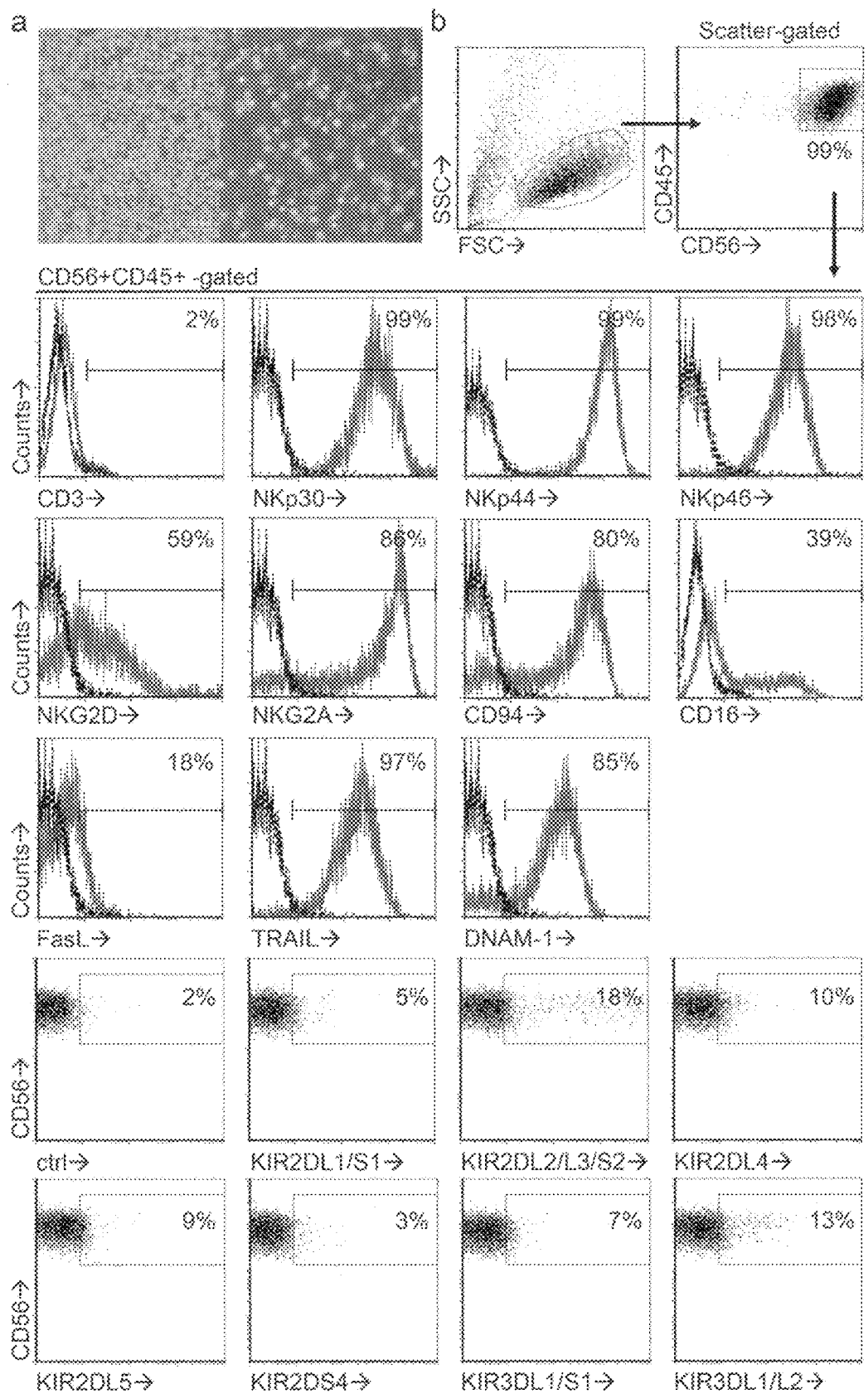
FIG. 4: Morphology and phenotype of PBC-iPSC-derived NK cells. (a-b): Morphology (a) and phenotype (b) of NK cells derived from PBC-iPSC #9.

Using the optimized cytokine combination, high-purity lymphoid cells were derived from PBC-iPSC #9 (FIG. 4). These cells showed typical NK cell morphology (FIG. 4a). They were a homogenous population as indicated by the cell images (FIG. 4a) and the scatter plot (FIG. 4b). Most of them are CD56+CD45+CD3−, a typical NK cell phenotype (FIG. 4b). These cells also expressed activating receptors like NKp30, NKp44, NKp46 and NKG2D and inhibitory receptor like CD94:NKG2A (FIG. 4b). They were also CD16+ (FIG. 4b), which is important for antibody-dependent cell-mediated cytotoxicity (ADCC) of NK cells. In term of killer cell immunoglobulin-like receptors (KIR), they showed no or low expression for KIR2DL1, KIR2DL4, KIR2DL5, KIR3DL1, KIR2DS1, KIR2DS4 and KIR3DS1. Only a small fraction of the cells were stained by CD158b (18%) or CD158e/k (13%) antibodies, suggesting that most of the NK cells were negative for KIR2DL2, KIR2DL3, KIR3DL1 and KIR3DL2 (FIG. 4b). This inhibitory KIR-negative phenotype may potentially benefit the cytotoxicity of these NK cells. Thus, a large number of high-purity NK cells from PBC-iPSCs can be consistently generated using the optimized two-stage protocol.

Mimetic γδ NK T Cells
Flow Cytometry.

To study phenotypic change during iPSC differentiation, cells were harvested and stained using antibodies against CD3, CD56, γδ TCR, Vδ2 TCR, Vγ9 TCR, NKp30, NKp44, NKp46, NKG2D, NKG2A, CD94, CD16, FasL, TRAIL, DNAM-1, CD158a,h (KIR2DL1/S1), CD158b (KIR2DL2/L3/S2), CD158f (KIR2DL5), CD158i (KIR2DS4), CD158e1/e2 (KIR3DL1/S1) and CD158e/k (KIR3DL1/L2) (BD Biosciences; Beckman Coulter, https://www.beckmancoulter.com; Miltenyi Biotec, http://www.miltenyibiotec.com) and analyzed with a FACSCalibur flow cytometer (BD Biosciences).

Expansion of Donor-Derived PB-NK Cells.

To derive PB-NK cells, 2×10$^6$ PBMCs from healthy donors were co-cultured with 4×10$^6$ γ-irradiated (100 Gy) K562-mbIL15-41BBL cells in CellGro SCGM serum-free medium supplemented with 10% FBS and 50 IU/mL IL-2 using T75 flasks in upright position. Half medium was replaced with fresh medium and fresh IL-2 was replenished every 2-3 days until day 7. Hereafter, 2×10$^6$ cells were re-stimulated weekly with 2×10$^6$ K562-mbIL15-41BBL cells for another two weeks. The cells were harvested on day 21 for experiments.

Figure 5:
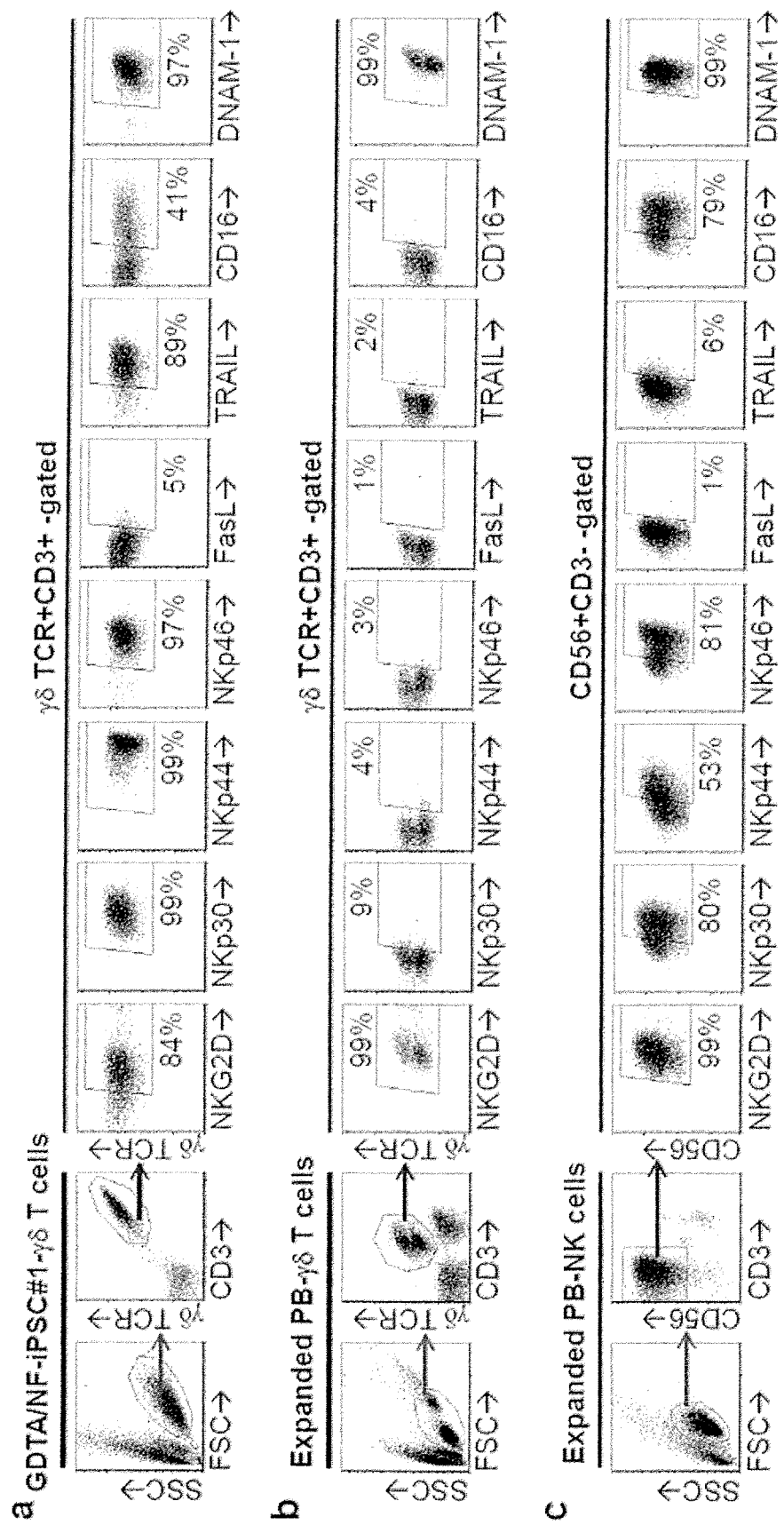
FIG. 5: Expression of activating molecules and death-inducing ligands on iPSC-γδ T cells, PB-γδ T cells and PB-NK cells. iPSC-γδ T cells were generated from GDTA/NNF-iPSC #1 line using established protocol in FIG. 1a. PB-γδ T cells and PB-NK cells were expanded from PBMCs of a healthy donor. Phenotypes of iPSC-γδ T cells (a), expanded PB-γδ T cells (b) and expanded PB-NK cells (c) were analyzed by flow cytometry.
Figure 6:
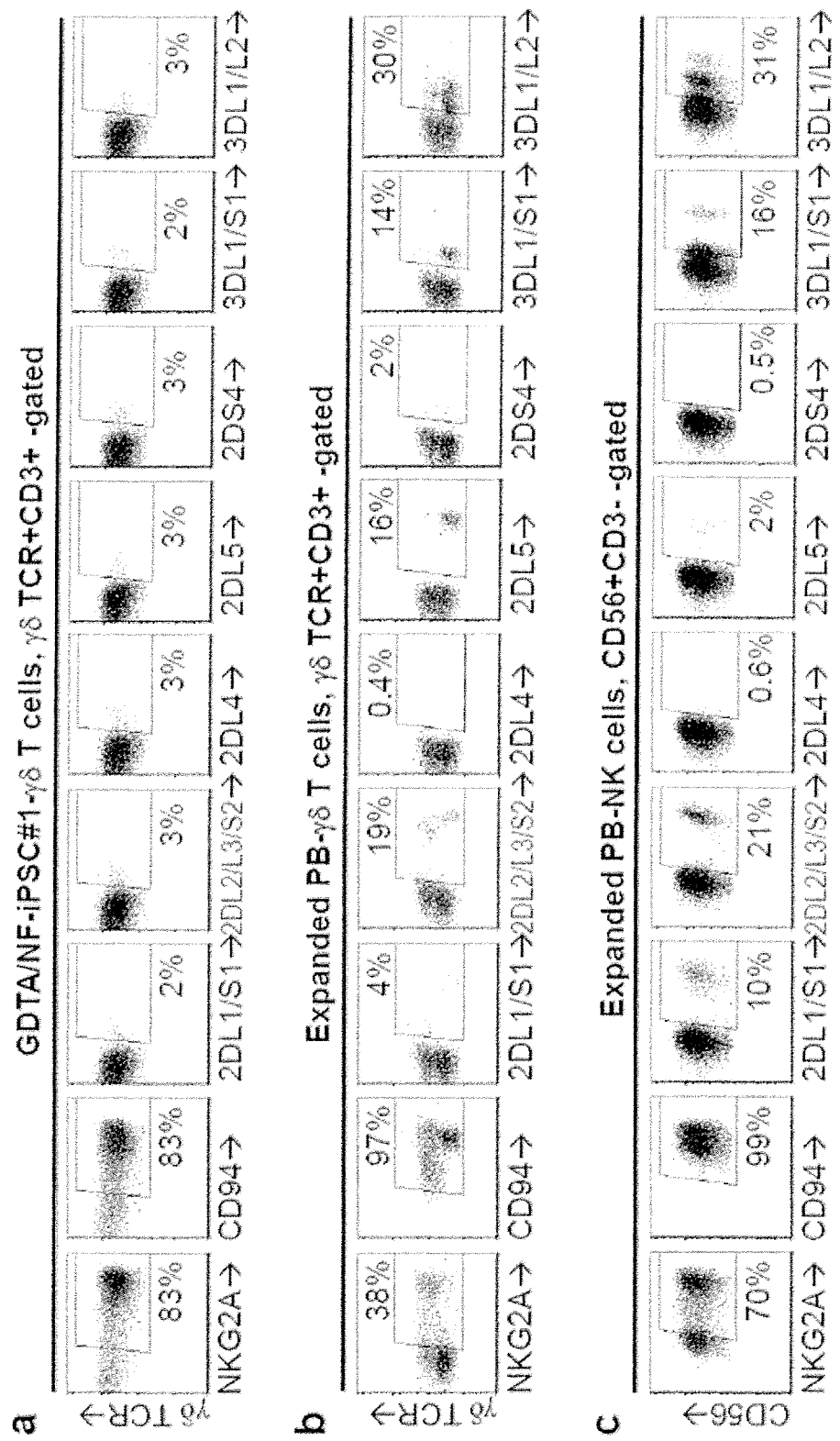
FIG. 6: Expression of Inhibitory receptor and KIRs on iPSC-γδ T cells, PB-γδ T cells and PB-NK cells. iPSC-γδ T cells were generated from GDTA/NF-iPSC #1 line using established protocol in FIG. 1a. PB-γδ T cells and PB-NK T cells were expanded from PBMCs of a healthy donor. Expression of inhibitory receptor and KIRs on iPSC-γδ T cells (a), expanded PB-γδ T cells (b) and expanded PB-NK cells (c) were detected by flow cytometry.

CD56 is a typical surface marker of NK cells. To find out whether such generated iPSC-derived mimetic γδ T cells (iPSC-γδ T cells) also express other surface molecules of NK cells, detailed phenotyping was performed (FIG. 5a). Flow cytometric analysis showed that most iPSC-γδ T cells highly expressed activating receptors: NKG2D and DNAM-1; natural cytotoxicity receptors (NCRs): NKp30, NKp44 and NKp46; and death-inducing ligand: TRAIL (FIG. 5a). In addition, 41% expressed CD16, a surface molecule mediates antibody-dependent cell-mediated cytotoxicity (ADCC); 5% expressed FasL, another death-inducing ligand (FIG. 5a). This surface molecule expression profile of iPSC-γδ T cells closely resembled that of expanded peripheral blood NK (PB-NK) cells (FIG. 5c), which had low-level TRAIL expression. In contrast, although the expanded peripheral blood γδ T (PB-γδ T) cells also expressed NKG2D and DNAM-1, they expressed no NCRs, death-inducing ligands and CD16 (FIG. 5b). In terms of inhibitory receptors and killer cell immunoglobulin-like receptors (KIRs), iPSC-γδ T cells expressed CD94/NKG2A receptor like PB-NK cells and PB-γδ T cells; however, unlike PB-NK cells and PB-γδ T cells, iPSC-γδ T cells did not express KIRs (FIG. 6a-c), which makes them unrestricted by recipient's HLA phenotype. Thus, the iPSC-γδ T cells are armed with both sets of "cancer-fighting" molecules observed in PB-γδ T cells and PB-NK cells and such novel GDT-iPSC-derived "γδ NKT cells" may fight against a broad spectrum of cancer cells.

Cancer Immunotherapy Using Mimetic Innate Immune Cells
Treatment with Mimetic NK Cells
Cell Culture.

K562 cells (ATCC), K562-mb15-41BBL cells (kindly provided by Prof. Dario Campana, Department of Paediatrics, National University of Singapore, Singapore) and Raji cells (ATCC) were cultured with RPMI 1640 (Thermo Fisher Scientific) supplemented with 10% FBS.

Cytotoxicity and ADCC Assay.

To detect direct cytotoxicity of PBC-iPSC-derived NK cells against target cells, a flow cytometry method was used. In brief, 0 to $0.5 \times 10^6$ NK cells were co-incubated with $2 \times 10^4$ carboxyfluorescein diacetate succinimidyl ester (CFSE; Thermo Fisher Scientific)—labelled K562 or Raji cells for 4-6 hours. The samples were then stained on ice with 7-Amino-Actinomycin D (7-AAD, BD Biosciences) for 10 minutes. After washing, the target cell death was assessed by FACSCalibur flow cytometer based on the percentage of 7-AAD-stained cells in the CFSE-positive population. To evaluate the ADCC function of PBC-iPSC-derived NK cells, co-cultures of NK cells and CFSE-labelled Raji cells were set up in the presence of human IgG1 (Sigma-Aldrich), anti-CD20-mIgG1 (InvivoGen, San Diego, CA, http://www.invivogen.com) or anti-CD20-hIgG1 (InvivoGen) of various concentrations, the target cell death was measured by flow cytometer as described above.

Functions of PBC-iPSC-Derived NK Cells.

Figure 7:
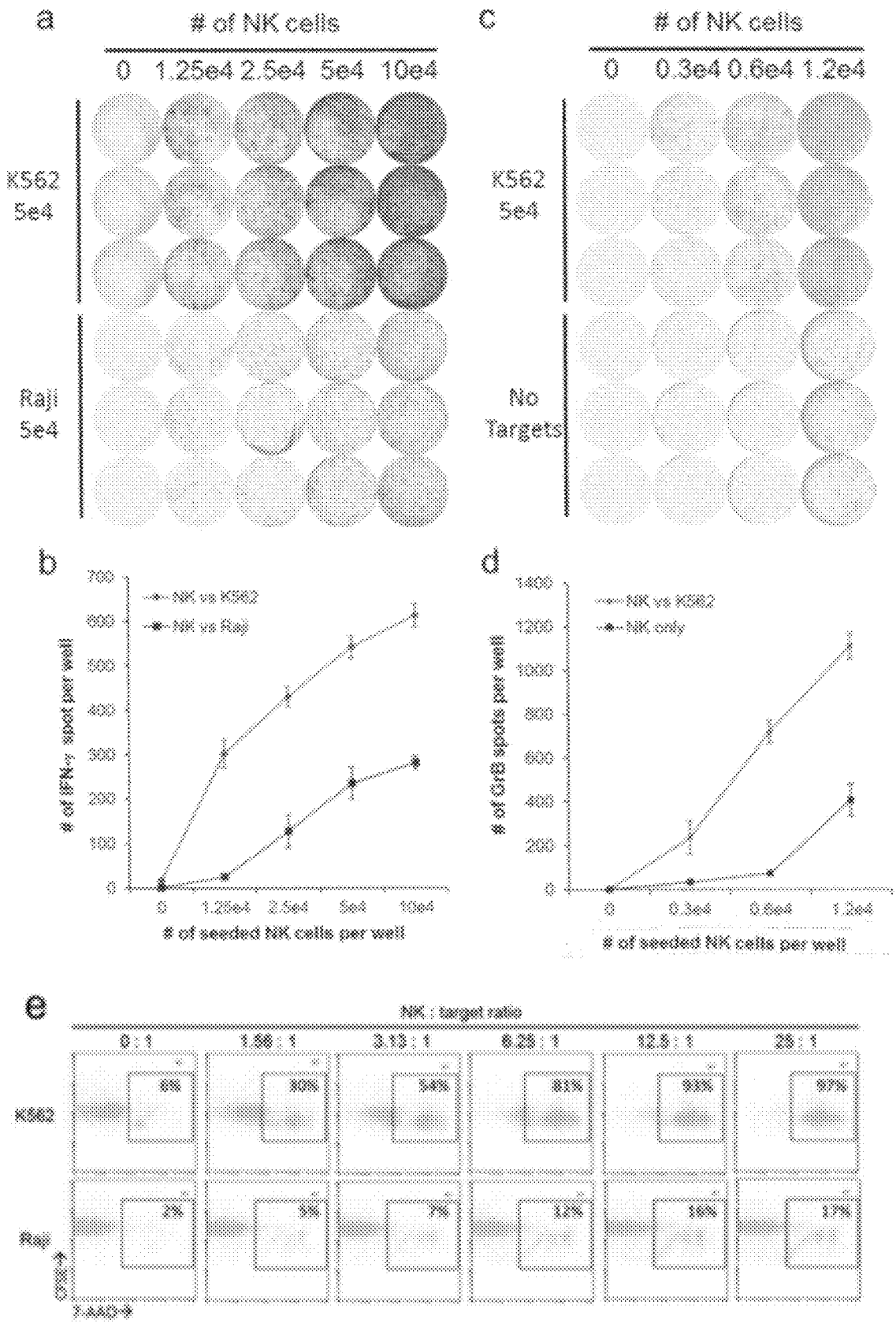
FIG. 7: Functions of PBC-iPSC-derived NK cells. (a-b): IFN-γ secretion by NK cells derived from PBC-iPSC #9 after stimulation by K562 and Raji cells detected by ELISPOT assay. ELISPOT images (a) and spot counting (b) are shown. (c-d): GrB secretion by NK cells from PBC-iPSC #9 after stimulation by K562 cells detected by ELISPOT assay. ELISPOT images (c) and spot counting (d) are shown. (e-f): Cytotoxicity of NK cells derived from PBC-iPSC #9 against K562 and Raji cells measured by flow cytometry. A representative flow cytometric analysis (e) and a result summary (f) are shown. (g-h): ADCC of NK cells against Raji cells in the presence of anti-CD20 humanized antibody measured by flow cytometry. A representative flow cytometric analysis (g) and a result summary (h) are shown.
Figure 7:
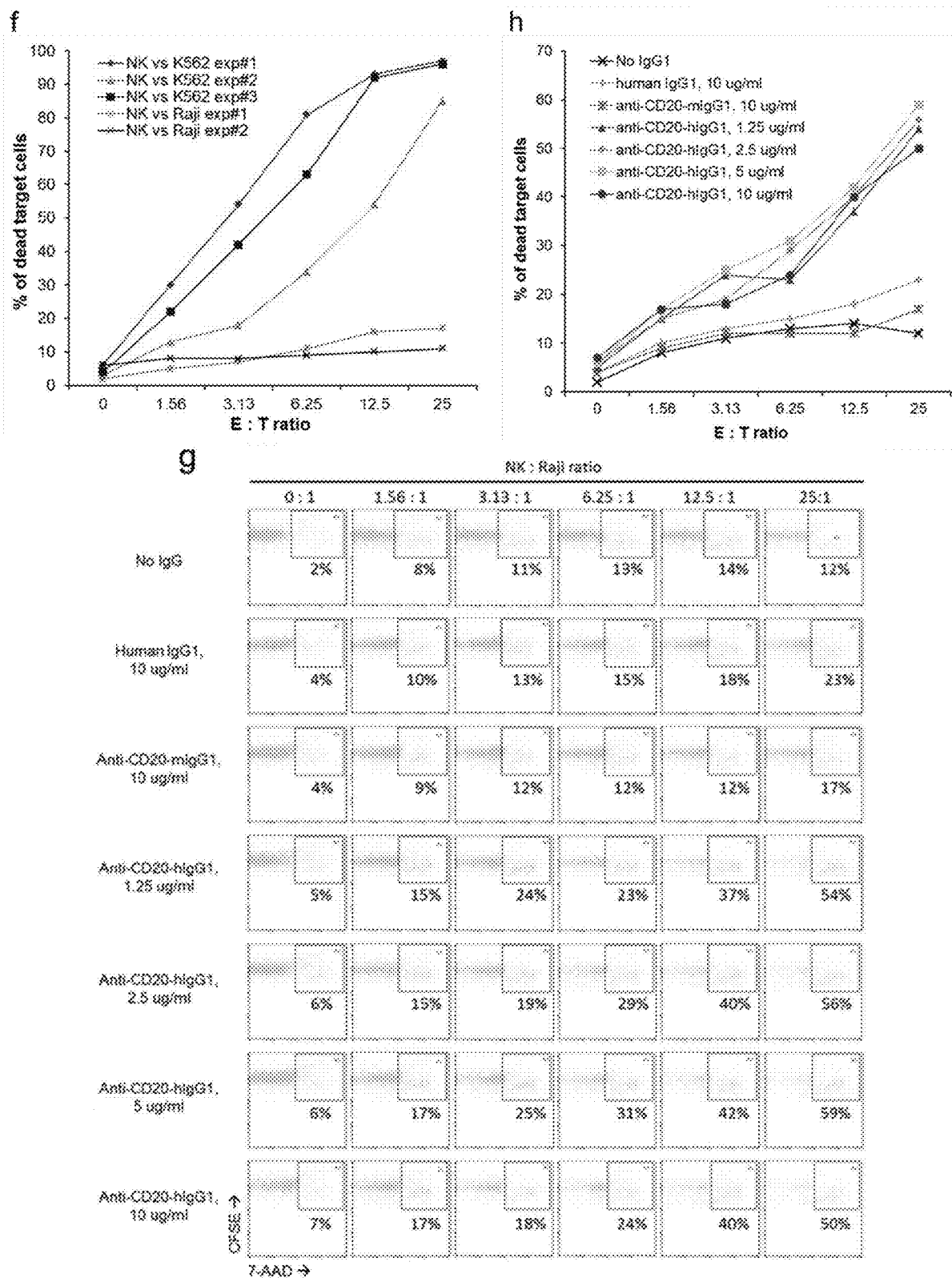

Secreting cytokines such as interferon-γ (IFN-γ) upon activation is an important functional feature of NK cells. To investigate IFN-γ secretion, PBC-iPSC-derived NK cells were co-cultured with stimulatory cells and an Enzyme-Linked ImmunoSpot (ELISPOT) assay was then used to detect IFN-γ-secreting NK cells. As shown in FIGS. 7a and 7b, K562, an NK cell-sensitive cell line efficiently stimulated IFN-γ secretion by NK cells derived from PBC-iPSC #9; in contrast, Raji, an NK cell-resistant cell line showed much lesser efficiency, suggesting that these PBC-iPSC-derived NK cells are capable of secreting cytokine in response to stimulation.

Cytotoxicity is another hallmark feature of NK cells, which depends on the secretion of cytotoxic molecules like granzyme B (GrB). ELISPOT result showed that a high frequency of PBC-iPSC-derived NK cells secreted GrB upon stimulation by K562 (FIG. 7c, d), which further confirms the functional competence of these iPSC-derived NK cells. More importantly, these iPSC-derived NK cells showed a similar direct killing profile as primary NK cells. As demonstrated in FIGS. 7e and 7f, they were able to directly kill the NK-sensitive leukemia cells K562, but not the NK-insensitive lymphoma cells Raji. Interestingly, by exploiting the ADCC function of these iPSC-derived NK cells, Raji cells were still able to be killed (FIG. 7g, h). As shown in FIGS. 7g and 7h, NK cells alone were not able to kill Raji cells; neither with the addition of human IgG1 or anti-CD20-mIgG1; however, in the presence of anti-CD20-hIgG1, obvious cytotoxicity on Raji cells were observed. Thus, the ADCC function of these PBC-iPSC-derived NK cells can significantly broaden their killing spectrum of malignant cells.

Treatment with Mimetic γδ NK T Cells

Cell Culture.

Cell lines: SK-OV-3, SW480, MCF-7 and BT474 (American Type Culture Collection [ATTC], Manassas, VA, http://www.atcc.org) were cultured as recommended by ATCC.

Cytotoxicity Assay.

To detect cytotoxicity of iPSC-derived γδ NK T cells against target cells, a flow cytometry-based method was used. In brief, 0 to $0.5 \times 10^6$ γδ NK T cells were co-cultured with $2 \times 10^4$ carboxyfluorescein diacetate succinimidyl ester (CFSE; Thermo Fisher Scientific)—labelled cancer cells at various effector to target (E:T) ratios for 4-6 hours. Samples were then stained on ice with 7-Amino-Actinomycin D (7-AAD, BD Biosciences) for 10 minutes. After washing, target cell death was assessed with flow cytometer by the percentage of 7-AAD-stained cells in CFSE-positive population.

Figure 8:
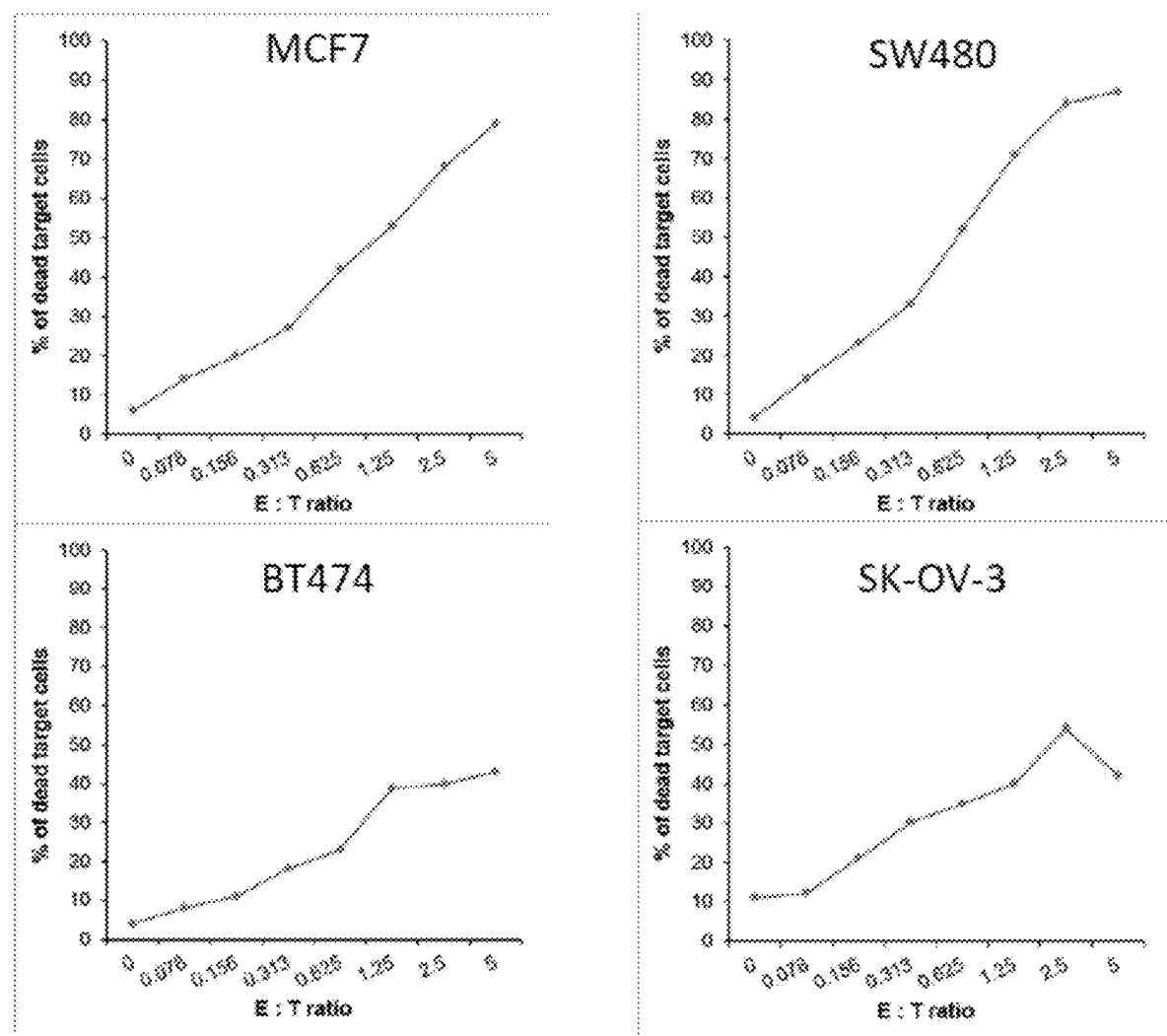
FIG. 8: Cytotoxicity of iPSC-derived γδ NKT cells against cancer cells. γδ NKT cells were generated from GDTA/NF-iPSC #1 line and used for cytotoxicity assay against a variety of cancer cell lines: MCF7, SW480, BT474 and SK-OV-3.

To test the cytotoxicity of γδ NKT cells, four different solid tumor cell lines were used as target cells: MCF7 (breast adenocarcinoma), SW480 (colorectal adenocarcinoma), BT474 (breast ductal carcinoma) and SK-OV-3 (ovary adenocarcinoma). Results showed that the γδ NKT cells were able to kill these cancer cell lines (FIG. 8). In some cases, the cytotoxicity was observed even at very low E:T ratios (FIG. 8), suggesting the high efficacy of the γδ NKT cells.

Generation of iPSCs from Peripheral Blood Cells

Generation of iPSCs from PBCs.

To generate iPSCs from PBCs, frozen peripheral blood mononuclear cells (PBMCs) from healthy donors (StemCell Technologies) were thawed and cultured with 5 μg/ml phytohemagglutinin (PHA; Sigma-Aldrich, St Louis, MO, http://www.sigmaaldrich.com) for 2 days in complete RPMI 1640 medium, which is composed of RPMI 1640 (Thermo Fisher Scientific), 10% heat-inactivated human serum AB (Gemini Bio-Products, West Sacramento, CA, http://www.gembio.com), 2 mM L-glutamine (Thermo Fisher Scientific), 0.1 mM nonessential amino acids (Thermo Fisher Scientific) and 0.1 mM 2-mercaptoethanol (Thermo Fisher Scientific). The cultured blood cells were then transduced with Sendai reprogramming vectors from a CytoTune iPS 2.0 Sendai Reprogramming Kit (Thermo Fisher Scientific) at MOI of 5:5:3 (KOS, hc-Myc, hKlf4) in complete RPMI 1640 medium containing 10 ng/ml of IL-2, IL-7 and IL-15 overnight. The transduced cells were then washed and cultured for 5 days before seeding to a six-well plate grown with mitomycin C (Sigma-Aldrich)—treated mouse embryonic fibroblasts (mEFs). Half of medium was replaced on day 1 to 3 after seeding with iPSC medium, which is composed of DMEM/F12 (Thermo Fisher Scientific), 20% knockout serum replacement (Thermo Fisher Scientific), 2 mM L-glutamine, 1% nonessential amino acids, 0.1 mM 2-mercaptoethanol and 5 ng/ml basic fibroblast growth factor (PeproTech). Three to four weeks after seeding, the resulting iPSCs were first expanded on mEFs in iPSC medium and later on Matrigel-coated plates in mTeSR1.

Immunostaining.

To detect pluripotency markers, PBC-iPSCs were fixed in 4% paraformaldehyde (Sigma-Aldrich) at room temperature for 15 min followed by blocking with 5% bovine serum albumin for 1 hour. The cells were then incubated with primary antibodies against SSEA-4, TRA-1-60, TRA-1-81 (Thermo Fisher Scientific) for 1 hour at room temperature. After washing, the cells were incubated with Alexa Fluor 594-conjugated goat anti-mouse IgG (H+L) antibody (Thermo Fisher Scientific) at room temperature for 1 hour for visualization under fluorescence microscope. To detect alkaline phosphatase (AP), Alkaline Phosphatase Live Stain (Thermo Fisher Scientific) was used according to the manufacturer's protocol. To demonstrate the feasibility of using PBC-iPSCs for NK cell generation, iPSC lines from PBCs using Sendai viral vectors carrying the reprogramming factors were first generated (FIG. 2a). These resulting PBC-iPSCs showed typical hPSC morphology and phenotype (FIG. 2a).

Expansion of γδ T Cells.

To expand γδ T cells for iPSC generation, frozen PBMCs from a healthy donor (StemCell Technologies) were thawed and cultured in PBMC culture medium [OpTmizer CTS T-Cell Expansion SFM (Thermo Fisher Scientific) supplemented with 10% heat-inactivated human AB serum (Gemini Bio-Products, West Sacramento, CA, http://www.gembio.com) and 10 ng/ml IL-2 (Thermo Fisher Scientific)] containing 5 µM Zometa (Novartis). Half medium was replaced with fresh PBMC culture medium without Zometa every 2-3 days.

Generation of GDT-iPSCs.

To generate iPSCs from the expanded γδ T cells, the cultured PBMCs were transduced on day 7 with Sendai reprogramming vectors from a CytoTune iPS 2.0 Sendai Reprogramming Kit (Thermo Fisher Scientific) at MOI of 5:5:3 (KOS, hc-Myc, hKlf4) overnight. The transduced cells were then washed and cultured for 5 days before seeding to a 6-well plate grown with mitomycin C (Sigma-Aldrich)—treated mEFs. Half medium was replaced on day 1 to 3 after seeding with iPSC medium, which is composed of DMEM/F12 (Thermo Fisher Scientific), 20% knockout serum replacement (Thermo Fisher Scientific), 2 mM L-glutamine, 1% nonessential amino acids, 0.1 mM 2-mercaptoethanol and 5 ng/ml basic fibroblast growth factor (PeproTech). Three to four weeks after seeding, the resulting iPSC colonies were picked up and expanded on Matrigel-coated plates in mTeSR1.

To generate iPSCs from γδ T cells using a non-viral method, PBMCs were cultured with Zometa and IL-2 as described above and used on day 7 or day 13. On day 0, episomal reprogramming vectors from a Epi5 Episomal iPSC Reprogramming Kit (Thermo Fisher Scientific) were delivered into the cultured PBMCs via nucleofection using a Amaxa Nucleofector 2b (Lonza, http://www.lonza.com). The nuleofected cells were then seeded on mitomycin C-inactivated mEFs. On day 2, the cells were adapted to a 1:1 mixture of PBMC culture medium: iPSC medium. From day 3 on, the cells were cultured in iPSC medium, which was changed every other day. Two to four weeks after seeding, iPSC colonies were picked up and expanded in Matrigel-coated plates in mTeSR1.

TCRB and TCRG Gene Clonality Assays.

Genomic DNA was isolated from iPSCs using a DNeasy Blood and Tissue Kit (Qiagen, https://www.qiagen.com) according to the manufacturer's instruction. To detect TCRG and TCRγ gene rearrangement in genomic DNA, PCR was carried out with master mixes provided in TCRB and TCRG Gene Clonality Assay kits (Invivoscribe Technologies, San Diego, CA, http://www.invivoscribe.com) and AmpliTaq Gold DNA polymerase (Thermo Fisher Scientific) using the following program: 95° C. for 7 minutes; 35 amplification cycles (95° C. for 45 seconds, 60° C. for 45 seconds, 72° C. for 90 seconds); and final extension of 72° C. for 10 minutes before holding at 15° C. PCR products were separated by electrophoresis in 2% MetaPhor Agarose (Lonza, http://www.lonza.com) gel.

Figure 9:
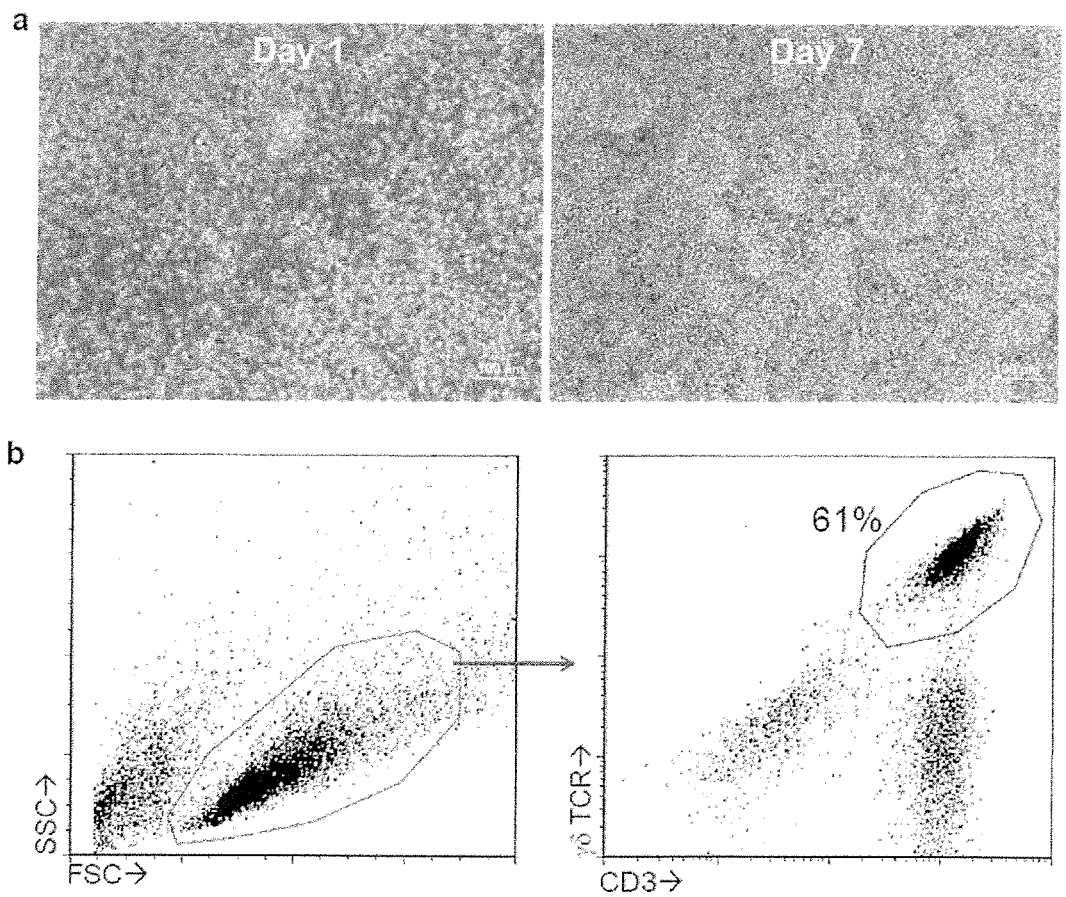
FIG. 9: Expansion of peripheral blood γδ T cells. PBMCs were cultured with Zometa and IL-2. (a): Morphology of PBMC culture on day 1 and day 7; (b): Phenotype of PBMC culture on day 7.

To activate and expand γδ T cells for iPSC generation, peripheral blood mononuclear cells (PBMCs) from a healthy donor was cultured using Zometa and IL-2. Total cell number and cell clumps in the PBMC culture increased over time (FIG. 9a), indicating a successful expansion of γδ T cells. Flow cytometric analysis further confirmed that up to 61% of the lymphocytes in a 7-day culture were γδ T cells (FIG. 9b). This γδ T cell-enriched PBMC culture was then used for iPSC generation.

Figure 10:
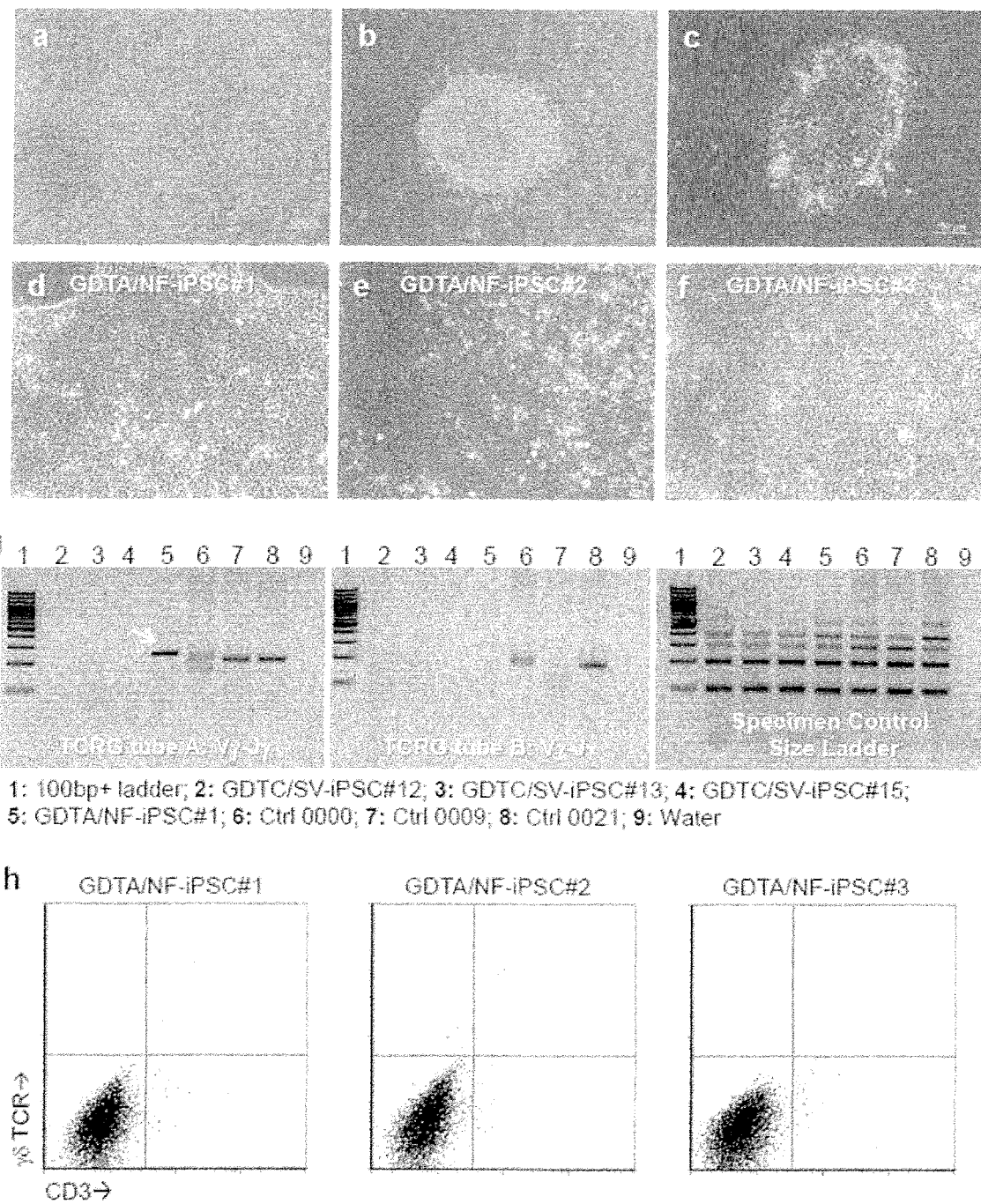
FIG. 10: Generation of GDT-iPSCs. Cultured PBMCs were reprogrammed into iPSCs using Sendai viral vectors or nucleofaction. (a-f): Morphological change during reprogramming of cultured PBMCs into iPSCs. Phase contrast images show that (a): cultured PBMCs survived on day 6 after transduction by Sendai viral vectors; (b): an iPSC colony appeared on mEFs on day 17 after seeding the transduced cells; (c): an iPSC colony attached to a Matrigel-coated plate after being transferred from a mEF plate; (d-f): three iPSC lines generated via nucleofaction were established. (g): TCRG gene clonality assay to identify γδ T cell-derived iPSC lines. The arrow indicates the detection of rearranged TCRG gene in a GDTA/NF-iPSC #1 line. (h): Detection of CD3 and γδ TCR expression in three established iPSC lines by flow cytometry.

To derive iPSC lines from γδ T cells, two reprogramming protocols were used. In one protocol, integration-free Sendai viral vectors carrying the reprogramming factor genes to transduce the cultured PBMCs was initially used. As observed on day 6 after transduction, most transduced cells survived (FIG. 10a). These cells were then seeded on mitomycin C-treated mouse embryonic fibroblasts (mEFs). iPSC colonies (FIG. 10b) started to appear as early as 9 days after seeding. These colonies could be picked up 3 weeks after seeding and directly expanded on Matrigel-coated plates in mTeSR1 medium (FIG. 10c).

In another protocol, nucleofection was used to deliver episomal reprogramming vectors into the cultured PBMCs and established three iPSC lines: GDTA/NF-iPSC #1, GDTA/NF-iPSC #2 and GDTA/NF-iPSC #3 (FIG. 10d-f). To identify iPSC lines derived from γδ T cells, TCRG gene clonality assay (FIG. 10g) and TCRB gene clonality assay were performed. Two iPSC lines, GDTA/NF-iPSC #1 and GDTA/NF-iPSC #2 were confirmed to be derived from γδT cells due to the presence of rearranged TCRG gene, whereas one iPSC line, GDTA/NF-iPSC #3 was from a non-T cell due to the absence of both rearranged TCRB and TCRG genes. Like the non-T cell-derived GDTA/NF-iPSC #3, the γδ T cell-derived GDTA/NF-iPSC #1 and GDTA/NF-iPSC #2 expressed no γδ TCRs and CD3 (FIG. 9h), suggesting the thorough reprogramming of γδ T cells.

For the first time the derivation of iPSCs from γδ T cells and the generation of γδ T cells using such γδ T cell-derived iPSCs (GDT-iPSCs) has been demonstrated. Moreover, by combining these novel GDT-iPSC lines with the above described differentiation protocol for generating NK cells from iPSCs, γδ T cells that highly expressed the "cancer-fighting" molecules of NK cells were generated and designated this unique cell type as "γδ natural killer T (NKT) cells".

Expansion of Mimetic Innate Immune Cells

Expansion of Fresh and Cryopreserved PBC-iPSC-Derived NK Cells.

Figure 11:
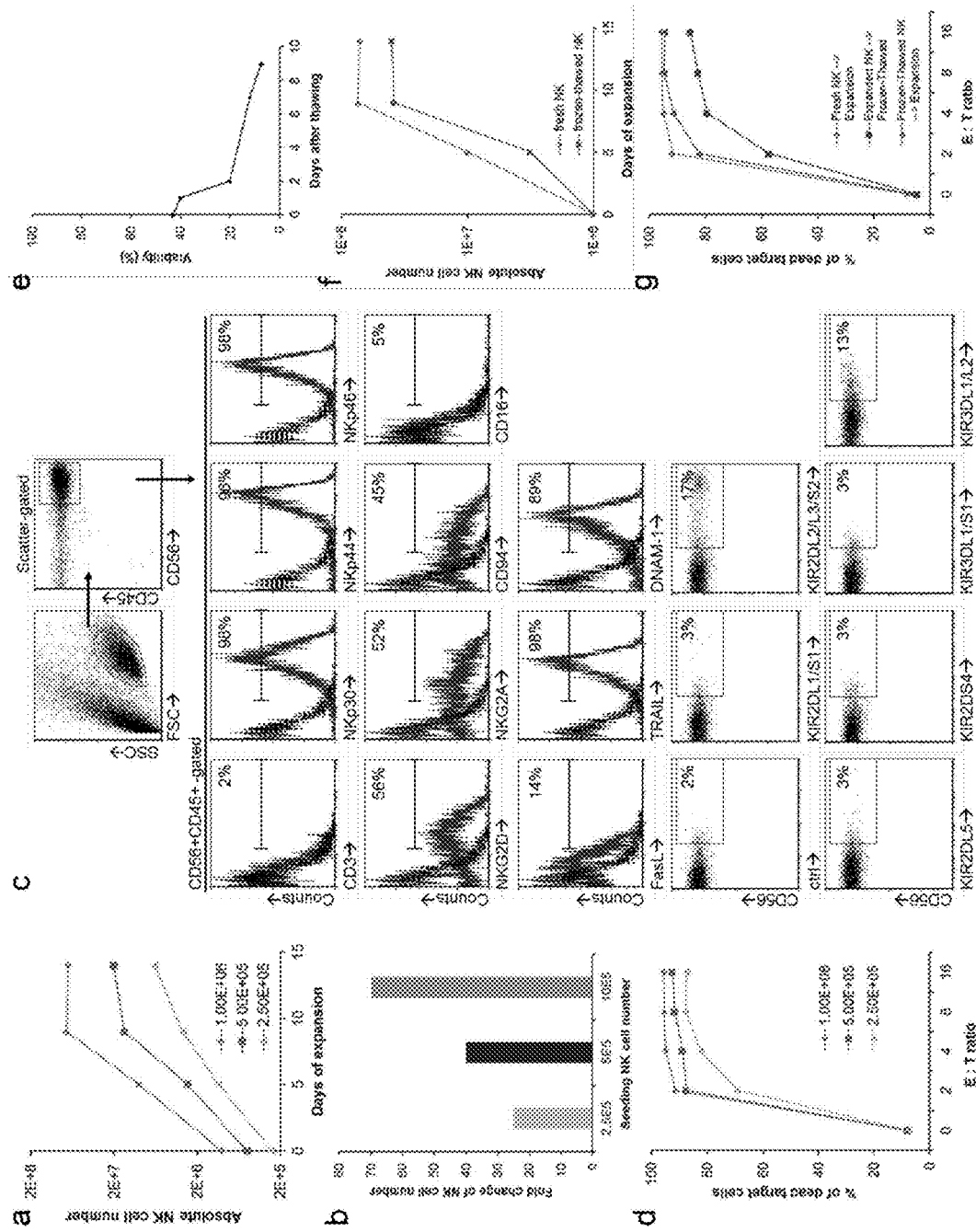
FIG. 11: Expansion of fresh and cryopreserved PBC-iPSC-derived NK cells. (a-b): Expansion of fresh NK cells derived from PBC-iPSC #9 by K562-mb15-41 BBL in G-Rex10 starting with different NK cell numbers. The absolute numbers (a) and fold changes (b) of NK cells during the 14-day expansion are shown. (c-d): Phenotype (c) and cytotoxicity against K562 (d) of fresh NK cells after 14-day expansion measured by flow cytometry. (e): Viability of expanded NK cells after freeze/thaw procedure. (f): Expansion of cryopreserved NK cells. (g): Cytotoxicity of cryopreserved NK cells against K562 after expansion.

Generating sufficient functional cells is a prerequisite to translate these iPSC-derived NK cells into clinical use. One possible way to obtain therapy-scale NK cells from iPSCs is to scale up the differentiation cultures, which, however, is not cost-effective. A more practical way is to expand the iPSC-derived NK cells using feeder cells. To investigate this possibility, various numbers of NK cells generated from PBC-iPSC #9 were co-cultured with irradiated K562-mb15-41BBL cells at an NK cell: feeder ratio of 1:10 in gas-permeable G-Rex10 flasks. The results showed that these iPSC-derived NK cells were quickly expanded during a 14-day co-culture (FIGS. 11a, b). With a starting NK cell number of $10^6$, a 74-fold expansion was observed on day 9, although no further expansion was achieved by extending the co-culture to 14 days (FIG. 11a). Interestingly, although there was no obvious change in phenotype except the down-regulation of CD16 expression (FIG. 11c), these expanded NK cells became more potent in killing K562 cells (FIG. 11d), probably due to their further functional maturation during expansion. These data indicate that it is feasible to produce functional iPSC-derived NK cells in clinical-scale through expansion with feeder cells.

Shipping cellular therapeutics from a centralized manufacturing site to a clinical site for injection without compromising product quality is crucial for the clinical efficacy of live cell products. Transporting conventional NK cell products in cryopreserved form can significantly reduce the viability and potency of NK cells. This was also true for the PBC-iPSC-derived NK cells (FIGS. 11e, g). The freeze/thaw procedure significantly affected the viability of expanded PBC-iPSC-derived NK cells (FIG. 11e), although the potency of these expanded NK cells was preserved to a certain extent after freeze/thaw procedure (FIG. 11g). To overcome these viability and potency issues caused by cryopreservation, a possible solution: the PBC-iPSC-derived NK cells are first cryopreserved before expansion at a centralized manufacturing site and shipped to a clinical site in cryopreserved form was proposed; these cryopreserved NK cells are then thawed, expanded and injected at the clinical site. The feasibility of such solution depends on the ability to expand the cryopreserved NK cells. As shown in FIG. 11f, the cryopreserved NK cells remained very expandable; starting from $10^6$ cryopreserved NK cells, a 38.5-fold expansion could still be achieved on day 9. Most importantly, these expanded cryopreserved NK cells showed comparable cytotoxic potency as those expanded from non-cryopreserved fresh NK cells (FIG. 11g). These results suggest that transporting pre-expansion NK cells is a practical solution for the logistics of PBC-iPSC-derived NK cell therapeutics.

The yield was up to $15 \times 10^6$ NK cells per $3 \times 10^6$ PBC-iPSCs with 99% purity. These PBC-iPSC-derived NK cells could be expanded by 74-fold in 9 days and by 38.5-fold after cryopreservation using a feeder cell line. These expanded NK cells became more potent functionally as shown by the increased cytotoxicity against K562 cells. Thus, the feasibility of generating NK cell therapeutics from PBC-iPSCs using an industry-compatible production scheme is demonstrated.

It should be further appreciated by the person skilled in the art that variations and combinations of features described above, not being alternatives or substitutes, may be combined to form yet further embodiments falling within the intended scope of the invention.

The invention claimed is:

1. A method of generating gamma-delta natural killer T cells (γδ NKT cells), the method comprising:
   (a) expanding γδ T cells of human peripheral blood cells in PBMC culture medium containing an amino-bisphosphonate and interleukin 2 (IL2);
   (b) transducing the expanded γδ T cells with reprogramming transcription factors to generate induced pluripotent stem cells (iPSCs);
   (c) screening the TCRG and TCRD gene configuration of the iPSCs to identify γδ T cell-derived iPSCs;
   (d) co-culturing γδ T cell-derived iPSCs with a stromal cell line deficient in expressing macrophage colony stimulating factor (M-CSF) to generate innate immune cell progenitors;
   (e) co-culturing the innate immune cell progenitors with a stromal cell line deficient in expressing M-CSF and ectopically expressing Notch ligand, Delta like 1 (DLL1) in a media comprising stem cell factor (SCF), Fms-related tyrosine kinase 3 ligand (FLT3L), interleukin 7 (IL7) and interleukin 15 (IL15) to generate differentiated gamma-delta NKT cells;
   (f) passaging the differentiated gamma-delta NKT cells weekly for 3 to 5 weeks to obtain gamma-delta NKT cells expressing gamma-delta TCRs (γδ TCRs); and
   (g) detecting the expression profile of the gamma-delta NKT cells obtained in step (f); wherein the γδ NKT cells expressing gamma-delta TCRs (γδ TCRs), express NKp30 in 99% of the cells, NKp44 in 99% of the cells, NKp46 in 97% of the cells, NKG2D in 84% of the cells, DNAM-1 in 97% of the cells, TRAIL in 89% of the cells, and NKG2A/CD94 in 83% of the cells in combination with expression of at least any one of CD56, CD16, FASL and less than 5% expression of killer cell immunoglobulin-like receptors (KIR) are γδ NKT cells.

2. The method according to claim 1, wherein the γδ T cell-derived iPSCs in (c) are co-cultured with the stromal cell line deficient in expressing M-CSF for 12 days.

3. The method according to claim 1, wherein the media comprises Fetal Bovine Serum (FBS); alpha Minimum Essential Medium (aMEM); or a combination thereof.

4. The method according to claim 1, wherein the amino-bisphosphonate is zoledronic acid or salts thereof.

5. The method according to claim 1, wherein the iPSCs generated in step (b) comprises a TCR gene arranged in a TCRG gene configuration and a TCR gene arranged in a TCRD gene configuration.

6. The method according to claim 1, wherein the method further comprises expanding gamma-delta NKT cells in the presence of feeder cells in a media comprising stem cell factor (SCF); Fetal Bovine Serum (FBS); Fms-related tyrosine kinase 3 ligand (FLT3L), interleukin 15 (IL15) and interleukin 7 (IL7).

* * * * *

SEQUENCE LISTING

<160> NUMBER OF SEQ ID NOS: 15

<210> SEQ ID NO 1
<211> LENGTH: 128032
<212> TYPE: DNA
<213> ORGANISM: Homo sapiens

<400> SEQUENCE: 1

```
atgcggtggg ccctagcggt gcttctagct ttcctgtctc ctggtgagtg cgctgcctac      60
agagaggatc acgggttttg ttttgttttg ttattttctt cttttgcaag gagcgacata     120
ctaagaaatg cctcattata ttttgtgttg ttcccattgc agccagtcag atatcttcca     180
acttggaagg gagaacgaag tcagtcacca ggctgactgg gtcatctgct gaaatcacct     240
gtgatcttcc tggagcaagt accttataca tccactggta cctgcaccag gaggggaagg     300
ccccacagtg tcttctgtac tatgaaccct actactccag ggttgtgctg gaatcaggaa     360
tcactccagg aaagtatgac actggaagca caaggagcaa ttggaatttg agactgcaaa     420
atctaattaa aaatgattct gggttctatt actgtgccac ctgggacagg cacagtgatt     480
cagacactga aaatctgcct gtggttgctt ctggtacaca agatagacca gccaactctc     540
atttcctgcc ctgaatttac tgtattctgt acaaagagaa acacagctta actcctgatc     600 tccctgcaa tatcacactc ccctggcagc agctgcaccc tgttccccac cctccccag     660 gactttcctg aagaccaagc tgccacctcc aagcctcagc taagcagcct ggctgagagc     720
aagtttctct cagctctcct agaacatggg gaaggcccac tcactctgct tcctaggaca     780
gacaggtaca gctagggtcc agctgtgaag caagacattt tggacaaaaa tgggaagggt     840
attcatactg aatcatacat ccaataatgg tccagagatc gcagctgaga gtggtgctta     900
ttccttatgt ctataacaat ataagcaata ctataatgac cactaaaaca ctaggccaat     960
atatgcagtt gaacattctc tctctctgcc ctcccttta ttctcgctct cctttcttac    1020
ttccatgctt gcttttatca ttttctctcc ctccctccct tcctcctttc cttccatcac    1080
cccaccctcc ttcctttctt tccttccttc cttccttgct tttctctctt tctctccttt    1140
ttgtgtacat aatcacaata cttttccac aaaatcattt gaaatagttt ttctctattt    1200
gttcatgcca acattgatat agctgcttta attgttcagt ttcatttta tattttggaa    1260 atttgtgtat tattttgttt tgtttcatat ttgttttgta tacgtaaaac atttagttgg    1320
aactgaagtc aaaattataa aagatgacac atttgaagat tttagcttcc attgtagact    1380
tctcattcct ctttctccc tgacactata ggtaacaata ttttatccg ttttcttgaa    1440 cttttcact ctgtcatagc gcagtatgta tcaattctat ttcaatgcca tatttatatt    1500
```

```
tttgttccta tatttggttt ttatacattt taatcaatct tatattttcc cgtgtctgga    1560
ttgtgtgtct tacttctaaa ggtgcacata cttcataagt atgcataaag acgtccatat    1620
catttatttg aatgttttta tgtgttgatt atttaatgat ggcatcattg atctatcagg    1680 aattttata caataattac tgtattagta ataataatac tggccaggcc cggtggctca    1740
tgcctgtaat cccagcattt gagtagtaca gtcgttagga atacttaggc cgggagattg    1800
cgaccagctt agccaacatg gtgaaaccct gtctctacta aaatacaaa aaattagctg    1860 gctgtggcgg tgcacacatg taatcccagc tacttggatg ctgaagcagg agaatctctt    1920
gagcctagaa ggtggagttt tcagtgagct aatatcacac tactgcagtc cagtttgggc    1980
aacacagtga gactctgtct caaaaagact aataataata ataatattga tggtaaatat    2040
gggtactgac attctggtag ttaatgtact aagcacattg catgcatatt gtatttaatc    2100
tacacagaaa cttcattaag gatttaaagt actgttgaat gtaacattag aaattggggg    2160
gttaattaac attccctaag tcatatactt taatttgata atgattgcaa tccaagctct    2220
gtggttcaga aaatgagatt tgttaattcg gtttgcattc ccccatcgta ggagtactag    2280
catcatttta caactttaca gttcatttat atttcttctt ttgagaattg ccttgtacac    2340
tcttttccta ttcttctatt ggaggattag ttttttctta ttggttcgta agaattaata    2400
tacaccattt tagagatact gacccttat ccaatgtgtt gaagatattt ctcctcattt    2460
gttattattt acatttggca ccttttggag aattgaactt tgaaaaaaac aaaatctatc    2520 aattttcta tggtgtctac tttgatgtca ggtttagaaa ggccaatctc acctagaatt    2580
tctatgcaat tcatcatcat ttaagtctaa tgattttctt tttattacaa ctaaatcact    2640
atttgtaact ggtaaggtag aaatgcagca atatttgttt ccatatggta agtcaatatc    2700
caaaagagaa cttatgaaat aattgactat ttccttgtgg atattaacat atcactttat    2760
cacatgataa aatattacat acatgcagct ttctttctgg attttccact gtgttccatg    2820
aatcttgtca ttctagtgcc agtattgcct tctcttcagc actgtagctt tatagttctt    2880
ttcacattct gatgaagttt ctctcattat cttttgttt taagaatttt ctgtgcatgc    2940
tagtgtgatc tcaatcctct cccttcccat ttttaaaccg tgagacttct gtccagcaag    3000 acttttcac gctccaaggc aggcaagctt ccctccttca caaggacctg agaattcagc    3060
tttcagagct gttcctgtgg aagcctcatg tcctgcacat atggtccaga ggcagaggga    3120
gaccaaccgg agcccctcc ctttctcatt cccagctgtg atgacagcaa aaactgaact    3180
ctgtgagcta ggccaacaac acaattaaga gagacattgt tctacatctc attatgcatc    3240
tttcaaacat gtgtctctat atacttctga cacaggtggt ggtaatctgt gtatgcctta    3300
ctgaattttc acaattatat tactgtacta cttttgtccc ctatatttcc atctgtgaat    3360
ccaggtgtac tgcagatctc agtcccctt ctgagggtag ggctgacaaa taaaatatac    3420
aataccaaac aatttggaag ttcagataaa caacaagttt ttagtttaag tatgttccaa    3480
atattgcatg acatggcacc ctgaactact tagaaaaaaa aaacaaaaaa acctcacact    3540
cctacttcag tgaacaaaaa tcctctaata aagagatcac acccacagga tcacacacac    3600
acaaacacac acacacacac acaccccaca tacacccatt tatcttagag cagagtccaa    3660
gacccaccaa cacacatgat cctcagtcct ttcattttta ttatttattt atttatttat    3720
atttattata ctttaagtgc tagggtacat atgcacaacg tgcaggtttg ttacatatgt    3780
atacatgtgc catgttggtt tgttgcaccc atcaacttgt catctacatt aggtatatct    3840
```

```
cttaatgcta tccctccccc ctccccccac cccactacag gccccagtgt gtgatgttcc   3900
cccactctgt gtccaagtgt tctccttgtt caattcccac ctacgagtga gaacatgcac   3960
tgtttggatt tctgtccttg gaatagtttg ctcggaatga tggtttccag cttcatccat   4020
gtccttacaa aggacatgaa cgcatccctt tttatggccg catagtattc catggtgtat   4080
atgtgccaca ttttcttaat ccagtctatc attgatggac atttggggttg gttccaagtc   4140
tctgctatcg tgaatagtgc cacaataaac atatgctttg cgtggtgcct ccaagtgtcc   4200
tcgcagatgc caaaaggaag gtggttcagt tccctaatca gagacttcct ggcaggacaa   4260
ggtcctggca tcagcattag ctgctgcaac tctgaagggc agggtgtgag cctgctgtgg   4320
gactgccccc tcctagggct gggcctgctg actccagggt ctgcttcccc cacctctgca   4380
ctccctctgc tgcaggcctg agctctcctt gccctggct ctcttctgca gagggcctgc   4440
tctcagctgc cacaagaggg cgccggagaa cggacctgag cagagaggca ggggctcctc   4500
tgcaggtcct cccaggcacc aacccttctg ggagggagga aggcttggga gtcctcttag   4560
acagatcctc agtcacttcc ctctgcttgt gtctcaggaa gaccacctcc tcctactgtc   4620
ttctgtgcta gggatcactt ccttgttgag tggaacctga gttttaagag gatcttctgc   4680
tcctcttcat ctggtccctt tccttccaag gccccagaga ggaaggcatg cagtgggccc   4740
tagcggtgct tctagctttc ctgtctcctg gtgagtgcgc tgcctacaga gaggatcacg   4800
ggttttgttt tattttcttc ttttgcaagg agtaccatac taaggaattc ctcattatat   4860
tttgtgttgt tcccattgca gccagtcaga aatcttccaa cttggaaggg agaacgaagt   4920
cagtcatcag gcagactggg tcatctgctg aaatcacttg tgatcttgct gaaggaagta   4980
acggctacat ccactggtac ctacaccagg aggggaaggc cccacagcgt cttcagtact   5040
atgactccta caactccaag gttgtgttgg aatcaggagt cagtccaggg aagtattata   5100
cttacgcaag cacaaggaac aacttgagat tgatactgcg aaatctaatt gaaaatgact   5160
ttggggtcta ttactgtgcc acctgggacg ggcacagtga ttcagatccg ccctacacca   5220
cactgaaaat ctgccttgtg gctgcttctg gtacacaaga tagagccgcc cctctcatt   5280
tcctgccacc aaatttaccg tgtgctgaac aagagaaaca ttgcttaact cctgatctcc   5340
cctgcaatat tacactcccc tggcagcagc tgcaccctgt tccccacccc cccccaggac   5400
tttcctgaag accaagccgc catctcagct aagcctcaga gaagcagcct ggctgagagc   5460
aaggttctct tagctctcct aggacatggg ggaggcccac tcactctgct tcctaggaca   5520
aatgggtacc cctagggtcc agctgtaaag caagatattt tggacaacaa atgggaaggg   5580
aatttatact aaattgtgta tcccatcatg atccagaaac cgcagctgag actggtgctt   5640
attcctatg tctataacaa tataagcaat actataatga ccactgaaac accaggccta   5700
ggtatgcagt tgaacattct ctccctctgc cctcccttt attctctctc tctttttct   5760
taattctttg cttgcttta ttatttttct ctctcccttc ctcccctcgct ccatcgctcc   5820
ctccgtcctt ccctccctct ctccctctct ccttccctcc cttcctctct tctttccttc   5880
catccattct ccttcgtttt ccttccttcc ttctttgctt ttctcttgct ttccttttg   5940
ggtacataat cagaatactt tttccacaaa atcatttgaa ataatttttc tctatgtgtt   6000
catgtcaaca ttgatatagc tactttaatt gttcagtttt cttttttaca ttttggaaat   6060
ttgttgtatt actttgtttt gtttcatatc tgttttgtat atataaaaca tttacatgga   6120
agtgaagtca aaattataaa agatgatgca tttgaagatt ttagcttcca ttgtagactt   6180
ctcattcttc ttttctcccct gacactatag gtaacaatat ttttggcagt tcacttgagt   6240
```

```
tttttcactg tttgtcatag cggagtatgt attgtttcta tttcaatgcc atatttatat    6300
tttctttctg atattcagtt tctatatatt ttaatcaatc ttatattttc ctgtgtctgg    6360
actgtgtgtc ttacttctaa aggtgcacat acttcataag tatgcataaa gacgtccata    6420
tcatttattt gaatgttttt atgcattcat tatttaatga tggcatcatt gatctatcag    6480 gaattttttat acaataatta ctgtattagt aataataata ctggccaggc ccggtggttc    6540
atgcctgtaa tcccagcatt tgggcagtcc agtcgttagg atcacttagg ccgggagatt    6600
gcgaccagct tagccaacat ggtgaaaccc tgtctctact aaaaatacaa aaaattagct    6660
ggctatagtg gcgcacacat gtaatcccag ctacttgaat gctgaagcag gagaatctgt    6720
agagcctggt aggtggagtt ttcagtgagc taatatcaca ctactgcagt ccagtttggg    6780
caacagagtg agactctgtc tcaaaaaaat gaataacgat aataataata ttgatgctac    6840
atatgggtac tgacattctg gtagttaatg tactaagcac attacatgca tattttattt    6900 aatctcacaca gaaatttcat tagggtttaa agtactgttg aatgtaacat tagaaattga    6960
gggggttaat taacattccc tgagtcatat actttaactt gataatgatt gcaatccaag    7020
ctctgtgatt ctgaaaacga gatttgtaaa ttcagttttgc attccctcat ctttgggagt    7080
actaacatta tttcacaact ttataggtca tttatagttc ttcttttgtg aattgccttg    7140
tcatactctt tgcctattcc tctcttggag gattaatttt ttcttattag tttgtaagag    7200
ttaatataca ctatttttaaa gatactgacc ctttatccaa tgtgttgaag atatttctcc    7260
tcatttgttg ttatttacat ttggcatctt ttggtgaatt gaactttgaa aaaaaaagca    7320
ttaaaatcta tcagttttttc tagggtgtct agtttgatgt caagcttaga aaggccaatc    7380
tcacctagaa tttctatgca attcatcatt gtttaagtgt aatgattttg ttttttattac    7440 aactaaatca ctatctatat ctggtaagaa cgaaatgcaa taatatttgt ttccatatgg    7500
taagtcaata cccaaaacag aacttataaa ataattgact atttccttgt gggtattaac    7560
atatcacttt atcacatgat aaaatattac atacgtgtgg ctctcttttct ggattttcca    7620 ctgtgttcca tgaatcttct cattctagtg ccagtattgc cctctcttca gcactgtagc    7680
tttatacttc ttttcacatt ttgatgaagt ttctctcatt attttttttgt tttaagaatt    7740 ttctgtgcat tctagtgtga tctcaatcct ctcccttccc attttttaaac catgagactt    7800 ctgtcctgca agacttttttc acgctccaag gcaggcaagc ttccctccttt cacaaggacc    7860 cgagaactca gctttcagag ctgctcctac agcagcctca tgtcctgcat gtgtgctcca    7920
gaggcagagg gagaccaacc agagcccccct cccttttctca ttcccagctg tgatgacagc    7980
agaaactgaa ctctctgagc tagcccaaca caacaactga gagggacact gttctccatc    8040
tcattatgca tatttcaaac atgtgtctct atatacttct tacagaggtg gtgataatct    8100
gtgaatgcct tactgaattt tcacaataat attactgtac ttgatttgtc cccttatttt    8160
catctgtgaa gccaggtgca ctgcagatat tagtctgctt tctgagggta gggatgacaa    8220
ataaaatata caataccggg ggaattggaa gttcagataa ataacaagtt tttagtttaa    8280
gtatgttcca atattgcat gacatggcac ccagttctac tttaaaaaca aacaagcaaa    8340
caaacaaatt cacactccta ctttaatgaa caaaaatctt ctaataagga ggtcacacac    8400
acaggattac aggcacaacc cccacacaca aacacacaca cacatttacc ttagagcaga    8460
gtccaggaca caccaacaca catgatcctc agtccttttta atttaaagca cgttcaaccc    8520
ttctcagagt ggccttgagt ggttgcctcc atgagtctgc agatgcgaaa aggaagttgg    8580
```

```
ttccgggccc taatcagagg cttcctgtca ggacaaggtt ctggcatcag cattacctgc    8640
tgcaactctg aagggcaggg tgggagcctg ctatgggact gcccctcca aggtgtgagc     8700 ctgttaattc cagggtcagc ttacccaaca tctgcagtcc ctcagctgga ggcctgagct    8760
cttaatgccc ctgcctccct tctgcccctgg gcctgctctc agctgccaca agagggcgcc   8820
gaagaaaggg cctgaggaga tgcaggagct cctctgcagg tcctcccagg caccacccct    8880
tctgggagga aggcttggga gtcccctaag acacatcttc agtcacttct ctctgcctgt    8940
gtctcaggaa accagctcct cctactgtct tctgtgctag ggatcacttc cttgttgagt    9000
ggggcctgag ttttaagagg atcttctgct cctcttcatc tggtccgttt ccttccaagg    9060
cccccgagag gaaggcatgc ggtgggccct actggtgctt ctagctttcc tgtctcctgg    9120
tgagtacgct gcctacagag aggctcacag gttgggtttt gttttgtttt cttcttgaaa    9180
ggggtgccat acaaaggaat acctcattgt attttgtgtt gttcccattg cagccagtca    9240
gaaatcttcc aacttggaag ggagaacgaa gtcagtcacc aggcagactg gtcatctgc    9300 tgaaatcact tgcgatctta ctgtaacaaa taccttctac atccactggt acctacacca    9360
ggaggggaag gccccacagc gtcttctgta ctatgacgtc tccaccgcaa gggatgtgtt    9420
ggaatcagga ctcagtccag gaaagtatta tactcataca cccaggaggt ggagctggat    9480
attgagactg caaaatctaa ttgaaaatga ttctggggtc tattactgtg ccacctggga    9540
caggcacagt gattcagacc tgtcctacac cacactgaaa atctgccttg tggctgcctc    9600
tggtacacaa gatagagccg cccccctctca tttcctgcca ccaaatttcc tgtattctga    9660
acaagagaaa gacagcttaa ctcctgatct ccctcctaat atcacactgt cctggcagca    9720
gctgcatcct gttccccacc cctcccccac aactttcctg aagatcaagc tgccatctcc    9780
aggcctcagc taagcagcct ggctgagagc aaggttctct cagctctcct aggacatggg    9840
ggaggcccac tcactctgct tcctatgaca cacaggtaca actagggtcc agctgtgaag    9900
cgagatattt tggacagcaa atgggaaggg tatttatact gaatcatgta tccactcatg    9960
gtccagagat cacagctgag agtggtgctt attccttatg tctataacaa cataagcaat   10020
actataatga ccactaaaac actaggccca ggtatgcagt tgaacatggt ctccctctgc   10080
cctccctttt attctctctc tcttttctta cttctttgct tgtttttatt tttctctccc   10140
tccctaactc cctccctcca tccatccttt cctcccttcc tcccttgttt ccttccatcc   10200
attctccttc cttgttttcc ttccttcctt ccttgctttt ctctctcttt ctttcctttt   10260
tgggtacata atcagaatac ttttccaca aaatcatttg atataatttt tctctatatg    10320
ttcatgccaa cattcataca gctagtttaa ttgttcagtt ctcttttca cattttggaa    10380 ttttgttgta ttactttgtt ttgcttcata tctgttttgt atatataaaa catttacatg   10440
aaactgaagc caaaattata aagatgatg catttgaaga ttttagcttc cattgtagat    10500
ttctcgttcc tcttttctcc ctgacactat aggtaacaat attttggca gttcacttga    10560 gcttttcac tgtttgtcat agcggagtat gtattgtttc tattttaatg ccatatttat    10620 atttcgttc tgatatttgg tttttataca ttttaatcaa tcttatattt tcccgtgtct    10680
ggactgtgtg tcttacttct aaaggtgcac gtacttcata agtatgcata agaagtcca    10740 tatcatttat ttgaatgttt ttatgcgttg attatttaat gatggcatca tcgatctatc   10800
aggaattttt atacaataat tactgtatta gtaataataa tacttgccag gccggtggc    10860 tcatgcctgt aatcccagca tttgggcagt ccagtcgtta ggaacactta ggccgggaga   10920
ttgcgaccag cttagccaac atggtgaaac cctgtctcta ctaaaaatac aaaaaattag   10980
```

```
ccggctgtag tggcgcacac atgtaatccc agctactttg gatgctgagg caggagaaac    11040
tcttcaacct ggaagttgga gttttcagtg agctaagatc acactactgc agtccagttt    11100
gggcaacaca gcgagactct gtctcaaaaa gactaataat aataataata ttgatggtaa    11160
atatgggtac tgacattctg gtagttaacg tactaagcac attgcatgca cattttattt    11220
aatctacaca gaaacttcat taaggtttta aagtactgtt gaatgtaaca ttagaaattg    11280
gggggttaat taacattccc taagtcatat actttatctt gataatgatt gcaatgcaag    11340
ctctgtggtt cctaaatgag atttgttaat ttggtttgca ttcccccatc tttaggagta    11400
ctagcatcat tttacaactt tacaggtcat ttatagttct tcttttgaga attgccttgt    11460
catactcttt tcctattctt tttttggaag attagttttt tcttattagt tcgtaagaat    11520
taatatacac cattttagag atactgaccc tttatccaat gtgttgaaga tatttctcct    11580
catttgttat tatttacatt tggcaccttt tggtgaattc aactttgaaa aaaaaacaat    11640
aaaagctatc aattttttcta gggtgtctag tttgatgtca ggcttagaaa ggccaatctc    11700
acctagaatt tctatgcaat tcatcatcgt ttaagtctaa tgattttcta tttattacaa    11760
ctaaatcact atttgtaact agtaaggtag aaatgcaaca atatttgttt ccatgtggta    11820
agtcaatacc aaaaagagaa cttatttaat aactgactat ttccttgtgg gtattaacat    11880
atcactttat cacatgataa aatattacat acatgcagct ctctttctgg attttccact    11940
gtgttccatg aatcttgtca ttctagtgcc agtattgccc tctcttcagc actgtagctt    12000
tatagttctt ttcacattct gatgaagttt ctctcattat tttttttgttt taagaatttt    12060 ctgtgcattc tagtgtgatc tcaatcctct cccttcccat ttttaaaccg tgagacttct    12120
gtccagcaag acttttttcac gctccaaggc aggcaagctt ccctccttca caaggacccg    12180
agaactcagc tttcagagct gttcctgtgg aagcctcatg tcctgcacgt gtgctccaga    12240
ggcagaggga gaccaaccgg agccccctcc cttttctcatt cccacctgtc attcccagct    12300
gtgaagacag cagaaaccga actctgtgag ctaggccaat accacaactg agaggaatat    12360
tgttctacat ctcattatgc atcttttcaaa catgtgtctc tatatacttc ttacagaggt    12420
ggtgataatc tgtgtatgcc ttactgaatt ttcacaatta tattactgta cttcctttgt    12480
cccctatatt tccatctgtg aatccaggtg tactgcagat ctcagtcccc tttctgaggg    12540
tagggctgac aaataaaata tacaatacca aacaatttgg aagttcaggt aaacaacaag    12600
tttttagttt aagtatgttc caaatattgc atgacatggc accctgaact acttagaaaa    12660
aaaaaaacaa aaaaaactca cactcctact tcaatgaaca aaaatcctct aataagaga    12720 tcacaaccac aggatcacac acacacaaac acacacacac acacaccccc aacacacaca    12780
cctttatctt agagcagagt ccaagaccaa ccaacacaca tgatcctcag ttctttatt    12840 tttattattt ctttatttat ttatatttat tatactttaa gtgctagggt acatttgcac    12900
aacgtgcagg tttgttacat atgtatacat gtgccatgtt ggtttgttgc acccatcaac    12960
ttgtcatcta cattaggtat atctcctaat gctatccctc ccccctgccc ccacccccact    13020 acaggcccca gtgcgtgatg ttcccccact ctgtgtccaa gtgttctcat tgttcaattc    13080
ccacctacga gcgagaacat gcactgtttg gatttctgtc cttggaatag tttgctcgga    13140
atgatggttt ccagcttcat ccatgtcctt acaaaggaca tgaacgcatc ccttttatg    13200 gccgcatagt attccatggt gtatatgtgt cacatttttct taatccagtc tatcactgat    13260
ggacatttgg gttggttcca agtctctgct atcgtgaata gtgccgcaat aaacacacgc    13320
```

```
tttgcgtggt gcctccaagt gtccttgcag atgccaaaag gaaggtggtt cagttccta    13380
atcagagact tcctggcagg acaaggtcct ggcatcagca ttagctgctg caactctgaa    13440
gggcagggtg tgagcctgct gtgggactgc cccctcctag ggctgggcct gctgactcca    13500
gggtcagctt ccgctacatc tgcattccct ctgctgcagg cctgagctct cctggccct    13560
ggctctcttc tgcagagggc ctgctctcag ctgccacaag agggcgccgg agaacggacc    13620
tgagcaagag aggcaggagc tcctctgcag gtcctcccag gcaccaatcc ttctgggagg    13680
gaggaaggct tgggagtcct cttagacaga tcctcagtca cttctctctg cttgtgtctc    13740
aggaagacca gctcctccta ctgtcttctg tgctagggat cacttccttg ttgagtgggg    13800
cctgagtttt aagaggatct tctgctcctc ttcatctggt cccttccctt ccaaggcctc    13860
agagaggaag gcatgcagtg ggccctagcg gtgcttctag ctttcctgtc tcctggtgag    13920
tgcgctgcct acagagagga tcatgggttt tgttttcttt attttcttct tttgcaagga    13980
ttgccatact aaggaattcc tcattatatt ttgtgttgtt cccattgcag ccagtcagaa    14040
atcttccaac ttggaaggga gaacgaagtc agtcatcagg cagactggt catctgctga     14100
aatcacttgt gatcttgctg aaggaagtac cggctacatc cactggtacc tacaccagga    14160
ggggaaggcc ccacagcgtc ttctgtacta tgactcctac acctcagcg ttgtgttgga     14220
atcaggaatc agcccaggga agtatgatac ttacggaagc acaaggaaga acttgagaat    14280
gatactgcga aatcttattg aaaatgactc tggagtctat tactgtgcca cctgggatgg    14340
gcacagtgat tcagatccgc cctacaccac actgaaaacc tgccttgtgg ctgcttctgg    14400
tacacaagat agagccgccc cctctcattt cctgccacca aatttaccgt gtgctgaaca    14460
agagaaacat tgcttaactc ctgatctccc ctgcaatatc acactcccct ggcagcagct    14520
gcaccctgtt ccccaccctc ccccaggact tccctgaaga ccaagccacc atctcagcta    14580
aacctcagag aagcagcctg gctgagagca aggttctctt agctctccta ggacatggcg    14640
gaagcccact cactctgctt cctaggacaa atgggtacct ctagggtcca gctgtgaagc    14700
aagatatttt ggacaacaaa tgagaagggt atttatacta aattgtgtat cccatcatga    14760
tccagaaatc gcagctgaga ctggtgctta ttccttatat ctataacaat gtaagcaata    14820
ctataatgac cactgaaaca ccaggcctag gtatgcagtt gaacattctc tccctctgcc    14880
ctccctttta ttctctctct cttttttaa ttctttgctt gcttttatta ttttttctctc    14940
tctcccttcc tccttccctc cgtccttccc tccctccttc cctccctctc tccctccctc    15000
cttccctccc ttcctctctt cttccttcc atccattctc cttcgtttc cttccttcct      15060
tctttgcttt tctcttgctt tccttttttgg gtacataatc agaatacttt ttccacaaaa    15120
tcatttgaaa taattttct ctatgtgttc atgtcaacat tgatatagct actttaattg      15180
ttcagttttc tttttacat tttggaaatt tgttgtatta ctttgttttg tttcatatct      15240
gttttgcata tataaaacat ttacatggaa gtgaagtcaa aatcataaaa gatgatgcat    15300
tgaagattt tagcttccat tgtagacttc tcattcttct tttctccctg acactatagg     15360
taacaatatt tttggcagtt cacttgagct gtttcactct gtttttcata gcggagtatg    15420
tattctttct atttgaatgc catatttata ttttctttct gatattcagt ttctatatat    15480
tttaatcaat cttatatttt cctgtgtctg gactgtgtgt cttacttcta aaggtgcaca    15540
tacttcataa gcatgcataa agatgtccat atcatttatt tgaatgtttt tatgcattga    15600
ttatttaatg atggcatcac tgatctatca ggaattttta tacaataatt actgtattag    15660
taataataat actggccagg cccggtggct catgcctgta atcccagcat ttgggcagtc    15720
```

```
cagtcgttag gatcacttag gccgggagat tgtgaccagc tcagccaacg tggtgaaacc  15780
ctgtctctag taaaaataca aaaaattagc tggctgtagt ggcacacaca tgtaatccca  15840
gctacttgga tgctgaagca ggagaatctg tagagcctgg taggtggagt tttcagtgag  15900
ctaatatcac actactgcag tccagtttgg caacagagt gagactctgt ctcaaaaaaa   15960
tgaataacga taataataat attgatggta catatgggta ctgacattct ggtagttaat  16020
gtactaagca cattacatgc atattttatt taatctacac agaaacttca ttaaggttta  16080
aagtactgtt gaatgtaaca ttagaaattg ggcggttaat taacattccc taagtcatat  16140
gctttaattt gataatgatt gcaatccaag ctctgtggtt ccgaaaatga gatttgtaaa  16200
ttcagtttgc attcccccat ctttgggagt actagtatta tttcacaact ttataggtta  16260
tttatagttc ttcttttgtg aattgccatg tcatactctt tgcctattcc tctcttggag  16320
gattaatttt ttcttattat ttcgtaagag ttaagataca ctattttaaa gatactgacc  16380
ctttatcgaa tgtgttgaag atatttcccc tcatttgtta ttatttacat ttggcacctt  16440
ttggtgaatt gaactttgaa aaaaaaagca ttaaaatcta tcaattttc tagggtgtct    16500 agtttgatgt caagcttaga aaggccaatc tcacctagaa tttctatgca attcatcatt  16560
gtttaagtgt aatgattttg ttttattac aactaaatca ctatctatat ctggtaagaa    16620
cgaaatgcaa taatatttgt ttccatatgg taagtcaata cccaaaagag aacttataaa  16680
ataattgact atttccttgt ggatattaac atatcacttt atcacatgat aaaatattac  16740
atgcatgcgg ctttctttct ggattttcta ctgtgttcca tgaatcttct cattctagtg  16800
ccagtattgc cctctcttca gcactgtagc tttatagttc ttttcacatt ctgatgaaat  16860
ttctctcatt attttttgt tttaagaatt ttctgtgcat tctagtgtga tctcaatcct    16920
ctcccttccc attttaaac catgagactt ctgtccagca agactttttc atgctccaag    16980
gcatggaagc tttcctcctt cacaaggacc ccgagaactc agctttcaga gctgctccta  17040
cagcagcctc atgtcctgca cgtgtgctcc agaggcagag ggagaccaac cggagccccc  17100
tccctttctc attcccagct gtgatgacag cagaaactga attctctgag ctaggacaac  17160
acaacaactg agagagacac tgttctacat ctcattatgc atctttcaaa catgtgtctc  17220
tatatattct tacagaggtg gtgataatct gcctatgcct tactgaattt tcacaataat  17280
attactatac ttttttgtc ccctatattt ccaactgtga atccaggtgc actgcagata   17340
ttagtctgct ttctgagggt agggatgaca aataaaatat acaataccgg gggaattgga  17400
agtacagaaa aataacaagt ttttagttta agtatgttcc aaatattgca tgacatggca  17460
cccagtacta ctttaaaaac aaacaagcaa acaaacaaat tcacactcct actttaatga  17520
acaaaaatcc tctaataagg aggtcacaca cacaggatta caggcacaac ccctgccccc  17580
ccaacacaca cacacacata tttaccttag agcagactcc gggacacacc aacacacatg  17640
atcctcagtc ctttaataa agcacgttca acccttctca gagtgacctt gagtggttgc   17700
ctccatgagt ctgcagatgc gaaaggaac ttggttcagg gccctaatca gaggcttcct    17760
gtcaggacaa ggttctggca tcagcattac ctgctgcaac tctgaagggc agggtgggag  17820
cctgctatgg gactgccccc tccaaggtgt gagcctgtta attccagggt cagcttaccc  17880
aacatctgca gtccctcagc tggaggcctg agctcttaat gcccctgcct cccttctgcc  17940
ctgggcctgc tctcaactgc cacaagatgg cgcagaagaa agggcctgag gagatgcggg  18000
agctcctctg caggtcctcc caggcaccac cccttctggg aggaaggctt gggagtcccc  18060
```

```
taagacacat cttcagtcac ttctctctgc ctgtgactca ggaagaccag ctcctcctac    18120
tgtcttctgt gctagggatc acttccttgt tgagtggggc cggagtttta agaggatctt    18180
ctgctcctcc tcatctggtc cctttccttc caaggccccc gagaggaagg catgcggtgg    18240
gccctactgg tgcttctagc tttcctgtct cctggtgagt acgctgccta cagagaggct    18300
cacaggttgg gttttgtttt gtttacttct tttgaaaggg gtgccataca aaggaatacc    18360
tcattaaatt ttgtgttgtt cccattgcag ccagtcagaa atcttccaac ttggaagggg    18420
gaacgaagtc agtcacgagg ccgactaggt catctgctga aatcacttgt gaccttactg    18480
taataaatgc cttctacatc cactggtacc tacaccagga ggggaaggcc ccacagcgtc    18540
ttctgtacta tgacgtctcc aactcaaagg atgtgttgga atcaggactc agtccaggaa    18600
agtattatac tcatacaccc aggaggtgga gctggatatt gatactacga aatctaattg    18660
aaaatgattc tggggtctat tactgtgcca cctgggacag gcacagtgat tcagacctgt    18720
cctacaccac actgaaaatc tgccttgtgg ctgcctctgg ttcacaggat agagccgccc    18780
cctctcattt cctgtcacca aatttactgt attctgaaca agagaaagac agcttaactc    18840
ctgatctccc tcctaatatc acactgtcct ggcagcagcc gcaccctgtt ccccacccct    18900
cccccacaac tttcctgaag atcaagctgc catctccagg cctcagctaa gcagcctggc    18960
tgagagcaag gttctctcag ctctcctagg acatggggga ggcccactca ctctgcttcc    19020
tatgacacac aggtacaact agggtccagc tgtgaagcga gatatttttgg acagcaaatg    19080
ggaagggtat ttatactgaa tcatgtatcc agtcatggtc cagagatcac agctgagagt    19140
ggtgcttatt cctatgtct ataacaacat aagcaatact ataatgacca ctaaaacact    19200
aggcccaggt atgcagttga acatggtctc cctctgccct cccttttatt ctctctctct    19260
tttttcttac ttctttgctt gtttttattt ttctctccct ccctaactcc ctccctccat    19320
ccatcctttc ctcccttcct cccttgtttc cttccatcca ttctccttcc ttgttttcct    19380
tccttccttc cttgcttttc tctctctttc tttccttttt gggtacataa tcagaatact    19440
ttttccacaa aatcatttga tataatttt ctctatttgt tcatgccaac atttatacag    19500
ctagtttaat tgttcagttt tcattttac attttggaaa tgtgttgtat tactttgttt    19560
tgcttcatat ctgttttgta tatataaaac gtttacatga aactgaagcc aaaattataa    19620
aagatgatgc atttgaagat tttagcttcc attgtagatt tttcgttcct cttttctccc    19680
tgacactata ggtaacaata ttttttggcag ttcacatgag cttttttcact gtttgtcata    19740
gtgccgtatg tattgtttct atttcaatgc catatttata ttttcattct gatattcggt    19800
ttttatacat tttaatcaat cttatatttt cccgtgtctg gattgtgtgt cttacttcta    19860
aaggtgcaca tacttcataa gtatgcataa agacgtccat atcatttatt tgaatgtctt    19920
tatgcattga ttatttaatg atggcatcat tgatctatca ggaattttta tacaataatt    19980
actgtattag taataataat actggccagg cccggtggct catgcctgta atcccagcat    20040
ttgggtggtc cagtcattac gatcacttag gccaggagat tgcgaccagc ttagccaaca    20100
tggtgaaacc ctgtctctac taaaaataca aaaaattagc cggctgtagt ggcgcacaca    20160
tgtaatccca gctactttgg atgctgaggc aggagaatct ctagagcctg gaaggtgaag    20220
gtttcagtga gctaagatca cactactaca gtccagtttg ggcaatagag tgagactctc    20280
tctcaaaaaa atgaataatg ataataataa tattgatggt acatatgggt gctgacattc    20340
tggtagttaa tgtactaagc acattacatg catatttat ttaatctaca cagaaacttc    20400
attaagggtt taaagtactg ttgaatgaaa cataagaaaa tgggggtta attaacattc    20460
```

```
cctaagccat atattttaat ttgattatga tagcaatcca agctctgtgg ttccaaaaat   20520
gagatttgtt aattcgattt gcattccccc atctttagga gtactagcaa tatttgacaa   20580
cgttataggt catttataat tcttcttttg agaattgcct tgtcgtactc tttgcctatt   20640
ctcccttggg aggattaatt ttttcttatt ggttcgtaag aattaatatg tactatttta   20700
gagatgatga ccctttatcc aatgtgttga agatattact cctcatttgt tattatttac   20760
atttggcacc ttttagtgaa ttcaactttg aaaaaaaaac aataaaaccc atcaattttt   20820
ctagggagtc tagtttgatg tcagcttaga aaggccaatc tcacccagaa tctgtatgca   20880
attcatcatc gtttaagtct attgattttc attttattac aactaaatca ctatttgtaa   20940
ctggtaaggt agaaatgcga caatatttgt tccatatgg taagtcaata cctaaaagag   21000
aacttattaa ataattgact atttccttgt gaatattaat atatcacttt atcacatgat   21060
aaaatattac atacatgcag ctctcttact gcattttcca ctgtgttcca tgaatcttct   21120
cattctagtg ccagtattgc cctctcttca gcactgtagc tttatagttc ttttcacatt   21180
ctgatgaaat ttctctcatt atttttttgt tttaagaatt ttctgtgcat tctagtgtga   21240
tctcaatcct ctcccttccc atttttaaac catgagactt ctgtccagca agactttttc   21300
acgctccaag gcaggcaagc ttccctcctt cacaaggacc cgagaactca gctttcagag   21360
ctgctcctac agcagcctct tgtcctgcat gtgtgctcca gaggcagagg gagaccaacc   21420
agagccccct cccttttctca ttcccagctg tgatgacagc agaaactgaa ttctctgagc   21480
tagcccaaca caacaactga gagggacact gttctccatc tcattatgca tatttcaaac   21540
atgtgtctct atatacttct tacagaggtg gtgataatct gtgaatgcct tactgaattt   21600
tcacaataat attactgtac ttgatttgtc cccttatttt catctgtgaa tccaggtgca   21660
ctgcagatat tagtctgctt tctgagggta gggatgacaa ataaaatata caatacgcag   21720
agaattggaa gttcagataa ataacaagtt tttagtttaa gtatgttcca aatgttgcat   21780
gacatggcac ccagtactac tttaaaaaca aacaagcaaa caaacaaact cacattccta   21840
cttaatgaac aaaaatcctc taataaggag gtcacacaca caggattaca ggcacaactc   21900 accccccccca acacacacac acatttacct tagagcagag tccaagacac accaacacac   21960
atgatcctca gtccttttaa tttaaagcac gttcaaccct tctcagagtg gccttgagtg   22020
gttgcctcca tgtgtctgca gatgcgaaaa ggaacttggt tcagggccct aatcagaggc   22080
ttcctgtcag gacaaggtcc tggcatcagc attagctgct gcaactctga agggcagggt   22140
aggagcctgt tgtgggactg cccccctccaa ggtctgagcc tgttaattcc agggtcagct   22200
tcccctaaat ctgcagtccc tctgctggag gcctgaactc tcaatgcccc tgcctcccct   22260
ctgccctggg cctgctctca gctgccacaa gagggcgccg aagaaagggc ctgaggagac   22320
acaggagctc ctctgcaggt cctcccagga accacccctt ctgggaggaa ggcttgggag   22380
tcccctaaga cacatcctca gtcacttctc tctgcctgtg tctcaggaat accagctcct   22440
cctactgtct tctgtgctag ggatcacttc cttgttgagt gggacctgag ttttgagagg   22500
atcttctact cctttccatc tggtcccttt ccttccaagg ccccagaaag gaaggcatgc   22560
ggtgagccct agcggtgctt ctagctttcc tgtatcctgg tgagtgtgct gcctacgag   22620 aggctcacag gttgggtttt gttttgtttt cttctttga aggggtgcc atacaaagga   22680 atacctcatt atattttatg ttttttcccat tgcagccagt cagaaatctt ccaacttgga   22740
agggagaatg aagtcagtca ccaggccgac tgggtcatct gctgaaatca cttgtgacct   22800
```

```
tactgtaata aatgccgtct acatccactg gtacctacag caggagggga agaccccaca   22860
gcatcttctg cactatgatg tctccaactc aagggatgtg ttggaatcag gtctcagtct   22920
tggaaagtat tatactcata caccgaggag gtggagctgg aatttgagac tgcaaaatct   22980
aattgaaaat gattctgggg tctattactg tgccacctgg ggcaggcaca gtgattcaga   23040
tctgccctac accacactga acatctgcct tgtggctgcc tctggtacac aagatagagc   23100
cgcccctct catttcctgc caccaaattt actgtattct gaacaagaga aagacagctt   23160
aactcctgat ctccctccta atatcacact gtcctggcag cagctgcacc ctgttcccta   23220
cccctccccc acaactttcc tgaagatcaa gctgccatct ccgggcctca gttaagcagc   23280
ctggctgaga gtaaggttct ctcagctctc ctaggacatg ggggaggccc actcactctg   23340
cttcctatga cagacaggta caactagggt ccagctgcga atctagatat tttggacagc   23400
aaataggaag gttatttata ctgaatcatt tatccagtca tggtccagag atcacagctg   23460
agagtggtgc ttattcctta tgtctataac aatataagca atagtataat gaccactaaa   23520
acactaggcc taggtatgca gttgaacatt ctctccctct gccctccctt ttattctctc   23580
tctcttttt cttacttctt tgcttgtttt tattttctc tccctcccta actccctccc   23640
tccatccatc ctttcctccc ttcctccctt gtttccttcc atccattctc cttccttgtt   23700
ttcctccttc cttccttgtt tttctctctc tttctttcct ttttgggtac ataatgagaa   23760
tacttttcc acaaaatcat ttgaaataat ttttctctat ttgttcatgc caacatttat   23820
acagctagtt taactgttca gttttcattt ttacattttg gaaatttgtt gtattacttt   23880
gttttgtttc aaatctgttt tgtatatata aatatttac atggaactga agtcaaaatc   23940
ataaaggtg atgcatttga agattttagc ttccattgta gatttcttgt tcctcttttc   24000
tccctgacac tacaggtaac aatatttttg tcagttcact tgagctgttt cactctgttt   24060
gtcatagcag agtatgtatt gtttctattt caatgccata tttatatttt cattctgata   24120
tttggttttt atacatttta ataaatctta tattttcctg tgtctggatt gtgtgtctta   24180
cttctaaagg tgcacatact tcataagtat gcataaagac gtccatatca tttatttgaa   24240
tgttttatg tgttgattat ttaatgatgg catcattgat ccatcaggaa ttttttataca   24300
ataattactg tattaataac aataatactg gccacgcccg gtggctcatg catgtaatcc   24360
cagcatttgg ccagtccagt cattaggatc acttaggccg ggagatttgg acccgctcag   24420
ccaacatggt gaaaccctgt ctctactaaa tatacaaaaa attagccggc tgttgtggcg   24480
cacacatgta atcccagcta ctttggatgc tgaggcagga aatttctag agccaggaag   24540
gtgaaggttt cagtgagcta atatcacact actacagtcc agtttgggca atagagtgag   24600
actctgtctc aaaaaaatga ataatgataa taataatatt gatggtacat atgggtgctg   24660
acattctggt agttaatgta ctaagcacat tgcatgcaca tttatttaa tctacacaga   24720
aacttcatta agggtttaaa gtaccgttga atgtaacata agaaattggg gggttaatta   24780
acattcccta agtcatatac tttaatttaa taatgatggc aatccaagct ctgtggttct   24840
gaaaatgaga tttgttaatt tgatttgcat tcccccatct ttaggagtac tagcaatatt   24900
tgacaacgtt ataggtcatt tatagttctt cttttgagaa tcgccttgtg atactctttg   24960
cctattctcc ttttggagga ttaattttt cttattggtt cgtaagaatt aatatatact   25020
attttagaga tactgaccct ttatccaatg tgttgaagat attactcctc atgtgttatt   25080
atttacattt ggcacctatg gtgaattgaa cttgaaaaa taaataata tctgtccatt   25140
tttctagggt gtctagtttg atgccaggct tagaaaggcc aatctcacct agaacttcta   25200
```

```
tgcaattcat catcgtttaa gtctaatgat tttcatttta ttacaactaa atcactattt   25260
gtaactagta aggtagaaat gcaacaatat ttgtttccat acagtaagtc aataccaaaa   25320
agagaactta ttaaataatt gactatttcc ttgtgaatat taatatatca ctttatcaca   25380
tgataaaata ttacatacat gcagctctct tactgcattt tccactgtgt tccatgaatc   25440
ttctcattct agtgccagta ttgccctctc ttcagcactg tagctttata gttcttttca   25500
cattctgatg aagtttctct catttttttg ttttaagaat tttctgtgca ttctagtgtg   25560
atctcaatcc tctcccttcc cagttttaaa ccgtgagact tctgtccagc aagacttttt   25620
cacgctccaa ggcaggcaag cttccctcct tcacagggac ccgagaactc agctttcaga   25680
gctgttcctg cggaagcctc atgtcctcca cgtgtgctcc agaggcagag ggagaccaac   25740
tggagcccct tcccttttctc attcccagct gtgatgacag cagaaactgc aaaatttgag   25800
ctaggacaac acaacaacca agagagacat tgttctacat ctcattatgc atatttcaaa   25860
catgtgtctc tatatacttc ttacagaggt ggtggtaatc tgtgcatgcc ctactgaatt   25920
ttcacaatta tattactgta cttgttttgt ccccttattt ccatctgtga atccaggtgc   25980
actgcagata ttagtctgct ttctgagggt agggatgaca aataaaatat acaatacccca  26040 gggaatttgg aagttcagat atataacaag tttttagttc aagtatgttc caaatatttc   26100
atgacatggc acccagtact actttaaaaa caaacaagca aacaaacaaa cttacactcc   26160
tactttaatg aacaaaaatt gtctaataaa gagatcacac ccacaggatt acaggcaccc   26220 cccccccgc ccccgccac acacacacac atttaccta gagcagagtc caaggcccac    26280
caacacacat gatcctcagt cctttaata aagaacattc aaccctcctc agagtggcct   26340
tgggcagttg cctccaagtg tccttgcaga tgtgaaaagg aagttggttc acagccctaa   26400
tcagaggctt cctggcagga caaggtcctg gcatcagcat tagctgctgc aactctgaag   26460
ggcagggtgt gagcctgctg tgggactgcc ccctcctagg gctgggcctg ctgactccag   26520
gggtcagctt tccccatatc tgcactccct ctgctggagg cctgaactct ccatgcccct   26580
ggctctcttc tgcagagggc ctgctctcag ctgccacaga gggtgctgca gaactggcct   26640
gagcagagag gcaggagctc ctctgcaggt cctcccaggc accacccttc tggaaggaag   26700
gcgtgggagt cccctaagac acatcctcag tcacttctcc ctgcttgtga ctcaggaaga   26760
ccagccttcc ccactgcctt ctgtgctagg atcacttcc ttgttgagtg ggacctgagt    26820
tttgagagga tcttctgctc ctgttcatct gggcccttc tttcaagacc ccagagacga    26880
aggcatgtgt tgggccctag ccctgcttct agctttcctg tctcttggta agtgtgctgc   26940
ctacagagag gctcacaggt tgggttttgt tttggatttt tcttctttag caagggacgc   27000
catactaagg aatacctcat tatattttat gttgttccca ttgcagccag tcagatatct   27060
actaacttgg aagcgaaaat aaagtcaggc accaggcaga tggggtcatc tgctgtaatc   27120
acctgtgatc ttcctgtaga aaatgccttc tacatccact ggtacctacg ccaggagggg   27180
aaggccccac agcatcttct gtactatgac atctgcaact ccagggatat gttggaatca   27240
ggagtcagtc aggaaagcat gatacttatg gaagtagaag gataagctgg aaatttatac   27300
ctccaaaact aaatgaaaat gcctctgggg tctattactg tgccacctag acaggcagaa   27360
gtgattcaga cctgctctac accacactga atatctgtct tgtggctgct tctggtacac   27420
aagagagagc cgtccctct catttcctgc cctgaattta ctgtattctg tacaaagaga    27480
aacagcttaa ctcctgatct ccccctaat attacactct cctgtcagca gctgtaccct    27540
```

```
gttccccacc ctcccccagg actttcctga agactaagct gccatctcag ctaagcctca    27600
gctaagcagc ctggctgaga gcaaggtttt ctcagctctc ctaggacatg ggggaggccc    27660
actcactctg tttcttaggg tccagctgtg aagcgagata ttttggacag caaatgggaa    27720
gggtatttat actgaatcat gtatccaatc atggtccaga gatcgcagct gagagtgctg    27780
cttactcctt atgtctataa caatataggc aatattataa ataccactaa aacactaggc    27840
ctagatatgc agttaaacac tctctccctc tgccctccct tttattctct ctcctttctt    27900
acttccttgc ttgcttttat tattttttct tccctccctc cctccctccc tctctccctc    27960
ccttccttcc ttccttttt catttcttcc tccttgctt ttctctctct ttctttcctt     28020
tttgggtaca taatccgaat attttttcaa caaaatcatt tgaataatt tttctttaca     28080 tgttcatgcc aacattgata tagctagttt atttgttcag ttttcatttt aaaattttag    28140
acatttgttg tattattttg ttttgtttca tatttgtttt gcatatgtaa actatttaca    28200
tggaactaaa gtcataattt taacgaagat gcatttggag attttaactt acattctaga    28260 tttcttttc tctctctttt ttttttttt ttttttttga cggattct cagtctgtca        28320 ctcaggctgg agtgcagtgg agcaatctcg gctcactgca acctccgcct cctgggttca    28380
agagattctc ctacctcagc ctcccaagta gctgggattt caggtgcccg ccagcacatc    28440
cagctaattt ttgtattttt ggtagagaca gggtttcctc atgttggcct ggctggtctc    28500
gaactcctga cctcagatga tccccctgcc tcggcctccc taagtgctgg gattacaggc    28560
atgagcaacc tcaccaggcc ccattctgga tttctctttc ctcttctctc cctgaccccta  28620 taggtaacaa tattttatc agttcagttg aactttttca cttttctta ttcagaacaa     28680 gtctttcagt attacagaaa agtcttttgt ttgtcatagt gcagtatata ttgtttctat   28740
ttgaccgtca tatttatatt ttcattctga taaggtttta tacatttaa tcaatctttt   28800 atcttccagt gtctagattt tgtgtcttgc ctctaaaagt gcatacactt cataagtatg    28860
aataaagaag tccatatcat ttatttgaat gctttatc atagactatt taatgatggc     28920
atctctgatc tattgggaat tttaatacaa taattaccgt agtaataata atatgctaat   28980
gataaacacg ggtactgaca ttctggtagt tactgtacta atcacattgc atgtaagttt   29040
tatttaatct tcacagaaac cccattgagg ggttaaagta ccattgaata caccagatga   29100
gaaataaagg gctaactaa cattcccta gtcatatact ttattcgata gcaatttcaa     29160
tccaagcgct ggggttcaga aaatgagatt tgttaattca atttgcattt tcttacctgt   29220
gtgaatgcta gcattactta acaactttgt aggccattta tacttcttct tttgtcaact   29280
gccatttcat actcttcgcc tattcttctg ttggttatca ttttttcttt attggtttgt   29340
aagaattaat acacctcatt ttagagatat tgatccttta tcaaatgtat tgaaaatatt   29400
tctcgtggtt tgctattatt ttcagcacct tttggtgaac tgaactttgt gtactacttt    29460
taataaaacc tatcaatttt tctaaggggt ctattttgat gttaggatca gagaggcaaa    29520
tctcacttac aatatgtgtg caattcatca tggttaaagt ctaatgattt tctgttttca    29580
gttttattac aagaaaatct ccatttgtag ctggcaacat agtaacttaa gaagatttgt    29640
ttctggccgg gtgcagtggc tcacgcctgt aatcccagca ctttgggagg ctgaggtggg    29700
tgaatcacga gatcaggaga tccagactat ccggggtaac acggtgaaac cccatctcta    29760
ctaaaaatat aaaaaattag ctgggcatgt tggcaggtgc ctgtagtccc agctactgag    29820
aaggctgagg caggagaatg gcgtgaaccc aggaggcgga gcttgcagtg agccgagatt    29880
gtgccaccgc actccagcct gggggacaga gagagactct gtctcaaaaa aaaaaaaaaa    29940
```

```
aaaaaattgt tccatatgg taagtcaatt cccaaaagag aacttattac ataatccagt    30000
agtttctcaa ggatattaac gtacaacttt atcatgtgat aaaatattac atacacatgg   30060
ctctctttct ggactttcca gtgtgttcca tgaatctttt cattctagtg ccagtattgc   30120
cgtctcttca gcactgtagc tgtatagttc ttttgacatt acagtggagt tactttcctt   30180
tattgctttt ttgttttaag ggtgttctat gcattgcaat gtaatggcaa atctctccct   30240
tctaattttt aaaccgtgag acatcggtcc cagcaaggat tttccaggct tcaaggcacc   30300
tgagcttccc tccttcacag tgacccaag aactcagctt tcagagctgc tcctgcggca    30360
gcctcatgtc ctccacgtgt gctccagagg cagagggaga ccaaccagag cccctccctt   30420
tctcattccc agctgtgatg acagcagaaa ctgaattctc tgagctaagc caataccaca   30480
accaagaggg atgttgttct acatcttatt aggaatattt taaacatgaa tctaaacata   30540
tttgttatag aggaggtgaa tatctgtgta tacactactg aatgttccca attattttat   30600
tctacttgtt ttatcaccca tatcttcatc tatgaatcca ggtgcactgc acatattagc   30660
ctgctttcca aggatagagt tgccaaataa aatatgcaat acccaggtaa attggaagtt   30720
cagataaata acaaataagt tttgagttca agtatgtacc acatattgca tatggcactg   30780
caccctgtac ttttttttt cttttttga gacggagtct cactctgttg tccaggctgg    30840
agtgcaatgg cacaatctcc gctcactgca agctccacct cccgggttca acacattctc   30900
ctgcctcagc ctcctgagta gctgggacta caggtgccca cccccacaac cggctaattt   30960
ttttgtattt ttagtagaga cagggtttca tcgtgttagc caggatggtc tcaatctcct   31020
gacctcgtga tctgcccacc tcggcctccc aaagtgctgg gatacaggc gtgagccaat    31080 ctcacactcc tacttgatgt ggccttttta cttgagaatg aacagaaatc ctctaacaaa   31140
gaggttacaa acacaaggtc acacacaccc cctcctgacc cccacacacc catttaccat   31200
tgaggagagt ccatggccga ccaacatacc tgattctcac tcctgttgag aggaggggcc   31260
agctgggctt cctgggtcga gtaggggctc agcaagctgt gaaacgcact catttcctgc   31320
atcacgactt acttcggtcc tggatgaata atattgaaga tatatgctta aaatattccg   31380
aacaccagga tttgtgcatg tgttttcttc cccatgaaag ctatgaacag cgaaaatttt   31440
cctgtaagtt tccctgtgtt ctctctccct ctcttccttc cccctgcccc aaaactaaag   31500
taaaataacg ttaactgccc gttttctgt aaccagcaga cctatctat actcccaatt     31560 ccaattcctt gtaaacatac tttgtaaagt cctgtaagat cctgtctcct ttgccatgac   31620
gctgcaaggt cataaagtag ataaaaccta agttgcaatt ccggttttcc tcaagatcta   31680
agacatgtta caaatggtta attgcctttg tttctcgctt tggtaacatc ttcccgcctc   31740
aggtatttcc cgccttgaag agtttaaaag gcaatcctat aatctaactc tggctaccca   31800
ttctggaccc cctccatgct ttggaagctt tgtactttca ctctgctcaa taaagcctac   31860 agcttttct ctctctcggt ccgtgtttct atcactcgct gcggtcagcc gccacaccaa    31920
ttctatggcg tggctaggca agaaccttag gtgttacact gttaataaag caggttcagg   31980
ccttctcaga gtggccctgg gtattttgcc tccaagtgtc cttgcgaatg tgaaaaggaa   32040
agcagttgaa agaccaaatc aagcttcctg acaggacaag gccctggaag cagcatcaac   32100
tgctgaaact ctgaagggca gggtgtgagc ctgctgtgga ctgccccgtc ctatggccct   32160
ggccagctgg cgccagggtc agctttcccc acatctgcac tccctctgct ggaggcctga   32220
gctctccatg cccctggctc tcttctgcag agggcctgct ctctgctgcc acaagatggc   32280
```

```
gctggagaag gggcctgagc agagaggcag gagctcctct gcaggtcctc ccagacacca    32340
cccctctggg aggaaggctg gggagtcccc taagacagat cctccatcac ttctccctgc    32400
ctgtgactca ggaagaccag ctcctcctac tgccttctgt gctagggaac acttcctgtt    32460
tgagtgggac ctgagttttg aaagcgtctt ctgctcctct tcatctggtc cctttccttc    32520
caagacccca gagaggaagg catgcggtgg gccccagccc tgcttctagc tttcctgcct    32580
cttggtaagt gtgctgccta cagagaggct gatgggtttt attttgttct gttttgtttt    32640
ctcattttgc aaggggtgcc gttctaagga gttcctcatt atattttgtg ctgttcccat    32700
tgcagccagt cagaaatctt ccaacttgca agggagaagg aagtcagtca ccaggccagc    32760
tgggtcatct gctgtaatca cttgtgatct tactgtaata aataccttct acatccactg    32820
gtacctgcac caggcgggga aggccccaca gcatcttcca tactatgacc cctactactc    32880
cagggttgtg ttggaatcaa gaatcagtag aggaaagtat tttacttatg caagcatgag    32940
gaggagctgg aaattgatac tgcaaaatct aattgaaaat gattctggat ctattactgt    33000
gccacctggg acaggcacag tgattcacac ctgccctaca ccacactgaa aatctgcctt    33060
gtgactgctt ctggtacaca agatagacca gcccctctc atttgttgcc accgaattta    33120
ctgtattctg tacaaagaga aacacagcat aattcctgat ctctcccta atatcacact    33180 ctcctggcag cagctgcacc ttgttcccca ccctccccca ggactttcct gaagacaagc    33240
tgtcatcttc aggcctcagc caagcagcct ggctgagagc aagactctct cagctctccg    33300
aggacatggg ggaggcccac tcactctgct tcctcggacc aacaggtaca cctagggtcc    33360
aactgcgaag cgagatattt tggacagcaa atgggaagga tatttatact gaatcatata    33420
tctagagatc acagctgaga gtgttgctta ttctttatgt ctataacaat ataagcaata    33480
gtataattac cactataaca ctaagcctag gtatgcagtt gaacattgtc tccctctgct    33540 ttccttttg tctctctctc tactttcttg gttacttgct attttctac acatcccttt    33600 ttctggcctc cctccctcc ctccctagct ccctccctag cttgccttcc ttccttcctt    33660
ccttccttcc tttcttcctc cctctctcct tcccttcctt acttccttcc tttctttctt    33720
cctccctctc tccttccctt ccttacttcc ttcctttctt cctccctcct tctcttactt    33780
ccttcttttt ttcctttctt cctttttctct ctctttcttt cttttttggg cacacaatca    33840
gaatacagaa tcattctcta tatgttcatg ccaactttga tacagctagt ttattcgttc    33900
agttttcatt tttatatttt ggaaatctgt tgtattattt tgatttgtat atgtaaaacc    33960
tttacatgga actgaagtca aaattataaa acaagatcaa tttagagatt ttagcttcca    34020
ttctagaatt ctcttttctc ttctgtgtct caccctatag gtaacaatat ctttattagt    34080
tcagttgaac ttttttcactt tttcttattt attcagaagt ctatcactat tacagaaata    34140
cctcttttgc ttgtcatata tgtgcagtat gcattatttc tatttgaatg gcatatttat    34200 gttttgttc tgatattctg ttttataca tttcaatcaa tcttttagtt tctggtgtct    34260 ggatttgtg tcctacttgg aaaggtgaac atacttcaga agtatgccta aagaaattca    34320
tatcatttca ttaatatttt attcatttat tacttgatat gatctatctg gaattttat    34380 acaataatta ctatagcaat aataataata ctgatgataa atatgggtac tgactttccg    34440
gtagttactg tactaagcac attacatgta tattttattt aatcttcaca gaaaccttat    34500
caacgggttt aagtaacatt gaatatagca gatgagaaag tgagggtta actaacattc    34560 cctaagtcat atagttttaat ttgatagcaa ttgcaatcca agctctgggg ttcagaaaat    34620
gagatttgtt cattcaattt gcattttctt atctttatga atactagcat tattttacaa    34680
```

```
ttttataggc catttatact tcttcttttg tgaattgcct tttcatactg tttgcctatc   34740
cttctgttgg ggtattaatt tttctttatt tgtttgtaag aattaatata caccattttc   34800
gagatattga tcctttatca aacgtgttga aaatatttct catcatttgc tattattttat  34860 tttcagcacc ttttggtgaa ctgaactttg tatattactt taataaaat ctatcaattt    34920 ttctagggtc tgtattatga tgtcaggctc agcgagacca atgtcaccta caattagtgt   34980
gcaattcatc atcgtttaag tctgatttcc ttttttcagt tttattacaa ctaaatctct   35040
atttgtacct tttaagttag caacccaagg atatttgttt ccatatggta agtcaattcc   35100
caaaggagaa catagtaaat aatcaagtat ttccttgtgg atattaacat acaactttat   35160
gacatgataa atattacat acacgtggct ctctttctgg actttccact gtgttccatg    35220
aatcttttca gtctagtgcc agtattgtcc tctctttgtt gtatctgaat gagttagaga   35280
aaatgccaca ctttgagaca aattaagatt ccgtttattt agccggcggc caagagacgg   35340
ctaatgctca aaattctctc ggccccgaag aaagggctag attttctttt atactttggt   35400
ttggaaaggg gaggggtgtc tagttaaaac aattttacag aaataaagta ggcaaaaagt   35460
taaaaggata aatggttaca ggaaagtaaa cagttccagg tgcaggggct ttaagactat   35520
tacaaggtca tagacttggg gctttgggcg ttatcaatca gatggattcc tgggaattgc   35580
ggatatagct tgccacagta tcttatcagt taattgcatt cttggatgtg ctgggagtca   35640
gcttgcacaa gttaagtcct tgaggaaggg gctgccagtg aaagagccaa gatggagtct   35700
gtctggctct cttagctaag ggagagtcaa ttcaggtgga aacaaggcca ggtgattaaa   35760
ggaaaaggga gagtctaaaa acagggttag taaaaacacg gttgggcatt acatcttcag   35820
cactgtagtt ttgtagttca ttttatattc cagtggagat tgtttctctc attacttttt   35880
tgttttaagg attttctgtg cattctaatg tgatggcagt tctctccctt ctcatttttta  35940 aaccatgaga gttctgtccc aggcaggatt ttcctggctc caaggcaggt gagcttccct   36000
ccttcacaag gaccccaatg actcagcttt cagagctcct cccctggcag cctcaagtcc   36060
tgtacgtgtg gtggagaggc agagggagac caactggagc cccctgcctt tctcattccc   36120
agctgtgatg tcagcaaaaa ctgaactctc tgagctaggc caaaacaaca accaagaggg   36180
acattgttct acgttttatg aatatcttaa acatgtgtcc aaactttttt ttttttttac   36240
cgaagtgaaa atcgtgtat gcactactga attttcacaa ttatttact atacttgttt    36300 tatcacctgt atctccatct atgagtccag gtccactgca gacatcagtc agctttctga   36360
ggatacggtt gctaagtaaa atatgcaata ctcaggaaat ttggacgttc agataaataa   36420
caagttttta gctgaagtat gtcccaaata ttgcatgaca tggcaccctg tattacttta   36480 aaaaaaaac tcacacttct acttgaatga acggaaatcc tctaataaag agatcacaca    36540
cacaggcata cactcccaac acacacacac acacaaactc acagaggatc acacaaacac   36600
ccgccccacc cccacacacc catttacctt agaggagagt ccaagaccca ccaacatacc   36660
tgaccctcga tcctgttaat aaagcaggtt caggccctct cagagtgacc ctgggtgttg   36720
cctctagtgt ccttgcagat gtgaaaagga tggtggttta gggccctaat cagaagcttc   36780
ccggcagaat gagggtcttg cagttgcctt acttgctgaa actctgaagt gctgggtgtg   36840
aacctgctgt gagactaccc cctttaaggt ctgagcctgt taactccagg gtcagcttcc   36900
cccacatctg cactccctct gctgcaggcc tgagctctct atgcccggag ctctcttcct   36960
tagagggcct gctctcagcc gccacagagg gcgctggaga actggcctga gcagagaggc   37020
```

```
agaaactcct ctgcaggtcc tcctaggcac cacccagagt cccctaagac agatcctcaa    37080
tcacttatct ctgcctgtga atcaggaaga ccagctcctc ctactgtctt ctgtgttagg    37140
gatcacttcc ttgttgagtg ggacctgagt tttgagaggg tcttctgctc ctcttcgtct    37200
ggtcccttac ttccaagacc ccagagagga aggcatgctg ttggctctag ctctgcttct    37260
agctttcctg cctcctggta agagtgctgc ctacagagag gctcacaggt tttattttgt    37320
ttcgttttgt ttattttctt cttttgcaag ggataccata ctaagaaatg cctcattaca    37380
ttttgtgttg ttcccattgc agccagtcag aaatcttcca acttggaagg gagaacaaag    37440
tcagtcacca ggccaactgg gtcatcagct gtaatcactt gtgatcttcc tgtagaaaat    37500
gccgtctaca cccactggta cctacaccag gaggggaagg ccccacagcg tcttctgtac    37560
tatgactcct acaactccag ggttgtgttg gaatcaggaa tcagtcgaga aaagtatcat    37620
acttatgcaa gcacagggaa gagccttaaa tttatactgg aaaatctaat tgaacgtgac    37680
tctggggtct attactgtgc cacctgggat aggcacagtg attcagacct gtgctacacc    37740
acactgaaaa tctgccttgt gactactcct ggtacacaag atagaccagc ctcatctcat    37800
ttcctgccca tgaattcact gtattctgta caaagagaaa cacagcttaa ctcctcatct    37860
ctcccctaat atcacactcc cctggcggca gctgcaccct gttctccacc ccaccctcat    37920
gagttaccta aagaccaaac tacaatctcc cagctgtgtc agccaagcag ccttgctgac    37980
agcaaagttc tttcagctct tctatgggct ggtggagacc cattccacct gcttcctaag    38040
acagacaaat tcctcaagga ctggtctgta aagggattca tttaggagac tatatgggaa    38100
gactagcttc actcaagcat ttatccaatt attgtctata ggctaaaata gtgcttattc    38160
attgctcagg ataaatgttg gaataacaac tttgcacttc agtaagacat ctaacgtgta    38220
tcagatctgc tatcttttgg acacactgac atttttttct acataacaaa tcatggtact    38280
attggtctgc aggagaatgg gtaaaaaagt gatagtcata ggtacgccaa cttgtgggtc    38340
atatcatagg ttttcaacca tttcaagcat ccctgcccta atgcaagtat ctgaaggatc    38400
tgacccttgc cctgcagcag aattcattcc atgtcccctc tggatattag actgataatt    38460
tggatcaggt ctcagcatgg gccattgagg aacactacag ccctgctgag agataaaaag    38520
gattatccac tcaaggagtt cacacctccg ggccgacatg gagaacgtgc ctagaagcag    38580
acttggaggg tgctcagtgg tgggttgtgg aatgtaagcc tgaagaagca gagtttaatt    38640
ctacggggt gctttcataa tttagtaccc tgacagggct cctggtgttg gtccttagac    38700
actcctggga tggctccctg gaaacatgga ggaaaccttg gtcgcatgac atgatacgga    38760
gatgttggag ctgcctggac acagttacag agggaggcat taaaaggctt cgagaggtag    38820
gcatgctaga gtggactttc ccactaaacc tgagaactca ctggataact gtattccctg    38880
cgagagccca gagaaccctc tgaattagga aagaagggca tgttctgaaa tgggaggaat    38940
cagcgttctt gagagtcttg gtggaagctg tgccctgtgg ggcagggttg actataggag    39000
acgctgttaa ggaattagct cccaagggtc aatggagatg atgtaatttc aaaataagag    39060
tccaaatggg cagaattagt gtgagaagac ataaagccag aaaagcagcc aaggagccct    39120
gctctacaga aatctggggt gacagctaat aaaccacagt gttcctaggg gtaaggaaat    39180
tgggctacca cagtggtatt ccacatatgt attccatata tacatatata tctctcccat    39240
atatatatat atatatatga gatatatata tgagatatat atgggagaga tatatatgat    39300
atatatgaga tatatatgag atatatatga tatatatatg agatatatat gagatataga    39360
tatgtatatc tctctcatat atacataata catatctctc tcatatatat atatatatat    39420
```

```
atatatatat atatatgtaa ttggaacgta ttaagagaag atgaatgaaa gaatgatgtc   39480
agctcctcct gttctccaac tcagagtcct ttgaatgaag gggaaggcag attgccttga   39540
gggagaacct tgtaatgttc tagcaagtat atatggcagt gattctccga gccttttccc   39600
ccaaaagatc gaagactagt tacctgagaa atttgtacac ctagggaagg ggataaacta   39660
ggtctttcaa ggctgttgga gacggcatct gagctaactt tgataccaag aaatgcatac   39720
tgtcaacgtg gtcccccatt agagtgagga cacatagaag ctcccctct aatgctagtt    39780 ttaaaggccc aagtctatct aaaagggcag tcccataggt ggatggactg actgtggtct   39840
ctaccctgtg tctgaggata tcagagtgga tatgatgaat ggacataaaa taaggaggct   39900 gccccctac ccccggatag tccaggcagc cttcattcct ttatttcatt tggaacccat     39960
atggcttatt ctcttcact gactggagct cacagtctgg ctattgtaac ctgtcttaaa    40020 tcttttctc tttaaaatat cttgactttg aggcaggtct tagaaaatga ctcttcctgt    40080
ctcaaaatgc agtccttcat tctgattgat gaattggaag cacatggctg gtgtaaagaa   40140
taagaaacta attataagcc aggaaacagc aggagaagaa agcagagaag caacgcttac   40200
cctgaagaat taatttccgt ttagaaaata tcacagctga tgtgtcaaag gccccggtat   40260
gcaggaatga gattaaacaa atgtggtcat gaggaagagg tttctgaata atgatagaga   40320
agcttgagtc tacaagaaat ccagagtcca gaatactgca ggggagcagt gctgggttca   40380
tgtttatctg gtctcttgtc tattggatcc tctttcttcc agaaccctaa accttgaatc   40440
agccttatag tcctggctcc tagaagagtg tttctcaaag tgtactccac ggaccacctg   40500
gataagaagc acgtgaggct tttaattaaa aaaaaaaaa aaagtacagg ttctgggaag    40560
catccaacac aataagacag aatcttggaa tgaagggtga aaatgtgcat tttaaaataa   40620
cctccagagc tgattcttat tcaaactgac tttttaaaaac tgctgcacta gtggcaagag   40680 atcgagggc tgtcctgagc ctgacacaga aaggtgttct agaaagctgc tcacaggctc    40740
cttcgcagcc caccaaatcc gcctcactct tatctccccc agcccctcaa agcagctgct   40800
ttgacagttt ctcacatttt tgcatgataa tcccacaact gcaattcctt ctggcttcct   40860
gtgacctcac gcaagaaaaa gttgtgtact aaatgaatct gctttaactt gctctccttc   40920
ctcggggatc acaccttttt aagaaagcct gtcccttacc ttgaagcaca aacatattct   40980 cattttatt ctcccaatac cttgaaggtt ttcttctgca catgtatttg tttgatctgc    41040
cttttgtgcg tggggtggga gttaggtagg aatcttaaag tggagagcca gtttcttccc   41100
aaattactga cctaacccat ccttaacccc cagttcaagg ccacctttgt gatagtgaag   41160
cttccacatg ctcactcagc cccttctgct ctctcttctt ctctactgtg catgtcggct   41220
tgtacttttg ccagtttctc taaagacaca accagaggtg gggtggctgt gtgtgcacaa   41280
cttcaacttt acatgtgggg ctgagtccct atgttgtata tccttgtgca aaagcacaat   41340
atgttaattg ctatagcttt taaaaaaata attaatagtt tttcataatc aaattttctt   41400
gcttttttgt tttttcaaaa aagcatactt ttattgaaga ataaacccct tatatatgta   41460
cacttattta taactatgaa ccatgaacta ggatagaaat gcattgtgta tattacaaaa   41520
cataacaaaa ataataggg tagggaggtg cagatgttgg tcaaaggata taaacctgca    41580
gttctatgat gaataagttc tggacatctg gaatacagca tggtgactat acttagtaat   41640
actatattgt acacttgaag cttactgaaa gagtaaatct caagtgttct caccacacaa   41700
acccaaaggt aactatgttc tcaccacaca aacccaaagg gaactatgta ttaattagct   41760
```

```
tgattgtggt aaccatttca caatgtatac atttgccaaa acattatgtt gtatacctgg    41820
aatatataat tttatttatc aattatacct caataaagct gaaagagggg attactaatt    41880
cccacaaaat acagatttaa caaaaacttt tattcaacaa acagtgctat gaagttgtaa    41940
attggaaaca aaagaaataa aatttcatcc acagtcttct catcaaaacc cttcagtggc    42000
attcctcttt ctggtgtccc agtcttgtca attttgctaa taactgtcat cctgggaata    42060
cccaatttat cctacatgac aaaatgacaa agtctgatta gatgagttct cagattctag    42120
catggccaga gagcactgt cctgggtcgg ataaatcacg tggaagatgc aggggatgcg     42180
tgactttaaa ggtccagccc ttagtccctg gatcttcatg caggggccgc ctcagcctgg    42240
atctgctctt cctcaccact gcagccctat cccacgctgg ctgaggtctg cttccacctg    42300
ggcagtgact ggatgacatg ggatgagagg acacacctct ccctcgccca gcatcgcatt    42360
tctctttccc tggagatctg ggatcttggt cagaatcctt caaacgccac ccagggcttg    42420
agagggcaag ccctcctaca ccttgactgc gttttgccca agatttcccc catattatta    42480
ttttaaacgt gtctaattta gacaaataga acctgtaagt gctacattga aaagagcaca    42540
gggccaccga attgggaaga caagtagagg aaaggaaagc aaatgtcacc agacagaatg    42600 tatgctgca ggtttacagc agattctatt aaaatctatg gttgggctgg gtgtggtggt     42660
tcacccctct aatctcagca ctttgggagg ccaaggcaga gagatcacct gaggtcagga    42720
gttcaagacc agccaggcca acagagcaaa accctgtctc taccaaaaat acaaaagtta    42780
gcaaggcgtg gtggcacgcg cctgtaatcc cagctactgg ggaggctgag gcaggagaat    42840
ctctggaacc caggaggtgg aagttgcaat gagcagagat cacaccactg cactccagcc    42900
tgagctaaag agtgagaccc tgtctcaaaa aacaaacaaa caaaaaatct atgattggct    42960
gattggctat tgctaacaac ttttgagtct ttaatgatca gtaattgaat taaaacggtt    43020
aaaacaacaa ttgagagaaa catagttttg aacactgaca acacaaaata acttatccat    43080
gtaaccaaaa gctacctatt cccccgaaac tattgaaata aacaaacaaa aaattagaa     43140 agcggaaact ttacaaaaat tattctcacc aatgaggttg tccaaatgtc accaaattta    43200
ttatagaata gtaataacca aatttgtgca tgaatcggtg atgacataag tatcttgtaa    43260
gcattactga agtttttttt ttttctatta aatttacctt caagatatgc cttcaggatg    43320
aggctttcca ctgcacttca ttatgcaatg ccatgttgac ttggtatatt acctcagatg    43380
tgactctaat atggtttgat tgttatgac gagactaaaa tgaaacatat cacttttttc      43440
atgtgcatat tgcaccttat aagcacaagg tgcaattaaa taaccaattt gaatattgaa    43500
aacatatgta gttgttataa tttttttctc ctctaaaata atattttctt atttctaaaa    43560
aaatctagaa aatagagaaa gattgaagac aaataatttg cccatttcca ttgctcactg    43620
tctgtatttt gcactttcta cctgtcattt ccctgcgttg acctttttctg accatagctg   43680 tcactttctt tcccattacc ctagcccacc cctgggctaa aggtctatag agtgtataaa    43740
tgatagcccc agaatatccc tctgtcaaaa cgttctgcta gctttgtatt tgaccacctt    43800
ctcaccaact cagcacaacc ctaagccctg catgtgagaa tgctgaaaac tggaatcatg    43860
actttcagtt tttgccatcg aagagaagct caggaactgg gtctggtcgt gggagcccag    43920
ggactcacag cttcccttcc caagccagac ccctttttctt gccatgccca aaccttccc    43980 ctcatggcca tctcttttgac tactcaggag gtcctgggtg tcattagcaa agctgaaaat    44040
gaaccttcat ttcagtagga actcaaggct gggtctattt ctccaagcct ttggcaggtg    44100
tgtccttcgc tggcccttcc caatgcacag tcttcaccat ttccaaggac gtgccactgg    44160
```

```
cagaggatga gctggtcctg cctccaggcc ctctctgtct gctggcctga cttagccttc    44220
ttcctttgga gacacacaca cactcacaca cacgcacgca cacacctggt tcttgaaaac    44280
tgcattagtc cctataattt ctactttgtg tgaacccag agatcattta ctggaaccca    44340
tccagtttcc aggtgaaaca acaacacccc acatttcttg agcatggtct atgcagctgg    44400
gattgtgctg cgtgctctgc tcacattctc ctgtttactg tccatgtggc cctatgacac    44460
ctctctttac agatgaggaa aaagaggtga acaacttgc ccaagactac acagctatca    44520
tgttatttta gggcactgaa aatctccttc tactaggacc tctgggtgac acgctccgat    44580
gctggctcag acgttggca tgggtttttt tagggattgc tgttttgtgt ttgtcccttc    44640
ctctggagca agcagcacac tcattgttct ctgagtataa gatggttaca tgaagcagaa    44700
atttgtcacc agcctggcct ggcttctctc ccaactctga ttctctttag gtattacagc    44760
cttggaaaag ctacttaaaa taacagcctt actccttcat ttctaaactg aagataacat    44820
ttgtcctata gagttatttt aggatttaat aaagcaatgg ccctaaacca attagtgcag    44880
tgcaagagtt tgctggtgt ccaaccaatg attgctatta ttgctaatta taccagcaac    44940 actcttaag cctttttcag cactctagcc attggtcatc cctcccttca ccttgtggtc    45000
agatttctgt ctctcctctg gaacttcttt cttcctcccc catttctctc atcagttacc    45060
tccttgcacc accagggaaa tagcagttca ggcctaagc tggtcgctac cataactcag    45120
gaaagtgtgg ctcaggtcca tagttgaaa caggtcactc tgggctcctc tcccccagtc    45180
aggatcagag atatggtggg ctgccctgcc ttcctttggg tcatcctgtt tccaggtcag    45240
tctcctacct aaggacctgt gtagaggtgg cgaggctttg ggacatccct acctcactgc    45300
tctctccctg acagctggct ggtggctcat caggccggag cagctggccc atgtcctggg    45360
gcactaggga agcttggtca tcctgcagtg cgtggtccgc accaggatca gctacaccca    45420
ctggtaccag cagaagggcc aggtccctga ggcactccac cagctggcca tgtccaagtt    45480
ggatgtgcag tgggattcca tcctgaaagc agataaaatc atagccaagg atggcagcag    45540
ctctatcttg gcagtactga agttggagac aggcatcgag ggcatgaact actgcacaac    45600
ctgggccctg cgcagccttg catgctgccc cagccctaca caaaaggact cttcctcccg    45660
atccaacaag gccttgggca ttttcactta ctcttggtcc cttgggtttc cctgtggcat    45720
agaagaaaaa agtcttatcc cctgtccctc acctccccat ctatcctgga ggtccccttcc    45780 ccggtcccac tacagatgag gctttcagct tgtgcagact cagtgatcta tatctcatcg    45840 aaagggtct gtttaaagat gctccagttc agtgtctctg aagcctttgc aggatgacct    45900
gtgctcctga atgcaggtgc cactagccac ctgtggctat tgagcatggg aaacatacca    45960
agtgcaatag tccaagctga gatgggctgt gtgtctaaaa tcatattttg aagctttagt    46020
gttaaaagtg agataactct tataatgatc aaaagttgaa atgattaggt atcttggact    46080
aaagccaata gcattaaaac taattttacc tgtttctctt tacttttttt aatgcagcaa    46140
ctaaaaaaat taaagtgtgt gactcacatt ggtgactcat ttatttctgt tggacagtgc    46200
tgttagagac tgatcattta agaatctgac catctcccct gaagaatgca caaataaaat    46260 attttgaag agatttcaag ggtggaggac ttgctgagat ttaccacaaa atggttgaaa    46320
agctgagact agaagcctac tcctgtttcc agcttccaag ctcttggccc tgggactgtt    46380
atcattttgc aatagagtca gcaattagaa gcatgggaaa catgactgcc cacttctcag    46440
tactttcacc cgtgggcggg ctgcatagga actgatgtga gtagacagtc gccatggcag    46500
```

```
ggtgatgcag tcctccctgg atgagacatt taccttccac ttctccttca acagcacccc    46560
agtgtggaac acgtgtgtat cccaagcttc tctagacttt tgttctccta tctgacaaat    46620
gagggggttt agccaaatgt ctgctaagtt atatgactat gattttttgta ttaaagcaaa   46680
gccatacaca taagatcact atgcccacta ccttcatata aagcagtctt ttttaacata    46740
gaataaatga agaaaaaaa agaaagcct gtgttactga tcctccagca ccaaacagga      46800
aacccctctg ctgctctatg tgcagaaaaa aagaaattc tttgaagtct aagctgaatt     46860
taaatgcctt ttcaagagaa tgcttaatac actgttgatg agaatgtaaa ttagtacaac    46920
ttctctagaa aacagtatgg aaatttctca aagaactaaa aatagaacta ccattcaatc    46980
cagcaatccc ataactggat atccacccaa agaaaaataa atcattatat tagactgcat    47040
tcatatattt atcacagcac tgttcataat agcaaaaata tggaatcaac ctaaatgtcc    47100
attagtggat ggctggataa agaaaatgtg gtatatatac acagtggagt actattcatc    47160
cataataaat gtggtatata cacacaatgg aatactgctt atccatacaa aagaatgaag    47220
tcctgttttt tgcagaaaca tggaggaagc tggaggccat tatctaaagt gaaacaactc    47280
agaaatagaa agacaaatac tggatgttct cacttataag tgggagctaa ataatgtgta    47340
caagtggaca tagggtgtgg aaccagacat tggaggcttg taagggtggt gggggcaga    47400
aggaatacag atggaaatta agtaatttca catcacaatg agtattatcc aggtgtgggg    47460
tatactaaaa gccaagactt taccactgtg cattatatgt gtgtaacaaa attgcacttg    47520
tactccttaa atttatacaa ataaaaaaca aaaggagaat cacttggacc caggaggcag    47580
gggttgtggt gagccgagat cgtgccattg cactccagtc tgagcaacaa gaaataaaaa    47640
aaaaaaacgc tacgccttgc ttctgaaaca gcccagcgtc tctaacctct actgaaggct    47700
cagttcacgg ctaaggcctt ccaacttgtg tgagaaggac agaggccata caggaggaaa    47760
cttttcattct gttttggagt tgttccttca tttcatttttt ctaattgtgc tgataaaacc    47820
aaatgggcac agagaggaga tgcctcctct tctgcctgcc ccctctctca gtgctttact    47880
ccaaacaaga gtaaatttgg tgaaatggtg actatcaggg tgtggccaaa tggaggcgca    47940
agctccccag tcacctcctt atggaacaac atctttcatt tcctcaagag gagactctgc    48000
cactgcagtg aaccttcacc accacaaacc tccaccttca ctcctcacca acacctgctg    48060
tactcttcat gaatgctgtg agcttgagcg agttcttaaa tttcctagcc atcagtttcc    48120
tcatctccaa aataaagaaa acagcaatgt ccaaaatcaa tctccctctg aattatacta    48180
cctggtttca gcctcaacct ccagggtgat agaccagctt agagaccaag attttatctt    48240
tcctaagtga tctcaccttc agaggcatca tcaccagact tttcaagttt tgtttcttag    48300
aaatggtccc aagttctttc cctctcatcg tctcttgctt tagggagcct cccagctagt    48360
ctgtcttagc aagacaaggg catagctggt gcattgctgc tggtgagcag gggcaagttc    48420
acagaaggca gcatgggaga gtataacaga aatcaccatc agtttccaag ggcttgctct    48480
gtgtcaggca ttgccctaaa cagtctacct gggcaaacat ttattctttg caacatccag    48540
taaggtaggc tgtgatttta ttctcctttg gtagataaga aaacagaggc agagagaact    48600
actcaaagag ctcaggcttt gcagcccgat agaattaatc ttaaatctgt caccaacaag    48660
ctgttaaacc ttgacccatt acctgacctg ctttgagtag ggctttgtga agattatact    48720
aaatttatgg tattaaacat cataatggct acaaactgct tgacacatta aggcattcac    48780
taagtgtcca ttgcttggta actctttaaa aactgtattt taaatggtga tgttttgtta    48840
acatcagaac gacaaaaaaa tactacaatg gccatccatt ccctcactcc acccttctat    48900
```

```
ctattcaaca aacacctggg aatagagaga taaacagcac atgatcttac tccccctggga    48960 actcttaact gtcgtttaga atgagagaga aatgggtaaa caggccaaga cttgggtagg    49020
aggtgctagg agagaggaag gcactaggtg gcgtgaagag aaagcaattt gaagcatctc    49080
catcctggac ttactgggtg aggtaagctt cctggggaag actgcctggg gctgagccca    49140
gaaggataaa caggaattag ccagggaatg tggagtagaa tgcagtccaa acacaaaaaa    49200
attcaagtca atccatagaa gtgggtcgtg gaattccagg cagaaagtga ctaaatgaag    49260
atggaaggac agggaggggg tggccacatc acagagaacc tcttatccta agaactctgg    49320
acttcatctt cagaggcaag gtagagagag caaggacttt agagcaggaa aaggaccagg    49380
tcagtctagt ggccatgggg aaggtgggtg ggaggggccg agatgggatg tatggaggtg    49440
cgtgaggtgg aggcagtggt gagccaggaa atgtttagga cgtagaatcc tcaggaatta    49500
gagtgcggtg aattagaggg gagaattgag gctgatgctc aagctcctgg cttgggcaat    49560
gtgggtagtt atgtcataca gggaactcgg aagaagatat ggtttggggg aagggaatga    49620
gttcactctg gctatgagca gactttgttt gagatcccat gtcagacgta cttgaaaatg    49680
tccaagagtt agctggatat gggtacagac agctttcgat ttaactgagg tccgacttaa    49740 gattttttt tactttatga tggtgcaaaa gtgacacgca tttggtagaa aacataattt    49800
gacctttgct gtttccccag gacagtgata taaggttatg atactctctt gcgatgctgg    49860
gcagtggcag tgagctgcag ctcccagtgg gtaaattaag catggaaatc tggaacacag    49920
cagcttttaa gggatgcact ggggagagca gtttgtaaaa ataccttggg acggattaaa    49980
tgtcttggct tagagaaaga acaacagaca ataggaaact gtcattgagg agaagccggg    50040
attcaggaga tgtacattat tcaggtagct gagggagggg acaggaacct gaatcttcaa    50100
cagaagcaaa caaactggga tggagggccc agcctcatga aggtgaccag aaggacccgg    50160
tgctgcaggc tgtgtgggta gctgagcaga gctaagcggc ttgacggacc aacatctctc    50220
cagctggttg aagacaagct ctcagaagac aatgctgcat gtcacagccc cagcaaccaa    50280
caacaccagc ctgacaactt gctggggtgg ccgccttgtg gtctgaggtg gccgtctaaa    50340
ctatgtggtc tgatctcagg ctgcagacct tgcaggactg tcttcacaca gactggaagt    50400
gctaacaggt ggtgaggaca ccgctttaca acgatgcagg gggcccccatg tcaccctcac    50460 ccatgggaag tttgacttgg tggactcagc caagccacag aggtctaacg cttctctgcg    50520
gtgatttcag gctgccctgg cagaaagcac agtgcctgca gacatgctgt cactgctcca    50580
cacatcaacg ctggcagtcc ttggggctcg taagtagttt tgctcccca atcactttgg    50640 actgatattc tctattgtta tatattttta taaattccaa attcttggtt tatttactcc    50700
ctcccatttt ttttccccagt gtgtgtatat ggtgcaggtc acctagagca acctcaaatt    50760
tccagtacta aaacgctgtc aaaaacagcc cgcctggaat gtgtggtgtc tggaataaca    50820
atttctgcaa catctgtata ttggtatcga gagagacctg gtgaagtcat acagttcctg    50880
gtgtccattt catatgacgg cactgtcaga aaggaatccg gcattccgtc aggcaaattt    50940
gaggtggata ggatacctga aacgtctaca tccactctca ccattcacaa tgtagagaaa    51000
caggacatag ctacctacta ctgtgccttg tgggaggtgc acagcagcag acagtttgag    51060
ccatcccatt caataaatgt ttattgagtc tttgtttata attcgaatt gggaagccac    51120 agttaccacc agtgtgcttg taaacagttt ttaagataaa cattcatgtg gtgactctac    51180
ttggagttgc caaattccac atattttctc aaagcagaag ctttgcataa gtctatacaa    51240
```

-continued

| | | | | | |
|---|---|---|---|---|---|
| gtgaccagcc | tcctcttttt | cagggttgta | ctctctcacc | aacagctttt | ctaggtcacc | 51300 |
| catgcttatt | tttctggttc | aacctctcct | actcattata | tattttttt | ctggtataat | 51360 |
| atatacacat | ttttagtgtg | attcttttgt | actagtcaat | atgcattaca | taagttttct | 51420 |
| ctgaccttcc | tatttctctc | gattaaaaaa | tggatatgac | attaaatggt | attcattttt | 51480 |
| ctggaggtta | acatgtaaca | aacgcagcat | gatctaacca | cgagcagggc | agactgcaat | 51540 |
| gacaaatcta | tcacatgcat | gccttgagtg | gtgatgtttg | attttgtaca | aaatccgtaa | 51600 |
| acacttccac | taatcgaatc | taagtcaaag | tccactttgg | attggggttt | gagaaaaaat | 51660 |
| tcatttgctg | caacctctgc | ctcccgggtt | caagcgattc | ttctacctca | gtttcccaag | 51720 |
| tagctgagac | tacaggtgcg | tgccaccacg | cccatctaat | ttttttgtat | ttttaataga | 51780 |
| gacgggtttt | cgccatgttg | gccaggatgg | tctctatctc | ctcctgacct | cgtgatctgc | 51840 |
| ccacctcagc | cttccaaagt | gctgggatta | caggcgtgag | ccaccgtgcc | tggtcatcca | 51900 |
| accatgagct | tttgatagac | tactctgagc | caggcattat | gcacagcaga | aattacaagg | 51960 |
| cccatacgct | ctgcaaaggc | ccgaggttgc | ttctgttgaa | ccacattctg | ctactgggct | 52020 |
| gccattcacc | actaaaatgg | cagtcctcaa | cttgaatata | actcatgatt | gtaagtctct | 52080 |
| tatgaatttt | cgttacttct | agttcaactc | aggcttgca | atttattatt | gttgatggtg | 52140 |
| ttgttttaat | ttatgttttt | gccatgaaac | cctttcttga | aatgtgatct | tacaaatata | 52200 |
| aaatagagaa | aagtagattt | ccactgggaa | agagttcaga | gatgaatgat | ccttagtctc | 52260 |
| atcttctcaa | atttctctga | tactttgatt | tttcaacagc | tcaataatta | tctgagtata | 52320 |
| catataatgt | acaagtggt | caagacctgg | gcctgtcatg | tcagaaggac | ataggtccaa | 52380 |
| atggggctct | acttaccacg | gataagctgt | gtggcaaggc | cttgagcttc | tctagcccca | 52440 |
| tttcctcacc | tgtgaggcaa | tggtcctgtg | gttatcatat | gggtggctgt | gagaactcct | 52500 |
| gacatgatgc | atttcaagga | tttggcctag | tgcttggcat | attgtgacag | cccagcgtta | 52560 |
| tctgacaaga | gacaaaacta | gatacaacaa | aaaaataaca | gcaagcacac | atatatagtc | 52620 |
| atgtgtccct | taacgacagg | aaaacatcct | gagaaatgca | tcctttggca | atgtccttgt | 52680 |
| tgtgcagata | ttgtagagtg | cccttaacac | acacctacat | ggtacagcct | actacatacc | 52740 |
| taggatatat | ggtatagctt | attgctccta | agctgcaaac | ctgcatagca | tgttgctgta | 52800 |
| ctgaatgcta | tatgcgattg | taacactgat | aaatatttgt | gtatttaaac | atagcataga | 52860 |
| aaaggtacag | taaaaataga | atataaaaaa | aatgctacac | atgtgtaggg | cagtttcatt | 52920 |
| ataatttgtc | catctttgac | tgaaacatta | ttattcagcg | tatgactata | tacaagaa | 52980 |
| aacatacaca | cacacacaca | cacacataca | cacatctggt | ttttttttt | ttgagatgga | 53040 |
| gtttcactct | tgttgcccaa | gctggagtgc | aatggcgcga | tctcggctca | ctgcaacctc | 53100 |
| tgcctcccag | gttcaagcga | ttctcttgcc | tcagcctcca | gtagctggg | attacaggca | 53160 |
| cgcactacca | tgcccggcta | attttttgta | tctttagtag | agatggggtt | tcgccatgtt | 53220 |
| ggccaggctg | gtctcgaact | cctgagctcg | tgatcacccc | acctcggcct | cccaaagtgc | 53280 |
| tgggattaca | ggcatgagcc | aacacgcctg | gcccatatac | acatctttat | atatccaggg | 53340 |
| cttagtgcta | cgtctatcat | agtgtggcta | ttacatttta | tagagagaat | agctaagtat | 53400 |
| gaagaaactc | ttacaagagg | ttatcccaga | ttaatttaat | tctaagcttt | tggtcatggt | 53460 |
| tccctaagac | ctttgactca | cacacagctg | gacaggacag | tggccttgtg | catagtgcag | 53520 |
| atgaccatta | taggggaaaa | acaagtcgaa | attcatagtc | ctttactcct | cctgcccttc | 53580 |
| tccttttgct | taaggtgagc | ttcaccagga | acattttcgc | cacaccaaag | gaaaactagc | 53640 |

```
cagaggcaaa ccagctctaa gttaatattt gccaattaaa tggtttaagt tttggattca   53700
cagaaacact gacagcatct tattagaata tactgtactg catatagtag gggctcaatg   53760
aatatctgtt gaattgagat tgatactttc attattattg atgggttcat tttacctaat   53820
gggtcaacgc gttgtatgga tggatgccct gaatattctg atgatttggg ttcgacttct   53880
tttcttttct acctgaggtg ggtgagctac aatgactctg aataatagaa tcaacattat   53940
attatctagt aatataaaa tctgaataaa atctaaggaa atcttggaaa gcaatatttt   54000
cataaaccat atcatctgtt gccgaactcc ccacacatac aagtactatg gaaaagtaa   54060 tgtctactgc ccaggagtca tcttatagaa accacaattc tagaagttgc tgtacccacc   54120
tggaaatcca tgctgactgt tttgtctcgg gtgctttttg ctttcagtcc tgtgaagggg   54180
ttcacaagag gcagactggg gtagacaaaa aaagggcaca gactttgaaa tgcttatctc   54240
cagacattgc gctcatgagt attttatct gtgtcatttc tgtactttg aaatggtcta   54300 atagaaaaca cattactttt taattttatt ttaaaattga cttaaaaaaa gaattcctgt   54360
tttataatat taaacatatc cctgcacatt attgagcacc tagagacaat atgtaaaatg   54420
tgttggttag aaggacctgg aagggctct gcttgactac ttttctttc ctcttctcta   54480 acaacgtttg cttcttgtaa aaagcaaaat cttaccttt ctcctgttc ctactgatca   54540 ctgtgctgag ctaaagaaaa tgttagtgat ttgaatgctc aaggcagctt attgggcttg   54600
tatgtcttcc tggaacacta ggattttca agcctgtaga tcaaggtct tgggaaaaaa   54660 gaaacaactt ttttcagtga gctaactgaa atagaagaga atggcgactc ctacccacac   54720
ctcttggatc ctggacatca gctctggctg tggggcaaat ggcactgcat attggccaat   54780
gtggggagga tgcagccaac ttaaggcccc ttttcaggga gggaacgctg accccacgct   54840
cctatttccc agctgcctgc tgatgttcc attttctacc cccaaacaac acctgcagga   54900
tagggaagac catccatgca gcccagggcg gtcagacttt taaggcagag ttatgtggaa   54960
aatggacttg gatgagccaa ggaggaaatc ctgcagatgg cccaataagt ggattatgtt   55020
tgacttcaga taagtaggac aagctaggga gccagaaggt tttattagtt ttgtttcact   55080
ttccacaaaa ccaccaaggt cccatctcca acagaacagg atgtgtgact gttccttgag   55140
taaaaaaaca ggaaactgga caaatcttga gagatcatca ttaattagta cttctttagt   55200
tgatttctta atatggagga gcatgtagat tattaataat gcttttgttc ttgagttaag   55260
tgaaggagtc ttaggtattt gttgactcat taaataaatc accaacatgt agtagactca   55320
aataagaaac ataaagtga tacacattta gataaatgat tatagtgctt tatgcttgta   55380
gtgcttcatg aatcgatagt atgattaatc caattgtgct cgtagtgttc tttacaacaa   55440
ctaagtttaa aatagagaaa caatctcaac tctcattaga tgattgagga tagagaaatg   55500
cctgtcacgt tcatgtcaag tagaatttat cccctcaccc ctgttgctat aattgatgtg   55560
tctcttctgt agatccctaa tttaatttct tgtcacttttt aagtcaactt ttaactagca   55620
aattagcaaa gtgctaaggg attcagagag attgaatcac gtgctatact ttactgtagt   55680
cccgttctct ttatatttta cttataaact aaagttacag agtaattatc aaaactccat   55740
atttgtgttc tgaaattggc agaatttgaa tttgcagtcc ataggtcagc agatttctct   55800
gactttcctt attttctttg cttagccaca gaaaaacaga aaaatcagtg agtttacatg   55860
cacagaatta aatgtacaga ctattctctg aaagagctca gttctatgtg aaaatgaata   55920
atgtaataaa tattcttatg agtgtagtaa tagtagctat tgtttattga gtacttctta   55980
```

```
tgtgcatggc actttatact gcatgcttta tgtcatttga gcctaacaaa atactatcat    56040
tattattatc tcattttat agatattttc ttttttaat aaactctttt atttgcacgt      56100
ttgtgtcttg ggttattcgt ggggtgagaa acctccacac ttccaatccc agccatctgg    56160
tacaatctgg tgttgtggtc cagctgtcgg caaagggtag aggtgggtgc agggctggcc    56220
ccccagtctg caccaacctc ttcagagcag ggagctcaga ccatggttgt acttgcactg    56280
cttcagggcc tcgctgaagc cttcacacag ggacaggtca ctctgcgtgg tcgaacagtc    56340
caggaactgc cggatctcgt aggcgcagga ccccatctgc aggggctggg gggcagcgcg    56400 tgtggggtc tgctgggcag caggctggac gggctccgag ctcccccatc tgaaggctca     56460
ggtcagggcg ctgcccatga cgtgtcccac agccgagccc acggctaccc ctgcggccat    56520
ggacgccatc taagccatga ggctcggctg gccggaaggg gcggagatgg ggcggctgcc    56580
ggaggcggtg gctgtgtggg ggcaggtggg cagagggcgc ggcgggaggg ggctgggtgg    56640
tcggaccgcc gcgctgcggc ttcccagaga catggtggcg gcggagggac ccgggcgatc    56700
ttaaatgaca gcgatggcgg cagcggttct gtcgcgggga caaatgccct ttatagatat    56760
tttctaagta cagatttgag actttgataa attaagatac ttgatagtaa gcagcgaggc    56820
tgggatctga atccaggtct gtctgactac aaaatctatt gccttgatct cctacagtga    56880
tgagaaaaac aaaaccaaac acgaactttt aaatagagac atttcagggg gaaataaaaa    56940
aatttataat tcgttttatg agtttttttt ttttcatttg cggccttaag ctcctttccc    57000
cagggtcaca tgaagttagt taaattgatg ctaacggtgt ttacttacag acaatctgca    57060
gagaattctc tacagagaat tttcttatgc aatcaagttt ttctgacttc tgggttctaa    57120 gattttttc ttttttaac aagaaaaaaa agcgtaacca aaactgtgtt tattgagcaa      57180
cagaaaagca gcgagatgga acacagagat attcccctg attatcacct ttccgctgca    57240
ctcccttacc ctcagtccgc tggggagcac agaaatgtta tccaaggtg gatgggaaag     57300 ggtgaaagg ctgagaccca actgcagcct ggcctgagat ggccacatca tgttctgctt     57360
cctgcctggc tgcccaggga gggcctggat gggcagaggg ccaagtcagt gtcaggctgg    57420
gaactttaca tgcttttctc acttaaatat tgtcatctcc tttctcagag gaggaaccag    57480
agattcagag agactctgta gcctccaaga tcacgcaggc atcactagta gcagagaagg    57540
gatgtagagc aagtgtgacg gtccataaga cttactctct tcccaccaca ccacactcac    57600
ccagcaagaa ctggaataaa tgacaaggga gggaagaggg gctcagactt ctctgtatat    57660
tcacaaggat gtgaatgtg ttcctgtaag cgtacccaag ttgggaattt ggtcctttaa     57720
agaaaaaggt tgaagcagga agacttccag tttgctggat gaaacataat gcagcaatca    57780
aacagcccga ctcttttgag tgaatatcaa taggaatacc actataccat tcacttgttc    57840
ttcaaaggaa aaaatgaaac taatgagtcc ttgattccat gacatagata aatgttctga    57900
gaaggaagaa gttaatggat cactgggaag gcttcataga gccagaagat tcaagtaaaa    57960
gtcttgccaa acaagaaaag gagaaagttc attttgtca cagtctggtt gcaacagtaa     58020
aaactagctt ttgtcatcat cacattttct aatatcgaaa ggacatattt taggaaaaag    58080
catcccaaat ttataggtat gttgttattt atagaacttc attttttaa atcaaactct     58140 tcagtgaatt aattttacc acctcctcag gtacaggata aatgggacat ttgcagccag     58200
tttcctcctt gcccatgttt gctgcgaggt ggggcgtgga tgtggggaac ctctctgggg    58260
gaagaggatg ggtgcagcag cccgacgact ggtcgtgagg ccccaccaca aaaagcctcc    58320
acttaaaggg caatgctgag agccccacca cacctcatga tggggaattc ctctgtctag    58380
```

```
agatgttatt tattgtcatt caagtcaagg aactaaaatc ctaagaaaaa gagcataccc    58440
caaagccaaa ctaggcctcc taacagtagc tctgtgctca tcctgcttca acaaggaggc    58500
agagtagaga ggaaggaggt gaaagatatg gaacccactg agctcccact ttattccagg    58560
cgtattatgc acctatctaa gccaatgctg gtagataggg atttcaattt cattttcata    58620
gttgagggca ctgggtgtca gatagcaaca agtcaagcta acagcaggct gaactggaat    58680
taaaagcagg actgaatgat tgcatgctcg cctgtatagc acactacgtg gatttgcttg    58740
gcattgaaga aataggtttt agttccagct ctaccattta ctagctgaga ggccttacat    58800 tacccctct tccccatggg gaatcccttc ctgcctcaaa atattgtttg gattaaataa    58860
gccaatgttt gtaaaagagt tttggaaatt gtagacacca taacaaagta aagagttata    58920 gttttttta aacacatttt cattcattct aatatgattt ctcatatgaa ttatctccta    58980
aggatagtca atatttatgg agctcccact atagggaagg catccttctt gatgaaataa    59040
ggggctttaa caatccctac aacttatgac tttgacttaa caaaaacgaa atctagcatg    59100
tgttatatga aagtagcagg taacaagtgg tctagcaaag ctgcagtgct atatgctgag    59160
tgatagaggt atttgttgta acatccactc caattcctca agaaaataga tggtggcaaa    59220
gaagattaag tgatattgct cattaaatga tgagaatttt tacatactgg atattcagtg    59280
ggagtttcat tttgtcccaa tctccgctga cactctaagc tcaggagaat ggtagtaata    59340 caaagaagg ggacaaaacc agagattcac agtggagggc aagcccctct ccagcagaca    59400
ttggtaatgt ctgagacatt ttttactgtc acaaacagag tgagaatgct actggtatct    59460
agtgagtaga ggccagaagt gttactaaac atcctacaat gcacaggaca gccccacaac    59520
aaagaattat ccagcccaaa atgtcaataa tgcagaggct gagaaaccct ggggtagttg    59580
gccatatttc tcaaagactt gctaagaggt agacaaaact gatgactcca acctttggct    59640
catgagctat atccaggcta attacagtaa gagctttcct ggggactcta attttgcaaa    59700
gactttctct gaaaagcact gttgggattt ccctggaaac cccctcctct cccagtgagg    59760
aggtgatgag gtagctcttc tacttccaca ccaaatagga ctctcaggtc ctacatccac    59820
catgggtcca gagcagagcc ctgtgtgtgg gtcatggaag tgttgggtct gtgccgtgag    59880
cgtttggtgg ccagataaac cagtgaggac tctcacctgg aaaagtggac aggtggcttc    59940
aggtcatagc ccacgtggta acttggacca actctcccct gaaatcagtt agataatcat    60000
gatgaaataa taataatgaa aaagaatctt tctaaaagtt tctaagagtt agcaagataa    60060
caaggtgaat aacttttacc ctggcaaatg gactgattat catggtgtca tacagctatg    60120
ggtaaagttc ccatgtgatc ctgaccaatc agcaacctca gaaatgactg atctgggcgc    60180
agggcctaag gacacccatt ttctctgtga acactctttg aggttcccct tcctcatcct    60240
ggtgcagctt ctcctgctcc aggttcccta tttcctcagc cttgtctcag gcactcagcc    60300
tgagcagacg gacgtcaca gctacagata tgcacctgtt cttcactctg gaatgtgaa    60360 cttgttctcc tacttctcag attggctgag ggattttttt gaaaatgaat gtctcatttc    60420
ttgataactt tggtttcatt gaaaatgcta ttttgtttct aattgaaatt gggtaaaaac    60480
aattgaagca agtaaaaatc tttatttcat tagcagaaat gaagcatata ttttcactgt    60540
agggtattta gatagaactt ttcatacaca ctcaggtact gaccaacacc aaatcaggct    60600
tttgaggatt tgatatttac ttggaaaaaa accctgttcc aggtcaatta caggcaaaga    60660
gctgcaacca tatataaaat tctgtatata aattctctat ataaaattct gtctacttcc    60720
```

```
ctttagttct taatataaaa ttcctagaaa aatagaaaga catgatgacc caatataatg   60780
gcccccagga aactagcatg acattggagc tgaggtaatg ggcacttgcc ccattatcat   60840
gtctgcgacc acatccttcc caatgtggaa gagcctcgtc cagccctctg ccccagctag   60900
gcctcagcct cagcttgcag cacttcctgt gttcctcaga tgatgcctct gtgatcacag   60960
gaaaccagaa agggagtctg atgactatca atttcacccc acaaatgcca gtacctatac   61020
ccccaagtgt ctgatttgac atcatttcct attgacttag gttcctattt agagactatg   61080
tttgttgaaa ctgcatgatt atttcagaga gaaagcaagg tccattatat catttcttag   61140
aaacttctag tcatggtgaa ttgctcaggg tgaagatgcc agcaaggaac aagatggaat   61200
tcatatccac tcagttccca ctggctgcca gaaaatggga tagatgttct acatattcag   61260
aatttcaggt gattgtcata agaacctggt aaataaactt attcatgaaa gaataactg    61320 atgtttagac aggggcagtt atctgtccaa acaaatagtt catgctcttt caagtgcact   61380
attgggccac tttgaatacc ctttgggttt attaacttaa tggaaatagg gccaggggca   61440
gtggctcagg cttataattc cagcgctttc agaggctgag gcaggcagat catttgtcct   61500
caggaattca agaccagcct gggcaacatg gtgaaactcc atctctacaa aaacacaaaa   61560
attaaccagg tgtggtggag cttgcctgta gtctcagcta ttccggaagc tgaggtggga   61620
ggatcacttg agcccaggag gcagaggttg cagagagaca agattgcagc actgcactcc   61680
agcctgggat acagagcaag actctgtctc aaaaacaaac aaacaaaact ttataggaat   61740
gaactgtggc atttgtgggt aattatgcgc tggcccggac ttactgccta gtcctgcaga   61800
gctaggtcaa gacagaatgg gcagtgactc aagacagaat gggcagtgac tcaagaagcc   61860
atggctaaag ggtcatgctg aacacacatt tggaagagtt cccacccccc accccacccc   61920
caccctgctc cccaccggca ttctgcctta ggacccttct tctcactgga ggggaaaagg   61980
ctaagaaaac agaaaaccct ctctgttctt gtgaacttgc tttagcagat aatatcatgg   62040
gtgggatacc tggagaggga tcaaaacctc acagcccaga cttaagtaaa tgatcaaaat   62100
gtgtaatgag gatcatgttt tggaaatgtg gccaacatat ttttattctc taaaataaat   62160
catgtcacct tttgtccttt ctttattgta gctaatccat gatatttact acccatagaa   62220
agagatggta gttgcccaga acaaactcac tttttttttt tttttttttt tttttgaga   62280 tgaagtgtta ctctgtcgcc caggctagag tgcagcgcac aggcgcccgc caccacgcct   62340
ggctaatttt tttttgtttg tttgttttta gcagagacgg ggtttcaccg tgttagccag   62400
gatggtctca atctcctgac ctcgtgatac gcccgcctca gcctcctaaa gtgctgggat   62460
tacaggcgta agccaccaca gcctgccaca aactcacttt ttgaattaat tgtgagatgt   62520
tgggcttgaa aatcaggttc aattttttttt taaagagttt tctatagttg tgattctctc   62580
attcataggt caaaaggcca cactggcaaa gtaacaacac agaattttat tacagctgct   62640
agatatgaag actcagcata tgatatcggt gacgttaata ccttcccagg gagaagcgct   62700
gttccttctg gctgggaagt gcgagccggt gggggggagag agaggagtag agcattatgt   62760
ggaggtactt cccggttccc ttgcgtctga gggtcttatg ccagagggga tagaaagccc   62820
aacagaaact caagatagaa gaaggagaat ctgcgagtgt ctgtctcctg tcaagcttcc   62880
ctaatacagc cctggtagaa cttcatcaac agtggaaggc atttgcaaag gtgagcccaa   62940
accagcaccc ctttccacac aggctgtcca tgtagaaggc ccagatgctt ctcagggtct   63000
ctgagaggat acaaagctac tgagggggcc agagggcaca gcacctggga tttggatgag   63060
aagctgcagg aagggaactt tgcaccccaa gggcatggtg tggagtcaat agtggcaagt   63120
```

```
tcagtctggt tttttacatc agccggttca gaggaagagt gaaatcccca agatcagcag    63180
ggcaaaatgc tggaagttgt cgaggatgca gagagtagca ggaagacacc tctgagaact    63240
cactcacaca ccctgcccct gtgtagagat gtcatcctgg ggatgagaag gaggaagaca    63300
gagaaacgca gaaaagccta agcaggcacc acaaagagac cgagcccgtc tgaaagaggc    63360
tgctctaacc tggtggaaac tattttaagt tggtaagttt agtgcctccc cacaatatca    63420
gaacgagcaa gagacgacag gtataggttg tgtacatttc ccctctgcgt tgaatgatag    63480
cgtgtgcgtg ttccaccact gtgccctgct caaagttagc tgggtggctg tgccctgctc    63540
aaagtcactt gggtgagggg cgcccgtggg agccaaaaat cccatcttac acccaccccc    63600
tgcacactct ggagttgggc tgtgacatgc tggagaaagg tgtctttgtc taattattct    63660
gcctaagggc atgccttttg ttaattagta aaaggaagcc ttatttgtgc tctgcagagt    63720
gggggtgctg tttaggaggt aattcgtgat agaaccacac agacaagata gattcaattt    63780
aaataaattg aatctatgaa gcttcctaac cccatggaaa cacaaaatta gtttacacaa    63840
aaataatcat taaagaacta atgaaaataa tgtttgaatt cagccaccag acattacatt    63900
ccagagcctt gagaaaaact gatgaaaaaa aagtcatgaa aaaaagtcat tcgcacaagt    63960
gacaccatgg tgtgaagtca aggagcacag actctggagt cagagggctt gagtcaacct    64020
gagcatcttc agctttgact gtgaagacac agctttgact ctctgtgttg cagagatggt    64080
agtgcccact ccagtgacgc ttgtgaggat tagttgagat aataaataca aaatgctgag    64140
catcaaacct agagtagaga aaggtctcaa gtaagtactc attaccagta tttgttattt    64200
aatttcactt ttgtctacat tcccttgtgt gaaatggttt ggataattaa ttaaggaaaa    64260 ctttcccctca gggacattgc tgatattgca atcttcacta gatacactta tctctacctc    64320
cgcctccacc tccaccttca cctccatctc ttctctgtct ctatctctat cttcctgttg    64380
tttatctatc taattattta taaatgaact ggtgggtttg ttgttgttgc agcctggcta    64440
atgttatcca gacatatctg aaacctcatg agtggcatgg aatggcagtc cctgcttgaa    64500
ccatttacct cctttcctaa caccaacaat cacacacacc tgacactgac ctgaagcctc    64560
tggcctgtcc tcggaggcaa agactgggta gacaagatgc ctggttacca gcaatcttct    64620
gcaatttcct ctgagctatt gagattgctt ttctctttgc tcaaattatg tgagaaactt    64680 ttaaaaaga atttaatgtg ctcttttgat atttcaggtg ttcattcaaa agcctatgtt    64740
attctctgtc tctctgtctc ttttcctagt tgggtaatca aaatggcaca atcagaaata    64800
tttatatctg caacagaaaa gaagaataaa tttattcatg cacaagtaca ttatgtacat    64860
atatatgttt gtgtatacat atatctgtat aattgatata tttgggagaa ataaaggtt     64920 tcattaagca cacaagttct agagttagac cctctgtcgc aaattactgt cctgtcactt    64980
aactcctgcc agaacaaagt gcatacttga acaaaatgcc tgctctgtaa aaatgccttg    65040
atcttgaata aaatgcctgc taggtcaaag cttctatttt cccacctaga aaatgggaac    65100
aataataaga atcctcactt aatagataat ggaaaaagtt gcttgcagca cagagcctgc    65160
tacagacaat gccttcaatt aatgcaaact attaatatta tgaaaagtga gtatctgttt    65220
tctgacaatg ttttcaataa tataaattct gcctttgttc actttatttg tttgaaaaaa    65280
caaataaaaa accaaacaaa aaagtgtctt aaaagtgtcc atttgtcttt cttcttgact    65340
cctagtaacg ctttcctgtg tttagggaat tttcacctca tgggttttgg tgagtgaatg    65400
aattcatctc cctctacaga aaagaagaat gcctgatgca ttttctcagc ctttattcca    65460
```

```
ggtagtcagg tagactatgg actccagcaa ttagatacac tcctcacaac ccctccatta    65520
cacacacaca cacacacaca cacacacaca cacacacaca cacacacggc tgctggagtt    65580
gcagggtctg gaaggaactg tctggcaggg atggagtgtg cagggtgcct agtgagttcc    65640
agcgtggccg tggctgccct ggctgtggca gcaccagggc tctaagccgg ccctgcaga     65700
ctggctcaat ctgcagcatg ggcgctctct cttacttccc attcccagga cacatcctgt    65760
gcaggggaag agtgagtcct tctagttgta gccacaggcc cattggtctg ctgacctcca    65820
cctcctcaat attcgactcc ccagcattga gtgtctcaaa acagtatttt ttcagaaaag    65880
agggtgaaca gggcaactgc tttaggagga gccatccgag ccagctgctt cctctcctgt    65940
ctcctaggga ggacccaagc tgtcggagtt catacctgtc ccacaaaaca cgagccagag    66000
ctggacaaaa gtgacaggga caaccactgt ccaaggttaa gtgagccctg aggcaccaga    66060
agatctccaa gaaagccaca tggaaatcat aaaatggagc tgaatggagg aaaagagaag    66120
ttctgtaatg tggaaaaatg aagtactaac aatatttgac tgttttccct tgatttagcc    66180
aggttactac ttcaaaacag tcagcaaagc attttaacaa tgaaagctgt tggggaaatt    66240
aaatggctgg aagtggaggg aaactgtgca ttgtggtgca tgcctgttgt cctagctact    66300
caagaggctg aggcaggagg gtggcttgag cccaggaatt caaggctgca gtgagccatg    66360
atcacaccac tgcactccag cctggccaac atagcaagac cctatctcta caaaaataaa    66420
aataagaagt ggaggggaga taaaaatgta gtggtaggag tagtagtaat aatatctaat    66480
aattactgaa aatttactat atgtcaggaa ctatactagg tgtacttagc tatttagtct    66540
gcataaaatt ttaataccag tgttattatt gtatccattt tcagatgaga gatttgaggc    66600
acaaagagat taagaagttt gcacagggtc agacagcccc tatgtgataa agatgaacag    66660
ttagacatta aaacatgttt tggttgggtg cagtggctca cgcctgtaat cccagcactt    66720
tgggaagctg aggtgggtgg actgcttgag ctcagaagtc ggaggccagc ctgggcaaca    66780
tggtgaaacc ccgtctctac aaaaaataca aaattagcca ggcatggtgg tgtgcacctg    66840
tattcccagt tactcaagag gctggggatg aaaggattgc ttgagcctca gaggttgagg    66900
ctgcagtgag ccatgagtgt gccactgcac tccagggtgg gtgacagaac aagatcttgt    66960
ctcaaaaaat atatgtaaag aaaaaattct ccaatgacat gggaagttgc tcagaatata    67020
agctgaactg aaagaataca gaacactata catgtaaata tatctatagt ccataaaatc    67080
atattaatat tcatgtatcc aaaatgaaaa tatctacaag tgagcatatg ataatgtgaa    67140
tagtagtggg cctttgtgat atgaccgtag atgttttat tgttatcttt ccccattgct    67200
ctgagtttct tcaatgagca ctgttaccag catgttctac ctatcagctg tgtgacttct    67260
gtggagttga tgactctgtg cctcattccc tcatccaaaa aatgaaaatt ccaagtaccc    67320
atattaagtg atcattgtga agattagaag gtgaaaaacg tttagaaaaa aaaaaggcta    67380
gcaaatagaa aatgctcaat aagtatttgc tattataaaa gttaatgttt attaaatatg    67440
caacaattta aaatattatg ctgaggaaaa gtgttcacga acaactccta ggcaattaga    67500
aatccttctc atttccacag aaattaagca accccatgg ccccctcaca ttcgtgcaga     67560
gaacaccatc gagattgcta gcctgatttg agataagcag ggtgagcagg agggggctc     67620
agtgctgagc ctgcaggagg cactgaaggg cccaaaaaac catttctttt ctctccccag    67680
ttcaggccac accctccaga acctgaccag agtcgtctag ccaccaggtc cgcactttcc    67740
tgccttctcc ttgggtacac cgccccgaag acaggatgtc actgctggaa gcatttgcct    67800
tctcctcctg ggctcctgag ttgctgtccg aacatttcag tctagctgcg tgaccaaaat    67860
```

```
cattcttcaa tgtttccctc ttctactgtc agatgttcat tggaaattct cctcttttac   67920
ttacagttgg acttggatta tcaaaagtgg agcagttcca gctatccatt tccacggaag   67980
tcaagaaaag tattgacata ccttgcaaga tatcgagcac aaggtttgaa acagatgtca   68040
ttcactggta ccggcagaaa ccaaatcagg ctttggagca cctgatctat attgtctcaa   68100
caaaatccgc agctcgacgc agcatgggta agacaagcaa caaagtggag caagaaaga    68160 attctcaaac tctcacttca atccttacca tcaagtccgt agagaaagaa gacatggccg   68220
tttactactg tgctgcgtgg gattacacca tactagaact gttgaaacaa catgcacaaa   68280
atcccctccc agggtctgtg cccaccacat ccttcccaac aggggcaacc acagccagtc   68340
cccagctggg ctcccagact caggctcgcc ttctctgagg ctcttccggg ctttccagg    68400 aagctgttat gggttatacc ttcgttccca cctgatccca ggacttgtgc tccagaatct   68460
ttatttgaca ctgtttctta atgcattaaa gacttgtctg gggactgaga gaacataggt   68520
cgtgccactg tccatcatat caccacctag agacttccag taagtagcaa ggtgcagttg   68580
agacagggat ccttattacg tacagtcaag acaaccccc tgcaatataa ctatcactgg    68640
cccagtttac aatgaaagaa atgaaagctt agagaactga ggttgcatga tctgccagac   68700
aagtcatgtc tttgagctgg tctatgagac cacaccgaac agtttaagga ttgcaattct   68760
ctaagtaaat gctaggatat ctgggataaa ttcgggaagg agtaagtgcc ctttttctg    68820 ggaggggtag ggaggagaat ttgcctgcat gagatcgtca gaatagagct ccaagtcatc   68880
ccaggggcca ttggatgaga cccttcatgt tggaataacc tttggtctta cctgtaaagg   68940
aagagagaat tgtatcgtgt gtgtgtgtgt gtgtgtgtgt gtgtgtgtgt aagttctcta   69000
cagtgttctc aattctttgc atatattagc tcctttaacc cacactacct atagtgtctg   69060
ctctgttgtt ctcatcaaac atatctaact cctgaaataa gtggagtatt agttcatgca   69120
cttgtccaaa tcacagagct gataggtggc aggacagcct agggagggac ccaggtaatc   69180
tggttcctct tgaatatgac actaaactgc ttctgaatca caggagtata aagaaaaga    69240 cacattgttc ctgtccccat ggaggagaca gaactgacca tcatggaaca gtaactgaca   69300
cacattacta ccgtgtgctg aaacttgtgc ccagggttcc agtgattagg tgtattcaga   69360
gaacaagtaa aatgccaata aagtaccaaa tgacttttct ttctttttt ttttttttga    69420 gactgagtct cgctctgtcg cccaggctgg agtgcagtgg cgccatctcc actcactgca   69480
agctccgcct cccgggttga ccccattctc ctgcctcagc ctcccgagta gctgggacta   69540
ctggcgcccg ccaccacgcc cagctaattt tttgtatttt tagtagagac ggggtttcac   69600
tgtgttagcc aggattgtct cgatctcttg acttcgtgat ccgccagcct ggcctccca    69660 aagtgctggg attacaggcg tgagccactg cacccggcca ccgattgact tttcaatata   69720
aaaacataag aaatttgggt tttccatatc taggtacgtg acaggtactg ttatctatac   69780
ttcatgttca ttatcattat tatgtgatca tgtaaatttc ttaagtctct ggaagccatt   69840
taggcactta tagatgtaga actgagacct aaagatttca ataactcag ctgatgttag    69900 atagggtaag tagtctagaa gggtgcatat tgtcataggt cattaatagt aatattcaga   69960
tgagcttttg aaggacctga tatatttta aatataaaat taaagatca gaatataaaa     70020 ctgtaaatgt aaaacccatt aaaaaacgtt taatcatggc tgggtgcagt ggttcacgcc   70080
tgaaatccca gcactttggg aggccagggt gggcggatca cgaggtaagg agtttgaaac   70140
cagcctggcc aatatagtaa aacacgtttc tactaaaaat acaaaaatta gccgggtgtg   70200
```

```
gtggtgcacg cctgtggtcc cagctactca ggaggctgag gcaggagaat tgcttgaatc   70260
cgggaagtgg aggttgctgt gagccgagat cgtgccactg tactccagtc tgggtgacag   70320
agcaagactc tgtctaaaag aaaaaaaaaa tttaatcctg tgatcctgtg taatgatcca   70380
aacaaatata ttactatcta caaatgtgta gagaacatgc ttaaaagtaa attctgattg   70440
ctcttatttt ctttatttta attaactaat taatgttcta ctagagtctt ctcaaaatat   70500
tttcatcatt ttgcaacatt tggtcaggtt ttcttcagtg aggattgggt agttatccaa   70560
gctcccatgt ttaccaactt tgtgatctgg gacgtcatgc gtgccacact gttcttgtct   70620
atcagagaga gataataata ccactgcctc tcaacgctgg tgagaagtgt gaaggaagta   70680
atggaagaaa acgtttagaa caatgttagc aagtctacaa tagatgtttg atataacgtt   70740
aattttaaag gcttatgatt acacataaaa atgaacttta tttaaaaaca cccctctctg   70800
tgacatagtg ttcatgagat agttctgaag tccaaggtga gttcccacag actgccctgt   70860
cggtccctcc agcaatttca atcaagtttc ctcttgaggt gcaccctctt tataagtgaa   70920
attggatttc tctgagttat aatctgcatt gtgacatccc aattaattat aaaccaaata   70980
ctttactgta tttcaaacag aaatgactat agcttttttaa atgaggtatg aataatgcta   71040
gtgtaaaatt tcagtttgcc tttttttaaaa ttgtaaaata ctgtccatgt tttatactcc   71100
tgagtcctgc atccccaaaa cattaacaga gggatcaatt tttacgtgag gtaaagaaag   71160
ttatatgctt atatatctgg aaaaatattg tacagtctga aaatcaagga gagaacagct   71220
aagtttgaag cagaattagt tcaactccag agctgctccc atccctttcc acagacacat   71280
tcttgtcagg taatgcaccc tacaccccgt cagtggtcag tgtaatgctc ctgggaactg   71340
ctcagctctt cagtaggcca tgaagtcccc agagggcacc tgacccacca cattttctc   71400 tctcaccaag tcatgccatg ctgtctcccc actgactggg gccagccagc aaccagggtc   71460
cttctcctgg ggatatggct cagcagacag caggatgtcc ctgctgagaa tattcatatt   71520
tttctcccct tgcagcggtg agttgctcct caattatttc aacatagatg agagatgaaa   71580
gtgattcttt ttttctttta ttttaagaca gtctcgttct ttcacccagg ctggagtgca   71640
gtggtgtgat ctcagctcac ttcaacctct gcctcctggg ttcaagcaat tctctcttgt   71700
gcttcagcct ccaaagtagc taagattaca ggcatgcgcc actgtgccta gcttattttt   71760 ttattttttag tagaggcagg ttttgccat gttggtcagg ctggtctcga tctcctggcc   71820
tcatgtgatc tgccctcctt ggcctcccaa agtactgtga ttacagtcat gagccaccac   71880
acctggccag atgaaagtgt ttcattatca tttcctcttt ctatgtccca ggttcatggg   71940
gatttctctt ttttgtttgc agttgaactt ggtaagttaa atttaaagca ataaaaaatg   72000
tcaactacat ttttgtcaac agagcaacag ataaaagtgt ctaggtatct tgtgtggtgt   72060
ccactgaaga ctttgtaaat atagttatac actggtacca gcagaaactg aatctaaatt   72120
atgagccatc tgacaaatat cacttcaata acaagcccca gttcgagttt gcttaggtga   72180
gaaaaacaag aaacttgagg caagaacaaa ttttcaaatg tctacttcag tctttaccat   72240
aaacttcata ggaaaggaag atgaggccat ttactactgc actgcttagg acccacagca   72300
tcagtgccac actgtcccac acaacaacct ctgttgggtc tctgcccaac cacatccttc   72360
ccatgggagc aaactctatg gactcctagc tgggctccca ccctcagcct tgccttctct   72420
gcggcacttc tggatctttc tgggaagcca tcttgggtta atgctttaag caggaagcat   72480
gcctgatcat gacgttccca gatattcatt gaacactact tcctaatgaa ttaaggtttg   72540
gcctgggaat gagtggacac aggctaaggt cccattcctg tcagcatcca gataattcta   72600
```

```
ttaactgcaa acggcttagg ccaagggaga gaatcgttgt gtataggaat cccatatata    72660
attatttcaa cacctctgca acagaactat tatttgccca ttttaataaa gaaattaaag    72720
cttacaagtt caaatgact ggtcgaagtt gagaagtgca tgttttttgt tttttaaaac     72780
tggatcatga ggccaccttg aatatctaaa agtcacagtt gtacaacaga ctctttgagg    72840
tgactttggg gtggagcaag tgtcttttt ctgtagagaa gaagatggtt cctcacttca     72900
cactaagggg tgtgacagtg tgatatcatc agaaaagagc cccaggcatc ggactgttaa    72960
atgagccata ctttgcattt attaactcct ttaacctctg gcaacctctg aggtctgttc    73020
tgttatgaac agaagtgcat tttactcagg taagtgagat ctatttgtcc tagccactca    73080
tccaggtcac acagctggtt catggcagtg taggattgga cccagctagt ctggctccag    73140
agtctgtact cctcagtcac agaagggtaa agagaagtac attgttccta ctcccatgga   73200
gaagacaata ctgacaactt ctgtaaaaca tttactggca caattattat tttgaactga    73260
atcaggtgac cagaatttga gcaattagga atccttgttg aataagtgaa ataccaataa    73320
attatccatt ttttcaaaat ataaagtgat acaaattcga ttatttatg atgccatctc     73380 taaaataatt gagaaagaaa tgaagaatac ctttaatcca tgtacttttc ctatagcagt    73440
acatactagg caccccatg gaaaaatata gataccacct tgcattcgtg ccacgtgttg     73500
tcttacttat tcgataattt ccaaggtcag gacaacatat tcatcctcat catcccttt     73560 tccaaggagc caggaaggct actgaaggaa ataaggggg ttccaggaaa ggctgacctg     73620
gggctggaat cagacaatcc gtcatccttt atcctccac cccgatgcac tcagcctttt     73680
gtgatccaca tcctgtctgt gtaattcctg accatcatat tccctcaggg tgggccacac    73740 ttggttctt gaacctatat gggcctttac ttgttaactt taatattagc taaagtagac     73800
agtaagatct gaggaaaaac acagcgaatc tgagaggata agctgttttc agacagggat    73860
gcatagacag gcttgcggaa atacttgtgt caccctcttc tcgtggttgt ctcatctact    73920
actcaaaaca gcctcagaga gcagcaatga ggtatccact gccagatccc tgtgtccaga    73980
tcatagagca gagctctcct gcagccttc aggcatcaga ctaaatggtg agaaacagag     74040
aaagagatac tagattcata gtgcattcaa atgcacagaat actatgcagc ctgtgaaaat   74100
gatattgtat gcatttatta ataaaattca aacatcttca caatacaatg taaagaaaag    74160
ttcttgaagt gtacaaaacc tcttaaaaat ataaatgtct gtgttgatag aataattttt    74220
taaaaacaga aagaaattat ccaaaatttt agaataatta ttcccgaggg aataattatt    74280
taaattattc tatgtactttt tactaatttt tatatatttt cttaagtgag atactaaggc   74340
tttgttgtaa gatatactta acaaagtaat tttctcttgt ttggtagtaa tactaagaca    74400
cgataacgtc attaaggact catgctgtgc caggtactga tatctgagta ttttatgcat    74460
taccattgtg taacacgata atataagccc cttagtacct ctagaagata tatatgtagg    74520
caaggtacac atgtagaaac tgaggcccaa gagcttaaat aactcagccc acattctata    74580
gggttaagtg gtataggagt gtttaattgt attcggtcac taaaaataat gtgcacatag    74640
actcaagacc tgcagtattg ctcatgataa taaagtaacc aaaataagag agtataaagc    74700
caaatatgta aatcccaccg aaatatatac atatatcata tgtataaaata ataccaagcc   74760 attctatttc ttttttaaaa attttttaact tttaagttct gaggtacatg tgcaggatgt    74820
gcatgtttgt tacataggta aacgtgtgct gtgtggtttg ttgcacctat caacccatca    74880
cctaggtact gagcccagca tgcattagct attttttccta atgctatcct tccccacacc   74940
```

```
ctgcccgcca ataggcccca gtgtgtgttg tttctctccc tgtgtccatg tgttctcatc   75000
attaagctcc cacttataaa tgcggacatg cagtgtttgg ctttctgttc ctgcattagt   75060
ttgctgagga taatggcttt cagctcatcc gttttcctgt gaaggacatg atctccttcc   75120
attttatggc tgcatagtac tccatggtat atatgtacca taatttcttt atccaatcta   75180
tcattgatgg gcatttgggt taataccatg tctttgctac cgtgaatagt gctgcaatga   75240
acaataccaa gctattctat ttccaaccat aaatatgttg agaaaaattc aaaggaaaag   75300
taaatgatgg gtgccttttg ttgtcaattt ttatatctca ttttactcag attttcctta   75360
acggatgact gctactcacc tgagttctta tgtttaccag ctctgtgttt ttgaatgagt   75420
cactcaaact ctgtttgccg ttgtcctcat ttgacacatg gagataatca taaaacttac   75480
tgcacaggac tgttgagagg atcaagtaaa ataatataag aaaacatcta gacaagtagc   75540
aagttgtaaa tggatattag atgcttgtca agtttcttac tgcagttctg aattaacagc   75600
taattacaga aagatagtca ttgggacaga acactgcagg tttatcttca cattttcaaa   75660
gccatatttc tgcaatatgg tactgctggg gaatgggaga gtgggcaaga gaacatccct   75720
gccccacccc tagaggtaca cattcatact aggtatttct ttccagatag ttaacccact   75780
tacccgatct gcccagcact catgggatgc aggaaaccct ggaactgctc ataactgtag   75840
cagctcatga agaaccctaa ggaaccacct catctagtac ttctgagaga cctcaacagc   75900
cccgccttct gccactgact tgagacctcc agtgaacagg gttaccttct ccctggggaa   75960
ccagactggc agaaagcatg ccactggtag tagctgttat cttcttctcc ctctgggttt   76020
gtgagttgcc ccctaatcat ttcagtctac agaagagatt gaagtcattc tgtattatta   76080
cctcttcacg tatcgttggc ttatgggaat ttctcttcac ttgcaattgc acttgggcag   76140
ttggaacaac ctgaaatatc tatttccaga ccagcaaata agagtgccca catatcttgg   76200
aaggcatcca tccaaggctt tagcagtaaa atcatacact ggtactggca gaaaccaaac   76260
aaaggcttag aatatttatt acatgtcttc ttgacaatct ctgctcaaga ttgctcaggt   76320
gggaagacta agaaacttga ggtaagtaaa aatgctcaca cttccacttc cactttgaaa   76380
ataaagttct tagagaaaga agatgaggtg gtgtaccact gtgcctgctg gattaggcac   76440
cacagtgtta gagttgtcaa gataacctac acagaaacta tctccgagtc tgtgcctgtc   76500
cacatccttc tccatgtggg caaccacagc ggtttgctca gctgggtgcc cagccggagc   76560
ctgccctccc tgcagctctt ctggaatgtt gcaggaagac atcttagatt ctgctccctt   76620
ggtgtgcaga atcacattgg tgattcatgg tgtccaaacg ggaaaagttt tcttgttccc   76680
tctcagggcg tgcgataagg atgtggctcc cttcttggtg cccctctcct caaacctcta   76740
gggggagcat gcacacgtgc aggttgtggg gctccgaccc cacagcagtg tctagggtg    76800 aatgcttata actcctgagg ccccagtggg cctgtgttac aaggtgtcct tttagtttgg   76860
ctgtccatag gtgacttgct ttagccagct caattagacc ccctgcctta ttgcaaggac   76920
ggagggcttt ctgtatccct gggtttcttg ccttggtgta ctgaaagaat tggataacat   76980
gtgggcttgg agaatgagtg caagtttttt attttttgttt ttgttttgag acggagtctc   77040
gctttgtcgc ctgggctgga gtgcagtggc gcaatctcgg ctcacgcaag ctccgcctcc   77100
cgggttcacg ccattctcct gggcagtctc ccgagtagct gggactacag gcgcccccca   77160
ccatgcctgg ctaatttttt gtattttag tagagacggg gtttcaccgt gttagccagg    77220
attgtctcga actcctgacc tcgtgatctg cccacctcgg cctcccaaag tgctgggatt   77280
acaggtgtga gccaccgcgc ctggccgagt gcaaggtttt attgagtgga agtagctctt   77340
```

```
agcagatggg ggagccagac gggagatgga gtgggaaggt ggttttcccc tggagttgac   77400
tgctcagcgg ccaggctttc ctccaaccac cccgccaaac tctgctttgt tctgccagtc   77460
gatggcctgc agcccgccag tctcgccaaa ctctgctttg ttctgccagt cgatggcctg   77520
cagcccgcca gtctctgtag gtgtgctttt ccacattagt gttcctctcg atgtccagcc   77580
acttgtgtgt gtgcccacta gggtctcagg ggttttatag gcacaagatg gaggcgtggc   77640
gggccagggt ggtcttggga aatgcaacat ttgggcgtgg aggcaggagt gcctgtcctc   77700
acctaggtcc gtgggcacag gcctgggagt ggggccctcg acagggacca cgtccttcct   77760
ttccctgcac ttccctcccc caatcccata tcagtgtcag caattaggat ccaaattagg   77820
gacattttga cactatttcc tacaacatta ggatatctgg gaactctgaa aatacagagt   77880
gggtggctta gagcaaaatt catctgtcta gtaattcgct acgtagagat ttctagtaac   77940
tggttcagaa tgaaagtagg aagcagtata tattttacat agatattccc tgctgttatc   78000
attattttcc catttggttc atgagcattg gaggttttca aagttagagt gatctgtcaa   78060
acatagtaac tgtgtgcttt ttattcgcac ctgaggccat cctgaagaaa tctagggaca   78120
agtaagtaga tctgtaagta aacaatcacc tgtttggggt atatgagaga tgaaagtata   78180
aatcctgtgt cctagaggaa gagcatgcag ctcacttcac actcagggct cagtgctggg   78240
acaaaacaag cactgtgcag tggaacccag ctcctaggca cagtggggga tctcaggatg   78300
ggggctatgc tttggagatc ttgtctttca gggttctgca aagaaaacta aaaatcctga   78360
gtaaaatagg attagatagt taagaagaaa gataatacat gcttcctgca tcggtaaagg   78420
aaataaccat aataataccc ctcagaaatt aataaataag aaataatgat tgacaattat   78480
tttatgttta ttccatgatt aatcattggg tggttgggaa ctttcaaaaa ataatgaaac   78540
aaaatataaa actgtaaaac tgtaaaagtc ctctctcact tctttgaaac tttcaaacaa   78600
caaattaatg atgaaaaatc cggagtttca aagattttct cctatttata cctttagtac   78660
tatggatatc tgacagcata ttgccataca tgcagtctac ttacagtcct tgaagtaatt   78720
gcaacgtatt ttttctccat tctcccttct gagaatcagc ttgtaccatc ctgataggat   78780
aagaggagaa atgctattga aagcccaatg agggaatacc aggagcctcc atggcaggtc   78840 agccccttc caggtgcaga ctcagaatct ggagtcccgc atcctgtccg ccatgattcc   78900
tgaccatggt ggtccacagg gagaatgacc tgagcgcctg agtgagtcct caacagacct   78960
cacctctcac ctgatgcata cataaaagca aagggaagaa gattgttaag gaaatacaga   79020
gcctgagaac atgaactttt caagaaatag gtgaatgaaa agatggaatt cagcttttca   79080
caatgtcagt gttaagtatt ttacatggat tattttattt aatcctcaaa agagcagtgt   79140
agagtgactg tagtggccac acaaggtcag gtcttagaag atgcagtcac tttgactttt   79200
taagagactc ctgggagatt tatggggaag aaaacttaga gacacactag agtgaggaag   79260
aggaaggaaa gagacaccgt atctgtgtga atttaaagta atgaaatact atgtagcaat   79320
taagcagtgt ttttgaagaa ctataagtaa aattgaaaat attcaccatg tatttagcag   79380
gaggatattg aacacagaac tgatttaaat agtaagctct catgtacata catgtatata   79440
ttgaagaacg agcaaaagga aaaaaattct ccaaagttta aagagtgggt gtctctgaaa   79500
ggatgggtga ttttaacatc ttcttggtac ttgcacagat tttacacatt gtaacaaaaa   79560
gctgctacta cttttaaaga tgtatgccat aatggcttca atattttatt gattcatgca   79620
tttaataatg aaactgttta tataacaaca taaaatataa ctatatatgg cacacttaaa   79680
```

```
attattttta tgttttttcca cttaatcata tcactactct atagctctca gaaaaaaaaa    79740
aacaaaaata ccaaccttca tgttaatact ggttactatt gagcagaagg tcagcaaact    79800
atgtctatga ccagcagtct ccagttttgt aaataaagtt ttattgaaat acaaccatgc    79860
ctatttattt atatattgtt tatggctgct tttgctagct gcttttgcac ttgaatggta    79920
gagtacattc agtcagtctt cactatctgt gcattaaata cctgcgaatt caaccaacag    79980
tggatcaaaa atatttgaaa aaataaaaa attacaatac agcaataaaa ataatacaaa    80040
taaaaacaat ataatatagc aactacatac atagtattta cattgtatta ggtattatac    80100
ataattagag atgatttgaa gtgtagagga ggatgtgcat ttgttatatg caggtactat    80160
gccattttat atcagggact tgagcataca tggattttgg tatctgtcgg ggatcctgga    80220
acaaatcccc tgaagattct gagagatgac tgtagctata acagagaccc acaaagccca    80280
aaatatttat tatttgggtc tttacagaaa atgattttca gtcactgtcc tagagtgata    80340
gactcatgag tgacatttat tcatatttag tgtttcccaa tttctcaatt tttctttaat    80400
gacccttgt tacacatcca ccctccccat attagctgtg tgacttcaga taaattagtt    80460
agcatatatt tgattcattt tcctaattgt aaaatggaga acataataat gattactcaa    80520
ataaactgtt gagaaaagta acttaaataa tacaaataaa gttcttgcaa gtgcttgggg    80580
catgcctaat gctcaacaaa ttgaagcact acattaatca tatgagttat tattgcatat    80640
tagaaaataa aattatttag actaatactc taagtccttg gtactcaaag tttgatttgt    80700
gaaccagcag cattggcttc acttaggagc ttcttttaaa tccagtcagt caagcctcag    80760
cccaggccta ctgcgtcaga agctcttttc agaaggtccc tcctacatac tatggtgtgg    80820
ggagtgggag tctaagggcc aaactgttca agatataagc tccacagtct ggtacaagtg    80880
caagccaatc ccatttccat aggatggttg tgtctagtgt cctctctaat ttctggagag    80940
caatattgaa ctgatatttg gcctctctgg ggctgaaata gatggcatcc tcccaattaa    81000
ttaaacaaat atactcaatt gtccacgtat atgtactttt attttcattt ataaatttg    81060
ttataaaatc agcacaaatt ttcagtattt tatatagtga gaaatacagg tgttttataa    81120
ccttgagttt tagatccaca ttcaacccac aggaagagta atttttgctt tgagtacaaa    81180
atacatatca ctgtatcctc atatccacat atcacatatc ctcatatcac tagggctact    81240
gaaaaacgaa ataggaggca acagggaagg ggagagaaat tgaagttaat tgccactgtc    81300
accactcacc cacacctcac ccttcatagg aagagttctc ctctaaccat caccatattg    81360
ccagatctcc tgggcactgg agtatttaga gggccagcca tttcagatct gacaacgctg    81420
cactctacag aaagggttgt cagggaatca ctgtgaccca ctacttcttt ccctgacacc    81480
tgctcagacc aagctaccct tgccacacac taaacattct aggcacaggc atcctcactt    81540
tcctgcttct tcttgggaac acagcctggc agaccagagc atgtcagcac caggagcatg    81600
tagggattca ccttggggtt tgctccagtc atttcacttt gtatatcagg tgaagaaatt    81660
ctttatcact tcatctttac atatcaggtg ttcatgagaa ttaattttct ttgcttacag    81720
ttattctcag ggcgttaaag ttggcacaaa tttaaaatac ccagggcaaa agataaggat    81780
gcttttatac cttgtaaaat atccagccaa gactaaaaat gaagtcaaat actggtgtca    81840
gctgaaacct aagtcggcat tggatgtgtg ttgacaatcg cacctgctca gggtccatta    81900
ggtgttgtgg cttacaatga tgctcatcct tccacttcaa ccttgaaagt aaatttcaca    81960
aacatgaaga tgaggtcatt tactgctgtg attattgagc ccactgggca tcaagcacac    82020
acttccctgc cttctccttg ggacacagca ggatgtcgtt gctggaagca tcatctttc    82080
```

```
ctctctctgg actcttacgg gttccccatc attttgactc ttgaggagag agcaagtaaa    82140
ttatttaatg gtgcatcttt atacctcagg tcttcatatg gatttctctt ctttgcttac    82200
agcttgtttt ggatacaaga aattggagca acctgaaata ttaatttcca gagaaaaata    82260
ttaaaagtcc aaatactatc tggggtggta tctagccgct tatactggct gagacataac    82320
ttgatgcatt ttcctcaaca acatgaccct ctcaattcac ttaggggctg tagctgaaaa    82380
tgatgttcct agatctgttt tgacctacaa gataaattct caggaaaaag gaaatggaga    82440
tagttatgtg cttgctggaa tcacagatga gagatgtcag gacacccgca cagaatccct    82500
ctttaggtct gtgtgtacca gcccccttcc aacaggagca taggcttagc agggttgtca    82560
gggttggact gcacctccca ggacttcccc ttcaacctct ggaaacttga ttatgttcac    82620
acattaggac atacagaaat cagtgtactc tgtgctcaag gtccagggat tacctgaaag    82680
tttatatgat ccagactcaa agagggaatc actgagtggc aggaaacgtg ctgggtatct    82740
tacacatctt atataaccat tgcaatactt tcgcaatgtc atcttcattt ttttccactt    82800
taatatgaaa taatttgaaa gataaaatac cttcttaaac cccaaatgcc catgtttcct    82860
cagctgtgtc ctgtgacctt gaagaagtta gcattcattt gctccactca tgttgggggt    82920
gagtgtgaaa tgaagctcct gccctctcct caggctcatt ccactctgag ggatcctcct    82980
acagtccagc cagcacactt cctttgcaca ggtctcagat cctcctaggg aagggagggg    83040
gcattagatg atccaccgac aaggtggatc cccaccagga tggatcctct tcccggcttc    83100
tgcctgtgat tgcagcagcc gtttattcag ggtactctgc tccctcttgg gcactgctct    83160
aaatccttta catgtaactc atctcatcct tgggacatct tttcacattg gtctgttgtg    83220
attctcatct tacgggggag gaaacagagg cagagcgatg tgatttactt tgtggtcaga    83280
gttcttaact ggggggggggg aggggctggg gttctggctt cagcgtctgt cctcgtaacc    83340
acgctgtgtc ctgactctga gagggaggt aaaaatagca tctaatatgt ggtctctacg    83400
gctagaaaga aaactgatag gaaattaaac tagacatttt agtgaaatta taaaggctga    83460
atgcagacta gtgggagagt gtgagccgct gggggccaaa attttaggga atttcccacc    83520
atcttttaga ctttttctcc aggaacccta tgcaggctct tgcagggaag agcatggaga    83580
atccagagaa agctcccctt tttggtactg gcttagaagg ggaacagtag ccactgtcta    83640
aattcaccca gacctacccc acctcttctc cactgtagaa ggacttaatc tgcaagaaa    83700 ggtttctatg gaatttcatt ttagttgagg gagggaaaag gaagccacca tcaactctgc    83760
ccaatacttt atccctatct ccacagagta atgagtttta atgtgcagaa gggtgggtgt    83820
caaaatcata gcccaaggac actggtgggt gcctcctatg actggaaatg tgccacctct    83880
ggaataagag cagcaacagt tgtgaagtta cattctcaag tcccggtttg accctgcctg    83940
tttaagacag aagctgaatg aaaatagcag agaatggctc ccttcctcac ctcaccacca    84000
tactaccttg agcaaaagca acagtagaat gcagtgaaga gagcttcaaa agacagactg    84060
tctctgggga gcagaacaaa gggatggctc aaagccaaga acaagggatg attagagaaa    84120
tctaaagtct ctaatgtcct atgaagaaca aactccaatc cagacaactt agtagcaaca    84180
acaaacttct aacccagtct aactcctaac tagattaaca caaactccca cactaaaggt    84240
ctggcagaaa gaaagatgca ggcatttttt ttttcttttt tcttttttct tttttttt    84300 ttttttgagg cggagtcttg ctctgtcacc caggctagag tgcagtggct gatctcagct    84360
cactgcaacc tctacctccc gggttcgagt gatttacctg cctcagcctc ccgagtagct    84420
```

```
gggactatag gcatgcgtca ccatgcctgg ctaatctttc tattttagt agagacgggg    84480
tttttaccat attggccagg atggtctcaa tctcttgacc tcgtgatctg cccaccttgg    84540
cctcccaaag tgctgggatt acaggcatga accagcgtgc ctggccaatg taggcatttt    84600
taagcatcaa atatagttat ctcagtatct actgtgttat acaacatcgt cccctttcaa    84660
taaaaaaatc taagtacctt accccaaaac aagaaggaac acagtcttga agccacaaag    84720
caatcatacg catcggactc tgatatgact cagatgtttg agctgtcagg cagggagttt    84780
aaaataactg atgagtatgt taaaggctct aatggaaaag gtagacaaca tgcaaggtca    84840
gacagagaat ttcagcaaag agacagcaat tacataaaaa aattcaaatg aaaatgcaag    84900
acataaaaaa aaaacacagt aacagaaatc aagaatgcct ttgaagggct caccagtaga    84960
ccctatggag ataaggaaag atttggttaa cataaagata ggccactaga tatgacccaa    85020
actgcaatgc aaggagatga gaaagaaaga acaggagaga aagcatatct tcatggaaga    85080
acagaactgt ggacaatatc atattttcaa acatatttgt aactagaatc cctgaaacaa    85140
aagagacaaa gagcagaaca atatttgaa aaaataatgg ctgagagtat tccaaatgta    85200
gtgatagata ccaaaccaca gaacaaaaaa gctaggaaaa caccaaccag gataaatatt    85260
aaaaacagaa caaaatacct agacatatta gatttaaact gttgaaaacc aaaaataaag    85320
agaaactctt gaaggtagct agagggaaaa aagcagattt tccatctgaa accacgcaag    85380
caagaagaca ttggagtgaa atctacaaag tgttaaatga aaaaactgtc acttggcata    85440
aagacagctt cagacaaaat aaaaaactgag agaattcatt gccagcagtt gcacttcaca    85500
agaaatgtct gaagttattc aggcaaaaaa aaaaaaaatg atatgggtca aaaacttgaa    85560
ttcacacaag gaaatgataa gaactggaaa taaaataaat gaaggtaaaa catagtcctt    85620
taaaccttaa ttgctctaaa acaggagttg gcaaactatt tttgcaaagg acccaatagt    85680
aaatatattc tacgttggtg gacaacatag tctctgttgt aactacacaa atgggctatt    85740
gcaacacaaa agtccttgct actcttaagt ctggagggac atggaactgt tataacaacc    85800
gggagggtat ctgtattgaa agggacacag ccaaccggtc ttagtttgag ttcccccagg    85860
aagtgagcct caggctttga ggacagctag ttttgtttggg agacacagga agactagtag    85920
gagagtgagg atgatgtt aagaaaagga aggcagataa ttaaattact ttcattaatt    85980
agatactaaa tgagcaacag gaacctcata gaagttcaaa acctaacaga tcaattaaat    86040
cataatttct tgttttctg ttccttaat tcgtgggact ggccatgtaa aataaataaa    86100
atctgcagac cccatgtgag tctgatggtt agtgtggtag tgaaccaggg aatcttgcta    86160
agtgtcagaa cgtgataaga aagtaaccac agagcagaaa aatattcctg gtgttaccttt   86220
aagttataaa gacagagctt aaaatcgagc acacatatta tatctatgtg aagcaaatga    86280
aaaagatgag cagatattag cctgtaaggg aatacaccaa actgttaata gtagttgtct    86340
ctggttggtg gggacaaaaa gtgactgttt tctctgcatt tctttctgac ccatctaccc    86400
atgttgtctt cccatagcta tttactgccc tttgttctta cagcttccta actgttctga    86460
aatcccttac taatcagagc agtttccctg gtatgcccat cacacatatg ggcatgtggg    86520
acatagagat tagctttttt tctgactaga ttagtaaatt cttataatag aaggacctgc    86580
tgaaccaagg ctggaatttc ctactcttca ctctgaaagc tggaaccaat cccaagggc    86640
tggccacaca cttggttcaa attgggtagt cctggcctgc tttctgcctt cttagagtga    86700
cctaggactt gttcatgtcc aaggccttac cagccacacc tagaaaatag caagaacaat    86760
agtagcaacc atatctatac cattacattt agctcagtac ctctctttt ggatgtctga    86820
```

```
caagtagcca aaaaaattat tgattccaat tccactccct tcccccaatc tccaagcatg  86880
tattattttc ctccccagac tttcctattg cagtaaatgg caacagtata ttgtatcatc  86940
tgatggaatg gcaagggtgt tttctcaagc agatagtgtt ttgttgactt ctgtgttttt  87000
tgtttctcct agtaatgaga gaagagtgca gagacccaac tattactgag tttcctgtga  87060
tatgagatct gaagggagtt tacaggagct cttgaagcta tggtttcacc tgcgagaaag  87120
acacccacaa accaggccca accctgtgtg gtccaatctg agactggagt aggctgtctc  87180
aacagagccc ctgaccgaaa cactacagac ccaatgcagg gaagacccag tcttctctct  87240
aacttactgc aggtttagaa actctttgtg ttcccctga catgtgcagg gcaataggcc  87300
agccatgacg gcaatgattg tcattctgaa gtgcatggcc caaatggccc catggatgta  87360
taatctcctg gtgtcactga agacaaata aaaagaaagt aaattgtgag atataatttg  87420
atattcagat tcaactagcc ccgctcctca cagattattt tgctaggtgt tgtcactgac  87480
tactcaatgc ttttagaat atgcaaatca accatttcat ctgcttttta tttcgtttaa  87540
tatgttctgt gattcctaga aagcaatacc cagcatcctc tatatggcca tttgagatac  87600
agattctcta tattatacag acctagacta tacttgggaa ctgcgttcct tccacacata  87660
tctctccaac tgtgaagtaa ttgatgaaca gggtttggga tctggaaaac ttgaactgaa  87720
atcctggctc agtttgaact ccctaattct gtttcctcac atgacttta atggtaataa  87780
ccatttatag ggtaaagcag aaagagataa atgcatagtt agtgcctgac tcatggtaga  87840
cactatattt atgagttttc ttctctttca ctatcagaaa gcacaggccc atggattgtc  87900
atcctgcagc aggggaagg taagtgaaaa ggagatttgg ggcttagagt agcatatcaa  87960
tttctcaaga catttttcca gacacgagtc ttttatgcaa acatttcttg tttgccaaaa  88020
agaaacaagt gtttcaccag gcatgtttgc ctgtgggagc agtatcagtt gaaaagtatc  88080
tataaatcta caatatgcat agtggcatgt taagtacccc aagtgcaaaa gaaaccctaa  88140
aagactaaat cttcaggtta agaatgaaga caggtggcac aattgctaaa agggagaatc  88200
tgattgaaag tgcagtgacc cggcctctcc caaacactgc cctggtgttt ttagaaacaa  88260
gtgaagatcc actggactat attgtaacat atctgatatt atctaagtga tgacatatgt  88320
gaaatcaaat tatgctaatt tatgaaagtt agtggtccac agattgtcag tatgtgattt  88380
ttttatctct tgtacatgtc agataatgtg tttttttttg cttcagaggg tggtctctct  88440
cagaagtgtc ttaacttact gctgtacctg atttaattaa gatccactac aatttctgaa  88500
agataaacca atgtgaaaaa aatgtgcaaa ttattatttt ggttcatgtt ggcaaccaaa  88560
ccctgaaatg aaatgtgaga tatattttcg tatcttttga tggtctaaca aatttggttg  88620
aagctgttct ctatgaaaat tattatcatc agacttgaaa aagtgatgca aaacttcaag  88680
caatgcagta tcaacttgtg ctttacctca cttgacttac ttgttattta tatatttgtt  88740
cattcataac ccatcttctt ggaagcagga tttaagttgc ctcagtttgt taactcaaga  88800
catgacaaat gtggcgggga ggatgtatgt gttccaaaac acagggttag aggcgaaact  88860
gcttatcttt atacacattc atttgggttt cattttacgc ctttagtaaa actgaacatc  88920
atggtcttca catagttctt ttttttttgta aacttaataa aatatgttat aattcattac  88980
ttactttta cattgtatta cttaaatctt tcatggctgt tgaaatgtag acagcttcta  89040
agacttctga tacttcccca catggttctg gaataaggaa aagcagagga caaagaggga  89100
ttgaatgggc atcatcccat ctatgacagg tgcaaagggt aattgacagt acgaagtaac  89160
```

| | |
|---|---|
| aataacttat tatttttcaga taaaaagaca cagaaataag atctttccat tctaccttat | 89220 |
| gaagtgaagt ctctctgtct gaattattac ataaatgata agagaaaatt aaacagtttt | 89280 |
| tagcccctac tgtgtcccat gctcgattat aaatatcgta caaaagtcct gggaaatagg | 89340 |
| tctaattctc tccatttaaa agatgaggaa acccaggctc tgagaagtgt gtgtgcccaa | 89400 |
| gggcacatca ccaggagtgg aagaactgga atctgaacct gggttttcca attttaaagt | 89460 |
| gtcttttttct tcattcccaa cttcctgaga taataaattta tttcataaga atcctttaaa | 89520 |
| agctcgagta aacttgttaa tgtttattgc tgcagccact ctgtccatct ccaccatcac | 89580 |
| tgcaacaatt caggtcctgg ttgcctctta ttggattatg cgaccaccct ataaaaccat | 89640 |
| ctgcttcagc caaattgctg tcctggggag cgccccttcc tttctgcttg cacatctatc | 89700 |
| tttctccagt gcaaatgtga tcatgtcact ttcctctcta aatttttttag caagtcctca | 89760 |
| ttgtctattc tttcaaaaac atttatttga aaatactata aaaatagaaa attttccaca | 89820 |
| tgcttacttc ctaaaaatta atgtgttaag tttctcctac cccatttcca tcccatgccc | 89880 |
| ctttactcaa tggatacaat aaatctccaa tatgttcctt ctggccacgt gttgctttgt | 89940 |
| aattttaatt ttaatctatt tggaccctgt gttatctggg atgaggtaga gtggtatttt | 90000 |
| tattttctaa ggtaattatt ttcctaatgc ccgtttccaa acaatccatc atttcctttc | 90060 |
| aatttaaaaa tgctgcagcg tgttttaaat atgcacacat atttgacaca ttttctggag | 90120 |
| aatttctgtt ttatttgtct gtttcattat tcttacatca ttatcatatt atctcagtag | 90180 |
| ctttgtgata aaaattaaga tctactatgc caaatgtcta ttcactgtac cattttttcag | 90240 |
| aaaatctttt tcaatcatct catatttatt cactcctgta gaatttaaaa tcaacttatc | 90300 |
| tagcccaaca ttaaacctca cagcctagaa caacaacaac atgtcgtagt aattctgact | 90360 |
| ggaattgctg gaaattttata gatgaattta ggatgtattg gcctctttat gataggagct | 90420 |
| ttttattcat caatgtatgt ttctccattt atttaggttt tatttatgc ccttaggaaa | 90480 |
| actaaacact gtgttcttca tatcattctt gtattttttt ggtaaattta ataaaagatt | 90540 |
| ttataattca ttacttttcc acattttatt agttaaatcc ttcatggctc ttgaaatatt | 90600 |
| gacagctgct aagacttctg atgcttcgcc tcatggtcct gaaataagga aggccagagg | 90660 |
| acaagaagag attgagcggg cgtcattcca tctatcacag gtgtaaaggg tcattgacag | 90720 |
| cgccacataa taattttgaa ttttctatta agaagaaacc cttttccaaac ataattttca | 90780 |
| cccagcccca ttgtcctctc cattgaattg ggggctgtga gctgctgtgt atggacaggt | 90840 |
| accctctgtg acctcattca tatcttcctg aatgaggact caggggactt aggctggagc | 90900 |
| agggtggatc tggagtggac atggaggttg tcaaggcttg tcctcctcag cccttgcaag | 90960 |
| tgaacacctc atctgtactc aggagatcac acagctgacc ccggcttaag atggcagatt | 91020 |
| tttcaacata ttagataact ggatttgttt tttttggtca tgcctcagta taattaaaga | 91080 |
| atgtattatt tcatgggaga tagaattcta caaatttctt ctattattcc aggagaaata | 91140 |
| ataagtcatt gcagaacaca ttttttcatt tggcattgcc ttggtaaagc atcatgttgc | 91200 |
| caaatgataa aagtggcttt ttgaaagtgg agaccgttgt tcaaatttct caagtatatc | 91260 |
| tgcattgaca catttgcatt ttcagttact aaagagcttc ctcctttcag aagtatcttc | 91320 |
| ccaaattgct agcagagagg ctctggtgtt tgtgggaaca aagggctttt tcctttgatg | 91380 |
| taatctcaaa gcagtttcaa cacaattgaa cccctggaaa aaaaaaagac aattctctga | 91440 |
| atacttttcc tggtaattta gaaaagcagt gggttgaccc attaaacctg ctgttttctc | 91500 |
| ttcctgctttt ttttttttcca tttcccttttt ctgttggtgc ttttcaagaa ttactgcctt | 91560 |

```
agaagaaaac aggcaattta tgaggaaaaa ttacaaacta tcacatgtca caaaacctat    91620
attcaaggac ttccaaaaaa gccagaagat gaaattgcta gttcaaagtt gttggattgc    91680
tagtcgtgtc ccgaggatca gaaggctgag attttgtag aagcttagac cggtgtgata     91740
ccactggttg gttcaagata tttgctgaag ggactaagct catagtaact tcacctggta    91800
agtaactttt ctttctgttt ttattccagt aatgaaaaac tgatagatga tttttagaaa    91860
aaaatgatca accttatctg aatatgtcac attcctggcc tcagtatacg aacagcaatt    91920
ttgcagatta gctgaatatg gaaacaaaac gattttgtac atgatatctt cccttccctg    91980
tctgtaagcg gattaaaatt ctactttaag aatacacaca cacacacaca cacacacaca    92040
cacacaaaag atagactctg gcaagaaatt aaaatgtttt gaggcccatg tctatacacc    92100
attagtgtaa gtccttggtc caagttactt ttttgttggt cttttaagtg agagacataa    92160
aaatggagtt ttattaatta cttcttctct gtattttgag atataacata gtgctcccett   92220 cttctgctag cctgccaaac ccatgttatt gattttgatc tcatcctgag aaatagtata    92280
gaaaaaaatt acttcttata gtaaattact atagaaggtc aatacatccc acttattagt    92340
gttctagttt ctttgaggga ggctgaagtc agtcaaaatt tatgcaattg ggactcttgt    92400
tatatcacct ggaaatggcc cggtttaata gaatttgtaa gttcaaccag ccatgtcagc    92460
tccaaggtca atgaaaagag tcttcatcat tttacatctt catttgttca ttcatcctct    92520
cagcaaatat ttatcaaaaa cagttttttgt tctggatgct agagataaaa gggcaaagaa   92580
gacacagtct caacactcaa aagctgccag tctggcagat aagtattcta gattctggct    92640
tggttgggcc ctgtccacgt tctttggcct gtggctgccg gagaagcaga aggtcttggg    92700
ttcatgagct catttttcttt cttaatttgt gtagcagtta ttgcttataa gatctatgta   92760
ttgcgtttgg tgggaggatt tgataaaatg acccaatatt gtccttttaa ggagaaaatt    92820
aatattagca aagtttattg agagccagac accatgctaa atagtttcaa tgctttatct    92880
ccttcctcat cagacctatg caggagatcc tcttagtccc atttcacaga tgaggaaact    92940
gaggcctaga gaagctcagt tactttcttta agtcacatg actagtcact gtggaaaagt    93000
ctgggatcta tctaagcttg tctactccaa agtgcctggt ctggacccctt atgtgatatt   93060 tagaaatatt aagtcatatt tttatacttt gaatatttct tcttctgtag cttgacccta    93120
tgaatggact ctttagttga ctattttctct agtaacaact cccaatttgt attactttt    93180 gtgtattaat acaattcttc tacttctaat tatggcactg aaatgacctc tctcctccaa    93240
aaagtcatat gggatataca tttattaaat actcaaaata taattttag ggtatttctg     93300 tagaatgagt cattttgacg tcattccact cagctgtctt tctgtattgg catcaaattt    93360
gctagatatg ttgaaactga tgtaggagct atcgcagcta tgctatattg cagtgctaag    93420
tcgcataact cagagctgcc tcagattctc tgttgagtag cacacgattt aatttgatga    93480
aactgtatag atattttcaa gtcaaaagta gcagtcttttc agcaatgaat catcattaag   93540
aattcatatt ttctaacaac tcatcagtat tctatcagtg agaactggat tctaaaaga     93600 acttactta ttttattttt ttattttttg agatggagtc tcactctgtc gcccagctgg     93660
aatgcagtgg catcatctct gctcactgca acctccgctt cccagtttca agagattctt    93720
ctgcttcggc ctcctgagta gctaggatta caggctcctg ccactacgcc caactaatgt    93780
tttgggtttt ttttgtattt ttagtagaga tggggtttca ccatgttgac caggctggtt    93840
ttcaactcct gagctcaagt gatccgcttg cctcagcctc ccaaagtgct aggattacag    93900
```

```
ggatgagcca ctgtgcctgg ccaaaaagaa gttattttag aatcaatcta gatacccatc    93960
cctccataca tatgaatccc aaaataccta taaatcatat tgaatatcta tttattaaat    94020
gtcaaacata ggaatcctat tattgtctct ctttgaaaat taaggaaata ttaactctaa    94080
attacactta agacaaagtg tatacaagaa aactttttag ggaagattta gaagattcag    94140
gcaaaatcat gagaaaaggt aaaatcagac tctctaatgt atgggataca aggagagaat    94200
gtacatagcc caaagtgccc agggcaaggt gaggtcagtt cttaaattcc tgattacatt    94260
cagatccagt gtgattttgt ttgacctttg tcttgactta acgtcagcag ggccaatttt    94320
tatgtattta tgtaaatatt gaaaaaaatg ttggcacaat tttaagcaaa acacaaaggg    94380
agattcttat aaaggcttct caggtggtgg gcaagagttg ggcaaaaaaa tcaaggtatt    94440
tggtcccgga acaaagctta tcattacagg taagttttct ttaaattttg caatgtaaag    94500
aagggatggg aggctggcag gcaggagctg gctcagaatt ctaggattcc ctccttggtc    94560
actaatcatg gtgaaatctc cagagaggtc aggtgacttg gttcatgcct taggagtcag    94620
aacttttcct gccctagcat gggagacatt actaaggagc ttagaccaac tgcaaatctc    94680
taaaggatgg aggccttatg ttgttccatt ggtatctctc tgttgaaagt tttgtgaaca    94740
agtttagttt tgagatttta tttcttcagt tctaaaaata accaatggaa aaaattaaaa    94800
aaaaaaaaag taaaatcagc taccctcctt atttggtcac caaaagatga aatatttgat    94860
aatttgacca agaatggtt aatatcaaat gttaaatat ttctcggtgt gaccatattt    94920
agaagtaaca taagctgcat ttattgttat ttaaattggt ccaatgagtt tgtttattat    94980
ttgttagctt aagtttaaag atgtaatttt gcctggatga gagaaacat ctcataaaga    95040 tactcttagt ctgttagatc cactgaaatg aaagttttca gagaattttc acaaagttga    95100
taaagcatcg gaaaaaatga aagcagtttt acatttttaa ttccttagtg gttgagatct    95160
tatgataaaa tgaacttata agttaaaaag tgaccttccg attctctttt atccaattga    95220
cttaatgaga attgtagcaa tcaaattcat aatttgtaat tttctgagaa gtgatttttc    95280
aggaaagtgc ggtgcaagaa aaggtatgga ctttgtttct cgactcctgg agctagcact    95340
ttctatgtaa ctccctttta ggaagtgtat tttgatttac cagttgttca aattataaaa    95400
atgctggttc attatagaaa aattggaaaa cacaaaaata aacaaaaaat tataatttga    95460 tattgacccct catcacatta tcattttgtt atatttttat ttaaacattt ttctctgctt    95520
tttgtttgtt tgttttacaa agttggaatc atactagata cacaataata gatctggctt    95580
tttcacttca cactgcttca taaacattct tttcaaatgt ccttaatatt tttcaatacc    95640
agaacaaagt tgaaacttct gttttcacgt tgatctgtac aaagaagata atggagatta    95700
tttatctaaa gtggatgtta taaagattaa atgaaattaa atatggaaat tacctaccag    95760
aatgcctggc acttggtagg tgatagaaat attatttcct cttctagaat tcaagttact    95820
acccacgaaa ggtctttata cactcaggaa tacagataaa tgtatcgact cccatctatt    95880
cagcagctca cttcagaaca aatatcacta tttgtaaaat gctttctatg tctaaaagac    95940
taattgtacc tgcttctaaa agtaattaga atgttttacg tattatctca aatatgatct    96000
acctgaatac aaggtgattt ttcattttca agagaaaatt tatgtttaag aaaatatgta    96060
ttttcccctc ccccaactcg aatatgtaaa tttatagggc tacaggtaaa acagtcaaat    96120
gtctacctat aacatttaat ttcttacctg gttcatactt tcaaagttaa aaattatatc    96180
aatatcaata tcagttgaga aatattgcct ttttgccct tatatttcat taaaactttt    96240
gttttgatgc ttcacatgca tgtaaagcat ctatctcaga acagctttct aaggcatctc    96300
```

```
aggtcaaagc gtccactttg gaatcctctt atgatggtgt ctctgaatat tttattctaa    96360
gacacaatta ttcactcaca aaataaaagg atatatttt ttccaattta ttctgttatt    96420
ctacagttgt atgaagtaaa aactacagag acattacccc aagtaataat gaccaaatcc    96480
gtgataaatt tctttgcctt ttttttttcct tttaccagtg ctattcccca aactagcatc    96540
attgagttca tttcatgtcg atatctcctc cagttagtcc ttctggatca aagcagagta    96600
ttagaagaac attttttaat atgagaagtt acacaaagac tgtaccatac ataaggcacc    96660
tccccatgtt gtgagagaaa attttgggga aaaaagctt cattttaagt tctggcactt    96720
tctatctaaa tttagtatgt aggtgtccct atcacagagc taggatttgc aaacatagtc    96780
tccattcctt gtgtcttatt tgagcttgac cttacaaaac catcaactcc tggggcaaa    96840 ggagaaacat gctaaatgca caaactcttt gttatttatt taagctatct ctttccaaaa    96900
tctatttgag aagacctaaa ttaaaatata caagcacagt cagaccatta aatatataca    96960
gatgatctaa agccctaagg aaaggagaag gaaaaggcc tgtgattacc tagtgaggag    97020
cacagtttaa aattttatgc tcaaagaag gagaaaaagg taggggaata catacatctt    97080
actaattgat aaaagaagc acaccaaatt ttcaaatatc atattttttt ctattactag    97140
attggaaaaa gacttcaatg catgagtcct ttagaaggaa atggaagagt gggcagtgcc    97200
ttcaacttcc attttggaaa atgaaaggaa tggtcatgaa aaacccactg catattacca    97260
ctgcatcagt gctatgggca tcctgacatt taatgaaatg cgcagatggt gatgctcagc    97320
agacatggtc aggcagataa catgtagtga tctaaagtga caacagagag atggatttga    97380
ggaccaggcc tcttgccttt tctctaccca ttctgccttg aagggtaaag ccaggtgttt    97440
caagctggac tttggcatga actagacaga agtcagtttc aggctgaagt ttctggtgaa    97500
acttggaagg caaataagtt gtgctgctga ttagaaaaag gctcacttgt tttgaaaaac    97560
acaagtgaag aattcccata cactgactgc atatattaga cttttagccaa tgttcccttt    97620 gactttctta acacggtagg taaggcaaag gataacctat taaagattgg gcgtgtgaaa    97680
gccatgtttc ttgtgatgat ggggacgatg gctttgagaa tcccagagca aagtggaatg    97740
caaacagagg aactgagaaa ttattcctcc tgcttaattg ctatggattt aactgccact    97800
ccaaaatgct gaattttttt tagtaagggc aatgcttggt cctataggggt taaaatgtca    97860 tgtcaaggca cacaatcata gcaaacagat tgctaatcat aacaatgaca tcatcatcat    97920
cataatctct tatatttcca tagcattat ttttgaggca gggtcttccc ctgttgccca    97980
ggcaggagtg cagtggtgtg atcaattctc actgcagcct cgaactccta ggctcaagtg    98040
accctcctgc ctcagcttct cgagtagctg ggcctacagt cgtgcacatc atgctcagct    98100
aatgcttttt gtattttag tgaatatggg gtctcactgt gttgcccagg ctggcctcaa    98160
aattctgagc tcaagcaatc ctcccacctc agcctcccaa agtgctggaa ttataggcac    98220
aaaccactgc actgggacct ataacatttt aatcaaattg ctttttata tcttgtttca    98280 ttttggtctc acttcagtgc tggtagcgat gttgaactga ttttgaaaca tcactgtttt    98340
tagacaaata aaacaccaaa agctttaagt tatttgattt gtggagcaac agaacttgtt    98400
atgagcaaaa tgaaccagga ctggaaccct ggtcttttga gaatcccaga ccaccagaat    98460
ttgaagaact cagggaaact gaattagagt ttttgatatg gactgaatca ctgtggaatt    98520
attataagaa actctttggc agtggaacaa cacttgttgt cacaggtaag tatcggaaga    98580
atacaacatt tccaaggtaa tagagggaaa gcaggaaatt attaaactgg aataatgtaa    98640
```

```
taatgtttag aaaaaagagg aattggatgg ggatttgatg tagaaaactt aggagagact    98700
ttaaaacaaa cgctcatact aaaagagaac atagataaca ttgcacagat atcataataa    98760
gatttggctt tgtgcatata cggacttcca taaagggctc atatgtaatg tatgaaatga    98820
tctcattaaa atgtctggcc ctgagaccaa atgtattatg acaggtaagt ttgtgataga    98880
ctctacagag tggacacata ttcatctctg atggtcaaag acatgtttac tcttgttgtg    98940
aaggagcccg ggtgttggag tcaggtccac ctggaactct ggctccacca ctcactgctt    99000
agtgaaattg agtgattatt ctctggcctc agttttctaa tccataaaat gggataacag    99060
tatgaattca gcagggttgt ataagaattg cacaacatag tgtgaattaa gtacttggca    99120
cattgtccaa cccaaaatag gtgcccaaca aatgttttct ggattcacat gtaaagagac    99180
aatgggatct actatggaga gttgctctca gtccatctaa tttacagagc agcaattctc    99240
cagaggattc agctgtactt ctaactgctc aaatggaagg ttatcaacat cagctcacac    99300
acgcaaaaat tgaacttatg gattcgtttc ttgttagcag gcttttttaat cacgtggcaa    99360
aaacattgta ttaagatgtc tgttttttat ttttgttgtt ctatgtgctt tacttaatcc    99420
tttatcttaa ttgatatcat ttctaacacc aacatattgg tcctaagatt tatagccaat    99480
tagtttaggg ttctgttcat atgtctcagg aaaaaaggt taaaatctta ccaaaaatgg    99540
tcaagatatc aaatcaatta aatccagttg gaaacatcat aaatctgaaa tacatattta    99600
aacataaaat ggctataact atttagctaa tgaaaaaata agaatagag aacacttaaa    99660
taaatatcca tatgtagatt taatatatca taccgtctct aaaaactgta gttgatattt    99720
ggtaaattta caatgctgca ttttaataaa ctacaaacaa cttaggcaat ttaactcaaa    99780
tatactattt gattttgcaa ataaatgtac ataaatgaat ccaacaataa aataaatttt    99840
atttattatt ttaaataaaa tatgtaaatt ctatttgtta ttgaagtaag taaaaatgta    99900
ccatacttgg ccataaaaaa ctcttaatat gtacatttta aaagtagtat tttaaaaatc    99960
atgtgagagg atgatccaca atatcggccc ttaccatgtg taatcaagta tgctatttaa   100020
tgattcgtta actactacgt tgagaaagtt ttggaagttc cagattcatt ttgtcctgaa   100080
aagaatgaaa cttaaagaat ctagctaaag aaagggaca agaggcaatg aatgctgtgg   100140
taccgtacag aaaatgtcca agtttatcat ttgatttta atttctttag tacaatgaat   100200
tagaagtatt tcaatgaaga gacactagtt cttaggatga aaattagatt ggaaaatata   100260
ttgactagag actacaatta tataaatata atgtacaatt gaaaaattac tcatatttta   100320
taacatgctt ttaaaattag aagcaaaacta tatggtggag aaatatacac tgtctcacaa   100380
gtataacaag taaaatacta tttgcactaa aagcaaagag tatgaaatta agatgagcac   100440
attatgccta attaaattta tagcatgctc acaaattaat atttctgtat atgtttacta   100500
attttgtatg aaaatcagaa gctttgctac acagacagaa attatcaaga ctgttttctt   100560
ttcttctgaa atgagaaatt taattcttat tttcttagaa attgttcaat tattaaattc   100620
acttcaaacc agccaaagca ttggagtttc aattggaaat caaatagaa agaattgtaa   100680
catttataat ttcagttatt agattaaaaa tacgtgtata acccattaac attccagatt   100740
caagtgatat gcctttgtaa acatatgatg ctttgttatg tatcttgacc ctatccctat   100800
aagaagctct gaaatcatga cttttaatag agcaattata tgtacatttt attcagcagg   100860
ctaagatgaa gagaataatg gagctttaaa acagttaagc agcatatagg acagataaaa   100920
attctgggag agacataaag agtcaaaata tagatacact gatttacaca gaccttctca   100980
ttaatggggt aaatttatat aaaacccagt ataaaaaata caccctggt gcattcttag   101040
```

```
tcattcttaa acttcaaatg aaattccaaa ataaaatgtg cttttggtga atattttctg   101100
aagcaaaatg aaattttgat aagtgcgtta ctgcagaaga ttaacacaag agtatttctg   101160
aaaataatca agaaaaaatt taaataagag ttttggaaag ttgccatttt gtttctaaat   101220
tcaggagatg gtgaataatc tggaggtaca gctgtaaata ctgctgcatc ccaaaacttg   101280
gagggtgcag atgtgaaatt gagatgttat ataaagttag atattaacta ggggactgc   101340 tcatggtata cacattgaag ctacatggtc aacttgatag acagtatgta catgcggaag   101400
tagattctct ttaaaacaag tgactgtgta tgttaaaaat aaaagtgaac aaaatggcta   101460
ggcatggtgg ctcacaccta atcccagg atttgggagg ctgaggcagg cagatcactt   101520
gagcgcagga gttttaaacc agcctggtca atatggtgaa acatgttcct agaaaaaaaa   101580
tattagccag gcatggtgat gcatacctgt agtcccagct acttgggagg ctgaggtggg   101640
aggatcactt gagcctggga agtcgagact gcagtgagct atgatcttgc cgctgcattc   101700
caacctggac gacagagcaa gccccagtct caacaacaac aaaaattttg acattgattc   101760
atatgggaaa taagataaat aataagataa atatggtgca tcgcagaatc agttaaatga   101820
agagtgggag tacacgaaat tgcagaacat gagaatgtgt catatttggc caaagaacat   101880
aagttacaaa ggatggaaaa gggaagtggg aaaaggacca agagtctca tctgtagaga   101940 gatcattaag gttttctgac cttccacttt ccctgccat ccaccttgaa aacctgcttc   102000
actatgatga aacaaagag attaaaaaat aaaataaata tgctcatgaa ctttggaagc   102060
cctggtagga ggcagttaaa aatcacactc atcacagcat gtgcagaata aacaaaggcc   102120
aggttttcgt ccagcatctg acatttgaga gctgtgactt ttggcaagtt atttaatgtc   102180
ttgattctct tttcaacatc tgtaaaataa gcacaataat aagtactgtg cagcctatcc   102240
tggatgaaag gccgcagtgg acaccagctc aatggcatct tctcttttta tggttatgta   102300
ctaggccact ccaaactgtg caatgtgtgt gtttctctaa tgattctttt aaactcatat   102360
ttcatttctc cccatagata aacaacttga tgcagatgtt tcccccaagc ccactatttt   102420
tcttccttca attgctgaaa caaagctcca gaaggctgga acatacccttt gtcttcttga   102480 gaaatttttc cctgatgtta ttaagataca ttggcaagaa agaagagca acacgattct   102540 gggatcccag gagggaaca ccatgaagac taacgacaca tacatgaaat ttagctggtt   102600
aacggtgcca gaaaagtcac tggacaaaga acacagatgt atcgtcagac atgagaataa   102660
taaaaacgga gttgatcaag aaattatctt tcctccaata aagacaggta tgtgttacg   102720 catatcatct gtcagaacac ttctttgaaa gtgaatgctg cattttttcc tttcagtatt   102780
aatgaaaaac aaacataaat ctttcttaaa tattgttaca tttaatggta gcataaatgc   102840
cctgctactt ttctatagaa ttaaaatggt ataggttttg gagaaaacaa aattgaaaaa   102900
gttactgaag gtttgtcagc ctcagctcca ttatccaaaa taagaaagtc acgtgctggt   102960
ttttagggtt gttagatgga ttaaagaaac aacatacaca gaagcatcta gcaacgtgac   103020
acgtggtaaa cgctcaaaaa gtgttctccc ttcttttgat gactttactt gatcaggaaa   103080
taacatatat atgtctttca ggaatgttct gcccaagcag gagagtcact cacctcaatc   103140
ttgctaccca caaagtttaa cctaaaaaca acgggttcat tgttgacaaa atgatgttta   103200
tctgttgttg acagaatgat gtttatctaa aaacagttcc aatttctat ttcctttgct   103260 gagacacaaa ggggaggcaa atgtgcaaag cttgagggta gtcttaccac tgtgcttaag   103320
tgttctgatt tttctagtga tcagggcaaa ataaaaagta tagtaagttc caaggcagtg   103380
```

```
aatattatac aggagagaag ttacagtttt ataatgtgtt ttcctttaca ctaaattcta    103440
aaagtaaaaa gtctttttt tttttttgaca gagtttcact cttgttgccc aagcaggtgt    103500
gctatggtat gatctcagct cactgcaacc tccacctccc gggttcaagt gattctctta    103560
cttcagcctc ccgacaggct gggattgcag gcgcctgcca ccacacctgg ctaattttg    103620 tgttttagt agagatgggg tttcaccatg ttggccaggc tggtctcaaa ttcctgacct    103680
caagtgatcc atccacctcg gcctccaagt gctgggatta gggcgtcag ccactgtgcc    103740 cagcctaaaa gtaaaatgtc tttcatgagc ttcccaaggc agctacgtta aggaggacac    103800
ttctcttaat gtcattctac agtagatttc taatgctctt tcttggaagt ttgttttct    103860 gagaaaagct aaaatataa catggaagtg atcatattat ataatcaatg aagtgctttt    103920
caaggagata aaactaatct ggtccacact tgcaaccaac cttgattgag agagagagag    103980
aactcaggat acacttgaag attttattat ggggaacagt tactttattc ttttacctc    104040 aatcaatgca tggaaataag tgatagtcat tttcatttat cttttaataa atgaagtcac    104100
catgaggaaa ataaaaagac attgaaaacc cattaaagtc agcccttaaa gatatttgga    104160
catgcagact tgataactaa cgtttgcatt cttgagactt acccaaaacc catacctcaa    104220
gtccaagttt ttagaattca tgaaataaag atctcagtga gtgcataaaa ttgcgcacca    104280
gaatcatatc cgtatagaca gaacacatc tactagaaaa ataataaacc aacacaccaa    104340
tgcaactgtg ttttcttctg ttttaaagta tgttgtcttt gtatgcatgt ttgcttcttc    104400
cttttttttt ttaacatcac agataaattc aactctcacc tcaggtttta ttgagagaac    104460
tgtcaatgtg acttggcctc tgtctttcta gtcccagaaa gaattgcact gaaatctgag    104520
ctcctgtaat aaaaacaacc atttgctgag agtaattaac atactgaaag agattttctt    104580
agagtacaca atggtgacat tatattgcct ctttataaat aactttctat ctatttctgt    104640
ggattattcc tacaaagtac ttttcatatg tccaatttct tttcttcccc tacaactact    104700
gtctgaatac tggctctgct attttgctgat atgattctcg gcaagttgcc tgcacttttt    104760
aaactttatt tcctcattca gaacatgggg ccatacataa tacaactcac ttcagtgtta    104820
ttggggaatt aaacaaaaaa tgcatgggaa gcatttaaca tagtgcctga cacaataatg    104880
agtactcagt agatgttagc ttttattaat attgttgttg ttatgtccag aaacactata    104940
cctccagaaa atcatgggta cttgctgggg acattgggga tatgcatgat ttggaaagaa    105000
atgactgctt tttttgctta gatgagaaat ttttctaagc cagactcctt caaatatgta    105060
agattctgtt gtggattcaa ggactgaaag aattcttggc cgagtgtggt ggcttatccc    105120
tgtaatccca gcattttgtg aggacaaggc aggaagattg cttgagtcca ggagtttgaa    105180
accagcctgc gcaacatggc gaaaccctgt ctctacaaaa aatacaaaca ttagctcgga    105240
gtgagtgctg acatgtgcct gtactcccag ctactcagaa ggctgagatg ggaggatctc    105300
atgagcctgg ggagtttgag gcttcagtga gccgtgatga caccgtacta tactccactc    105360
cagcctgggt gacagtgaga ccctgcctca aaaacaaac aaacaaacaa acaaacaaa    105420 attaatcttt ttgctgatgt catgtcagca gtgtgtgttg aaggctgtaa agcagccatt    105480
tgttcagttt atttttccat tgaacaagta tttatcaaaa acatactttg tggcagtcac    105540
tatgctagga gctatgaata cagaaggaaa agtaaatgct cttggatact acactccagt    105600
tgtgataaaa aagaaaaaat gtattcttca ccaacttcaa catcttgatg tgcaaaaaca    105660
taatacatga attagatcta cctaattaca cagaattaga ccaattgttt ctggaattgt    105720
gggctcatat ttttaataac tgtcctcctg cctctctgtc gacaggtttt ataaatattc    105780
```

```
atttaattac acacacacac acgaacaatt gactagtact tgctctcatt cttctagatg    105840
tcatcacaat ggatcccaaa gacaattgtt caaaagatgc aaatggtaag cttttgtgtt    105900
tttcccttcc tcctgatcat tttgttttga acttctctgg cttgaaaaat cagggaatgg    105960
attttgctag gttggatgct gcagaatgga cctagtgata ttttaaatta gtccctcatt    106020
ttctaggagt tgtattaaca aacctaacta ctgctttggg gtatgagatg actgtaaatt    106080
agagagggta cagtggtata gtgatatgct tttaattatt tcaaaaaaaa gattttattc    106140
attcatgtgt ctttttttctt tttcttttct ttttttttttt ttttttggaca gagtcttgct    106200 ctgtcaccca ggctggagtg cgtggcagt atctcagctc accacaacct ccgcctcccg    106260
gcttcaagtg attctcctgc ctcagcttct cgagtagctg ggactacagg cgcgtgccac    106320
catgcccggc taattttgt attttagta gagttgggt ttcaccatgt tggccaggat    106380
ggcctcgaat tgtgacctc gtgatctgcc ccctcgccct cccgaactgt tgggattaca    106440
ggcgtgagtc actgtgcccg gcctcctgtc ctgtcttttg tttaatgact gggaaaaaca    106500
tgataccatg ttgcttctcg agttgttttg tttagtctt tggtctttgc tagtagctaa    106560
taacacgaac tagtgtttat caagtgcttt ttacacagaa gggcttgggc tgtgttctgc    106620
attttcttgt ttaaccctct taaaactcct ataaaatggt acatattttt ctcccaattt    106680
acagtccctt taaagcaaat aattataaaa atccctatac atgtcacaca gctagatctg    106740
ggatttcaaa tcaggccatc aaacaaagag tttatgtact tagtaagttt tctgttcttt    106800
ttctacaata gagtcagata gcaagaaatt accagccag gaacctgaaa caaaacggac    106860
atcatgtggg gctgggtggg tgcatgggct ttgcagactg gactttcact ccagctcttt    106920
taatgattag gtgtaagtga cctacatttt gtgagcaaca gttttctcat cagccaacaa    106980
agaataatta caccagattc acagttattg aagagataaa ggcatgaatg tgagatgtct    107040
ggcatagggc atctcattta gcagacacag aatgagtact tgtttctggc ttttctctc    107100 tacatatgca caaagaatgc gactagaagc atgggctcta gccctgctca actttcctct    107160
atttccaata ccaagggct ctgacttagg ctgccacacc aggcaaggag ggcagtacca    107220
cctcacttga ccaagggcag ggagtcacgg acacatcact tcttgagatc cttttccaca    107280
ccaaggactg atgtttctgg aattctcact ttatgaagac aaaacatata aatggaaatt    107340
ttctcaggta gagactcact cttgtagctc attgagtagg cactagtggt ccaccccac    107400 tgtctttact tattccttga catcacatat ctcttgcaaa acctcaaata atattaaatg    107460
caatcaccca ataatagcat agccataatt agaggcattt aggaaagaca ggtgagtgtg    107520
ccacaactac ctaacacatc agcaaatctg gattaaccac tttctttgat tttccacaat    107580
gcaaccttac tttttaatag ttgggaatgt tctaagtgaa tttagcagag gttgttaatc    107640
aacttgaaag ctgaattctg acttgtctga ctcttggtgg tgctggtagc agtagatgtt    107700
tacttttagg ttttggtggt ggtggaatat cacttcaacg taaatcatca gaaataagta    107760
tttgtgaacc cctctcgcat taatgtatct tattctgtaa aaagaacatg tgcaatttct    107820
cttagataca ctactgctgc agctcacaaa cacctctgca tattacatgt acctcctcct    107880
gctcctcaag agtgtggtct attttgccat catcacctgc tgtctgctta aagaacggc    107940 tttctgctgc aatggagaga aatcataaca gacggtggca caaggaggcc atcttttcct    108000
catcggttat tgtccctaga agcgtcttct gaggatctag ttgggctttc tttctgggtt    108060
tgggccattt cagttctcat gtgtgtacta ttctatcatt attgtataac ggttttcaaa    108120
```

```
ccagtgggca cacagagaac ctcactctgt aataacaatg aggaatagcc acggcgatct   108180
ccagcaccaa tctctccatg ttttccacag ctcctccagc caacccaaat agcgcctgct   108240
atagtgtaga catcctgcgg cttctagcct tgtccctctc ttagtgttct ttaatcagat   108300
aactgcctgg aagcctttca ttttacacgc cctgaagcag tcttctttgc tagttgaatt   108360
atgtggtgtg tttttccgta ataagcaaaa taaatttaaa aaatgaaaa gttgacttt   108420 gtccatggta ttttaattgg atgacatcaa attgaacatc caaggtaaga aacagcatgg   108480
caattgggct gtggaattct gtattggttg taagaatggt ccaacacccc atttctaatt   108540 cttccctga atcgtggtt atcacacctt ctaagaagaa ctacaaccaa atgaaggagc   108600
tcatgtgact tctgtttgaa aggtcaccag agtcagattc attcggttta ggacattcca   108660
gtggctatag acactatct actgtgacgc gtaccgtgtg agctcagctc tagagtgttt   108720
cacagacact gtgtttcctg atcctcacga tacccccatg agagctgccc taaaagcaga   108780
gaggcagcgt gatggagagg ttcagcacat gctctctgat cccaggaatc ctgggtatgg   108840
tgtttcgtat ctgtgtgacc tcaggtgagt tccaggaact ctatgtgcca taatctcctc   108900
atgtaaaatg aagttataat gccccgtttc ctggagttat gtggattaga tgagttaatg   108960
acacctggca catgcaagtc ctccacagtg tcggcacgca ctgttggtag ctctactcta   109020
gagacagtaa taaccaaaa agtatctgac acaggcctca atcaacttag aagtttattt   109080
tgcctatgtt aagggcatgc ccaacttcct gagataataa tttatttcat aagaatattt   109140
taaaaactcg agtaaacttg ttaatgttta ttgctgcagc cactctgtcc atctccacca   109200
tcactgcaac aacgcaggtc cttgttgcct cttattggct tatggtgacc acctataaaa   109260
ccatctgctt caccccaaatt gctgtcctgg ggagtgcccc ttccttttctg cttgcacatt   109320 tatcttcctc aagtgcaaat gtgatcatgt gactttcctc cctaaatctt ttagcaagtc   109380
ctcattgtct attcttcttt caaaaacatt tattttgaaaa tactattaaa atagaaaatt   109440
ttccacattc ttacttctta aaaattaatg tgttttaagt ttctcctact ccatttccat   109500
cccatgcctc tttactcaat ggatgcaatt attcttctac atgttccttc tggccatgtg   109560
tagctttgtc attttaatttt taatctattt ggaccctgtg ttatctggga tgaggtagag   109620
tgatattttt atttctcag gtaattattt gcctaatgcc tgttccaaa taatccacca   109680 tttccttaca atttaaaaat gctccagcat gttttttaata gctacacata tttgacacat   109740
tttctggaga atttctgttt tatttgtcta tttcattatt cttgtatcat tatcatatta   109800
tctcagtagc tttgtggcaa gtattaagat ctactatgcc aaatgtctat tcactgtacc   109860
atttttcaga aaattctttt tcaatcatct catatttatt cactcctgta gaatttaaaa   109920
tcaacttatc tagcctaaca ttaaacctca caccctagaa caacaacatg tcgtagtaat   109980
tctgactaaa attgctggaa atttatagat gaatttaggg tgtattggcc tctttatgat   110040
agaagctttt tattcatcaa tgtatgtttc tccatttatt taggttttat tttatgcccct   110100 taggaaaact aaatactgtg ttcttcatat cattcttgta ttttttttggt aaatttaata   110160 aaagatttta taattcatta cttcttcaca ttttattagt taaatccttc atggctcttg   110220
aaatattgac agctgctaag acttctgatg cttcccctca tggtcctgaa ataaggaagg   110280
ccagaggaca aaaagagatt gagtgggcgt cattccatct atcacaggtg taaagggtca   110340
ttgacagcgc cacataataa ttttgaattt tctattaaga agaaacccctt tccaaacata   110400 atttttcaccc agcccccattg tcttctccat tgttgtgggg gctgtggcct gccgtgtatg   110460
gataggtgcc ctctgtgacc tcactcatac cttcctgaat gaagactcag gagacttagg   110520
```

```
ctggagcagg gtggatctgg agtggacatg gaggttgtca aggcttgtcc tcctcagtcc    110580
ttgcaactga acacctcatc tgtacacagg agatcacaca gccgacacca gcttaagatg    110640
gcagattttt caacatatca gataactaaa tttttttttt tggttatgcc atagtttaaa    110700
taaagaatgt attacttcat gggacataga attctacaaa tttcttctgc tattccagga    110760
aaaatgataa gtcattgtgg aaaacatttc ctcatttggc attgccttgg taaagcatcg    110820
tgttgccaaa tgatacaagt ggcttttga aagtggagac ctttgttcaa atttctcaag    110880
tatatctgtg ttgacacatt tgcattttca gttactaaag agcttcctcc tttcagaagt    110940
atcttcccaa attactaaca ggccctggtg tttgtgggaa cagaagggct tttcctttga    111000
tgtaatctca aagcagtttc aacacaattg aaccctggaa attaaaaaa gaaaaaaaac    111060 gacaattctc tgaatacttt tcctggtaat ttagaaaagt agtgcattga cccactgagc    111120
ctgctctttt ttctctctat cgcccaggct ggagtgcaat ggcacgatct cggctcactg    111180
caacctctgc ctccctggtt caagcaattc tcctgcctca gcctcccgag tagctgtgac    111240
tacaggcaca cgccaccacg cccggataat atttttttgt atgttagtag agacggggtt    111300
tcactgtgtt gccaaagctg gtcttgaact cctgagttca ggcaatccac ctgactcagc    111360
ctctgaaagt gctaggatta caggcgtgac ccactgcgcc cggcctttct tttttgttg    111420 ttgttggttt tttatcttaa catttctttt ttctgttgat gctttcaag aattactgcc    111480 ttagaagaaa gcaggcaatt tatgaggaaa aattacaaac tatcacatgt cacaaaacct    111540
atattcaagg acttccaaaa aagccagaag atgaaattgc tagttcaaag ttgttggatt    111600
gctagtcatg tcatgaggat cagaaggttg agatttttgt agaagcttag accagtgtga    111660
tagtagtgat tggatcaaga cgtttgcaaa agggactagg ctcatagtaa cttcgcctgg    111720
taagtaattt tttttctgtt tttattccag taatgaaaaa ctgatagatg tttttagaa    111780 aaaaatgatc aaccttacct gaatatgtca cattcctggc ctcagtatac gaacagcaat    111840
ttttcagggt agctgaatgc ctggcacttg gtaggtgata gaaatattat ttcctcttcc    111900
agaattcaag ttactaccca agagaggtct ttatacactc aggaatacag ataaatgtat    111960
caatccccat ctattcaaca gctcacttca gaagaaatgt cactattcat aaaatgcttt    112020
ttatttctaa aagcctaatt gtacctgctt ctaaaagcaa ttagaatgtt ttacgtatta    112080
tctcaaatat gatctgcctg aatacaaggt gattttcat tttccagaga aaatttatac    112140
aagtttaaga aaatatgtat tttcccctcc cccaacttga atatgtaaat ttatagggat    112200
acaagtaaaa aagtgaaatg tctaattata acattcaatt tcttaactgg atcatacctc    112260
aaagttaaag attatatcaa taccaatatc agttgagaaa tattgccttt tttgcccta    112320 tatttcatta aaattttgt tttatgcttc acatgcatgt aaagcatcta tctcagagca    112380
actttctaag gcatctcagg tctcagtgtc cattttggat tcctcaaatg atgatgtccc    112440
tgaatatttt actctaagaa acaatgatcc actcacaaaa taaaggaaa ttattttttc    112500 cgatttattc tgttattcta cacttgtatg aagtaagtaa gaactacagg gactttagct    112560
ccaagtaata atgaccaaat ccatgataaa tttctttgct ttttttcctt ttaccagtgc    112620
tatccccaaa actagcattc attgagttca tttcatgtcg gtatctcctc cagttagtcc    112680
ttctggatca aagcagagta ttagaagaac attttttaat atgagagttt acacaaagac    112740
tgtaccatac ataaggcacc tccccatgtt gtgagagaaa aattttggaa aaaaagcctc    112800
attttaggtt ctggcacttt ctatctaaat ttagtatgta ggtgtcccta tcacagagct    112860
```

```
aggatttgca aacatattct ccattccttg tgtcttattt gagcttgacc ttacaaaacc   112920
atcaactcct ggggacaaaa gagaaacatg ctaaatgcac aaactctttg ttatttattt   112980
aagctatctg tttctaaaat ctatttgaga agacctaaat taaaatacac aagcacagtc   113040
agaccattaa atatatacag atgatctaaa gccctaagga aaggagaagg aaaaaggcct   113100
gtgattacct agtgaggagc acagtttaaa attttatgct caaagaagg agaaaaaggt    113160 aggggaatac atacatctta ctaattgata aaaagaagca caccaaattt tcaaatatca   113220
tattttttct attactaaat tggaaaaaga cttcaatgca tgagtccttt agaaggaaat   113280
ggaagagtgg gcagtgcctt caacttccat tttggaaaat gaaaggaatg gtcatgaaaa   113340
acccactgca tattaccact gcatcagtgc tatgggcatc ctgacattta atgaaatgcg   113400
cagatggtga tgctcagcag acatggtcag gcagataaca tgtagtgatc taaagtgaca   113460
acagagagat ggatttgagg accaggcctc ttgccttttc tctacccatt ctcccttgaa   113520
gggtcaagcc aggtgtttcg agcgggactt tggcataaac tagacagaag tcagtttgag   113580
gctgaagttt ctggtgaaac ttggaaggca ataagttgt gctgctgatt agaaaaaggc     113640
tcacttgttt tgaaaacac aagtgaagaa tttccataca ctgacactga ctgcatatat    113700
tagactttag ccaatattcc ctttgatttt cttaacacgg caggtaaggc aaaggataac   113760
ctattaaaga ttgggtgtgt ggaaggcatg tttcttgtga tgatgggac gatggctttg    113820 agaatcccag agcaaagtgg aatgcaaaca gaggaactga gaaattattc ttcctgctta   113880
attgctatgg atttaactgc cactccaaaa tgctgaattt tttttagtaa gggcaatgct   113940
tggtcctata gggttaaaat gtcatgtcaa ggcacacaat catagcaaac agattgccaa   114000
tcataacaat gacaccatat tcatcataat ctcttatatt tccacagcat ttttttttga   114060
ggcagggtct tcccctgttg cccagtcggg agtgcagtgg tgtgatcaag ctcactgca    114120 gcctcgaact cctaggctca agtgaccctc ctgcctcagc ctctcgagta gctgggcgta   114180
cagtcgtgca catcatgctc agctaatgct ttttgtattt ttagtaaata tggggtctca   114240
ctagatactg ggttgcccag gctggcttca aaattctgag ctcaagcaat cctcccacct   114300
cagcctccca aagtgctggg attataggca cgagccactg cactgggacc tataacattt   114360
taatcaaatt gcttttttat atcttgtttc attttggtct cacttcagtg ttggtagcga   114420
tgttgaactg attttgaaac atcactgttt ttagacaaat aaaacaccaa aagctttaag   114480
ttatttgatt tgtggagcaa cagaacttgt tatgagcaaa atgaaccagg actggaaccc   114540
tggtcttttg agaatcccag accaccagaa tttgaagaac tcaggaaac tgaattagag    114600 ttttttgatat ggactgaatc actgtggaat tattataaga aactctttgg cagtggaaca  114660
acacttgttg tcacaggtaa gtatcggaag aatacaacat ttccaaggta atagagggaa   114720
ggcaggaaat gattaaactg gaataatgta ataatgttta gaaaaagag gaattggatg    114780 gggatttgat gtagaaatcc taggagagac tttaaaacaa atgctcatac taaaagaaa    114840 catagataac atggcacaga tatcataata ggatttggct ttgtgcatat acggacttcc   114900
ataaagggct catatgtaat gtatgaaatg atctcattaa aatgtctggc cctgagacca   114960
aatgtattat gacaggttag tttgtgatag actctataaa gcggacacat gttcatctct   115020
gatggtcaaa gagatgttga ctcttgttgt gaaggagccc gggtgttgga gtcaggtcca   115080
cctggaactc tggctccact actcactgct tagtgaaatt gagtgattat tctctggcct   115140
cagttttcta atccataaaa tgggataaca gtatgaattc agcaggggttg tataagaatt  115200 gcacaacata gtgtgaatta agtacttggc acattgtcca acccaaaata ggtgcccaac   115260
```

```
aaatgttttc tggattcaca tgtaaagaga caatgggatc tactatggag agttgctctc   115320
agtccatcta atttacagag cagcaattct ccagaggatt cagctgtact tctaactgct   115380
caaatggaag gttatcttaa catcagctca cagacaaaaa ttgaacttat ggattcgttt   115440
cttgttagca gactttttaa tcacgtggca aaaacattgt attaagatgt ctgttttta    115500
tttttgttgt tctatgtgct ttacttaatc ctttatctta attgatatca tttctaacac   115560
caacatattg gtcctaagat ttatagccaa ttagtttagg gttctgttca tatgtctcag   115620
gaaaaaaagg ttaaaatctt accaaaaata gtcaagatat caaatcaatt aaatccagtt   115680
ggaaacatca taaatctgaa atacatattt aaacataaaa tggctataac tatttagcta   115740
gtgaaaaaat aagaaataga gaactcttaa ataaatatcc acatgtagat ttaatatatc   115800
ataccgtcta taaaactgta gttgatactt ggtaaattta caacgctgca ttttaataaa   115860
ctacaaacaa cttaggcaat ttaactcaaa tatactattt gattatgcaa ataaatgtat   115920
ataaatgaat ccaacaggtt tatttaaata aataaaatat atatattcta tttgttactg   115980
aagtaagtaa aaatgtacca tacttgacca taaaaaacac tcttaatatg tacattttaa   116040
aagtagtatt ttaaaaatca tgtgagagga tgatccagaa tatcggccct taccatgtat   116100
aatcgagtat gctatttaat gattcgttaa ctattacctt gagaaagtta tggaagttcc   116160
agattcattt tgtcctgaaa agaatgaaac ttaaagaatc tagctaaaga aaggggcaag   116220
agacaatgaa tgctgtggta ccgtacagaa aatgtccaag tttatcattt gatttttaat   116280
ttctttagta caatgaatta gaagtatttc aatgaagaga cactagttct taggatgaaa   116340
attagattgg aaaatacatt gactagagac taaaattata taaatataat gtacaattga   116400
aaaattactc atattttata acatgctttt aaaattagaa gcaaactata tggtggagaa   116460
atatacactg tctcacaagt ataacaagta aaatactatt tgcactaaaa gcaaagagta   116520
tgaaattaag atgagcacat tatgcctaat taaatttata gcatgctcac aaattaatat   116580
ttctgtatat gtttactaat tttgtatgaa aatcagaagc tttgctacac agacagaaat   116640
tatcaagatt gttttctttt cttctgaaat gagaaattta attcttattt tcttaagaaa   116700
ttgttcaatt attaaactca cttcaaacca gccaaagcat tggagtttca atgggaaatc   116760
aaaatagaaa gaattgtaac atttataatt tcagttatta gattaaaaat acgtgtataa   116820
cccattaaca tcccagattc aagtgatatg ccttttgtaaa catatgatgc tttgttatgt   116880
atcttgaccc tatccctata agaagctctg aaatcatgac ttttaataga gcaattacat   116940
actcatttta ttcagcaggc taagacaaag agaataatgg agatttaaaa cagttaaata   117000
gcatattagg acagatacaa attctgggag agacataaag agtcaaaata tagatacact   117060
gatttacata gaccttctca ttaatggggt aaatttatat aaaaaccagt ataaaaatta   117120
cacccctggt gcattcttag tcattcttaa acttcaaatg aaattccaaa ataaaatgtg   117180
cttttggtga atattttcta aagcaaaatg aaattttgat aagtgcatta ctggagaaga   117240
ttaacacaag agtatttctg aaaataatca agaaaaaatt taaataagaa ttttggaaat   117300
gttgccattt tgtttctaaa gtcaagagat ggtgaataat ctggaggtac agctgtaagt   117360
actgctgcat cccaaaactt ggagggtgca gatgtgaaat tgagatgtta tataagtta    117420
gatattaact aggggggactg ctcatggtat acacattgaa gctacatggt caacttgata  117480
gacagtatgt acatgcggaa gtagattctc tttaaaacaa gtgactgtgt atgttaaaaa   117540
taaaagtgaa caaaatggct aggcatggtg gctcacacct ataatcccag gatttgggag   117600
```

```
gctgaggcag gcagatcact tgagcgcagg agttttaaac cagcctggtc aatatggtga  117660
aatatgtctc tagaaaaaac aaatattagc caggcatggt gatgcatacc tgtagtccca  117720
gctacttggg aggctgaggt gggaggatca cttgagcctg ggaagtcgag actgcagtga  117780
gctatgatct tgccgctgca ttccaacctg gacgacagag caagcccag tctcaacaac  117840 aacaacaaaa attttgacat tgattcatat gggaataag ataaataaca agataaatat  117900
ggtgcatcgc agaatcagtt aaatgaagag tggaagtaca cgaaattgca gaacatgaga  117960
atgtgtcata tttggccaaa gaacataagt tacaaaggat ggaaaaggga agtgagaaaa  118020
ggaccaaaga gtctcatctg tagagagatc attaaggttt tctgaccttc cactttcccc  118080
tgccatccac cttgaaaacc tgcttcactg tgatgaaaca aaagagattt aaaaataaaa  118140
taaatatgct catgaacttt ggaagccctg gtaggaggca gttaaaaatc acactcatca  118200
cagcatgtgc agaataaaca aaggccaggt tttcgtccag catctgacac ttgagagctg  118260
tgacttttgg caagttattt aatgtcttga ttctcttttc aacatctgta aataagcac  118320 aataataagt actgtgcagc ctatcctgga tgaaaggccg cggtggacac cagctcaatg  118380
gcatcttctc ttttatggt tatgtactag gccactccaa accgtgcaat gtgtgtgttt  118440
ctctaatgat tcttttaaac tcatatttca tttctcccca tagataaaca acttgatgca  118500
gatgtttccc ccaagcccac tattttcctt ccttcgattg ctgaaacaaa actccagaag  118560 gctgaacat accttttgtct tcttgagaaa ttttcccag atattattaa gatacattgg  118620
caagaaaaga agagcaacac gattctggga tcccaggagg ggaacaccat gaagactaac  118680
gacacataca tgaaatttag ctggttaacg gtgccagaag agtcactgga caagaacac  118740 agatgtatcg tcagacatga gaataataaa aacggaattg atcaagaaat tatctttcct  118800
ccaataaaga caggtatgtg tttacacata tcatctgtca gaacacttct ttgaaagtga  118860
atgctgcatt ttttccttc agtattaatg aaaaacataa atctttctta aaaattgtta  118920
catttaatgg tagcgtaaat gccctgctac ttttctatag aattaaaatg gtataggttt  118980
tggagaaaac aaaattgaaa aagttgctga aggtttgtca gcctcagctc cattatccaa  119040
aataagaaag tcacgtgctg gttttttaggg ttgttagatg gattaaagaa acaacataca  119100
cagaagcatc tagcaacgtg acacgtggta aacgctcaaa aagtgttctc ccttcttttg  119160
atgactttac ttgatcagga ataacatat atatgtcttt caggaatgtt ctgcccaagc  119220
aggagagtca ctcacctcaa tcttgctacc cacaaagttt aacctaaaaa caacgggttc  119280
attgttgaca aaataatgtt tatctgaaga taactgtaga tcatatttat ctgtagataa  119340
tgtttatctg tggagtgtgg ctctacaaaa catagaatag tcttggtcac tgcagtttta  119400
tagaggcctt gggttttca gagtttcatt ttatatatca ccataaagta acatttcata  119460
attacaggtt ggtaaggctt acatgtacaa acattcttcc attttccata ataaatgcat  119520
ttcctgccat tggtgaatgc agctcaataa acatttattg tacaattatg acacgccagg  119580
cttagtggaa atgtggatga acagacaagg atgagttact gtcctaagga tgatgcatga  119640
cagtgcagag aatatactct cttcctgatc actcagggtc actcatgatt catgcgcgag  119700
gtcccaaaac agtgcctttg atgcagattc tgtacatctc tagacgattg gtccaagggc  119760
tgaatgtgct ctggcccagt ggtccagtct gtcactatat gtcaacatcc tgaatatgaa  119820
cataacagtc caacatctca agagtgggca tgaaaaggac tcattttgtg cttttttcctg  119880 tggttaacaa gtccttttta gcctggggga acaagcatta acaaaatgtt tgaagatctt  119940
tgccacgtac cattccaaat ttctagggta agtctttagc ttttcagatc ctgagtttct  120000
```

```
gcaatgatca aatgtgattt ggacagttgc gttgactttc tcctggggct ataatggagt 120060
gcaaaggaaa caatggcagg gaaaatgctt gctttcaaaa tggtagcatg gatgtgttca 120120
ttcgtgtagt tactgtatta ggtatagcct ttcctgaaac taactgaagt ggggttataa 120180
aaacagtccc aattttctat ttcctttgct gagacacaaa gaggagacaa agagcaaag 120240 cttgagggta gttttaccac tgtgcttaag tgttctgatt tttccagtga tcagggtgaa 120300
ataaaaagca tagtaagttc cagggcagtg aataccatac aggagacaag ttacagtttt 120360
ataatgtgtt ttactttaca ctaaattcta aaagtaaaat gtcttttttt ttttccgaga 120420
cagagtttca ctcttgtagc ccaggcagga gtgctatggt gtgatctcgg ctcacagcaa 120480
cctccacctc ccagtttcaa gcgattcttc tgcctcagcc tcccgagaag ttgaaattac 120540
aggtgcctgg caccatatct cgctaattat tctattttta gtagagatcg gttttacca 120600 tgttggccag gctggtctcg aactcctgac ttcaagtgat ccacccgcct cagcctccca 120660
aagtgctggg attacaggtg tgagtcactg tgccggacct aacagtaaaa tgtctttcat 120720
gtgcttctca aggcaactac attaaggagg acacatctct taatgtcatt ctacagtaga 120780
tttctaatgc tctttcttgg aagtttgttt ttctgagaag agctaaaaat ataataacat 120840
ggaagtgatc atattatata atcaatgaag tgctttcaaa ggagataaaa ctaacctggt 120900
ctgcatttgc aaccagcctt gattgagaga gagagaactc aggatacact tagagatttt 120960
attatgggga atagttactt tattcatttt acctcaatca atgcatggaa ataagtgaca 121020
gtcattttca tttatctttt aataaataaa gtcaccatga ggaaaatgaa acccattaa 121080 agtcagtcct taaagatatt tggacatgca gacatgataa ctaacatttc cattcgtgag 121140
acttacccaa aacctatacc tcaagtccat ttcttagaat acatgaaata aagatctcag 121200
tgagtgtata aaactgcaca ccagaatcat atccgtatag acaagaatac atctactaga 121260
aaaatataaa ccaaaacacc aaggtgactc tgttttttc tgttttaaaa tatgttgtct 121320
ttgtatgcat gtttgcttct tcctttttt ttttaaacat cgcagataaa ttcaactctc 121380
acctcagttg agagagaact gtcaatgtga cttggcctct ctctttctag tcccagaaag 121440
aattgcactg aaatgctgag ctcctgtaat aaaaatgacc atttgctgag agtaattaac 121500
atactgaaag agattttctt agaatagtgc acaatggccc aatggtgaca ttatattgtc 121560
tctttataaa ttattttcta tctatttctg tggattattt ctacaaagca cttttcatat 121620
gtccaattcc ttttattccc ctacaagtac tgactgacta ctggctctgc tgttcactga 121680
tatgactttc ggcaagttgc ctgcactttt taaacgttat ttcctcattc agaacatggg 121740
gccatacaaa atacaactca cttcagtgtt attggggaat taaacaaata aatgcatggg 121800
aagcatttaa catagtgcct gacacaataa tgagcactca gtagatgtta gcttttatta 121860
atattgttgt tgctatgtcc agaaacacta tacctccaga aaatcatggg tacttgctgg 121920
ggacgttggg gatatgcatg attttgaaag gagtgactgc tctttactgc tcagatgaga 121980 aattttcta agccagactc cttcaaacat gtaagattct gttgtggatt ctaggactga 122040
aagaattctt ggccgagtgt ggtggcttat cctggtaatc tcatcatttg ggaggacaag 122100
gcaggaagat tgcttgagcc caggagttgg aaacaagcct ggacaacatg gcgaaaccct 122160
gtctctacaa aaaatacaaa cattagctgg tcatgggagt gagtgcctgt actcccagct 122220
actcaggagg ctaagatagg aggatcacct gagcctgggc agtttgaggt ttcagtgagc 122280
cgtgatgaca ccatactata ctccactcca gcctgggtga cagtgacatc ctgcctcaaa 122340
```

```
aaaacccca aaattattct tttgctgat ttcatgtcag cagtgtgtgc tgaaggctgt 122400
aaagtagcca cttgttctgt ttatttttcc attgaacaag tatttatcaa aaacgtactt 122460
tgtggaaggc actgtgctag gaactatgca tacagaagga aaaccaaatg ttcttggata 122520
ctacactcca gttgtgataa aaaagaaaaa agtattcttc acaaacttca acattttgat 122580
gtgcaaaaac ataatatatg aattagatct acctaactac acagaattag accaattatt 122640
tctgggatta tgggctcata tttttaataa ctgtcctcct acctctctgt tgacaggttt 122700
tataaatatt catttaatta cacacagtca cagacacact cagacacaca cacatacaca 122760
cacacacaca ccttgacaaa taatgggcat gaacaattga ctggtacttg ctctcattct 122820
tctagatgtc accacagtgg atcccaaata caattattca aaggatgcaa atggtaagtt 122880
tttgtgtttt ttatttcctc ctgatcattt taagttttga acttctctgg cttgaaaaat 122940
cagggaatgg atttgctag gttggatgct gcagaatgga cctaatcata ttttaaatta 123000
gtccctcttt ttctaggagt tgtattaaca aacctaacta ctgcttcatg taagagatga 123060
ctgtaaattg aagggtacag tgatatgctt tcagttattt caaaaaacag actttactca 123120
tccatgtgtc ttttttcttt ttttttttt cttttttgag acggagtctc gctctgttga 123180
acaggctgga ttgcagtgac gcgatctcac ctcactacaa cctccgcctc tggagttcaa 123240
gcgattctcc agcctcagct tctcaagtag ctgggactac aggcacatgc caccatgtcc 123300
gggtcatctt tgtatttta gcagagaccg ggtttcacta tgttggccag ctggtctag 123360 aattcctgac ttcgtgatct gcccccctcag ccctccgaag tgctgggatt acagacgtga 123420
gtcactgtgc ccggcctaac agtaaaatgt ctttcatgcg cttctcaagg caactacgtt 123480
aaggaggaca cttctcttaa tgtcattcta cagtagattt ctaatgctct ttcttggaag 123540 tttgttttc tgagaaaagc taaaatata acatggaagt gatcatattg tataatcaat 123600
gaagtgcttt tcaaggagat aaaactaatc tggtccacgt ttgcaaccaa ccttgattga 123660
gagagagaga gaactcagga tacacttgga gatttttatta tggggaatag ttactttatt 123720 ctttttcct caatcaattc atggaaataa gtgatagtca tattcattta tcttttaata 123780
aatgaagtca ccatgaggaa aataaaaaga cattgaaaac ccattaaagt tagccctaa 123840 agatatttgg acatgcagac ttgataacta acgtttgcat tcttgagact tacccaaaac 123900
ccatacctca agtccatgtt tttagaattc atgaaataaa gatctcagtg agtgcataaa 123960
attgcgcacc agaatcatat ccgtatagac aagaacacat ctactagaaa aataataaac 124020
caacacacca atgcaactgt gttttcttct gttttaaaat atgttgtctt tgtatgcatg 124080
tttgcttctt ccttttttt tttaacatc acagataaat tcaactctca cctcaggttt 124140
tattgagaga actgtcaatg tgacttggcc tctgtctttc tagtcccaga agaatcgca 124200 ctgaaatgct gagctcctgt aataaaaatg accatttgct gagagtaatt aacatactga 124260
aagagatttt cttagagtac acaatggtga cattatattg tctctttata aataactttc 124320
tatctatttc tgtggattat tcctacaaag tactttttcat atgtccagtt tcttttcttc 124380
ccctacaact accgtctgaa tactggctct gctatttgct gatatgattc tcggcaagtt 124440
gcctgcactt tttaaacttt atttcctcat tcagaacatg gggccatgta atactcatgt 124500
acgtgagtat tacgtaataa tgctcactta agtgttactg gggaattaaa caaaaaaatg 124560
catggcaagc atttaacata gtgcctgaca caataatgag cactcagtag atgttagatt 124620
ttattaatat tgttgttgtt atgtccggaa acactatacc tccagaaaat catgggtact 124680
tgcttgggat gttggggata tgcatgattt ggaaaggtat gactgctttt ttctgcttag 124740
```

```
atgagaaatt tttctaagcc agactccttc aaatatgtaa gattctgttg tggattctag    124800
gacggaaaga attcttggtc aggtgtggtt tcttatccct gtaatccag  aatttttggga   124860
ggacaaggca ggaagattgc ttgagcccag gagtttgaaa ccagcctggg caacaagacg    124920
aaaccctgtc tctacaaaag tacataaatt agcttggctt ggtggtgtgt gcctgtatta    124980
ccagctattc gggagactga gatgggagga tctcctgaac ctgtgaagtt tgaggcttca    125040
gtgagccgtg atgacaccat actatactcg actccagcct gtgcgacagt gagactctgc    125100
gtcaaaaaaa aaaccccaaa attattgttt ttgctgattt caggtcagca gtgtgtgctg    125160
aagggtgtaa agtagccact tgatcagttt atttttccac tgaacaagta tttatcaaaa    125220
acatactttg tggtctgttt ttgataaata aaaaggcact gtgctaggag ccatgaatac    125280
agaaggaaaa ccaaatgttc ttggatacta cactccagtt gtgataaaaa agaaaaatgt    125340
attcttcacg aacttcaaca ttttgatatg caaaaacata gtatataaat tagatctacc    125400
tgattacgta gaatcagacc aattatttct ggaattgagg gctcatattt ttaataactg    125460
tcctcctgcc tctctgttga caggttttat aaatattcat ttaattacac acacacacac    125520
acacaccttg acaaataatg gacatgaaca attgactagt acttgctctc attcttctag    125580
atgtcatcac aatggatccc aaagacaatt ggtcaaaaga tgcaaatggt aagcttttgt    125640
gttttttcctt tcctcctgat cattttaagt tttgaacttc tctggcttga aaaatcaggg    125700
aatgggccgg gtgcggtggc tcacgcctgt aatcccagca ctttgggagg ccgaggcggg    125760
cggatcacga ggtcaggaga tcgagaccat cccggctaaa acggtgaaac cccgtctcta    125820
ctaaaaatac aaaaaattag ccgggcttag tggcgggcgc ctgtagtccc agctacttgg    125880
gaggctgagg caggagaatg gcgtgaaccc gggaggcgga gcttgcagtg agccgagatt    125940
gcgccactgc actccactcc agcctgggcg acagagcgag actccgtctc aaaaaaaaaa    126000
aaaaaaaaaa aaaagaaaaa atcagggaat ggattttgct aggttggatg ctgcagaatg    126060
gacctagtga tattttaaat tagtccctct ttttctagga gttgtattaa caaacctaac    126120
tactgcttcg ggtatgagat gactgtaaat tagagggtac agtgatatgc tttcagttat    126180
ttcaaaaaac agactttatt catccgtctg tcttttttt tttttttttt tttttttttt    126240
gagacggagg agtctcactc tatcacccag gctggagtgc agtggcgcga tctcggctca    126300
ccataacctc cgccttactg gttcaagcga ttctccagcc tcagcttctc aagtagctgg    126360
gactacaggt gcacaccacc atacctggct aattttttgta ttttttaatag agatgggggtt    126420
tcaccacgct ggccaggatg gtcttgaatt cttgacctcg tgatctgccc cctcgggctc    126480
ccaaacttct gggattatag gcgtgagcca ctgtgcccgg ccttctgtct tttgttataa    126540
tgactgggga aaacatgata ccatgttgct tcttgagttg ttttgtttta gtctttggtc    126600
tttgctagta gctaataaca cgaactagtg tttatcaagt gcttttttaca cagaagggct    126660
tgttctgcat tttctagttt aatcatctta atactcctat aaagtagtac aatatatttt    126720
ctcccatttt acagtcccctt taaagtaaat aactataaaa atcccttata catgtcacac    126780
agctaggtct ggcatttcaa atcaggacat caaacaaaga attcgtgcag ttactaagtc    126840
ctctattttt tctacaatag aaaaaatagc aagaattaca gatagcaaga cattacaagg    126900
caggaatctg aaacgaaagg gacataatgt ggggctgggt gggtgcatga gctttgcaga    126960
ctagactttc attccagctc ttttaatgat taggtgtaag tgacctacat tttgtgagta    127020
acagttttct catcagccaa ctaagaataa ttacaccaga ttcacagtta ttgaagagat    127080
```

```
aagggcatga atgtgagatg tctggcgtag ggtatctcat ttagcagaca cagaatgaat   127140
acttgtttct ggcttttct ctctacatat gcacaaagaa tgtgactaga agcattggct    127200
ctagccctgc tcaactttcc tctatttcca ataccaaggg gctctgactt aggctgccac   127260
accaggcaag gaggggcagt accacctcac ttgaccaagg gcaggagtc acggacacat    127320 cacttcctga gatcctttc cacaccaagg actgatgttt ctggaattct cactttatga   127380
agacaaaaca tataaatgga aatttctgca ggaagagact cactcttgta gctcattgag   127440
taggcactag tggtccaccc ccactgtctt tacttattcc ttgacatcac atatctcttg   127500
taaaacctca aataatgtta aatgcaatca cccaataata gcatagccat aattagaggc   127560
atttaggaaa gacaggtgag tgtgccacaa ctacctaaca catcagcaaa tctggattaa   127620
ccactttctt tgattttcca caatgcaacc ttactttta atagttggga atgttctaag    127680
tgaatttagc agaggttgtt aatcaacttg aaagctgaat tctgacttgt ctgactcttg   127740
gtggtgctgg tagcagtaga tgtttacttt taggttttgg tggtggtgga atatcacttc   127800
aacgtaaatc atcagaaata agtatttgtg aaccctctc gcattaatat atcttattct    127860 gtaaaagaa catgtgcaat ttctcttaga tacactactg ctgcagctca caaacacctc    127920
tgcatattac acgtacctcc tcctgctcct caagagtgtg gtctattttg ccatcatcac   127980
ctgctgtctg cttagaagaa cggctttctg ctgcaatgga gagaaatcat aa             128032

<210> SEQ ID NO 2
<211> LENGTH: 4249
<212> TYPE: DNA
<213> ORGANISM: Homo sapiens

<400> SEQUENCE: 2
agtgcagcgc agaagacaga gggtgactag gaagacgcgc gagcggggct ggccggccgg      60
cgggtggggg aggggaggcg ggggaaggcg gctgagtggg cctctggagt gtgtgtgtct     120
gtgtcagtgt gtgtgtgtgt gtgtgtatgt gtgtgtctgg cgcctggcca gggtgatttc     180
ccataaacca catgcccccc agtcctctct taaaaggctg tgccgagggc tggccagtga     240
ggctcggccc ggggaaagtg aaagtttgcc tgggtcctct cggcgccaga gccgctctcc     300
gcatcccagg acagcggtgc ggccctcggc cggggcgccc actccgcagc agccagcgag     360
cgagcgagcg agcgagggcg gccgacgcgc ccggccggga cccagctgcc cgtatgaccg     420
cgccgggcgc cgccgggcgc tgccctccca cgacatggct gggctccctg ctgttgttgg     480
tctgtctcct ggcgagcagg agtatcaccg aggaggtgtc ggagtactgt agccacatga     540
ttgggagtgg acacctgcag tctctgcagc ggctgattga cagtcagatg gagacctcgt     600
gccaaattac atttgagttt gtagaccagg aacagttgaa agatccagtg tgctaccta     660 agaaggcatt tctcctggta caagacataa tggaggacac catgcgcttc agagataaca     720
cccccaatgc catcgccatt gtgcagctgc aggaactctc tttgaggctg aagagctgct    780
tcaccaagga ttatgaagag catgacaagg cctgcgtccg aactttctat gagacacctc     840
tccagttgct ggagaaggtc aagaatgtct ttaatgaaac aaagaatctc cttgacaagg    900
actggaatat tttcagcaag aactgcaaca acagcttttgc tgaatgctcc agccaagatg    960
tggtgaccaa gcctgattgc aactgcctgt accccaaagc catccctagc agtgacccgg   1020
cctctgtctc ccctcatcag cccctcgccc cctccatgg ccctgtggct ggcttgacct      1080
gggaggactc tgagggaact gagggcaggct ccctcttgcc tggtgagcag ccctgcaca    1140 cagtggatcc aggcagtgcc aagcagcggc caccccaggag cacctgccag agctttgagc   1200
```

```
cgccagagac cccagttgtc aaggacagca ccatcggtgg ctcaccacag cctcgccct     1260 ctgtcgggc cttcaacccc gggatggagg atattcttga ctctgcaatg ggcactaatt     1320
gggtcccaga agaagcctct ggagaggcca gtgagattcc cgtacccccaa gggacagagc   1380 tttcccctc caggccagga gggggcagca tgcagacaga gcccgccaga cccagcaact     1440
tcctctcagc atcttctcca ctccctgcat cagcaaaggg ccaacagccg gcagatgtaa    1500
ctggtaccgc cttgcccagg gtgggccccg tgaggcccac tggccaggac tggaatcaca   1560
ccccccagaa gacagaccat ccatctgccc tgctcagaga ccccccggag ccaggctctc    1620
ccaggatctc atcactgcgc ccccaggcc tcagcaaccc ctccaccctc tctgctcagc    1680
cacagctttc cagaagccac tcctcgggca gcgtgctgcc ccttggggag ctggagggca    1740
ggaggagcac cagggatcgg aggagccccg cagagccaga aggaggacca gcaagtgaag    1800 ggcagccag gcccctgccc cgttttaact ccgttccttt gactgacaca ggccatgaga    1860
ggcagtccga gggatcctcc agcccgcagc tccaggagtc tgtcttccac ctgctggtgc    1920
ccagtgtcat cctggtcttg ctggccgtcg gaggcctctt gttctacagg tggaggcggc    1980
ggagccatca agagcctcag agagcggatt ctcccttgga gcaaccagag ggcagccccc    2040
tgactcagga tgacagacag gtggaactgc cagtgtagag ggaattctaa gctggacgca    2100
cagaacagtc tctccgtggg aggagacatt atggggcgtc caccaccacc cctcccctggc   2160 catcctcctg gaatgtggtc tgccctccac cagagctcct gcctgccagg actggaccag    2220
agcagccagg ctggggcccc tctgtctcaa cccgcagacc cttgactgaa tgagagaggc    2280
cagaggatgc tccccatgct gccactattt attgtgagcc ctggaggctc ccatgtgctt    2340
gaggaaggct ggtgagcccg gctcaggacc ctcttccctc aggggctgca ccctcctctc    2400
actcccttcc atgccggaac ccaggccagg gacccaccgg cctgtggttt gtgggaaagc    2460
agggtggacg ctgaggagtg aaagaaccct gcacccagag ggcctgcctg gtgccaaggt    2520
atcccagcct ggacaggcat ggacctgtct ccagagagag gagcctgaag ttcgtggggc    2580
gggacagcgt cggcctgatt tcccgtaaag gtgtgcagcc tgagagacgg gaagaggagg    2640
cctctggacc tgctggtctg cactgacagc ctgaaggggtc tacaccctcg gctcacctaa    2700
gtgccctgtg ctggttgcca ggcgcagagg ggaggccagc cctgccctca ggacctgcct    2760
gacctgccag tgatgccaag aggggatca agcactggcc tctgccccctc ctccttccag    2820 cacctgccag agcttctcca ggaggccaag cagaggctcc cctcatgaag gaagccattg    2880
cactgtgaac actgtacctg cctgctgaac agcctgcccc cgtccatcca tgagccagca    2940
tccgtccgtc ctccactctc cagcctctcc ccagcctcct gcactgagct ggcctcacca    3000
gtcgactgag ggagccccctc agccctgacc ttctcctgac ctggcctttg actccccgga    3060
gtggagtggg gtgggagaac ctcctgggcc gccagccaga gccggtcttt aggctgtgtt    3120
gttcgcccag gttctgcat cttgcacttt gacattccca agagggaagg gactagtggg    3180
agagagcaag ggagggagg gcacagacag agaggctaca gggcgagctc tgactgaaga    3240
tgggcctttg aaatataggt atgcacctga ggttggggga gggtctgcac tcccaaaccc    3300
cagcgcagtg tcctttccct gctgccgaca ggaacctggg gctgaacagg ttatccctgt    3360
caggagccct ggactgggct gcatctcagc cccacctgca tggtatccag ctcccatcca    3420
cttctcaccc ttctttcctc ctgacctttgg tcagcagtga tgacctccaa ctctcaccca    3480 cccccctctac catcacctct aaccaggcaa gccagggtgg gagagcaatc aggagagcca   3540
```

-continued

```
ggcctcagct tccaatgcct ggagggcctc cactttgtgg ccagcctgtg gtggtggctc    3600
tgaggcctag gcaacgagcg acagggctgc cagttgcccc tgggttcctt tgtgctgctg    3660
tgtgcctcct ctcctgccgc cctttgtcct ccgctaagag accctgccct acctggccgc    3720
tgggccccgt gactttccct tcctgcccag gaaagtgagg gtcggctggc cccaccttcc    3780
ctgtcctgat gccgacagct tagggaaggg cagtgaactt gcatatgggg cttagccttc    3840
tagtcacagc ctctatattt gatgctagaa aacacatatt tttaaatgga agaaaaataa    3900
aaaggcattc cccttcatc cccctacctt aaacatataa tattttaaag gtcaaaaaag    3960
caatccaacc cactgcagaa gctcttttg agcacttggt ggcatcagag caggaggagc    4020
cccagagcca cctctggtgt cccccaggc tacctgctca ggaaccccctt ctgttctctg    4080 agaagtcaag agaggacatt ggctcacgca ctgtgagatt ttgtttttat acttggaagt    4140
ggtgaattat tttatataaa gtcatttaaa tatctattta aagataggaa agctgcttat    4200
atatttaata ataaagaag tgcacaagct gccaaaaaaa aaaaaaaaa              4249
```

<210> SEQ ID NO 3
<211> LENGTH: 554
<212> TYPE: PRT
<213> ORGANISM: Homo sapiens

<400> SEQUENCE: 3

```
Met Thr Ala Pro Gly Ala Ala Gly Arg Cys Pro Pro Thr Thr Trp Leu
1               5                   10                  15

Gly Ser Leu Leu Leu Leu Val Cys Leu Leu Ala Ser Arg Ser Ile Thr
            20                  25                  30

Glu Glu Val Ser Glu Tyr Cys Ser His Met Ile Gly Ser Gly His Leu
        35                  40                  45

Gln Ser Leu Gln Arg Leu Ile Asp Ser Gln Met Glu Thr Ser Cys Gln
    50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
            100                 105                 110

Gln Glu Leu Ser Leu Arg Leu Lys Ser Cys Phe Thr Lys Asp Tyr Glu
        115                 120                 125

Glu His Asp Lys Ala Cys Val Arg Thr Phe Tyr Glu Thr Pro Leu Gln
    130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Cys Ser Ser Gln Asp Val Val Thr Lys Pro Asp Cys Asn Cys Leu
            180                 185                 190

Tyr Pro Lys Ala Ile Pro Ser Ser Asp Pro Ala Ser Val Ser Pro His
        195                 200                 205

Gln Pro Leu Ala Pro Ser Met Ala Pro Val Ala Gly Leu Thr Trp Glu
    210                 215                 220

Asp Ser Glu Gly Thr Glu Gly Ser Ser Leu Leu Pro Gly Glu Gln Pro
225                 230                 235                 240

Leu His Thr Val Asp Pro Gly Ser Ala Lys Gln Arg Pro Pro Arg Ser
                245                 250                 255
```

```
Thr Cys Gln Ser Phe Glu Pro Pro Glu Thr Pro Val Val Lys Asp Ser
            260                 265                 270

Thr Ile Gly Gly Ser Pro Gln Pro Arg Pro Ser Val Gly Ala Phe Asn
            275                 280                 285

Pro Gly Met Glu Asp Ile Leu Asp Ser Ala Met Gly Thr Asn Trp Val
290                 295                 300

Pro Glu Glu Ala Ser Gly Glu Ala Ser Glu Ile Pro Val Pro Gln Gly
305                 310                 315                 320

Thr Glu Leu Ser Pro Ser Arg Pro Gly Gly Ser Met Gln Thr Glu
                325                 330                 335

Pro Ala Arg Pro Ser Asn Phe Leu Ser Ala Ser Ser Pro Leu Pro Ala
            340                 345                 350

Ser Ala Lys Gly Gln Gln Pro Ala Asp Val Thr Gly Thr Ala Leu Pro
            355                 360                 365

Arg Val Gly Pro Val Arg Pro Thr Gly Gln Asp Trp Asn His Thr Pro
            370                 375                 380

Gln Lys Thr Asp His Pro Ser Ala Leu Leu Arg Asp Pro Pro Glu Pro
385                 390                 395                 400

Gly Ser Pro Arg Ile Ser Ser Leu Arg Pro Gln Gly Leu Ser Asn Pro
            405                 410                 415

Ser Thr Leu Ser Ala Gln Pro Gln Leu Ser Arg Ser His Ser Ser Gly
            420                 425                 430

Ser Val Leu Pro Leu Gly Glu Leu Glu Gly Arg Arg Ser Thr Arg Asp
            435                 440                 445

Arg Arg Ser Pro Ala Glu Pro Glu Gly Gly Pro Ala Ser Glu Gly Ala
450                 455                 460

Ala Arg Pro Leu Pro Arg Phe Asn Ser Val Pro Leu Thr Asp Thr Gly
465                 470                 475                 480

His Glu Arg Gln Ser Glu Gly Ser Ser Ser Pro Gln Leu Gln Glu Ser
            485                 490                 495

Val Phe His Leu Leu Val Pro Ser Val Ile Leu Val Leu Leu Ala Val
            500                 505                 510

Gly Gly Leu Leu Phe Tyr Arg Trp Arg Arg Arg Ser His Gln Glu Pro
            515                 520                 525

Gln Arg Ala Asp Ser Pro Leu Glu Gln Pro Glu Gly Ser Pro Leu Thr
530                 535                 540

Gln Asp Asp Arg Gln Val Glu Leu Pro Val
545                 550

<210> SEQ ID NO 4
<211> LENGTH: 3366
<212> TYPE: DNA
<213> ORGANISM: Homo sapiens

<400> SEQUENCE: 4
cgtgggattt ccagaccgcg gctttctaat cggctcggga ggaagctctg cagctctctt      60
gggaattaag ctcaatctct ggactctctc tctttctctt tctcccctc cctctcctgc      120 gaagaagctc aagacaaaac caggaagccg gcgaccctca cctcctcggg ggctgggagg      180
aaggaggaaa acgaaagtcg ccgccgccgc gctgtccccc gagagctgcc tttcctcggg      240
catccctggg gctgccgcgg gacctcgcag ggcggatata agaaccgcg gccttgggaa      300 gaggcggaga ccggctttta agaaagaag tcctgggtcc tgcggtctgg ggcgaggcaa      360
gggcgctttt ctgcccacgc tccccgtggc ccatcgatcc ccgcgcgtc cgccgctgtt      420
```

```
ctaaggagag aagtgggggc cccccaggct cgcgcgtgga gcgaagcagc atgggcagtc    480
ggtgcgcgct ggccctggcg gtgctctcgg ccttgctgtg tcaggtctgg agctctgggg    540
tgttcgaact gaagctgcag gagttcgtca acaagaaggg gctgctgggg aaccgcaact    600
gctgccgcgg gggcgcgggg ccaccgccgt gcgcctgccg gaccttcttc cgcgtgtgcc    660
tcaagcacta ccaggccagc gtgtcccccg agccgccctg cacctacggc agcgccgtca    720
cccccgtgct gggcgtcgac tccttcagtc tgcccgacgg cggggggcgcc gactccgcgt    780 tcagcaaccc catccgcttc cccttcggct tcacctggcc gggcaccttc tctctgatta    840
ttgaagctct ccacacagat tctcctgatg acctcgcaac agaaaaccca gaaagactca    900
tcagccgcct ggccacccag aggcacctga cggtgggcga ggagtggtcc caggacctgc    960
acagcagcgg ccgcacggac ctcaagtact cctaccgctt cgtgtgtgac gaacactact   1020
acggagaggg ctgctccgtt ttctgccgtc cccgggacga tgccttcggc cacttcacct   1080
gtggggagcg tggggagaaa gtgtgcaacc ctggctggaa agggccctac tgcacagagc   1140
cgatctgcct gcctggatgt gatgagcagc atggattttg tgacaaacca ggggaatgca   1200
agtgcagagt gggctggcag ggccggtact gtgacgagtg tatccgctat ccaggctgtc   1260
tccatggcac ctgccagcag ccctggcagt gcaactgcca ggaaggctgg gggggccttt   1320
tctgcaacca ggacctgaac tactgcacac accataagcc tgcaagaat ggagccacct    1380 gcaccaacac gggccagggg agctacactt gctcttgccg gcctgggtac acaggtgcca   1440
cctgcgagct ggggattgac gagtgtgacc ccagcccttg taagaacgga gggagctgca   1500
cggatctcga gaacagctac tcctgtacct gcccacccgg cttctacggc aaaatctgtg   1560
aattgagtgc catgacctgt gcggacggcc cttgctttaa cggggtgtcgg tgctcagaca   1620 gccccgatgg agggtacagc tgccgctgcc ccgtgggcta ctccggcttc aactgtgaga   1680
agaaaattga ctactgcagc tcttcaccct gttctaatgg tgccaagtgt gtggaccctcg   1740 gtgatgccta cctgtgccgc tgccaggccg gcttctcggg gaggcactgt gacgacaacg   1800
tggacgactg cgcctcctcc ccgtgcgcca acggggggcac ctgccgggat ggcgtgaacg   1860
acttctcctg cacctgcccg cctggctaca cgggcaggaa ctgcagtgcc cccgtcagca   1920
ggtgcgagca cgcaccctgc cacaatgggg ccacctgcca cgagagggggc caccgctatg   1980 tgtgcgagtg tgcccgaggc tacggggtc ccaactgcca gttcctgctc cccgagctgc    2040
ccccgggccc agcggtggtg gacctcactg agaagctaga gggccagggc gggccattcc   2100
cctgggtggc cgtgtgcgcc ggggtcatcc ttgtcctcat gctgctgctg ggctgtgccg   2160
ctgtggtggt ctgcgtccgg ctgaggctgc agaagcaccg gcccccagcc gaccccctgcc   2220 gggggggagac ggagaccatg aacaacctgg ccaactgcca gcgtgagaag gacatctcag   2280
tcagcatcat cggggccacg cagatcaaga acaccaacaa gaaggcggac ttccacgggg   2340
accacagcgc cgacaagaat ggcttcaagg cccgctaccc agcggtggac tataacctcg   2400
tgcaggacct caagggtgac gacaccgccg tcagggacgc gcacagcaag cgtgacacca   2460
agtgccagcc ccagggctcc tcaggggagg agaaggggac cccgaccaca ctcaggggtg   2520
gagaagcatc tgaaagaaaa aggccggact cgggctgttc aacttcaaaa gacaccaagt   2580
accagtcggt gtacgtcata tccgaggaga aggatgagtg cgtcatagca actgaggtgt   2640
aaaatggaag tgagatggca agactcccgt ttctcttaaa ataagtaaaa ttccaaggat   2700
atatgcccca acgaatgctg ctgaagagga gggaggcctc gtggactgct gctgagaaac   2760
```

-continued

```
cgagttcaga ccgagcaggt tctcctcctg aggtcctcga cgcctgccga cagcctgtcg    2820
cggcccggcc gcctgcggca ctgccttccg tgacgtcgcc gttgcactat ggacagttgc    2880
tcttaagaga atatatattt aaatgggtga actgaattac gcataagaag catgcactgc    2940
ctgagtgtat attttggatt cttatgagcc agtcttttct tgaattagaa acacaaacac    3000
tgcctttatt gtccttttg atacgaagat gtgcttttc tagatggaaa agatgtgtgt    3060
tattttttgg atttgtaaaa atattttca tgatatctgt aaagcttgag tattttgtga    3120
tgttcgtttt ttataattta aattttggta aatatgtaca aaggcacttc gggtctatgt    3180
gactatattt ttttgtatat aaatgtattt atggaatatt gtgcaaatgt tatttgagtt    3240
ttttactgtt ttgttaatga agaaattcct ttttaaaata ttttccaaa ataaatttta    3300 tgaatgacaa aaaaaaaaaa aaaaaaaaaa aaaaaaaaaa aaaaaaaaaa aaaaaaaaaa    3360
aaaaaa                                                               3366
```

<210> SEQ ID NO 5
<211> LENGTH: 723
<212> TYPE: PRT
<213> ORGANISM: Homo sapiens

<400> SEQUENCE: 5

```
Met Gly Ser Arg Cys Ala Leu Ala Leu Ala Val Leu Ser Ala Leu Leu
1               5                   10                  15

Cys Gln Val Trp Ser Ser Gly Val Phe Glu Leu Lys Leu Gln Glu Phe
                20                  25                  30

Val Asn Lys Lys Gly Leu Leu Gly Asn Arg Asn Cys Cys Arg Gly Gly
            35                  40                  45

Ala Gly Pro Pro Pro Cys Ala Cys Arg Thr Phe Phe Arg Val Cys Leu
        50                  55                  60

Lys His Tyr Gln Ala Ser Val Ser Pro Glu Pro Pro Cys Thr Tyr Gly
65                  70                  75                  80

Ser Ala Val Thr Pro Val Leu Gly Val Asp Ser Phe Ser Leu Pro Asp
                85                  90                  95

Gly Gly Gly Ala Asp Ser Ala Phe Ser Asn Pro Ile Arg Phe Pro Phe
            100                 105                 110

Gly Phe Thr Trp Pro Gly Thr Phe Ser Leu Ile Ile Glu Ala Leu His
        115                 120                 125

Thr Asp Ser Pro Asp Asp Leu Ala Thr Glu Asn Pro Glu Arg Leu Ile
    130                 135                 140

Ser Arg Leu Ala Thr Gln Arg His Leu Thr Val Gly Glu Glu Trp Ser
145                 150                 155                 160

Gln Asp Leu His Ser Ser Gly Arg Thr Asp Leu Lys Tyr Ser Tyr Arg
                165                 170                 175

Phe Val Cys Asp Glu His Tyr Tyr Gly Glu Gly Cys Ser Val Phe Cys
            180                 185                 190

Arg Pro Arg Asp Asp Ala Phe Gly His Phe Thr Cys Gly Glu Arg Gly
        195                 200                 205

Glu Lys Val Cys Asn Pro Gly Trp Lys Gly Pro Tyr Cys Thr Glu Pro
    210                 215                 220

Ile Cys Leu Pro Gly Cys Asp Glu Gln His Gly Phe Cys Asp Lys Pro
225                 230                 235                 240

Gly Glu Cys Lys Cys Arg Val Gly Trp Gln Gly Arg Tyr Cys Asp Glu
                245                 250                 255

Cys Ile Arg Tyr Pro Gly Cys Leu His Gly Thr Cys Gln Gln Pro Trp
```

```
                    260                 265                 270
Gln Cys Asn Cys Gln Glu Gly Trp Gly Gly Leu Phe Cys Asn Gln Asp
                275                 280                 285
Leu Asn Tyr Cys Thr His His Lys Pro Cys Lys Asn Gly Ala Thr Cys
            290                 295                 300
Thr Asn Thr Gly Gln Gly Ser Tyr Thr Cys Ser Cys Arg Pro Gly Tyr
305                 310                 315                 320
Thr Gly Ala Thr Cys Glu Leu Gly Ile Asp Glu Cys Asp Pro Ser Pro
                325                 330                 335
Cys Lys Asn Gly Gly Ser Cys Thr Asp Leu Glu Asn Ser Tyr Ser Cys
            340                 345                 350
Thr Cys Pro Pro Gly Phe Tyr Gly Lys Ile Cys Glu Leu Ser Ala Met
        355                 360                 365
Thr Cys Ala Asp Gly Pro Cys Phe Asn Gly Gly Arg Cys Ser Asp Ser
    370                 375                 380
Pro Asp Gly Gly Tyr Ser Cys Arg Cys Pro Val Gly Tyr Ser Gly Phe
385                 390                 395                 400
Asn Cys Glu Lys Lys Ile Asp Tyr Cys Ser Ser Pro Cys Ser Asn
                405                 410                 415
Gly Ala Lys Cys Val Asp Leu Gly Asp Ala Tyr Leu Cys Arg Cys Gln
            420                 425                 430
Ala Gly Phe Ser Gly Arg His Cys Asp Asp Asn Val Asp Asp Cys Ala
        435                 440                 445
Ser Ser Pro Cys Ala Asn Gly Gly Thr Cys Arg Asp Gly Val Asn Asp
    450                 455                 460
Phe Ser Cys Thr Cys Pro Pro Gly Tyr Thr Gly Arg Asn Cys Ser Ala
465                 470                 475                 480
Pro Val Ser Arg Cys Glu His Ala Pro Cys His Asn Gly Ala Thr Cys
                485                 490                 495
His Glu Arg Gly His Arg Tyr Val Cys Glu Cys Ala Arg Gly Tyr Gly
            500                 505                 510
Gly Pro Asn Cys Gln Phe Leu Leu Pro Glu Leu Pro Pro Gly Pro Ala
        515                 520                 525
Val Val Asp Leu Thr Glu Lys Leu Glu Gly Gln Gly Gly Pro Phe Pro
    530                 535                 540
Trp Val Ala Val Cys Ala Gly Val Ile Leu Val Leu Met Leu Leu Leu
545                 550                 555                 560
Gly Cys Ala Ala Val Val Val Cys Val Arg Leu Arg Leu Gln Lys His
            565                 570                 575
Arg Pro Pro Ala Asp Pro Cys Arg Gly Glu Thr Glu Thr Met Asn Asn
        580                 585                 590
Leu Ala Asn Cys Gln Arg Glu Lys Asp Ile Ser Val Ser Ile Ile Gly
    595                 600                 605
Ala Thr Gln Ile Lys Asn Thr Asn Lys Lys Ala Asp Phe His Gly Asp
    610                 615                 620
His Ser Ala Asp Lys Asn Gly Phe Lys Ala Arg Tyr Pro Ala Val Asp
625                 630                 635                 640
Tyr Asn Leu Val Gln Asp Leu Lys Gly Asp Asp Thr Ala Val Arg Asp
                645                 650                 655
Ala His Ser Lys Arg Asp Thr Lys Cys Gln Pro Gln Gly Ser Ser Gly
            660                 665                 670
Glu Glu Lys Gly Thr Pro Thr Thr Leu Arg Gly Gly Glu Ala Ser Glu
        675                 680                 685
```

```
Arg Lys Arg Pro Asp Ser Gly Cys Ser Thr Ser Lys Asp Thr Lys Tyr
    690             695                 700

Gln Ser Val Tyr Val Ile Ser Glu Glu Lys Asp Glu Cys Val Ile Ala
705             710                 715                 720

Thr Glu Val

<210> SEQ ID NO 6
<211> LENGTH: 848
<212> TYPE: PRT
<213> ORGANISM: Homo sapiens

<400> SEQUENCE: 6

Met Leu Gln Thr Lys Asp Leu Ile Trp Thr Leu Phe Phe Leu Gly Thr
1               5                   10                  15

Ala Val Ser Leu Gln Val Asp Ile Val Pro Ser Gln Gly Glu Ile Ser
            20                  25                  30

Val Gly Glu Ser Lys Phe Phe Leu Cys Gln Val Ala Gly Asp Ala Lys
        35                  40                  45

Asp Lys Asp Ile Ser Trp Phe Ser Pro Asn Gly Glu Lys Leu Thr Pro
    50                  55                  60

Asn Gln Gln Arg Ile Ser Val Val Trp Asn Asp Ser Ser Ser Thr
65                  70                  75                  80

Leu Thr Ile Tyr Asn Ala Asn Ile Asp Asp Ala Gly Ile Tyr Lys Cys
                85                  90                  95

Val Val Thr Gly Glu Asp Gly Ser Glu Ser Glu Ala Thr Val Asn Val
            100                 105                 110

Lys Ile Phe Gln Lys Leu Met Phe Lys Asn Ala Pro Thr Pro Gln Glu
        115                 120                 125

Phe Arg Glu Gly Glu Asp Ala Val Ile Val Cys Asp Val Val Ser Ser
    130                 135                 140

Leu Pro Pro Thr Ile Ile Trp Lys His Lys Gly Arg Asp Val Ile Leu
145                 150                 155                 160

Lys Lys Asp Val Arg Phe Ile Val Leu Ser Asn Asn Tyr Leu Gln Ile
                165                 170                 175

Arg Gly Ile Lys Lys Thr Asp Glu Gly Thr Tyr Arg Cys Glu Gly Arg
            180                 185                 190

Ile Leu Ala Arg Gly Glu Ile Asn Phe Lys Asp Ile Gln Val Ile Val
        195                 200                 205

Asn Val Pro Pro Thr Ile Gln Ala Arg Gln Asn Ile Val Asn Ala Thr
    210                 215                 220

Ala Asn Leu Gly Gln Ser Val Thr Leu Val Cys Asp Ala Glu Gly Phe
225                 230                 235                 240

Pro Glu Pro Thr Met Ser Trp Thr Lys Asp Gly Glu Gln Ile Glu Gln
                245                 250                 255

Glu Glu Asp Asp Glu Lys Tyr Ile Phe Ser Asp Asp Ser Ser Gln Leu
            260                 265                 270

Thr Ile Lys Lys Val Asp Lys Asn Asp Glu Ala Glu Tyr Ile Cys Ile
        275                 280                 285

Ala Glu Asn Lys Ala Gly Glu Gln Asp Ala Thr Ile His Leu Lys Val
    290                 295                 300

Phe Ala Lys Pro Lys Ile Thr Tyr Val Glu Asn Gln Thr Ala Met Glu
305                 310                 315                 320

Leu Glu Glu Gln Val Thr Leu Thr Cys Glu Ala Ser Gly Asp Pro Ile
                325                 330                 335
```

-continued

```
Pro Ser Ile Thr Trp Arg Thr Ser Arg Asn Ile Ser Ser Glu Glu
        340                 345                 350

Lys Thr Leu Asp Gly His Met Val Arg Ser His Ala Arg Val Ser
        355                 360                 365

Ser Leu Thr Leu Lys Ser Ile Gln Tyr Thr Asp Ala Gly Tyr Ile
        370                 375                 380

Cys Thr Ala Ser Asn Thr Ile Gly Gln Asp Ser Gln Ser Met Tyr Leu
385                 390                 395                 400

Glu Val Gln Tyr Ala Pro Lys Leu Gln Gly Pro Val Ala Val Tyr Thr
                405                 410                 415

Trp Glu Gly Asn Gln Val Asn Ile Thr Cys Glu Val Phe Ala Tyr Pro
                420                 425                 430

Ser Ala Thr Ile Ser Trp Phe Arg Asp Gly Gln Leu Leu Pro Ser Ser
        435                 440                 445

Asn Tyr Ser Asn Ile Lys Ile Tyr Asn Thr Pro Ser Ala Ser Tyr Leu
        450                 455                 460

Glu Val Thr Pro Asp Ser Glu Asn Asp Phe Gly Asn Tyr Asn Cys Thr
465                 470                 475                 480

Ala Val Asn Arg Ile Gly Gln Glu Ser Leu Glu Phe Ile Leu Val Gln
                485                 490                 495

Ala Asp Thr Pro Ser Ser Pro Ser Ile Asp Gln Val Glu Pro Tyr Ser
                500                 505                 510

Ser Thr Ala Gln Val Gln Phe Asp Glu Pro Glu Ala Thr Gly Gly Val
        515                 520                 525

Pro Ile Leu Lys Tyr Lys Ala Glu Trp Arg Ala Val Gly Glu Glu Val
        530                 535                 540

Trp His Ser Lys Trp Tyr Asp Ala Lys Glu Ala Ser Met Glu Gly Ile
545                 550                 555                 560

Val Thr Ile Val Gly Leu Lys Pro Glu Thr Thr Tyr Ala Val Arg Leu
                565                 570                 575

Ala Ala Leu Asn Gly Lys Gly Leu Gly Glu Ile Ser Ala Ala Ser Glu
                580                 585                 590

Phe Lys Thr Gln Pro Val Gln Gly Glu Pro Ser Ala Pro Lys Leu Glu
        595                 600                 605

Gly Gln Met Gly Glu Asp Gly Asn Ser Ile Lys Val Asn Leu Ile Lys
        610                 615                 620

Gln Asp Asp Gly Gly Ser Pro Ile Arg His Tyr Leu Val Arg Tyr Arg
625                 630                 635                 640

Ala Leu Ser Ser Glu Trp Lys Pro Glu Ile Arg Leu Pro Ser Gly Ser
                645                 650                 655

Asp His Val Met Leu Lys Ser Leu Asp Trp Asn Ala Glu Tyr Glu Val
                660                 665                 670

Tyr Val Val Ala Glu Asn Gln Gln Gly Lys Ser Lys Ala Ala His Phe
        675                 680                 685

Val Phe Arg Thr Ser Ala Gln Pro Thr Ala Ile Pro Ala Asn Gly Ser
        690                 695                 700

Pro Thr Ser Gly Leu Ser Thr Gly Ala Ile Val Gly Ile Leu Ile Val
705                 710                 715                 720

Ile Phe Val Leu Leu Leu Val Val Asp Ile Thr Cys Tyr Phe Leu
                725                 730                 735

Asn Lys Cys Gly Leu Phe Met Cys Ile Ala Val Asn Leu Cys Gly Lys
        740                 745                 750
```

```
Ala Gly Pro Gly Ala Lys Gly Lys Asp Met Glu Gly Lys Ala Ala
            755                 760                 765

Phe Ser Lys Asp Glu Ser Lys Glu Pro Ile Val Glu Val Arg Thr Glu
770                 775                 780

Glu Glu Arg Thr Pro Asn His Asp Gly Gly Lys His Thr Glu Pro Asn
785                 790                 795                 800

Glu Thr Thr Pro Leu Thr Glu Pro Glu Lys Gly Pro Val Glu Ala Lys
                805                 810                 815

Pro Glu Cys Gln Glu Thr Glu Thr Lys Pro Ala Pro Ala Glu Val Lys
            820                 825                 830

Thr Val Pro Asn Asp Ala Thr Gln Thr Lys Glu Asn Glu Ser Lys Ala
            835                 840                 845
```

<210> SEQ ID NO 7
<211> LENGTH: 233
<212> TYPE: PRT
<213> ORGANISM: Homo sapiens

<400> SEQUENCE: 7

```
Met Trp Gln Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Ser Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile
225                 230
```

<210> SEQ ID NO 8
<211> LENGTH: 177
<212> TYPE: PRT
<213> ORGANISM: Homo sapiens

<400> SEQUENCE: 8

```
Met Ala Trp Met Leu Leu Ile Leu Ile Met Val His Pro Gly Ser
1               5                   10                  15

Cys Ala Leu Trp Val Ser Gln Pro Pro Glu Ile Arg Thr Leu Glu Gly
                20                  25                  30

Ser Ser Ala Phe Leu Pro Cys Ser Phe Asn Ala Ser Gln Gly Arg Leu
            35                  40                  45

Ala Ile Gly Ser Val Thr Trp Phe Arg Asp Glu Val Val Pro Gly Lys
50                  55                  60

Glu Val Arg Asn Gly Thr Pro Glu Phe Arg Gly Arg Leu Ala Pro Leu
65                  70                  75                  80

Ala Ser Ser Arg Phe Leu His Asp His Gln Ala Glu Leu His Ile Arg
                85                  90                  95

Asp Val Arg Gly His Asp Ala Ser Ile Tyr Val Cys Arg Val Glu Val
            100                 105                 110

Leu Gly Leu Gly Val Gly Thr Gly Asn Gly Thr Arg Leu Val Val Glu
            115                 120                 125

Lys Glu His Pro Gln Leu Gly Ala Gly Thr Val Leu Leu Leu Arg Ala
            130                 135                 140

Gly Phe Tyr Ala Val Ser Phe Leu Ser Val Ala Val Gly Ser Thr Val
145                 150                 155                 160

Tyr Tyr Gln Gly Lys Tyr Ala Lys Ser Thr Leu Ser Gly Phe Pro Gln
                165                 170                 175

Leu

<210> SEQ ID NO 9
<211> LENGTH: 270
<212> TYPE: PRT
<213> ORGANISM: Homo sapiens

<400> SEQUENCE: 9

Met Ala Trp Arg Ala Leu His Pro Leu Leu Leu Leu Leu Leu Leu Phe
1               5                   10                  15

Pro Gly Ser Gln Ala Gln Ser Lys Ala Gln Val Leu Gln Ser Val Ala
                20                  25                  30

Gly Gln Thr Leu Thr Val Arg Cys Gln Tyr Pro Pro Thr Gly Ser Leu
            35                  40                  45

Tyr Glu Lys Lys Gly Trp Cys Lys Glu Ala Ser Ala Leu Val Cys Ile
50                  55                  60

Arg Leu Val Thr Ser Ser Lys Pro Arg Thr Met Ala Trp Thr Ser Arg
65                  70                  75                  80

Phe Thr Ile Trp Asp Asp Pro Asp Ala Gly Phe Phe Thr Val Thr Met
                85                  90                  95

Thr Asp Leu Arg Glu Glu Asp Ser Gly His Tyr Trp Cys Arg Ile Tyr
            100                 105                 110

Arg Pro Ser Asp Asn Ser Val Ser Lys Ser Val Arg Phe Tyr Leu Val
            115                 120                 125

Val Ser Pro Ala Ser Ala Ser Thr Gln Thr Ser Trp Thr Pro Arg Asp
            130                 135                 140

Leu Val Ser Ser Gln Thr Gln Thr Gln Ser Cys Val Pro Pro Thr Ala
145                 150                 155                 160

Gly Ala Arg Gln Ala Pro Glu Ser Pro Ser Thr Ile Pro Val Pro Ser
                165                 170                 175

His Pro Ser Ser Pro Leu Pro Val Pro Leu Pro Ser Arg Pro Gln Asn
            180                 185                 190
```

-continued

```
Ser Thr Leu Arg Pro Gly Pro Ala Ala Pro Ile Ala Leu Val Pro Val
        195                 200                 205
Phe Cys Gly Leu Leu Val Ala Lys Ser Leu Val Leu Ser Ala Leu Leu
    210                 215                 220
Val Trp Trp Val Leu Arg Asn Arg His Met Gln His Gln Gly Arg Ser
225                 230                 235                 240
Leu Leu His Pro Ala Gln Pro Arg Pro Gln Ala His Arg His Phe Pro
                245                 250                 255
Leu Ser His Arg Ala Pro Gly Gly Thr Tyr Gly Gly Lys Pro
                260                 265                 270

<210> SEQ ID NO 10
<211> LENGTH: 303
<212> TYPE: PRT
<213> ORGANISM: Homo sapiens

<400> SEQUENCE: 10

Met Ser Ser Thr Leu Pro Ala Leu Leu Cys Val Gly Leu Cys Leu Ser
1               5                   10                  15
Gln Arg Ile Ser Ala Gln Gln Thr Leu Pro Lys Pro Phe Ile Trp
        20                  25                  30
Ala Glu Pro His Phe Met Val Pro Lys Glu Lys Gln Val Thr Ile Cys
    35                  40                  45
Cys Gln Gly Asn Tyr Gly Ala Val Glu Tyr Gln Leu His Phe Glu Gly
    50                  55                  60
Ser Leu Phe Ala Val Asp Arg Pro Lys Pro Pro Glu Arg Ile Asn Lys
65                  70                  75                  80
Val Gln Phe Tyr Ile Pro Asp Met Asn Ser Arg Met Ala Gly Gln Tyr
                85                  90                  95
Ser Cys Ile Tyr Arg Val Gly Glu Leu Trp Ser Glu Pro Ser Asn Leu
            100                 105                 110
Leu Asp Leu Val Val Thr Glu Met Tyr Asp Thr Pro Thr Leu Ser Val
        115                 120                 125
His Pro Gly Pro Glu Val Ile Ser Gly Glu Lys Val Thr Phe Tyr Cys
    130                 135                 140
Arg Leu Asp Thr Ala Thr Ser Met Phe Leu Leu Leu Lys Glu Gly Arg
145                 150                 155                 160
Ser Ser His Val Gln Arg Gly Tyr Gly Lys Val Gln Ala Glu Phe Pro
                165                 170                 175
Leu Gly Pro Val Thr Thr Ala His Arg Gly Thr Tyr Arg Cys Phe Gly
            180                 185                 190
Ser Tyr Asn Asn His Ala Trp Ser Phe Pro Ser Glu Pro Val Lys Leu
        195                 200                 205
Leu Val Thr Gly Asp Ile Glu Asn Thr Ser Leu Ala Pro Glu Asp Pro
    210                 215                 220
Thr Phe Pro Asp Thr Trp Gly Thr Tyr Leu Leu Thr Thr Glu Thr Gly
225                 230                 235                 240
Leu Gln Lys Asp His Ala Leu Trp Asp His Thr Ala Gln Asn Leu Leu
                245                 250                 255
Arg Met Gly Leu Ala Phe Leu Val Leu Val Ala Leu Val Trp Phe Leu
            260                 265                 270
Val Glu Asp Trp Leu Ser Arg Lys Arg Thr Arg Glu Arg Ala Ser Arg
        275                 280                 285
Ala Ser Thr Trp Glu Gly Arg Arg Leu Asn Thr Gln Thr Leu
    290                 295                 300
```

<210> SEQ ID NO 11
<211> LENGTH: 216
<212> TYPE: PRT
<213> ORGANISM: Homo sapiens

<400> SEQUENCE: 11

Met Gly Trp Ile Arg Gly Arg Arg Ser Arg His Ser Trp Glu Met Ser
1               5                   10                  15

Glu Phe His Asn Tyr Asn Leu Asp Leu Lys Lys Ser Asp Phe Ser Thr
            20                  25                  30

Arg Trp Gln Lys Gln Arg Cys Pro Val Val Lys Ser Lys Cys Arg Glu
        35                  40                  45

Asn Ala Ser Pro Phe Phe Phe Cys Cys Phe Ile Ala Val Ala Met Gly
    50                  55                  60

Ile Arg Phe Ile Ile Met Val Thr Ile Trp Ser Ala Val Phe Leu Asn
65                  70                  75                  80

Ser Leu Phe Asn Gln Glu Val Gln Ile Pro Leu Thr Glu Ser Tyr Cys
                85                  90                  95

Gly Pro Cys Pro Lys Asn Trp Ile Cys Tyr Lys Asn Asn Cys Tyr Gln
            100                 105                 110

Phe Phe Asp Glu Ser Lys Asn Trp Tyr Glu Ser Gln Ala Ser Cys Met
        115                 120                 125

Ser Gln Asn Ala Ser Leu Leu Lys Val Tyr Ser Lys Glu Asp Gln Asp
    130                 135                 140

Leu Leu Lys Leu Val Lys Ser Tyr His Trp Met Gly Leu Val His Ile
145                 150                 155                 160

Pro Thr Asn Gly Ser Trp Gln Trp Glu Asp Gly Ser Ile Leu Ser Pro
                165                 170                 175

Asn Leu Leu Thr Ile Ile Glu Met Gln Lys Gly Asp Cys Ala Leu Tyr
            180                 185                 190

Ala Ser Ser Phe Lys Gly Tyr Ile Glu Asn Cys Ser Thr Pro Asn Thr
        195                 200                 205

Tyr Ile Cys Met Gln Arg Thr Val
    210                 215

<210> SEQ ID NO 12
<211> LENGTH: 336
<212> TYPE: PRT
<213> ORGANISM: Homo sapiens

<400> SEQUENCE: 12

Met Asp Tyr Pro Thr Leu Leu Leu Ala Leu Leu His Val Tyr Arg Ala
1               5                   10                  15

Leu Cys Glu Glu Val Leu Trp His Thr Ser Val Pro Phe Ala Glu Asn
            20                  25                  30

Met Ser Leu Glu Cys Val Tyr Pro Ser Met Gly Ile Leu Thr Gln Val
        35                  40                  45

Glu Trp Phe Lys Ile Gly Thr Gln Gln Asp Ser Ile Ala Ile Phe Ser
    50                  55                  60

Pro Thr His Gly Met Val Ile Arg Lys Pro Tyr Ala Glu Arg Val Tyr
65                  70                  75                  80

Phe Leu Asn Ser Thr Met Ala Ser Asn Met Thr Leu Phe Phe Arg
                85                  90                  95

Asn Ala Ser Glu Asp Asp Val Gly Tyr Tyr Ser Cys Ser Leu Tyr Thr
            100                 105                 110

Tyr Pro Gln Gly Thr Trp Gln Lys Val Ile Gln Val Gln Ser Asp
            115                 120                 125

Ser Phe Glu Ala Ala Val Pro Ser Asn Ser His Ile Val Ser Glu Pro
        130                 135                 140

Gly Lys Asn Val Thr Leu Thr Cys Gln Pro Gln Met Thr Trp Pro Val
145                 150                 155                 160

Gln Ala Val Arg Trp Glu Lys Ile Gln Pro Arg Gln Ile Asp Leu Leu
                165                 170                 175

Thr Tyr Cys Asn Leu Val His Gly Arg Asn Phe Thr Ser Lys Phe Pro
            180                 185                 190

Arg Gln Ile Val Ser Asn Cys Ser His Gly Arg Trp Ser Val Ile Val
            195                 200                 205

Ile Pro Asp Val Thr Val Ser Asp Ser Gly Leu Tyr Arg Cys Tyr Leu
210                 215                 220

Gln Ala Ser Ala Gly Glu Asn Glu Thr Phe Val Met Arg Leu Thr Val
225                 230                 235                 240

Ala Glu Gly Lys Thr Asp Asn Gln Tyr Thr Leu Phe Val Ala Gly Gly
                245                 250                 255

Thr Val Leu Leu Leu Leu Phe Val Ile Ser Ile Thr Thr Ile Ile Val
            260                 265                 270

Ile Phe Leu Asn Arg Arg Arg Arg Glu Arg Arg Asp Leu Phe Thr
            275                 280                 285

Glu Ser Trp Asp Thr Gln Lys Ala Pro Asn Asn Tyr Arg Ser Pro Ile
            290                 295                 300

Ser Thr Ser Gln Pro Thr Asn Gln Ser Met Asp Asp Thr Arg Glu Asp
305                 310                 315                 320

Ile Tyr Val Asn Tyr Pro Thr Phe Ser Arg Arg Pro Lys Thr Arg Val
                325                 330                 335

<210> SEQ ID NO 13
<211> LENGTH: 281
<212> TYPE: PRT
<213> ORGANISM: Homo sapiens

<400> SEQUENCE: 13

Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
                20                  25                  30

Pro Thr Ser Val Pro Arg Arg Pro Gly Gln Arg Arg Pro Pro Pro Pro
            35                  40                  45

Pro Pro Pro Pro Pro Leu Pro Pro Pro Pro Pro Pro Pro Leu Pro
        50                  55                  60

Pro Leu Pro Leu Pro Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
        115                 120                 125

Lys Gln Ile Gly His Pro Ser Pro Pro Pro Glu Lys Lys Glu Leu Arg
    130                 135                 140

Lys Val Ala His Leu Thr Gly Lys Ser Asn Ser Arg Ser Met Pro Leu

```
                145                 150                 155                 160
Glu Trp Glu Asp Thr Tyr Gly Ile Val Leu Leu Ser Gly Val Lys Tyr
                    165                 170                 175

Lys Lys Gly Gly Leu Val Ile Asn Glu Thr Gly Leu Tyr Phe Val Tyr
                    180                 185                 190

Ser Lys Val Tyr Phe Arg Gly Gln Ser Cys Asn Asn Leu Pro Leu Ser
                    195                 200                 205

His Lys Val Tyr Met Arg Asn Ser Lys Tyr Pro Gln Asp Leu Val Met
                    210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                    245                 250                 255

Leu Tyr Val Asn Val Ser Glu Leu Ser Leu Val Asn Phe Glu Glu Ser
                    260                 265                 270

Gln Thr Phe Phe Gly Leu Tyr Lys Leu
                    275                 280

<210> SEQ ID NO 14
<211> LENGTH: 101
<212> TYPE: PRT
<213> ORGANISM: Homo sapiens

<400> SEQUENCE: 14

Met Ala Met Met Glu Val Gln Gly Gly Pro Ser Leu Gly Gln Thr Cys
1                   5                   10                  15

Val Leu Ile Val Ile Phe Thr Val Leu Leu Gln Ser Leu Cys Val Ala
                    20                  25                  30

Val Thr Tyr Val Tyr Phe Thr Asn Glu Leu Lys Gln Met Gln Asp Lys
                    35                  40                  45

Tyr Ser Lys Ser Gly Ile Ala Cys Phe Leu Lys Glu Asp Asp Ser Tyr
            50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Thr Pro Arg Met Lys Arg
                    85                  90                  95

Leu Trp Ala Ala Lys
            100

<210> SEQ ID NO 15
<211> LENGTH: 233
<212> TYPE: PRT
<213> ORGANISM: Homo sapiens

<400> SEQUENCE: 15

Met Asp Asn Gln Gly Val Ile Tyr Ser Asp Leu Asn Leu Pro Pro Asn
1                   5                   10                  15

Pro Lys Arg Gln Gln Arg Lys Pro Lys Gly Asn Lys Asn Ser Ile Leu
                    20                  25                  30

Ala Thr Glu Gln Glu Ile Thr Tyr Ala Glu Leu Asn Leu Gln Lys Ala
            35                  40                  45

Ser Gln Asp Phe Gln Gly Asn Asp Lys Thr Tyr His Cys Lys Asp Leu
            50                  55                  60

Pro Ser Ala Pro Glu Lys Leu Ile Val Gly Ile Leu Gly Ile Ile Cys
65                  70                  75                  80

Leu Ile Leu Met Ala Ser Val Val Thr Ile Val Val Ile Pro Ser Thr
```

-continued

```
                    85                  90                  95
Leu Ile Gln Arg His Asn Asn Ser Ser Leu Asn Thr Arg Thr Gln Lys
            100                 105                 110

Ala Arg His Cys Gly His Cys Pro Glu Glu Trp Ile Thr Tyr Ser Asn
            115                 120                 125

Ser Cys Tyr Tyr Ile Gly Lys Glu Arg Arg Thr Trp Glu Glu Ser Leu
    130                 135                 140

Leu Ala Cys Thr Ser Lys Asn Ser Ser Leu Leu Ser Ile Asp Asn Glu
145                 150                 155                 160

Glu Glu Met Lys Phe Leu Ser Ile Ile Ser Pro Ser Ser Trp Ile Gly
            165                 170                 175

Val Phe Arg Asn Ser Ser His His Pro Trp Val Thr Met Asn Gly Leu
            180                 185                 190

Ala Phe Lys His Glu Ile Lys Asp Ser Asp Asn Ala Glu Leu Asn Cys
            195                 200                 205

Ala Val Leu Gln Val Asn Arg Leu Lys Ser Ala Gln Cys Gly Ser Ser
    210                 215                 220

Ile Ile Tyr His Cys Lys His Lys Leu
225             230
```